United States Patent
Hayashizaki

(10) Patent No.: US 6,365,350 B1
(45) Date of Patent: Apr. 2, 2002

(54) METHOD OF DNA SEQUENCING

(75) Inventor: Yoshihide Hayashizaki, Ibaraki (JP)

(73) Assignee: The Institute of Physical and Chemical Research (JP)

( * ) Notice: Subject to any disclaimer, the term of this patent is extended or adjusted under 35 U.S.C. 154(b) by 0 days.

(21) Appl. No.: 09/254,352

(22) PCT Filed: Jul. 6, 1998

(86) PCT No.: PCT/JP98/03039

§ 371 Date: Nov. 10, 1999

§ 102(e) Date: Nov. 10, 1999

(87) PCT Pub. No.: WO99/02729

PCT Pub. Date: Jan. 21, 1999

(30) Foreign Application Priority Data

Jul. 7, 1997 (JP) ................................. 9-196478
Jun. 4, 1998 (JP) ............................. 10-155847

(51) Int. Cl.[7] .................. C12Q 1/68; C12N 9/12; C07H 21/02; C07H 21/04
(52) U.S. Cl. ............... 435/6; 435/91.1; 435/194; 536/23.1; 536/24.33
(58) Field of Search .............. 435/6, 91.1, 91.2, 435/91.21, 194; 436/94; 536/23.1, 24.3, 24.33, 25.3

(56) References Cited

FOREIGN PATENT DOCUMENTS

| JP | 60-61594 | 9/1985 |
|---|---|---|
| JP | 7327698 | 12/1995 |
| WO | 93/02116 | 4/1993 |
| WO | 95/12689 | 5/1995 |
| WO | 95/29258 | 11/1995 |
| WO | 96/14434 | 4/1996 |
| WO | 96/12042 | 5/1996 |
| WO | 97/45555 | 12/1997 |

OTHER PUBLICATIONS

Chalfie et al., "Green Fluorescent Protein as a Marker for Gene Expression" *Science* 263:802–805 (1994).
Myers et al., "Recent Advances in the Development of Methods for Detecting Single–base Substitutions Associated with Human Genetic Diseases " *Cold Spring Harbor Symposia on Quantitative Biology,* 51:275–284 (1986).
Lu et al., "Detection of Single DNA Base Mutations with Mismatch Repair Enzymes", *Genomics* 14:249–255 (1992).
Gibbs et al., "Identification and Localization of Mutations at the Lesch–Nyhan Locus by Ribonuclease A Cleavage", *Science,* 236:303–305 (1987).
Schena et al., "Parallel Human Genome Analysis: Microarray–based Expression Monitoring of 1000 Genes", *Proc. Natl. Acad. Sci. USA,* 93:10614–10619 (1996).
Parsons et al, "Evaluation of MutS as a Tool for Direct Measurement of Point Mutations in Genomic DNA", *Mutation Research,* 374:2:277–285 (1997).

*Primary Examiner*—Bradley L. Sisson
(74) *Attorney, Agent, or Firm*—Burns, Doane, Swecker & Mathis, L.L.P.

(57) ABSTRACT

Disclosed are methods for determining DNA nucleotide sequences comprising reacting ribonucleoside 5'-triphosphates and 3'-dNTP derivatives in the presence of an RNA polymerase modified so as to enhance its ability for incorporating the 3'-dNTP derivatives and a DNA fragment containing a promoter sequence for the RNA polymerase to obtain a nucleic acid transcription product, separating the resulting nucleic acid transcription product, and determining a nucleic acid sequence from the resulting separated fraction. These methods can produce a transcription product of a long chain and afford more accurate sequence data where fluctuation of signals from labeled deoxyribonucleotides is reduced.

18 Claims, 64 Drawing Sheets

Fig. 1

```
AGGCACTAAATGAACACGATTAACATGCTAAGAACGACTTCTCTGACATCGAACTGGCTGCTATCCGTTCAACACT:3239
              M  N  T  I  N  M  A  K  N  D  F  S  D  I  E  L  A  A  I  P  F  N  T  :23
CTGGCTGACCATTACGGTGAGCGTTTAGCTCGCGAACAGTTGGCCTTGAGCATGAGTCTTACGAGATGGGTGAAGCA:3317
 L  A  D  H  Y  G  E  R  L  A  R  E  Q  L  A  L  E  H  E  S  Y  E  M  G  E  A  :49
CGCTTCCGCAAGATGTTTGAGCGTCAACTTAAAGCTGGTGAGGTTGCGGATAACGCTGCCAAGCCTCTCATCACT:3395
 R  F  R  K  M  F  E  R  Q  L  K  A  G  E  V  A  D  N  A  A  K  P  L  I  T  :75
ACCCTACTCCCTAAGATGATTGCACGCATCAACGACTGGTTTGAGGAAGTGAAAGCTAAGCGCGGCAAGCGCCGACA:3473
 T  L  L  P  K  M  I  A  R  I  N  D  W  F  E  E  V  K  A  K  R  G  K  R  P  T  :101
GCCTTCCAGTTCCTGCAAGAAATCAAGCCGGAAGCCGTAGCGTACATCACCATTAAGACCACTCTGGCTTGCCTAACC:3551
 A  F  Q  F  L  Q  E  I  K  P  E  A  V  A  Y  I  T  I  K  T  T  L  A  C  L  T  :127
AGTGCTGACAATACAACCGTTCAGGCTGTAGCAAGCGCAATCGGTCGGGCCATTGAGGACGAGGCTCGCTTCGGTCGT:3629
 S  A  D  N  T  T  V  Q  A  V  A  S  A  I  G  R  A  I  E  D  E  A  R  F  G  R  :153
ATCCGTGACCTTGAAGCTAAGCACTTCAAGAACAACGTTGAGGAACAACTCAACAAGCGCGTAGGGCACGTCTACAAG:3707
 I  R  D  L  E  A  K  H  F  K  K  N  V  E  E  Q  L  N  K  R  V  G  H  V  Y  K  :179
AAAGCATTTATGCAAGTTGTCGAGGCTGACATGCTCTCTAAGGGTCTACTCGGTGGCGAGGCGTGGTCTTCGTGGCAT:3785
 K  A  F  M  Q  V  V  E  A  D  M  L  S  K  G  L  L  G  G  E  A  W  S  S  W  H  :205
AAGGAAGACTCTATTCATGTAGGAGTACGCTGAGTCAATCGAGATATCGAGTCTTACATTGAGCTTACACCGC:3863
 K  E  D  S  I  H  V  G  V  R  C  I  E  M  L  I  E  S  T  G  M  V  S  L  H  R  :231
CAAAATGCTGGCGTAGTAGGTCAAGACTCTGAGACTATCGAACTCGCACCTGCTTACGAAGCCGTTGGAGCGAGCCGTGATTACTGGT:3941
 Q  N  A  G  V  V  G  Q  D  S  E  T  I  E  L  A  P  E  Y  A  E  A  I  A  T  R  :257
GCAGGTGCGCTGGCTATTGGGCTAACGGTCGTCGTCCTGGCGCGTGCACTAGTCCTCACAGTAAGAAAGCACTGATGCGCTACGAA:4019
 A  G  A  L  A  G  I  S  P  M  F  Q  P  C  V  P  P  K  P  W  T  G  I  T  G  :283
GGTGGCTATTGGGCTAACGGTCGTCCTGAGGTGTACAAGCCCTGAGGTGTACAAGCGATTAACATTGCGCAAAATCAACAAGAAAGTCCTA:4097
 G  G  Y  W  A  N  G  R  R  P  L  A  L  V  R  T  H  S  K  K  A  L  M  R  Y  E  :309
GACGTTTACATGCCCTGAGGTGTACAAAATCAACATGCCCTGAGGTCCGAGGACATCCCTGCGATTGAGCGCTGAAGAACTCCCG:4175
 D  V  Y  M  P  E  V  Y  K  A  I  N  I  A  Q  N  T  A  W  K  I  N  K  V  L  :335
GCGGTCGCCAACGTAATCACCAAGTGGAAGCATTGTCCGGTCCCTGTGTCCGAGGCTCTCACCGCCTGTGTGCTCCGCTGTGCCGCTGTACCGCAAG:4253
 A  V  A  N  V  I  T  K  W  K  H  C  P  V  E  D  I  P  A  I  E  R  E  E  L  P  :361
ATGAAAACCGGAAGACATCGACATGAATCCTGAGGCTCTAACTGCGTGGAAAAGAGCGCGCAGCCGCAGCCGTAAGAGTACCGCAAG:4331
 M  K  P  E  D  I  D  M  N  P  E  A  L  T  A  W  K  R  A  A  A  A  V  Y  R  K  :387
GACAAGGCTCGCAAGTCTCGCCGTATCAGCCTTGAGTTCATGCTTGAGCAAGCCAATAAGTTTGCTAACCATAAGGCC:4409
 D  K  A  R  K  S  R  R  I  S  L  E  F  M  L  E  Q  A  N  K  F  A  N  H  K  A  :413
ATCTGGTTCCCTTACAACGTAATGACTGGTGGCGCGGTCGTGTTTACGCTGTGTCAAGTTCAACGCAAGTAACGATATG:4487
 I  W  F  P  Y  N  M  D  W  R  G  R  V  Y  A  V  S  M  F  N  P  Q  G  N  D  M  :439
ACCAAAGGACTCTTACGCTGGCAGGTAACCAATCGGTAAGGTTACTACTGCTGAAAATCCACGGTGCA:4565
 T  K  G  L  L  T  L  A  R  G  K  P  I  G  K  E  G  Y  Y  W  L  K  I  H  G  A  :465
```

Fig. 2

```
AACTGTGCGGGTGTCGATAAGGTTCCCGTTCCCTGAGCGCATCAAGTTCATTGAGGAAAACCAGAGAACATCATGGCT:4643
 N   C   A   G   V   V   D   K   V   P   F   P   P   E   R   I   K   F   I   E   E   N   H   E   N   I   M   A  : 491
TGCGCTAAGTCTCCACTGGAGAACACTTGGTGGGCTGAGCAAGATTCTCCGTTCTTGCTTCTGCTTTGAG:4721
 C   A   K   S   P   L   E   N   T   W   W   A   E   Q   D   S   P   F   C   F   L   A   F   C   F   E  : 517
TACGCTGGGGTACAGCACCACCACGGCCTGAGCTATAACTGCTCCCTTCCGCTGGCGTTTGACGGGTCTTGCTCTGGCATC:4799
 Y   A   G   V   Q   H   H   G   L   S   Y   N   C   S   L   P   L   A   F   D   G   S   C   S   G   I  : 543
CAGCACTTCTCCGCGATGCTCCGAGATGAGGTAGGTGGTCGCGCGGTTAACTTGCTTCCTAGTGAAACCGTTCAGGAC:4877
 Q   H   F   S   A   M   L   R   D   E   V   G   G   R   A   V   N   L   L   P   S   E   T   V   Q   D  : 569
ATCTACGGGATTGTTGCTAAGAAAGTCAACGAGATTCTACAAGCAGACGCAATCAATGGGACCGATAACGAAGTAGTT:4955
 I   Y   G   I   V   A   K   K   V   N   E   I   L   Q   A   D   A   I   N   G   T   D   N   E   V   V  : 595
ACCGTGACCGATGAGAACACTGGTGAAATCTCTGAGAAAGTTCAAGCTGGGCACTAAGCACTGGTCAATGGCTG:5033
 T   V   T   D   E   N   T   G   E   I   S   E   K   V   K   L   G   T   K   A   L   A   G   Q   W   L  : 621
GCTTACGGTGTGTTACTCGCAGTGTGACTAAGACGTCAGTCAGTCAAGAGTTCGGCTTCCGT:5111
 A   Y   G   V   T   R   S   V   T   K   R   S   V   M   T   L   A   Y   G   S   K   E   F   G   F   R  : 647
CAACAAGTCTGGAAGATACCAGCTCAGCACTATTCAGCCAGTGTTCACTCAGCCGAATCAGGCT:5189
 Q   Q   V   L   E   D   T   I   Q   P   A   I   D   S   G   K   G   L   M   F   T   Q   P   N   Q   A  : 673
GCTGGAATACATGGCTAAGCTGCTGGCTGCTGAGGTCAAAGATCTGGAGAGAGACTGAAGAAGATAAGAACTGGCTT:5267
 A   G   Y   M   A   K   L   L   W   E   S   V   S   V   T   V   V   A   A   V   E   A   M   N   W   L  : 699
AAGTCTGCTGCTAAGCTGCTGGCTGCTGAGGTCAAAGACTGGAGAGAGACTGAAGAAGATAAGAAGACCGGCGAGATTCTTCGCAAGCGTTGCGCTGTG:5345
 K   S   A   A   K   L   L   A   A   E   V   K   D   K   K   T   G   E   I   L   R   K   R   C   A   V  : 725
CATTGGGTAACTCCTGATGGTTTCCCTGTGTGGCAGGAAGCCCTATTCAGACGCGCTGAACCTGATGTTC:5423
 H   W   V   T   P   D   D   G   F   P   V   W   Q   E   Y   K   K   P   I   Q   T   R   L   N   L   M   F  : 751
CTCGGTCAGTTCCGCTAACTTGTACACAGCCTACCATTAACACGGTAGCCACCTTCGTAAGACTGTAGTGTGGCCACACGAGAGTCTGGT:5501
 L   G   Q   F   R   L   Q   P   T   I   N   T   N   K   D   S   E   I   D   A   H   K   Q   E   S   G  : 777
ATCGCTCCCTAACTTTGTACACAGCCAAGACGGTAGCCACCTTCGTAGTGTGGCACACGAGAAGTACGGA:5579
 I   A   P   N   F   V   H   S   Q   D   G   S   H   L   R   K   T   V   V   W   A   H   E   K   Y   G  : 803
ATCGAATCTTTTGCACTGATTCACGACTCCTTCGGTACCATTCCGGCTGACGCTGCGAACCTGTTCAAAGCAGTGCGC:5657
 I   E   S   F   A   L   I   H   D   S   F   G   T   I   P   A   D   A   A   N   L   F   K   A   V   R  : 829
GAAACTATGGTTGACACATATGAGTCTTGTGATGTACTGGCTGATTTCTACGACCAGTTCGCTGACCAGTTGCACGAG:5735
 E   T   M   V   D   T   Y   E   S   C   D   V   L   A   D   F   Y   D   Q   F   A   D   Q   L   H   E  : 855
TCTCAATTGGACAAAATGCCAGCACTTCCGGCTAAAGGTAACTTGAACCTCCGTGACATCTTAGAGTCGGACTTCGCG:5813
 S   Q   L   D   K   M   P   A   L   P   A   K   G   N   L   N   L   R   D   I   L   E   S   D   F   A  : 881
TTCGCGT:5820
 F   A  : 883
```

Fig. 3

```
T7    1:MNTI-NIAKNDFSDIELAAIPFNTLADHYGERLAREQLALEHESYEMGEARFRKMFERQLKAGEVADNAAAKPLITT
T3    1:...I.E..E......E.............SA..K........L..R..L..L...A....I..........LA.
K11   1:..AL...GR....E......----------Y.I.SE...DQA.......A..L.RQ..L..L...V...F......VL.
SP6   1:--------------------------------MQDLH.I---Q..E.MFNG.IR..EADQQ..IA..SES.T.WNRR.LSE
                                              *    ** **    *  *   ** ** **  *

T7    80:KMIARINDWFEEVKAKRGKRPTAFQFL-QEIKPE-A---VAYI-TIK----------TTLA----CLTSADNT-TVQ--A
T3    81:.LTT..VE.L..YAS.K.RK.S.YAP..LL.....----S.F..L..------VI...--S...TNM..-I.---.
K11   80:QLTK...D..K..QANA...K.R.YYPIKHGVAS.L.VSMG.EVLKE.RGVSSEAIAL.TIKVV.GN.HRPLKGHNP.
SP6   52:P.AEG.QAYK..YEG.K.RA.R.LA..Q-CVEN.---VA---.YI.M.---V---M--DM--NT.A.L--Q--.
                *       *  *                  *

T7   140:AIGRAIEDEARFGRIRDLEAKHFKKNVEEQLNKRVGHVYKKAFMQVVEADMLSKGLLGG-EAWSSWHKEDSIHVGVR
T3   141:ML.K..............................H..Q...............IGR.-------D..TTM...I.
K11  160:QL.K.L............EQ..AY....AD..D...........I..M..-DN.A..KTDEQM...TK
SP6  110:SVAER...QV..SKLEGHA..Y.E.--KKS.KASRTKS.RH.HNVA.V.EKSVAEKDADFDR.EA.P..TQLQI.TT
              **                *   **    **  **          *

T7   219:MLIESTGMVSLHRQN-A-GVVG-QDSETIELAPEYAEAIATR--AGALAGISPMFQPCVVPPKPWTGITGGGYW-ANG
T3   220:.....L.E.Q.H..-.NA.-S.H.ALQ..Q..VDVL.K.---------------------VA-----------.
K11  239:L..-G..L.EMTKNKM.D.SDDVTSMQMVQ...AFV.LLSK.-----------H.............VETV....-SV.
SP6  189:I.--.GSVFYNGEPVFMRAMRTYGGKTIYYLQTS.SVGQWISAFKEHV.QL..AYA...I..R...RTPFN..FHTEKV
              *                                    *     ***  ***  *   **       *

T7   294:LALVRTHSKKALMRYEDVYMPEVYKAINIAQNTAWKINKKVLAVANVITKWK-HCPVED-IPAIEREELP--MKPED
T3   295:..........G.........................V.L.........V.EVN...-N..A...SL..Q....-P..D.
K11  317:...........................R.A..H.........V.L..P.V...........V.EVN..-...G.-V........-PR.D.
SP6  268:IR..KGN-REHVRKLTQKQ...K......AL...Q.Q...D....IEEVIRLDLGYG.PSFK.L.DK.NK.ANPV.VE
        **      *****                **   **     *          *

T7   367:I----D-MNPEALTAW-----KRAA---AAVYRKDKARKSRRISLEFMLEQANKFANHKAIWFPYNMDWRGRVY-AVSMF
T3   368:..----.T.EA..KE..---.K.-----K........GI..L...V...........................P...
K11  390:..----.T.EV.RK..----RKE.---........Q...CRC..VA.................................
SP6  347:LRGRELKEMLSPEQ.QQFINWKGEC.RL.TAETK.G.KSAAVVR.VG..R.YSAFES.Y.V.A..S..VQS.TL
                      *                                *  *   ***
```

Fig. 4

```
T7   436:GNDMTKGLLTTLARGKPI-GKEGYYWLKIHGANCAGVDKVPFPERI-KFIEENHENI-MACAKSPLENTWAEQDSPF
T3   437:..................................E..F.........-A...KHVDD.-L...D.IN.........
K11  459:......................S.........-LD.F..........EG.-L.S.AD..N...TQ..........
SP6  427:S...LG.A..RFTE.R.VN.V.ALK.FC.N...LW.W..KT.DV.VSNVLD.EFQDMCRDI.AD..TF.Q..KA.A.Y
         **       ********     *  **  ***    *      *  **   **  *    **      *      *

T7   513:AFCFEYA---GVQHHG-L-SYNCSLPLAFDGSCSGIQHFSAMLRDEVGGRAVNLLPSETVQDIYGIVAKKVNEILQA
T3   514:.........T..-...-............................................Q........KQ
K11  536:.........K..-...-..............................SI.....D......K..D....V.HQ
SP6  507:W.....QYLDLVDE.RADEFRTH..VHQ..................Y........AK...K..DAP....A.-Q.--V-I
         *  *****       *            **  ********* ****** *  ****  **  *      *  **

T7   588:NGTDNEVVTVTDENTGEISEKVKLGTKALAGWLAYGVTRSVTKRSVMTLAYGSKEFGFRQQVLEDTIQ-PAIDSGK
T3   589:..P..MI....KD....L...ST..Q..................D.....-...
K11  611:..SQTV.EQIA.KE...FH...T..ESV..A...Q...K...............SLV.....-...N.E
SP6  581:.ALYMDADDA.TFTS.SVTLSGT-ELR.M.SA.DSI.I...L..KP....P...TRLTC..ES..IDYIVDLEEKEAQ.
                  *         *   *  **  * **   *****    **          ***    ***

T7   667:FT-QPNQAAGYMAKLIWESVSVTVVAAVEAMNWLKSAAKLLAAEVKDKKTGEILR---KRC-AVHWVTPDGFPVWQE
T3   668:..-.-.............DA.........................K......----H......T.........
K11  690:.-H.................DA.T...............................K.V..---.I.........
SP6  660:EGRTA.KVHPFEDDRQDYLTPGAAYNYMT.LI.PSISEVVK.PI.AM.MIRQLA.FAA..NEGLMYTL.T..ILE.K
           *                                                                   *

T7   742:PIQTRLNLMFLGQFRLQPTINTNKDSEIDAHKQESGIAPNFVHSQDGSHLRKTVWAHEKYGIESFALIHDSFGTIP
T3   743:..L.K..DMI........L...G..............M...Y................S...
K11  765:QN.A..K.V...ANVKM.Y..G...............M..H.N.V..D........S....
SP6  740:TEML.VRTCLM.DIKMSLQVE.---.IV.EAAMMGAA......GH.A...IL..CELVD.-.VT.I.V......HA
           *                *         ******       ***         **       ****  **

T7   822:ANLFKAVRETMVDTYESCDVLADFYDQFADQLHESQLDKMPALPAKGNLNLRDILESDFAFA
T3   823:GK..........I...NN.......S.......T....P..K....Q..K......
K11  845:G..........K...DN..I.........V...D........
SP6  816:LT.RV.LKGQ..AM.IDGNA.QKL-LE-EHEVR-WMV.TGIEV.LE-EHEVR-WMV.TGIEV.EQ.EFD.NE.MD.EYV..
           *         **                     *      *    *
```

Fig. 6

```
T7RNApol   1:MNTI-NIAKNDFSDIELAAIPFNTLADHYGERLAREQLALEHESYEMGEARFRKMFERQL
T3RNApol   1:...I.E..E...............SA..K..........L..R..L...A
             ** * ** ***** ****************** ** *********  ** ***

T7RNApol  60:KAGEVADNAAAKPLITTLLPKMIARINDWFEEVKAKRGKRPTAFQFLQEIKPEAVAYITI
T3RNApol  61:....I..........LA......LTT..VE.L..YAS.K.RK.S.YAP..LL...S.F..L
             **** ********** ***** ****** ****** **  ** **** **   * **

T7RNApol 120:KTTLACLTSADNTTVQAVASAIGRAIEDEARFGRIRDLEAKHFKKNVEEQLNKRVGHVYK
T3RNApol 121:.VI..S...TNM..I..A.GML.K..................H........H.Q...
              ** ****   *** *  * *** *  *****************  ******** * ***

T7RNApol 180:KAFMQVVEADMLSKGLLGGEAWSSWHKEDSIHVGVRCIEMLIESTGMVSLHRQNAGVVGQ
T3RNApol 181:..........IGR...............D..TTM...I.L......L.E.Q.H...NA.S
              **********   *************** ** *** * * ******  * * *  **  *

T7RNApol 240:DSETIELAPEYAEAIATRAGALAGISPMFQPCVVPPKPWTGITGGGYWANGRRPLALVRT
T3RNApol 241:H.ALQ..Q..VDVL.K...............................VA.........
              *  *  * * ** * * **********************************  ************

T7RNApol 300:HSKKALMRYEDVYMPEVYKAINIAQNTAWKINKKVLAVANVITKWKHCPVEDIPAIEREE
T3RNApol 301:....G...............V.L.............V.E.VN..N..A...SL..Q.
             **** ***************  * ************* * * **  *  *  *** ** *

T7RNApol 360:LPMKPEDIDMNPEALTAWKRAAAAVYRKDKARKSRRISLEFMLEQANKFANHKAIWFPYN
T3RNApol 361:..P..D...T.EA..KE..K...GI..L....V.........SK...............
              ** *** *  * ***  ** * *** ** *** ********  ** ************
```

Fig. 7

```
T7RNApol  420:MDWRGRVYAVSMFNPQGNDMTKGLLTLAKGKPIGKEGYYWLKIHGANCAGVDKVPFPERI
T3RNApol  421:..........P.........................E..F..................
              **********.**************************.**.******************

T7RNApol  480:KFIEENHENIMACAKSPLENTWWAEQDSPFCFLAFCFEYAGVQHHGLSYNCSLPLAFDGS
T3RNApol  481:A...KHVDD.L....D.IN.........T...............................
              *.***.****.*.****.*.********.*******************************

T7RNApol  540:CSGIQHFSAMLRDEVGGRAVNLLPSETVQDIYGIVAKKVNEILQADAINGTDNEVVTVTD
T3RNApol  541:KD......L....ST..Q.................Q......KQ......P..MI....
              .*******.****..*.*.****************.*******.******.**.**.***

T7RNApol  600:ENTGEISEKVKLGTKALAGQWLAYGVTRSVTKRSVMTLAYGSKEFGFRQQVLEDTIQPAI
T3RNApol  601:KD......L....ST..Q.................................D.......
              .*******.****..*.*.*****************************************

T7RNApol  660:DSGKGLMFTQPNQAAGYMAKLIWESVSVTVAAVEAMNWLKSAAKLLAAEVKDKKTGEIL
T3RNApol  661:...........................DA.........................K...
              ***************************.**************************.***

T7RNApol  720:RKRCAVHWVTPDGFPVWQEYKKPIQTRLNLMFLGQFRLQPTINTNKDSEIDAHKQESGIA
T3RNApol  721:..H....T............R..L..K..DMI............L...G..........
              **.****.*************.**.**.**.****************.***.********

T7RNApol  780:PNFVHSQDGSHLRKTVVWAHEKYGIESFALIHDSFGTIPADAANLFKAVRETMVDTYESC
T3RNApol  781:.........M...Y..........................GK.......I...NN
              *********.***.**************************.*********.***

T7RNApol  840:DVLADFYDQFADQLHESQLDKMPALPAKGNLNLRDILESDFAFA
T3RNApol  841:......S........T........P..K......Q...K.....
              ******.********.********.**.******.***.******
```

Fig. 8

```
T7              617:AGQWLAYGVTRSVMTLAYGSKEFGFRQQVLEDTIQ-PAIDSGKGLMFT-QPNQAAGYMAKLIWESVSVTV
T7 F644Y        617:AGQWLAYGVTRSVMTLAYGSKEYGFRQQVLEDTIQ-PAIDSGKGLMFT-QPNQAAGYMAKLIWESVSVTV
T7 L665P/F667Y  617:AGQWLAYGVTRSVMTLAYGSKEFGFRQQVLEDTIQ-PAIDSGKGPMYT-QPNQAAGYMAKLIWESVSVTV
T3              618:..Q.............................D............................DA......
K11             640:..A...Q.......K...........SLV........N.E......H.............DA..T...
SP6             609:..SA.DSI.I....L..KP......P...TRLTC.ES.IDYIVDLEEKEAQ.AVAEGRTA.KVHPEDDRQDYLTPGAA
                      **  **** ***  *              ****  ***                *
                                           Motif B
                           ▲644                   ▲667
                                   ▲                 ▲
                                   ▲                 ▲
```

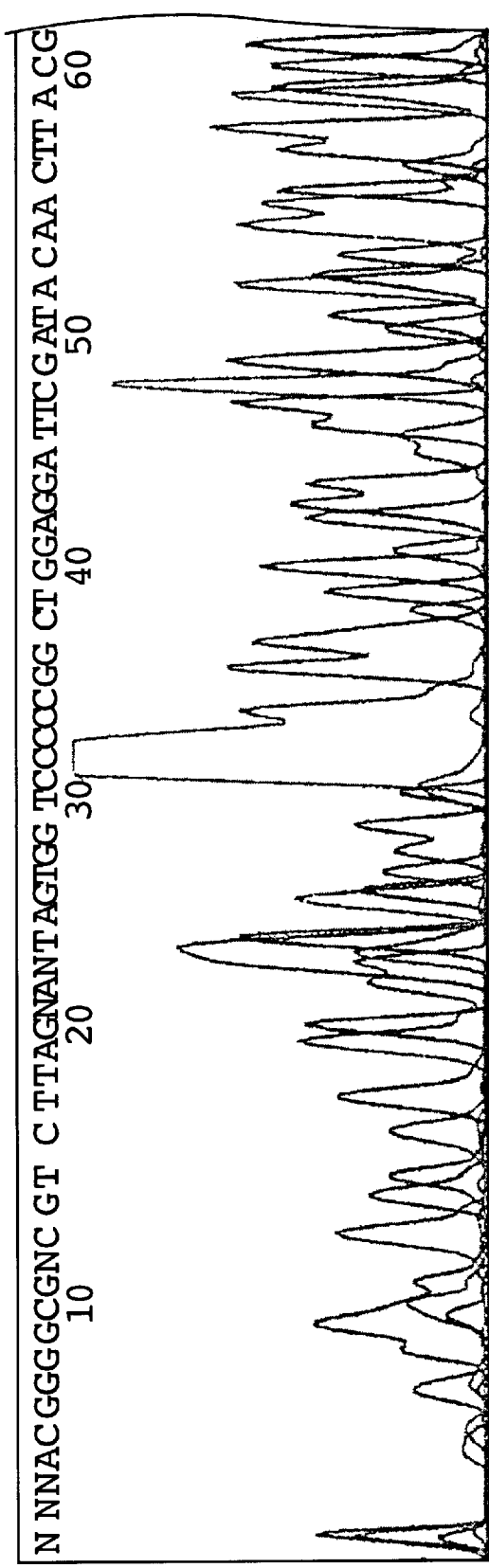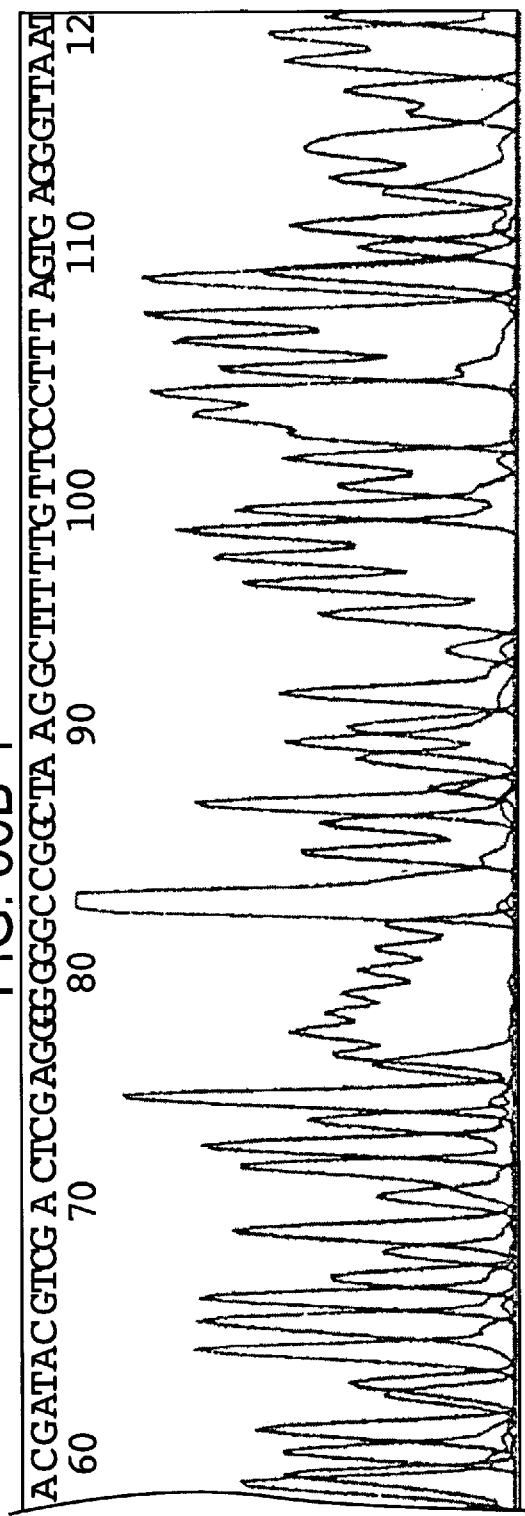
FIG. 36B-1     FIG. 36B-2

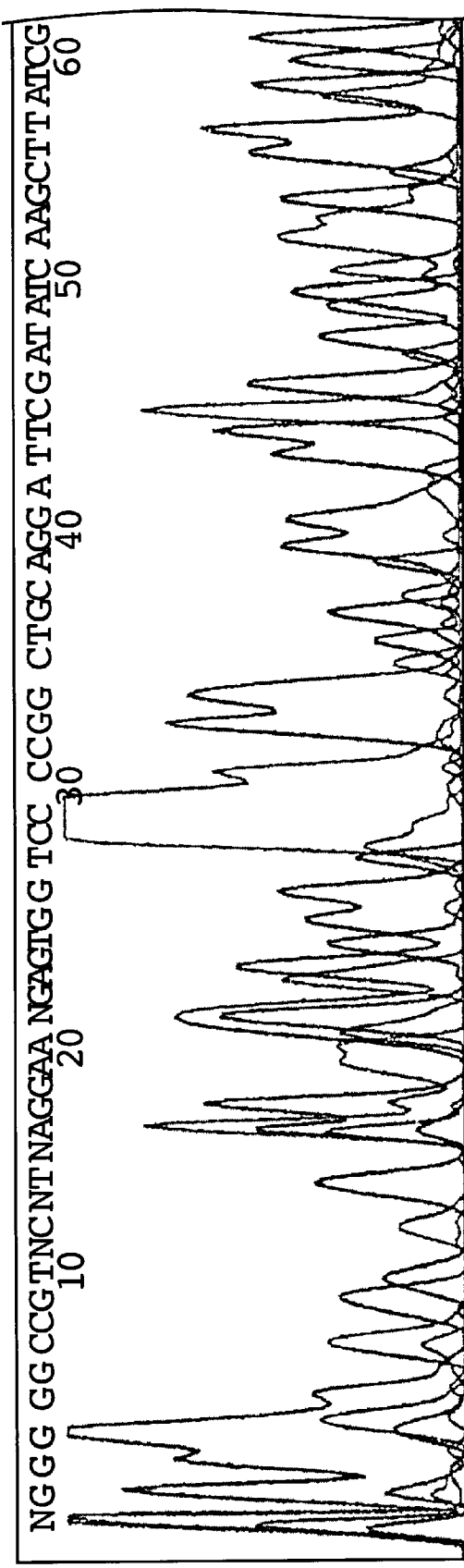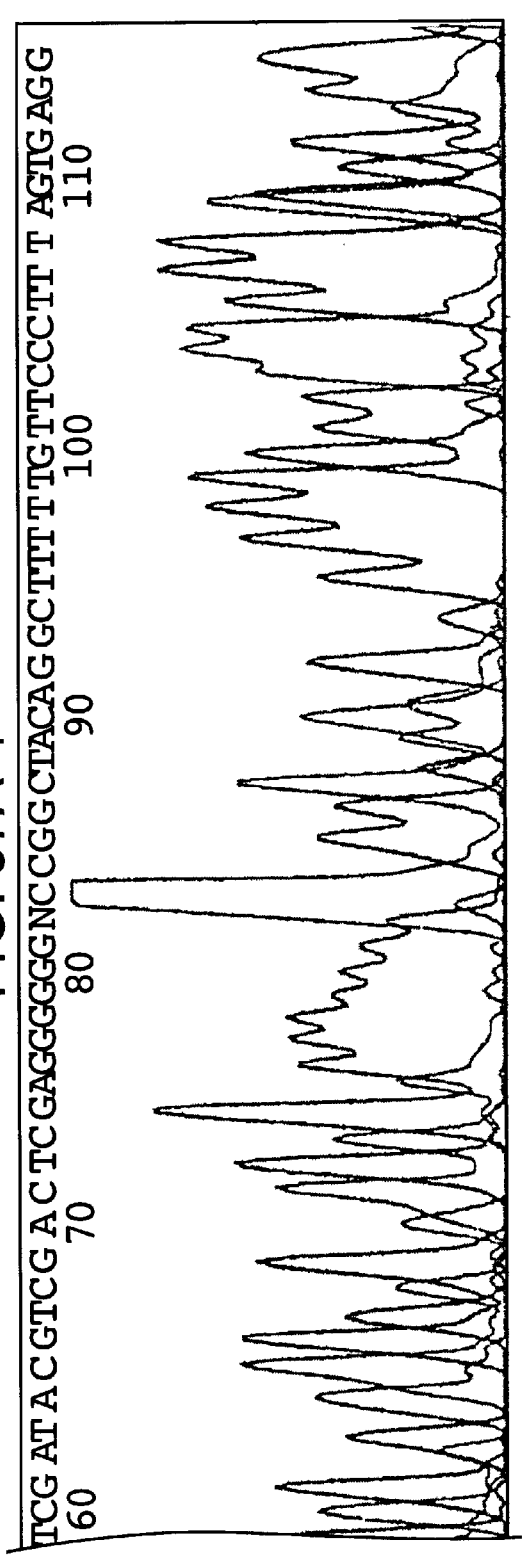
FIG. 37A-1
FIG. 37A-2

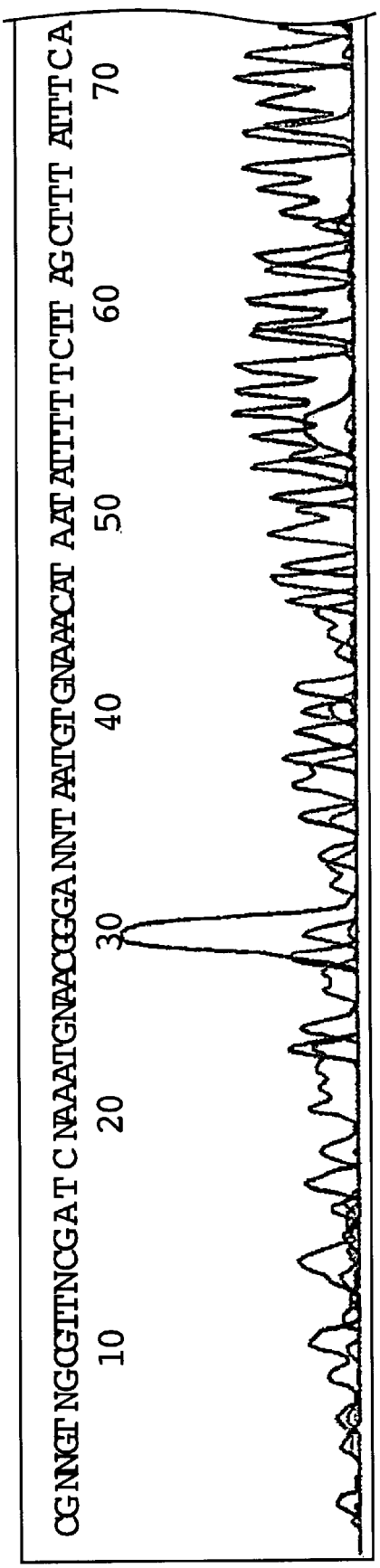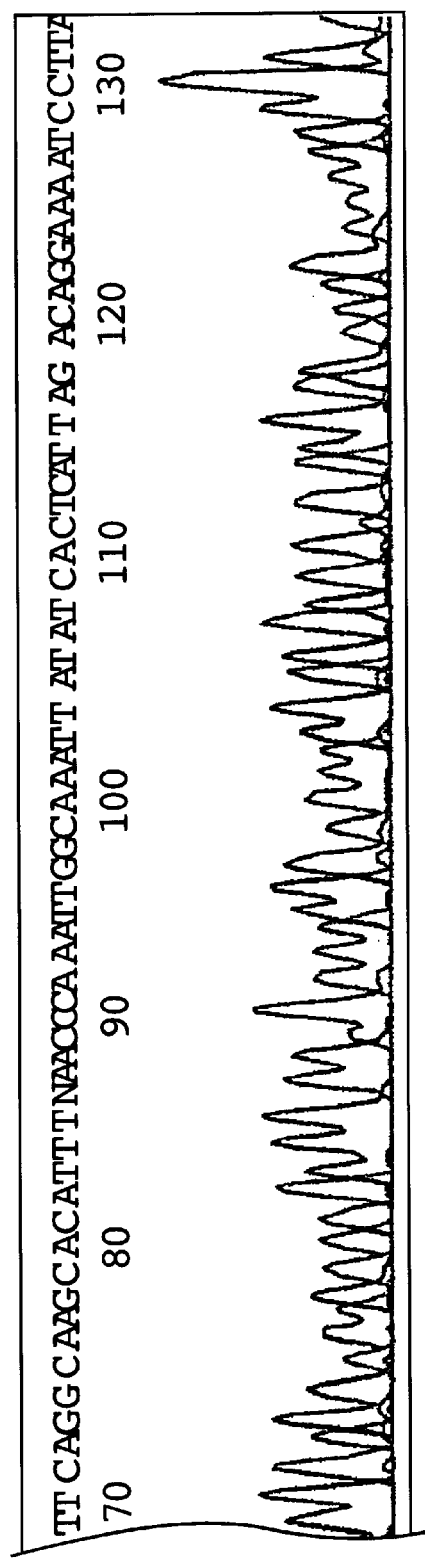
FIG. 40A
FIG. 40B

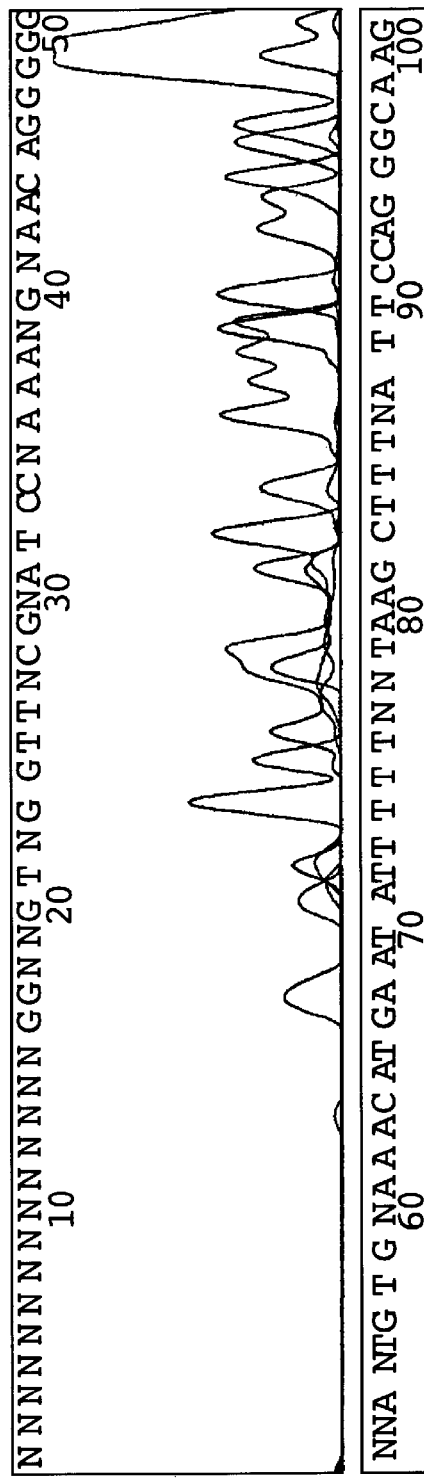
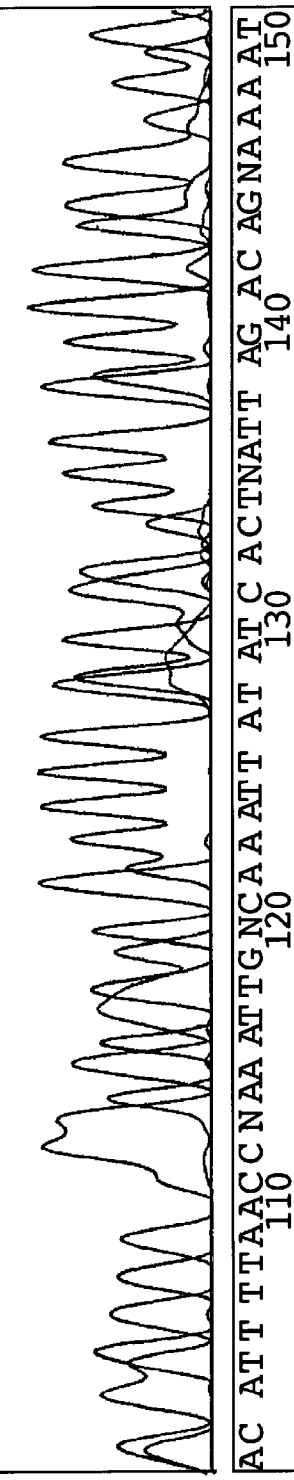
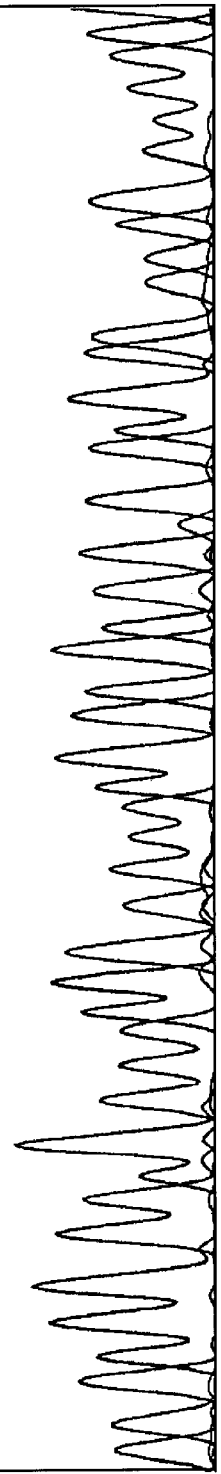
FIG. 41A-1
FIG. 41A-2
FIG. 41A-3

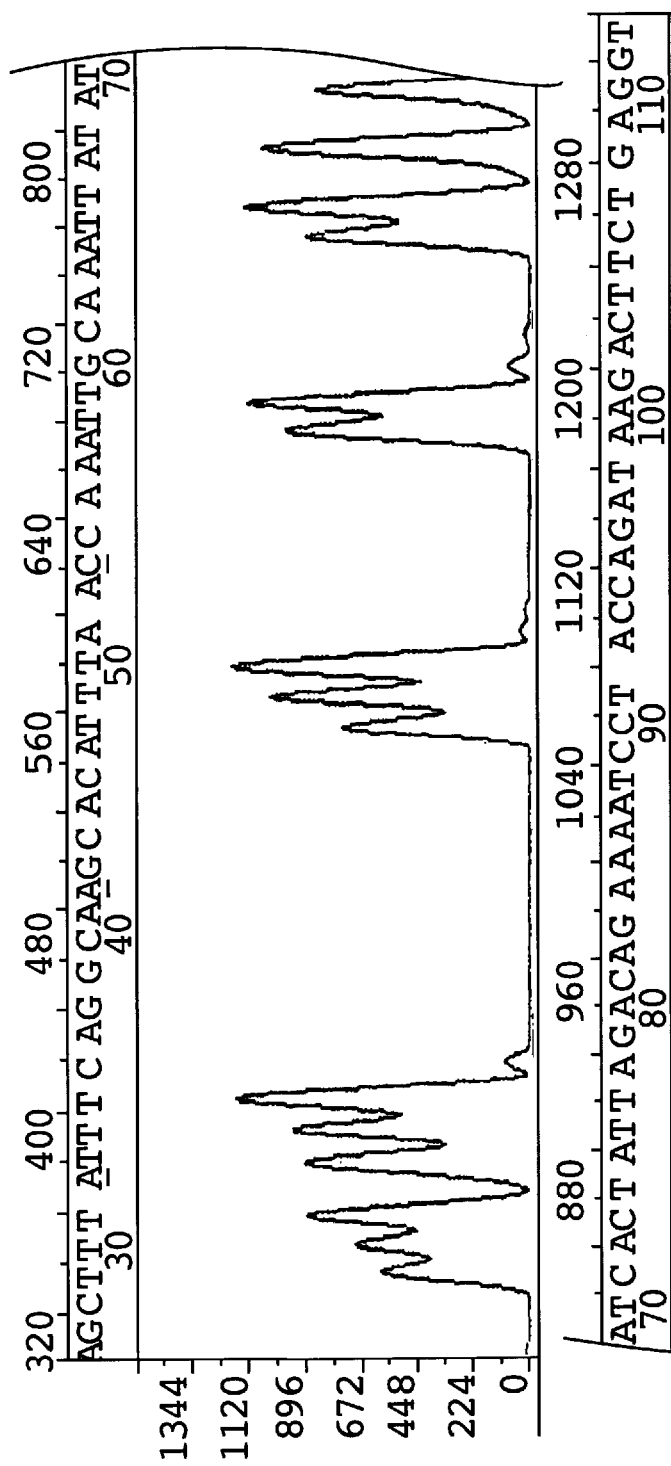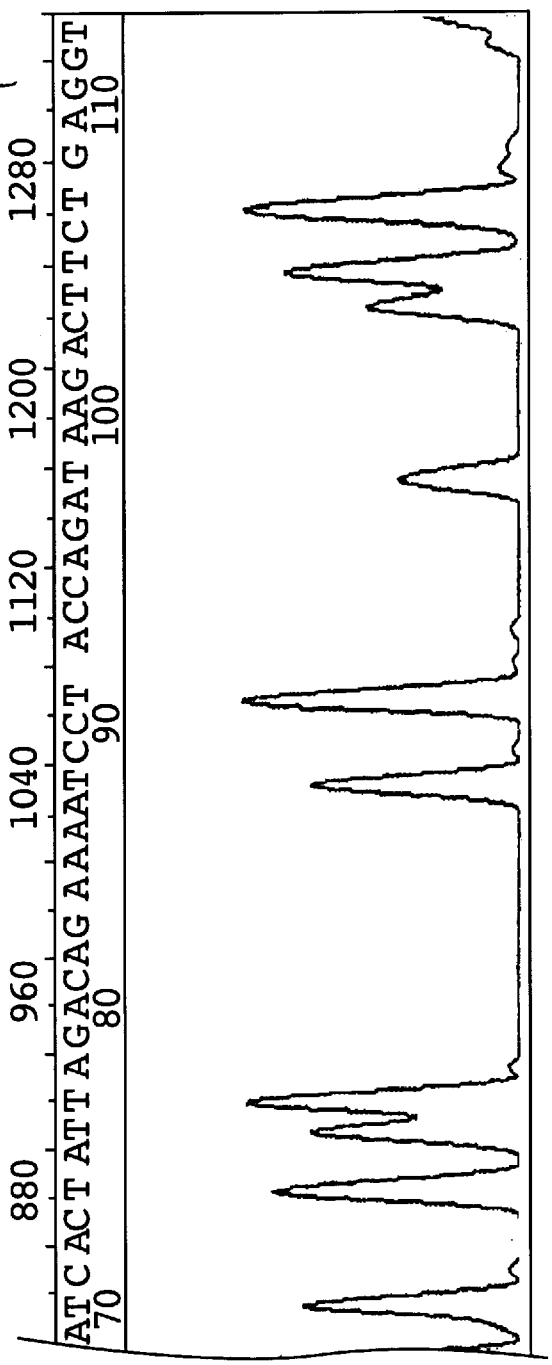

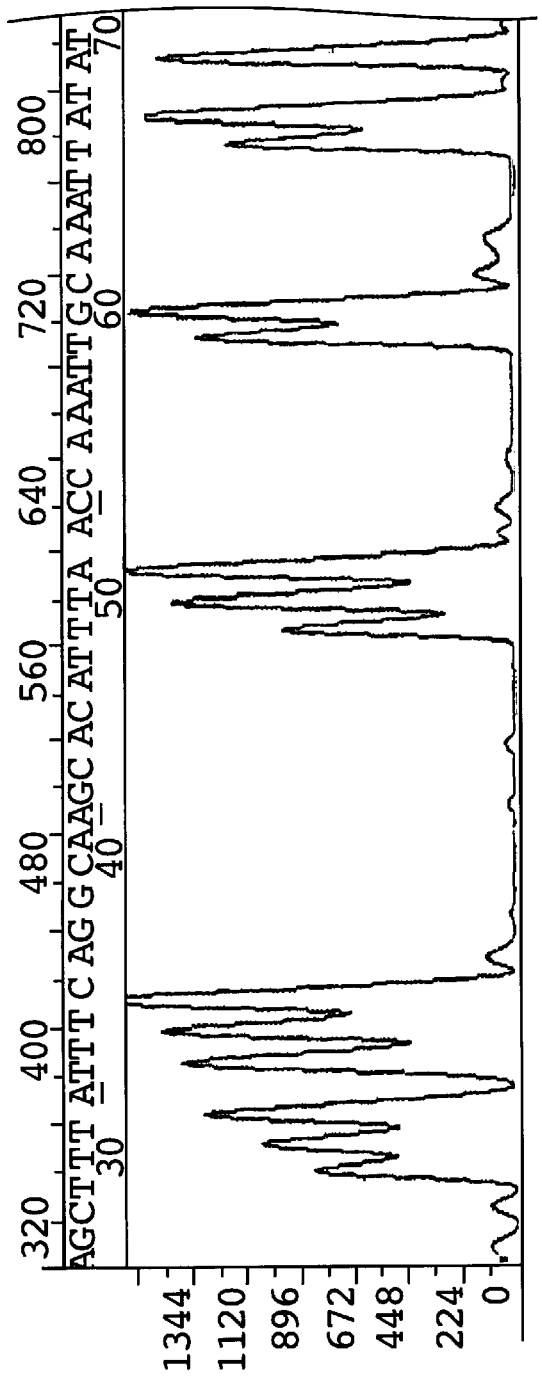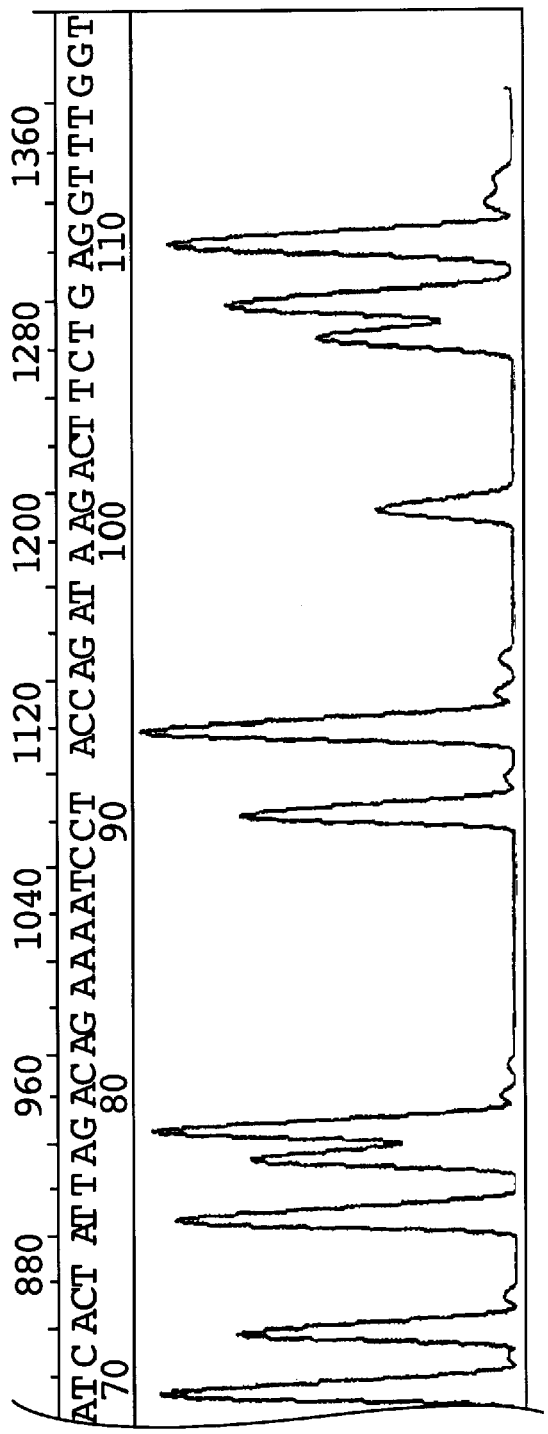

SEQUENCE LISTING

<160> NUMBER OF SEQ ID NOS: 64

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence:
    T7 RNA polymerase

<400> SEQUENCE: 1
atattttagc catggaggat tgatatatga acacgattaa catcgctaag          50

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: T7 RNA
    polymerase

<400> SEQUENCE: 2
atattttagc catggtatag tgagtcgtat tgatttggcg                     40

<210> SEQ ID NO 3

```
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 3
gttgacggaa gccgtactct ttggac                                    26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 4
gtccaaagag tacggcttcc gtcaac                                    26

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: T7 RNA
      P-HpaI-N primer

<400> SEQUENCE: 5
cgcgcggtta acttgcttcc tag                                       23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      pTrc99a-PstIC primer

<400> SEQUENCE: 6
gcatgcctgc aggtcgactc tag                                       23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer
      ApaF1

<400> SEQUENCE: 7
catctggtcg cattgggtca c                                         21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Xho-R
      primer

<400> SEQUENCE: 8
ccaagtgttc tcgagtggag a                                         21

<210> SEQ ID NO 9
<211> LENGTH: 26
<212> TYPE: DNA
<213> ORGANISM: Artificial Sequence
```

```
<220> FEATURE:
<223> OTHER INFORMATION: Description of Artificial Sequence: Xho-F
      primer

<400> SEQUENCE: 9
ctaagtctcc actcgagaac acttgg                                        26

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: AflII-R
      primer

<400> SEQUENCE: 10
cagccagcag cttagcagca g                                             21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer
      Xho-F and primer T7-DOUBLE-R

<400> SEQUENCE: 11
ctctttggac ccgtaagcca g                                             21

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:
      T7-DOUBLE-R primer

<400> SEQUENCE: 12
ttacgggtcc aaagagtacg gcttccgtc                                     29

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: L220 primer

<400> SEQUENCE: 13
taacaatttc acacaggaaa ca                                            22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: 1211 primer

<400> SEQUENCE: 14
acgttgtaaa acgacggcca gt                                            22

<210> SEQ ID NO 15
<211> LENGTH: 2659
<212> TYPE: DNA
<213> ORGANISM: Artificial Sequence
<220> FEATURE:
<223> OTHER INFORMATION: Description of Artificial Sequence: T7 phage
      genome
```

```
<221> NAME/KEY: CDS
<222> LOCATION: (10)..(2658)

<400> SEQUENCE: 15 aggcactaa atg aac acg att aac atc gct aag aac gac ttc tct gac atc        51
           Met Asn Thr Ile Asn Ile Ala Lys Asn Asp Phe Ser Asp Ile
            1               5                  10 gaa ctg gct gct atc ccg ttc aac act ctg gct gac cat tac ggt gag         99
Glu Leu Ala Ala Ile Pro Phe Asn Thr Leu Ala Asp His Tyr Gly Glu
 15                  20                  25                  30 cgt tta gct cgc gaa cag ttg gcc ctt gag cat gag tct tac gag atg        147
Arg Leu Ala Arg Glu Gln Leu Ala Leu Glu His Glu Ser Tyr Glu Met
                 35                  40                  45 ggt gaa gca cgc ttc cgc aag atg ttt gag cgt caa ctt aaa gct ggt        195
Gly Glu Ala Arg Phe Arg Lys Met Phe Glu Arg Gln Leu Lys Ala Gly
             50                  55                  60 gag gtt gcg gat aac gct gcc gcc aag cct ctc atc act acc cta ctc        243
Glu Val Ala Asp Asn Ala Ala Ala Lys Pro Leu Ile Thr Thr Leu Leu
 65                  70                  75 cct aag atg att gca cgc atc aac gac tgg ttt gag gaa gtg aaa gct        291
Pro Lys Met Ile Ala Arg Ile Asn Asp Trp Phe Glu Glu Val Lys Ala
 80                  85                  90 aag cgc ggc aag cgc ccg aca gcc ttc cag ttc ctg caa gaa atc aag        339
Lys Arg Gly Lys Arg Pro Thr Ala Phe Gln Phe Leu Gln Glu Ile Lys
 95                 100                 105                 110 ccg gaa gcc gta gcg tac atc acc att aag acc act ctg gct tgc cta        387
Pro Glu Ala Val Ala Tyr Ile Thr Ile Lys Thr Thr Leu Ala Cys Leu
                115                 120                 125 acc agt gct gac aat aca acc gtt cag gct gta gca agc gca atc ggt        435
Thr Ser Ala Asp Asn Thr Thr Val Gln Ala Val Ala Ser Ala Ile Gly
            130                 135                 140 cgg gcc att gag gac gag gct cgc ttc ggt cgt atc cgt gac ctt gaa        483
Arg Ala Ile Glu Asp Glu Ala Arg Phe Gly Arg Ile Arg Asp Leu Glu
        145                 150                 155 gct aag cac ttc aag aaa aac gtt gag gaa caa ctc aac aag cgc gta        531
Ala Lys His Phe Lys Lys Asn Val Glu Glu Gln Leu Asn Lys Arg Val
    160                 165                 170 ggg cac gtc tac aag aaa gca ttt atg caa gtt gtc gag gct gac atg        579
Gly His Val Tyr Lys Lys Ala Phe Met Gln Val Val Glu Ala Asp Met
175                 180                 185                 190 ctc tct aag ggt cta ctc ggt ggc gag gcg tgg tct tcg tgg cat aag        627
Leu Ser Lys Gly Leu Leu Gly Gly Glu Ala Trp Ser Ser Trp His Lys
                195                 200                 205 gaa gac tct att cat gta gga gta cgc tgc atc gag atg ctc att gag        675
Glu Asp Ser Ile His Val Gly Val Arg Cys Ile Glu Met Leu Ile Glu
            210                 215                 220 tca acc gga atg gtt agc tta cac cgc caa aat gct ggc gta gta ggt        723
Ser Thr Gly Met Val Ser Leu His Arg Gln Asn Ala Gly Val Val Gly
        225                 230                 235 caa gac tct gag act atc gaa ctc gca cct gaa tac gct gag gct atc        771
Gln Asp Ser Glu Thr Ile Glu Leu Ala Pro Glu Tyr Ala Glu Ala Ile
    240                 245                 250 gca acc cgt gca ggt gcg ctg gct ggc atc tct ccg atg ttc caa cct        819
Ala Thr Arg Ala Gly Ala Leu Ala Gly Ile Ser Pro Met Phe Gln Pro
255                 260                 265                 270 tgc gta gtt cct cct aag ccg tgg act ggc att act ggt ggc ggc tat        867
Cys Val Val Pro Pro Lys Pro Trp Thr Gly Ile Thr Gly Gly Gly Tyr
                275                 280                 285 tgg gct aac ggt cgt cgt cct ctg gcg ctg gtg cgt act cac agt aag        915
Trp Ala Asn Gly Arg Arg Pro Leu Ala Leu Val Arg Thr His Ser Lys
```

```
aaa gca ctg atg cgc tac gaa gac gtt tac atg cct gag gtg tac aaa    963
Lys Ala Leu Met Arg Tyr Glu Asp Val Tyr Met Pro Glu Val Tyr Lys
        305                 310                 315 gcg att aac att gcg caa aac acc gca tgg aaa atc aac aag aaa gtc   1011
Ala Ile Asn Ile Ala Gln Asn Thr Ala Trp Lys Ile Asn Lys Lys Val
320                 325                 330 cta gcg gtc gcc aac gta atc acc aag tgg aag cat tgt ccg gtc gag  1059
Leu Ala Val Ala Asn Val Ile Thr Lys Trp Lys His Cys Pro Val Glu
335                 340                 345                 350 gac atc cct gcg att gag cgt gaa gaa ctc ccg atg aaa ccg gaa gac  1107
Asp Ile Pro Ala Ile Glu Arg Glu Glu Leu Pro Met Lys Pro Glu Asp
            355                 360                 365 atc gac atg aat cct gag gct ctc acc gcg tgg aaa cgt gct gcc gct  1155
Ile Asp Met Asn Pro Glu Ala Leu Thr Ala Trp Lys Arg Ala Ala Ala
                370                 375                 380 gct gtg tac cgc aag gac aag gct cgc aag tct cgc cgt atc agc ctt  1203
Ala Val Tyr Arg Lys Asp Lys Ala Arg Lys Ser Arg Arg Ile Ser Leu
            385                 390                 395 gag ttc atg ctt gag caa gcc aat aag ttt gct aac cat aag gcc atc  1251
Glu Phe Met Leu Glu Gln Ala Asn Lys Phe Ala Asn His Lys Ala Ile
        400                 405                 410 tgg ttc cct tac aac atg gac tgg cgc ggt cgt gtt tac gct gtg tca  1299
Trp Phe Pro Tyr Asn Met Asp Trp Arg Gly Arg Val Tyr Ala Val Ser
415                 420                 425                 430 atg ttc aac ccg caa ggt aac gat atg acc aaa gga ctg ctt acg ctg  1347
Met Phe Asn Pro Gln Gly Asn Asp Met Thr Lys Gly Leu Leu Thr Leu
                435                 440                 445 gcg aaa ggt aaa cca atc ggt aag gaa ggt tac tac tgg ctg aaa atc  1395
Ala Lys Gly Lys Pro Ile Gly Lys Glu Gly Tyr Tyr Trp Leu Lys Ile
            450                 455                 460 cac ggt gca aac tgt gcg ggt gtc gat aag gtt ccg ttc cct gag cgc  1443
His Gly Ala Asn Cys Ala Gly Val Asp Lys Val Pro Phe Pro Glu Arg
        465                 470                 475 atc aag ttc att gag gaa aac cac gag aac atc atg gct tgc gct aag  1491
Ile Lys Phe Ile Glu Glu Asn His Glu Asn Ile Met Ala Cys Ala Lys
480                 485                 490 tct cca ctg gag aac act tgg tgg gct gag caa gat tct ccg ttc tgc  1539
Ser Pro Leu Glu Asn Thr Trp Trp Ala Glu Gln Asp Ser Pro Phe Cys
495                 500                 505                 510 ttc ctt gcg ttc tgc ttt gag tac gct ggg gta cag cac cac ggc ctg  1587
Phe Leu Ala Phe Cys Phe Glu Tyr Ala Gly Val Gln His His Gly Leu
                515                 520                 525 agc tat aac tgc tcc ctt ccg ctg gcg ttt gac ggg tct tgc tct ggc  1635
Ser Tyr Asn Cys Ser Leu Pro Leu Ala Phe Asp Gly Ser Cys Ser Gly
            530                 535                 540 atc cag cac ttc tcc gcg atg ctc cga gat gag gta ggt ggt cgc gcg  1683
Ile Gln His Phe Ser Ala Met Leu Arg Asp Glu Val Gly Gly Arg Ala
        545                 550                 555 gtt aac ttg ctt cct agt gaa acc gtt cag gac atc tac ggg att gtt  1731
Val Asn Leu Leu Pro Ser Glu Thr Val Gln Asp Ile Tyr Gly Ile Val
                560                 565                 570 gct aag aaa gtc aac gag att cta caa gca gac gca atc aat ggg acc  1779
Ala Lys Lys Val Asn Glu Ile Leu Gln Ala Asp Ala Ile Asn Gly Thr
575                 580                 585                 590 gat aac gaa gta gtt acc gtg acc gat gag aac act ggt gaa atc tct  1827
Asp Asn Glu Val Val Thr Val Thr Asp Glu Asn Thr Gly Glu Ile Ser
                595                 600                 605 gag aaa gtc aag ctg ggc act aag gca ctg gct ggt caa tgg ctg gct  1875
```

```
Glu Lys Val Lys Leu Gly Thr Lys Ala Leu Ala Gly Gln Trp Leu Ala
        610                 615                 620 tac ggt gtt act cgc agt gtg act aag cgt tca gtc atg acg ctg gct      1923
Tyr Gly Val Thr Arg Ser Val Thr Lys Arg Ser Val Met Thr Leu Ala
            625                 630                 635 tac ggg tcc aaa gag ttc ggc ttc cgt caa caa gtg ctg gaa gat acc      1971
Tyr Gly Ser Lys Glu Phe Gly Phe Arg Gln Gln Val Leu Glu Asp Thr
        640                 645                 650 att cag cca gct att gat tcc ggc aag ggt ctg atg ttc act cag ccg      2019
Ile Gln Pro Ala Ile Asp Ser Gly Lys Gly Leu Met Phe Thr Gln Pro
655                 660                 665                 670 aat cag gct gct gga tac atg gct aag ctg att tgg gaa tct gtg agc      2067
Asn Gln Ala Ala Gly Tyr Met Ala Lys Leu Ile Trp Glu Ser Val Ser
            675                 680                 685 gtg acg gtg gta gct gcg gtt gaa gca atg aac tgg ctt aag tct gct      2115
Val Thr Val Val Ala Ala Val Glu Ala Met Asn Trp Leu Lys Ser Ala
        690                 695                 700 gct aag ctg ctg gct gct gag gtc aaa gat aag aag act gga gag att      2163
Ala Lys Leu Leu Ala Ala Glu Val Lys Asp Lys Lys Thr Gly Glu Ile
            705                 710                 715 ctt cgc aag cgt tgc gct gtg cat tgg gta act cct gat ggt ttc cct      2211
Leu Arg Lys Arg Cys Ala Val His Trp Val Thr Pro Asp Gly Phe Pro
720                 725                 730 gtg tgg cag gaa tac aag aag cct att cag acg cgc ttg aac ctg atg      2259
Val Trp Gln Glu Tyr Lys Lys Pro Ile Gln Thr Arg Leu Asn Leu Met
735                 740                 745                 750 ttc ctc ggt cag ttc cgc tta cag cct acc att aac acc aac aaa gat      2307
Phe Leu Gly Gln Phe Arg Leu Gln Pro Thr Ile Asn Thr Asn Lys Asp
                755                 760                 765 agc gag att gat gca cac aaa cag gag tct ggt atc gct cct aac ttt      2355
Ser Glu Ile Asp Ala His Lys Gln Glu Ser Gly Ile Ala Pro Asn Phe
            770                 775                 780 gta cac agc caa gac ggt agc cac ctt cgt aag act gta gtg tgg gca      2403
Val His Ser Gln Asp Gly Ser His Leu Arg Lys Thr Val Val Trp Ala
        785                 790                 795 cac gag aag tac gga atc gaa tct ttt gca ctg att cac gac tcc ttc      2451
His Glu Lys Tyr Gly Ile Glu Ser Phe Ala Leu Ile His Asp Ser Phe
        800                 805                 810 ggt acc att ccg gct gac gct gcg aac ctg ttc aaa gca gtg cgc gaa      2499
Gly Thr Ile Pro Ala Asp Ala Ala Asn Leu Phe Lys Ala Val Arg Glu
815                 820                 825                 830 act atg gtt gac aca tat gag tct tgt gat gta ctg gct gat ttc tac      2547
Thr Met Val Asp Thr Tyr Glu Ser Cys Asp Val Leu Ala Asp Phe Tyr
                835                 840                 845 gac cag ttc gct gac cag ttg cac gag tct caa ttg gac aaa atg cca      2595
Asp Gln Phe Ala Asp Gln Leu His Glu Ser Gln Leu Asp Lys Met Pro
            850                 855                 860 gca ctt ccg gct aaa ggt aac ttg aac ctc cgt gac atc tta gag tcg      2643
Ala Leu Pro Ala Lys Gly Asn Leu Asn Leu Arg Asp Ile Leu Glu Ser
        865                 870                 875 gac ttc gcg ttc gcg t                                                2659
Asp Phe Ala Phe Ala
        880

<210> SEQ ID NO 16
<211> LENGTH: 883
<212> TYPE: PRT
<213> ORGANISM: Artificial Sequence
<220> FEATURE:
<223> OTHER INFORMATION: Description of Artificial Sequence: T7 phage
      genome
```

<400> SEQUENCE: 16

```
Met Asn Thr Ile Asn Ile Ala Lys Asn Asp Phe Ser Asp Ile Glu Leu
  1               5                  10                  15

Ala Ala Ile Pro Phe Asn Thr Leu Ala Asp His Tyr Gly Glu Arg Leu
             20                  25                  30

Ala Arg Glu Gln Leu Ala Leu Glu His Glu Ser Tyr Glu Met Gly Glu
         35                  40                  45

Ala Arg Phe Arg Lys Met Phe Glu Arg Gln Leu Lys Ala Gly Glu Val
     50                  55                  60

Ala Asp Asn Ala Ala Ala Lys Pro Leu Ile Thr Thr Leu Leu Pro Lys
 65                  70                  75                  80

Met Ile Ala Arg Ile Asn Asp Trp Phe Glu Val Lys Ala Lys Arg
                 85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
            115                 120                 125

Ala Asp Asn Thr Thr Val Gln Ala Val Ala Ser Ala Ile Gly Arg Ala
            130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Ala Val
            370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
```

-continued

```
                    405                      410                          415
     Pro Tyr Asn Met Asp Trp Arg Gly Arg Val Tyr Ala Val Ser Met Phe
                         420                  425                430
     Asn Pro Gln Gly Asn Asp Met Thr Lys Gly Leu Leu Thr Leu Ala Lys
                         435                  440                445
     Gly Lys Pro Ile Gly Lys Glu Gly Tyr Tyr Trp Leu Lys Ile His Gly
                         450                  455                460
     Ala Asn Cys Ala Gly Val Asp Lys Val Pro Phe Pro Glu Arg Ile Lys
     465                  470                  475                480
     Phe Ile Glu Glu Asn His Glu Asn Ile Met Ala Cys Ala Lys Ser Pro
                              485                  490                495
     Leu Glu Asn Thr Trp Trp Ala Glu Gln Asp Ser Pro Phe Cys Phe Leu
                         500                  505                510
     Ala Phe Cys Phe Glu Tyr Ala Gly Val Gln His His Gly Leu Ser Tyr
                         515                  520                525
     Asn Cys Ser Leu Pro Leu Ala Phe Asp Gly Ser Cys Ser Gly Ile Gln
                         530                  535                540
     His Phe Ser Ala Met Leu Arg Asp Glu Val Gly Gly Arg Ala Val Asn
     545                  550                  555                560
     Leu Leu Pro Ser Glu Thr Val Gln Asp Ile Tyr Gly Ile Val Ala Lys
                         565                  570                575
     Lys Val Asn Glu Ile Leu Gln Ala Asp Ala Ile Asn Gly Thr Asp Asn
                         580                  585                590
     Glu Val Val Thr Val Thr Asp Glu Asn Thr Gly Glu Ile Ser Glu Lys
                         595                  600                  605
     Val Lys Leu Gly Thr Lys Ala Leu Ala Gly Gln Trp Leu Ala Tyr Gly
         610                  615                  620
     Val Thr Arg Ser Val Thr Lys Arg Ser Val Met Thr Leu Ala Tyr Gly
     625                  630                  635                640
     Ser Lys Glu Phe Gly Phe Arg Gln Gln Val Leu Glu Asp Thr Ile Gln
                         645                  650                  655
     Pro Ala Ile Asp Ser Gly Lys Gly Leu Met Phe Thr Gln Pro Asn Gln
                         660                  665                  670
     Ala Ala Gly Tyr Met Ala Lys Leu Ile Trp Glu Ser Val Ser Val Thr
                         675                  680                685
     Val Val Ala Ala Val Glu Ala Met Asn Trp Leu Lys Ser Ala Ala Lys
         690                  695                  700
     Leu Leu Ala Ala Glu Val Lys Asp Lys Lys Thr Gly Glu Ile Leu Arg
     705                  710                  715                720
     Lys Arg Cys Ala Val His Trp Val Thr Pro Asp Gly Phe Pro Val Trp
                         725                  730                735
     Gln Glu Tyr Lys Lys Pro Ile Gln Thr Arg Leu Asn Leu Met Phe Leu
                         740                  745                750
     Gly Gln Phe Arg Leu Gln Pro Thr Ile Asn Thr Asn Lys Asp Ser Glu
                         755                  760                765
     Ile Asp Ala His Lys Gln Glu Ser Gly Ile Ala Pro Asn Phe Val His
                         770                  775                780
     Ser Gln Asp Gly Ser His Leu Arg Lys Thr Val Val Trp Ala His Glu
     785                  790                  795                800
     Lys Tyr Gly Ile Glu Ser Phe Ala Leu Ile His Asp Ser Phe Gly Thr
                         805                  810                815
     Ile Pro Ala Asp Ala Ala Asn Leu Phe Lys Ala Val Arg Glu Thr Met
                         820                  825                830
```

-continued

```
Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 17
<211> LENGTH: 853
<212> TYPE: PRT
<213> ORGANISM: Artificial Sequence
<220> FEATURE:
<223> OTHER INFORMATION: Description of Artificial Sequence: T7 RNA
      polymerase

<400> SEQUENCE: 17

Met Asn Thr Ile Asn Ile Ala Lys Asn Asp Phe Ser Asp Ile Glu Leu
  1               5                  10                  15

Ala Ala Ile Pro Phe Asn Thr Leu Ala Asp His Tyr Gly Glu Arg Leu
             20                  25                  30

Ala Arg Glu Gln Leu Ala Leu Glu His Glu Ser Tyr Glu Met Gly Glu
         35                  40                  45

Ala Arg Phe Arg Lys Met Phe Glu Arg Gln Leu Lys Ala Gly Glu Val
     50                  55                  60

Ala Asp Asn Ala Ala Ala Lys Pro Leu Ile Thr Thr Lys Met Ile Ala
 65                  70                  75                  80

Arg Ile Asn Asp Trp Phe Glu Glu Val Lys Ala Lys Arg Gly Lys Arg
                 85                  90                  95

Pro Thr Ala Phe Gln Phe Leu Gln Glu Ile Lys Pro Glu Ala Val Ala
            100                 105                 110

Tyr Ile Thr Ile Lys Thr Thr Leu Ala Cys Leu Thr Ser Ala Asp Asn
        115                 120                 125

Thr Thr Val Gln Ala Ala Ile Gly Arg Ala Ile Glu Asp Glu Ala Arg
    130                 135                 140

Phe Gly Arg Ile Arg Asp Leu Glu Ala Lys His Phe Lys Lys Asn Val
145                 150                 155                 160

Glu Glu Gln Leu Asn Lys Arg Val Gly His Val Tyr Lys Lys Ala Phe
                165                 170                 175

Met Gln Val Val Glu Ala Asp Met Leu Ser Lys Gly Leu Leu Gly Gly
            180                 185                 190

Glu Ala Trp Ser Ser Trp His Lys Glu Asp Ser Ile His Val Gly Val
        195                 200                 205

Arg Met Leu Ile Glu Ser Thr Gly Met Val Ser Leu His Arg Gln Asn
    210                 215                 220

Ala Gly Val Val Gly Gln Asp Ser Glu Thr Ile Glu Leu Ala Pro Glu
225                 230                 235                 240

Tyr Ala Glu Ala Ile Ala Thr Arg Ala Gly Ala Leu Ala Gly Ile Ser
                245                 250                 255

Pro Met Phe Gln Pro Cys Val Val Pro Pro Lys Pro Trp Thr Gly Ile
            260                 265                 270

Thr Gly Gly Gly Tyr Trp Ala Asn Gly Leu Ala Leu Val Arg Thr His
        275                 280                 285

Ser Lys Lys Ala Leu Met Arg Tyr Glu Asp Val Tyr Met Pro Glu Val
    290                 295                 300
```

-continued

```
Tyr Lys Ala Ile Asn Ile Ala Gln Asn Thr Ala Trp Lys Ile Asn Lys
305                 310                 315                 320
Lys Val Leu Ala Val Ala Asn Val Ile Thr Lys Trp Lys His Cys Pro
            325                 330                 335
Val Glu Asp Ile Pro Ala Ile Glu Arg Glu Leu Pro Met Lys Pro
        340                 345                 350
Glu Asp Ile Asp Met Asn Pro Glu Ala Leu Thr Ala Trp Lys Arg Ala
        355                 360                 365
Ala Ala Ala Val Tyr Arg Lys Asp Lys Ala Arg Lys Ser Arg Arg Ile
370                 375                 380
Ser Leu Glu Phe Met Leu Glu Gln Ala Asn Lys Phe Ala Asn His Lys
385                 390                 395                 400
Ala Ile Trp Phe Pro Tyr Asn Met Asp Trp Arg Gly Arg Val Tyr Ala
                405                 410                 415
Val Ser Met Phe Gly Asn Asp Met Thr Lys Gly Leu Leu Thr Leu Ala
            420                 425                 430
Lys Gly Lys Pro Ile Gly Lys Glu Gly Tyr Tyr Trp Leu Lys Ile His
        435                 440                 445
Gly Ala Asn Cys Ala Gly Val Asp Lys Val Pro Phe Pro Glu Arg Ile
450                 455                 460
Lys Phe Ile Glu Glu Asn His Glu Asn Ile Met Ala Cys Ala Lys Ser
465                 470                 475                 480
Pro Leu Glu Asn Thr Trp Trp Ala Glu Gln Asp Ser Pro Phe Ala Phe
                485                 490                 495
Cys Phe Glu Tyr Ala Gly Val Gln His His Gly Leu Ser Tyr Asn Cys
            500                 505                 510
Ser Leu Pro Leu Ala Phe Asp Gly Ser Cys Ser Gly Ile Gln His Phe
        515                 520                 525
Ser Ala Met Leu Arg Asp Glu Val Gly Gly Arg Ala Val Asn Leu Leu
530                 535                 540
Pro Ser Glu Thr Val Gln Asp Ile Tyr Gly Ile Val Ala Lys Lys Val
545                 550                 555                 560
Asn Glu Ile Leu Gln Ala Asn Gly Thr Asp Asn Glu Val Val Thr Val
                565                 570                 575
Thr Asp Glu Asn Thr Gly Glu Ile Ser Glu Lys Val Lys Leu Gly Thr
            580                 585                 590
Lys Ala Leu Ala Gly Gln Trp Leu Ala Tyr Gly Val Thr Arg Ser Val
        595                 600                 605
Thr Lys Arg Ser Val Met Thr Leu Ala Tyr Gly Ser Lys Glu Phe Gly
        610                 615                 620
Phe Arg Gln Gln Val Leu Glu Asp Thr Ile Gln Pro Ala Ile Asp Ser
625                 630                 635                 640
Gly Lys Phe Thr Gln Pro Asn Gln Ala Ala Gly Tyr Met Ala Lys Leu
                645                 650                 655
Ile Trp Glu Ser Val Ser Val Thr Val Val Ala Ala Val Glu Ala Met
            660                 665                 670
Asn Trp Leu Lys Ser Ala Ala Lys Leu Leu Ala Ala Glu Val Lys Asp
        675                 680                 685
Lys Lys Thr Gly Glu Ile Leu Arg Lys Arg Cys Ala Val His Trp Val
        690                 695                 700
Thr Pro Asp Gly Phe Pro Val Trp Gln Glu Pro Ile Gln Thr Arg Leu
705                 710                 715                 720
```

```
Asn Leu Met Phe Leu Gly Gln Phe Arg Leu Gln Pro Thr Ile Asn Thr
                725                 730                 735

Asn Lys Asp Ser Glu Ile Asp Ala His Lys Gln Glu Ser Gly Ile Ala
            740                 745                 750

Pro Asn Phe Val His Ser Gln Asp Gly Ser His Leu Arg Lys Thr Val
        755                 760                 765

Val Trp Ala His Glu Lys Tyr Gly Ile Glu Ser Phe Ala Leu Ile His
    770                 775                 780

Asp Ser Phe Gly Thr Ile Pro Ala Asn Leu Phe Lys Ala Val Arg Glu
785                 790                 795                 800

Thr Met Val Asp Thr Tyr Glu Ser Cys Asp Val Leu Ala Asp Phe Tyr
                805                 810                 815

Asp Gln Phe Ala Asp Gln Leu His Glu Ser Gln Leu Asp Lys Met Pro
            820                 825                 830

Ala Leu Pro Ala Lys Gly Asn Leu Asn Leu Arg Asp Ile Leu Glu Ser
        835                 840                 845

Asp Phe Ala Phe Ala
    850

<210> SEQ ID NO 18
<211> LENGTH: 854
<212> TYPE: PRT
<213> ORGANISM: Artificial Sequence
<220> FEATURE:
<223> OTHER INFORMATION: Description of Artificial Sequence: T7 RNA
      polymerase

<400> SEQUENCE: 18

Met Asn Ile Ile Glu Asn Ile Glu Lys Asn Asp Phe Ser Glu Ile Glu
  1               5                  10                  15

Leu Ala Ala Ile Pro Phe Asn Thr Leu Ala Asp His Tyr Gly Ser Ala
                 20                  25                  30

Leu Ala Lys Glu Gln Leu Ala Leu Glu His Glu Ser Tyr Glu Leu Gly
             35                  40                  45

Glu Arg Arg Phe Leu Lys Met Leu Glu Arg Gln Ala Lys Ala Gly Glu
         50                  55                  60

Ile Ala Asp Asn Ala Ala Ala Lys Pro Leu Leu Ala Thr Lys Leu Thr
 65                  70                  75                  80

Thr Arg Ile Val Glu Trp Leu Glu Glu Tyr Ala Ser Lys Lys Gly Arg
                 85                  90                  95

Lys Pro Ser Ala Tyr Ala Pro Leu Gln Leu Leu Lys Pro Glu Ala Ser
                100                 105                 110

Ala Phe Ile Thr Leu Lys Val Ile Leu Ala Ser Leu Thr Ser Thr Asn
            115                 120                 125

Met Thr Thr Ile Gln Ala Met Leu Gly Lys Ala Ile Glu Asp Glu Ala
130                 135                 140

Arg Phe Gly Arg Ile Arg Asp Leu Glu Ala Lys His Phe Lys Lys His
145                 150                 155                 160

Val Glu Glu Gln Leu Asn Lys Arg His Gly Gln Val Tyr Lys Lys Ala
                165                 170                 175

Phe Met Gln Val Val Glu Ala Asp Met Ile Gly Arg Gly Leu Leu Gly
            180                 185                 190

Gly Glu Ala Trp Ser Ser Trp Asp Lys Glu Thr Thr Met His Val Gly
        195                 200                 205

Ile Arg Met Leu Ile Glu Ser Thr Gly Leu Val Glu Leu Gln Arg His
    210                 215                 220
```

-continued

```
Asn Ala Gly Asn Ala Gly Ser Asp His Glu Ala Leu Gln Leu Ala Gln
225                 230                 235                 240

Glu Tyr Val Asp Val Leu Ala Lys Arg Ala Gly Ala Leu Ala Gly Ile
            245                 250                 255

Ser Pro Met Phe Gln Pro Cys Val Val Pro Pro Lys Pro Trp Val Ala
            260                 265                 270

Ile Thr Gly Gly Gly Tyr Trp Ala Asn Gly Leu Ala Leu Val Arg Thr
            275                 280                 285

His Ser Lys Lys Gly Leu Met Arg Tyr Glu Asp Val Tyr Met Pro Glu
290                 295                 300

Val Tyr Lys Ala Val Asn Leu Ala Gln Asn Thr Ala Trp Lys Ile Asn
305                 310                 315                 320

Lys Lys Val Leu Ala Val Val Asn Glu Ile Val Asn Trp Lys Asn Cys
            325                 330                 335

Pro Val Ala Asp Ile Pro Ser Leu Glu Arg Gln Glu Leu Pro Pro Lys
            340                 345                 350

Pro Asp Asp Ile Asp Thr Asn Glu Ala Ala Leu Lys Glu Trp Lys Lys
            355                 360                 365

Ala Ala Ala Gly Ile Tyr Arg Leu Asp Lys Ala Arg Val Ser Arg Arg
370                 375                 380

Ile Ser Leu Glu Phe Met Leu Glu Gln Ala Asn Lys Phe Ala Ser Lys
385                 390                 395                 400

Lys Ala Ile Trp Phe Pro Tyr Asn Met Asp Trp Arg Gly Arg Val Tyr
            405                 410                 415

Ala Val Pro Met Phe Gly Asn Asp Met Thr Lys Gly Leu Leu Thr Leu
            420                 425                 430

Ala Lys Gly Lys Pro Ile Gly Glu Glu Gly Phe Tyr Trp Leu Lys Ile
            435                 440                 445

His Gly Ala Asn Cys Ala Gly Val Asp Lys Val Pro Phe Pro Glu Arg
450                 455                 460

Ile Ala Phe Ile Glu Lys His Val Asp Asp Ile Leu Ala Cys Ala Lys
465                 470                 475                 480

Asp Pro Ile Asn Asn Thr Trp Trp Ala Glu Gln Asp Ser Pro Phe Ala
            485                 490                 495

Phe Cys Phe Glu Tyr Ala Gly Val Thr His His Gly Leu Ser Tyr Asn
            500                 505                 510

Cys Ser Leu Pro Leu Ala Phe Asp Gly Ser Cys Ser Gly Ile Gln His
            515                 520                 525

Phe Ser Ala Met Leu Arg Asp Glu Val Gly Gly Arg Ala Val Asn Leu
530                 535                 540

Leu Pro Ser Glu Thr Val Gln Asp Ile Tyr Gly Ile Val Ala Gln Lys
545                 550                 555                 560

Val Asn Glu Ile Leu Lys Gln Asn Gly Thr Pro Asn Glu Met Ile Thr
            565                 570                 575

Val Thr Asp Lys Asp Thr Gly Glu Ile Ser Glu Lys Leu Lys Leu Gly
            580                 585                 590

Thr Ser Thr Leu Ala Gln Gln Trp Leu Ala Tyr Gly Val Thr Arg Ser
            595                 600                 605

Val Thr Lys Arg Ser Val Met Thr Leu Ala Tyr Gly Ser Lys Glu Phe
            610                 615                 620

Gly Phe Arg Gln Gln Val Leu Asp Asp Thr Ile Gln Pro Ala Ile Asp
625                 630                 635                 640
```

```
Ser Gly Lys Phe Thr Gln Pro Asn Gln Ala Ala Gly Tyr Met Ala Lys
                645                 650                 655

Leu Ile Trp Asp Ala Val Ser Val Thr Val Ala Ala Val Glu Ala
            660                 665                 670

Met Asn Trp Leu Lys Ser Ala Ala Lys Leu Leu Ala Ala Glu Val Lys
            675                 680                 685

Asp Lys Lys Thr Lys Glu Ile Leu Arg His Arg Cys Ala Val His Trp
        690                 695                 700

Thr Thr Pro Asp Gly Phe Pro Val Trp Gln Glu Pro Leu Gln Lys Arg
705                 710                 715                 720

Leu Asp Met Ile Phe Leu Gly Gln Phe Arg Leu Gln Pro Thr Ile Asn
                725                 730                 735

Thr Leu Lys Asp Ser Gly Ile Asp Ala His Lys Gln Glu Ser Gly Ile
                740                 745                 750

Ala Pro Asn Phe Val His Ser Gln Asp Gly Ser His Leu Arg Met Thr
            755                 760                 765

Val Val Tyr Ala His Glu Lys Tyr Gly Ile Glu Ser Phe Ala Leu Ile
        770                 775                 780

His Asp Ser Phe Gly Thr Ile Pro Gly Lys Leu Phe Lys Ala Val Arg
785                 790                 795                 800

Glu Thr Met Val Ile Thr Tyr Glu Asn Asn Asp Val Leu Ala Asp Phe
                805                 810                 815

Tyr Ser Gln Phe Ala Asp Gln Leu His Glu Thr Gln Leu Asp Lys Met
            820                 825                 830

Pro Pro Leu Pro Lys Lys Gly Asn Leu Asn Leu Gln Asp Ile Leu Lys
            835                 840                 845

Ser Asp Phe Ala Phe Ala
    850

<210> SEQ ID NO 19
<211> LENGTH: 876
<212> TYPE: PRT
<213> ORGANISM: Artificial Sequence
<220> FEATURE:
<223> OTHER INFORMATION: Description of Artificial Sequence: T7 RNA
      polymerase

<400> SEQUENCE: 19

Met Asn Ala Leu Asn Ile Gly Arg Asn Asp Phe Ser Glu Ile Glu Leu
  1               5                  10                  15

Ala Ala Ile Pro Tyr Asn Ile Leu Ser Glu His Tyr Gly Asp Gln Ala
                20                  25                  30

Ala Arg Glu Gln Leu Ala Leu Glu His Glu Ala Tyr Glu Leu Gly Arg
            35                  40                  45

Gln Arg Phe Leu Lys Met Leu Glu Arg Gln Val Lys Ala Gly Glu Phe
        50                  55                  60

Ala Asp Asn Ala Ala Lys Pro Leu Val Leu Thr Gln Leu Thr Lys
 65                  70                  75                  80

Arg Ile Asp Asp Trp Lys Glu Gly Gln Ala Asn Ala Arg Gly Lys Lys
                85                  90                  95

Pro Arg Ala Tyr Tyr Pro Ile Lys His Gly Val Ala Ser Glu Leu Ala
                100                 105                 110

Val Ser Met Gly Ala Glu Val Leu Lys Glu Lys Arg Gly Val Ser Ser
            115                 120                 125

Glu Ala Ile Ala Leu Leu Thr Ile Lys Val Val Leu Gly Asn Ala His
        130                 135                 140
```

-continued

```
Arg Pro Leu Lys Gly His Asn Pro Ala Gln Leu Gly Lys Ala Leu Glu
145                 150                 155                 160

Asp Glu Ala Arg Phe Gly Ile Arg Glu Gln Glu Ala Ala Tyr Phe Lys
            165                 170                 175

Lys Asn Val Ala Asp Gln Leu Asp Lys Arg Val Gly His Val Tyr Lys
                180                 185                 190

Lys Ala Phe Met Gln Val Val Glu Ala Asp Met Ile Ser Lys Gly Met
            195                 200                 205

Leu Gly Gly Asp Asn Trp Ala Ser Trp Lys Thr Asp Glu Gln Met His
210                 215                 220

Val Gly Thr Lys Leu Leu Ile Glu Gly Thr Gly Leu Val Glu Met Thr
225                 230                 235                 240

Lys Asn Lys Met Ala Asp Gly Ser Asp Asp Val Thr Ser Met Gln Met
                245                 250                 255

Val Gln Leu Ala Pro Ala Phe Val Glu Leu Leu Ser Lys Arg Ala Gly
                260                 265                 270

Ala Leu Ala Gly Ile Ser Pro Met His Gln Pro Cys Val Val Pro Pro
            275                 280                 285

Lys Pro Trp Val Glu Thr Val Gly Gly Tyr Trp Ser Val Gly Leu
290                 295                 300

Ala Leu Val Arg Thr His Ser Lys Ala Leu Arg Arg Tyr Ala Asp Val
305                 310                 315                 320

His Met Pro Glu Val Tyr Lys Ala Val Asn Leu Ala Gln Asn Thr Pro
                325                 330                 335

Trp Lys Val Asn Lys Lys Val Leu Ala Val Val Asn Glu Ile Val Asn
                340                 345                 350

Trp Lys His Cys Pro Val Gly Asp Val Pro Ala Ile Glu Arg Glu Glu
            355                 360                 365

Leu Pro Pro Arg Pro Asp Asp Ile Asp Thr Asn Glu Val Ala Arg Lys
            370                 375                 380

Ala Trp Arg Lys Glu Ala Ala Val Tyr Arg Lys Asp Lys Ala Arg
385                 390                 395                 400

Gln Ser Arg Arg Cys Arg Cys Glu Phe Met Val Ala Gln Ala Asn Phe
                405                 410                 415

Ala Asn His Lys Ala Ile Trp Phe Pro Tyr Asn Met Asp Trp Arg Gly
                420                 425                 430

Arg Val Tyr Ala Val Ser Met Phe Gly Asn Asp Met Thr Lys Gly Ser
            435                 440                 445

Leu Leu Thr Leu Ala Lys Gly Lys Pro Ile Gly Leu Asp Gly Phe Tyr
450                 455                 460

Trp Leu Lys Ile His Gly Ala Asn Cys Ala Gly Val Asp Lys Val Pro
465                 470                 475                 480

Phe Pro Glu Arg Ile Lys Phe Ile Glu Glu Asn Glu Gly Asn Ile Leu
                485                 490                 495

Ala Ser Ala Ala Asp Pro Leu Asn Asn Thr Trp Trp Thr Gln Gln Asp
            500                 505                 510

Ser Pro Phe Ala Phe Cys Phe Glu Tyr Ala Gly Val Lys His His Gly
            515                 520                 525

Leu Asn Ser Tyr Asn Cys Ser Leu Pro Leu Ala Phe Asp Gly Ser Cys
            530                 535                 540

Ser Gly Ile Gln His Phe Ser Ala Met Leu Arg Asp Ser Ile Gly Gly
545                 550                 555                 560
```

-continued

```
Arg Ala Val Asn Leu Leu Pro Ser Asp Thr Val Gln Asp Ile Tyr Lys
                565                 570                 575

Ile Val Ala Asp Lys Val Asn Glu Val Leu His Gln Asn Gly Ser Gln
            580                 585                 590

Thr Val Val Glu Gln Ile Ala Asp Lys Glu Thr Gly Glu Phe His Ser
        595                 600                 605

Glu Lys Val Thr Leu Gly Glu Ser Val Leu Ala Ala Gln Trp Leu Gln
    610                 615                 620

Tyr Gly Val Thr Arg Lys Val Thr Lys Arg Ser Val Met Thr Leu Ala
625                 630                 635                 640

Tyr Gly Ser Lys Glu Ser Leu Val Arg Gln Gln Val Leu Glu Asp Thr
                645                 650                 655

Ile Gln Pro Ala Ile Asp Asn Gly Glu Phe Thr His Gln Pro Asn Gln
            660                 665                 670

Ala Ala Gly Tyr Met Ala Lys Leu Ile Asp Ala Ser Thr Ser Val Thr
        675                 680                 685

Val Val Ala Ala Val Glu Ala Met Asn Trp Leu Lys Ser Ala Ala Lys
    690                 695                 700

Leu Leu Ala Ala Glu Val Lys Asp Lys Lys Gly Val Ile Leu Arg
705                 710                 715                 720

Lys Arg Cys Ile Val His Trp Val Thr Pro Asp Gly Phe Pro Val Trp
                725                 730                 735

Gln Glu Gln Asn Gln Ala Arg Leu Lys Leu Val Phe Leu Gly Gln Ala
            740                 745                 750

Asn Val Lys Met Thr Tyr Asn Thr Gly Lys Asp Ser Glu Ile Asp Ala
        755                 760                 765

His Lys Gln Glu Ser Gly Ile Ala Pro Asn Phe Val His Ser Gln Asp
    770                 775                 780

Gly Ser His Leu Arg Met Thr Val Val His Ala Asn Glu Val Tyr Gly
785                 790                 795                 800

Ile Asp Ser Phe Ala Leu Ile His Asp Ser Gly Thr Ile Pro Asn
                805                 810                 815

Leu Phe Lys Ala Val Arg Glu Thr Met Val Lys Thr Tyr Glu Asp Asn
            820                 825                 830

Asp Val Ile Ala Asp Phe Tyr Asp Gln Phe Ala Asp Gln Leu His Glu
        835                 840                 845

Ser Gln Leu Asp Lys Met Pro Ala Val Pro Ala Lys Gly Asp Leu Asn
    850                 855                 860

Leu Arg Asp Ile Leu Glu Ser Asp Phe Ala Phe Ala
865                 870                 875
```

<210> SEQ ID NO 20
<211> LENGTH: 836
<212> TYPE: PRT
<213> ORGANISM: Artificial Sequence
<220> FEATURE:
<223> OTHER INFORMATION: Description of Artificial Sequence: T7 RNA
      polymerase

<400> SEQUENCE: 20

```
Met Gln Asp Leu His Ala Ile Gln Leu Gln Leu Glu Glu Glu Met Phe
 1               5                  10                  15

Asn Gly Gly Ile Arg Arg Phe Glu Ala Asp Gln Gln Arg Gln Ile Ala
            20                  25                  30

Ala Gly Ser Glu Ser Asp Thr Ala Trp Asn Arg Arg Leu Leu Ser Glu
        35                  40                  45
```

-continued

```
Pro Met Ala Glu Gly Ile Gln Ala Tyr Lys Glu Tyr Glu Gly Lys
    50                  55                  60
Lys Gly Arg Ala Pro Arg Ala Leu Ala Phe Leu Gln Cys Val Glu Asn
 65                  70                  75                  80
Glu Val Ala Ala Tyr Ile Thr Met Lys Val Val Met Asp Met Leu Asn
                 85                  90                  95
Thr Asp Ala Thr Leu Gln Ala Ser Val Ala Glu Arg Ile Glu Asp Gln
             100                 105                 110
Val Arg Phe Ser Lys Leu Glu Gly His Ala Ala Lys Tyr Phe Glu Lys
             115                 120                 125
Lys Lys Ser Leu Lys Ala Ser Arg Thr Lys Ser Tyr Arg His Ala His
130                 135                 140
Asn Val Ala Val Val Ala Glu Lys Ser Val Ala Glu Lys Asp Ala Asp
145                 150                 155                 160
Phe Asp Arg Trp Glu Ala Trp Pro Lys Glu Thr Gln Leu Gln Ile Thr
                165                 170                 175
Thr Ile Leu Glu Gly Ser Val Phe Tyr Asn Gly Glu Pro Val Phe Met
                180                 185                 190
Arg Ala Met Arg Thr Tyr Gly Gly Lys Thr Ile Tyr Tyr Leu Gln Thr
                195                 200                 205
Ser Glu Ser Val Gly Gln Trp Ile Ser Ala Phe Lys Glu His Val Ala
210                 215                 220
Gln Leu Ser Pro Ala Tyr Ala Pro Cys Val Ile Pro Pro Arg Pro Trp
225                 230                 235                 240
Arg Thr Pro Phe Asn Gly Gly Phe His Thr Glu Lys Val Ile Arg Leu
                245                 250                 255
Val Lys Gly Asn Arg Glu His Val Arg Lys Leu Thr Gln Lys Gln Met
                260                 265                 270
Pro Lys Val Tyr Lys Ala Ile Asn Ala Leu Gln Asn Thr Gln Trp Gln
                275                 280                 285
Ile Asn Lys Asp Val Leu Ala Val Ile Glu Glu Val Ile Arg Leu Asp
290                 295                 300
Leu Gly Tyr Gly Val Pro Ser Phe Lys Pro Leu Ile Asp Lys Glu Asn
305                 310                 315                 320
Lys Pro Ala Asn Pro Val Pro Val Glu Leu Arg Gly Arg Glu Leu Lys
                325                 330                 335
Glu Met Leu Ser Pro Glu Gln Trp Gln Gln Phe Ile Asn Trp Lys Gly
                340                 345                 350
Glu Cys Ala Arg Leu Tyr Thr Ala Glu Thr Lys Arg Gly Ser Lys Ser
                355                 360                 365
Ala Ala Val Val Arg Met Val Gly Gln Ala Arg Lys Tyr Ser Ala Phe
                370                 375                 380
Glu Ser Ile Tyr Phe Val Tyr Ala Met Asp Ser Arg Ser Arg Val Tyr
385                 390                 395                 400
Val Gln Ser Ser Thr Leu Ser Asn Asp Leu Gly Lys Ala Leu Leu Arg
                405                 410                 415
Phe Thr Glu Gly Arg Pro Val Asn Gly Val Glu Ala Leu Lys Trp Phe
                420                 425                 430
Cys Lys Asn Gly Ala Asn Leu Trp Gly Trp Asp Lys Lys Thr Phe Asp
                435                 440                 445
Val Arg Val Ser Asn Val Leu Asp Glu Glu Phe Gln Asp Met Cys Arg
450                 455                 460
```

```
Asp Ile Ala Ala Asp Pro Leu Thr Phe Thr Gln Trp Ala Lys Ala Asp
465                 470                 475                 480

Ala Pro Tyr Ala Trp Cys Phe Glu Tyr Ala Gln Tyr Leu Asp Leu Val
            485                 490                 495

Asp Glu Gly Arg Ala Asp Glu Phe Arg Thr His Leu Pro Val His Gln
        500                 505                 510

Asp Gly Ser Cys Ser Gly Ile Gln His Phe Ser Ala Met Leu Arg Asp
        515                 520                 525

Glu Val Gly Ala Lys Ala Val Asn Leu Lys Pro Ser Asp Ala Pro Gln
        530                 535                 540

Asp Ile Tyr Gly Ala Val Ala Gln Val Ile Asn Ala Leu Tyr Met Asp
545                 550                 555                 560

Ala Asp Asp Ala Thr Thr Phe Thr Ser Gly Ser Val Thr Leu Ser Gly
            565                 570                 575

Thr Glu Leu Arg Ala Met Ala Ser Ala Trp Asp Ser Ile Gly Ile Thr
            580                 585                 590

Arg Ser Leu Thr Lys Lys Pro Val Met Thr Leu Pro Tyr Gly Ser Thr
        595                 600                 605

Arg Leu Thr Cys Arg Glu Ser Val Ile Asp Tyr Ile Val Asp Leu Glu
        610                 615                 620

Glu Lys Glu Ala Gln Lys Glu Gly Arg Thr Ala Asn Lys Val His Pro
625                 630                 635                 640

Phe Glu Asp Asp Arg Gln Asp Tyr Leu Thr Pro Gly Ala Ala Tyr Asn
            645                 650                 655

Tyr Met Thr Ala Leu Ile Trp Pro Ser Ile Ser Glu Val Val Lys Val
            660                 665                 670

Ala Met Lys Met Ile Arg Gln Leu Ala Arg Phe Ala Ala Lys Arg Asn
        675                 680                 685

Glu Gly Leu Met Tyr Thr Leu Pro Thr Gly Phe Ile Leu Glu Gln Lys
        690                 695                 700

Thr Glu Met Leu Arg Val Arg Thr Cys Leu Met Gly Asp Ile Lys Met
705                 710                 715                 720

Ser Leu Gln Val Glu Thr Asp Ile Val Asp Glu Ala Ala Met Met Gly
            725                 730                 735

Ala Ala Ala Pro Asn Phe Val His Gly His Asp Ala Ser His Leu Ile
            740                 745                 750

Leu Thr Val Cys Glu Leu Val Asp Lys Gly Val Thr Ser Ile Ala Val
        755                 760                 765

Ile His Asp Ser Phe Gly Thr His Ala Leu Thr Leu Arg Val Ala Leu
770                 775                 780

Lys Gly Gln Met Val Ala Met Tyr Ile Asp Gly Asn Ala Leu Gln Lys
785                 790                 795                 800

Leu Leu Glu Glu His Glu Val Arg Trp Met Val Asp Thr Gly Ile Glu
            805                 810                 815

Val Pro Glu Gln Gly Glu Phe Asp Leu Asn Glu Ile Met Asp Ser Glu
            820                 825                 830

Tyr Val Phe Ala
        835

<210> SEQ ID NO 21
<211> LENGTH: 78
<212> TYPE: PRT
<213> ORGANISM: Artificial Sequence
<220> FEATURE:
<223> OTHER INFORMATION: Description of Artificial Sequence: mutated
``` sites of T7 RNA

<400> SEQUENCE: 21

Tyr Gly Val Thr Arg Ser Val Thr Lys Arg Ser Val Met Thr Leu Ala
 1               5                  10                  15

Tyr Gly Ser Lys Glu Phe Gly Phe Arg Gln Gln Val Leu Glu Asp Thr
            20                  25                  30

Ile Gln Pro Ala Ile Asp Ser Gly Lys Gly Leu Met Phe Thr Gln Pro
        35                  40                  45

Asn Gln Ala Ala Gly Tyr Met Ala Lys Leu Ile Trp Glu Ser Val Ser
    50                  55                  60

Val Thr Val Val Ala Ala Val Glu Ala Met Asn Trp Leu Lys
65                  70                  75

<210> SEQ ID NO 22
<211> LENGTH: 78
<212> TYPE: PRT
<213> ORGANISM: Artificial Sequence
<220> FEATURE:
<223> OTHER INFORMATION: Description of Artificial Sequence: mutated
      sites of T7 RNA

<400> SEQUENCE: 22

Tyr Gly Val Thr Arg Ser Val Thr Lys Arg Ser Val Met Thr Leu Ala
 1               5                  10                  15

Tyr Gly Ser Lys Glu Tyr Gly Phe Arg Gln Gln Val Leu Glu Asp Thr
            20                  25                  30

Ile Gln Pro Ala Ile Asp Ser Gly Lys Gly Leu Met Phe Thr Gln Pro
        35                  40                  45

Asn Gln Ala Ala Gly Tyr Met Ala Lys Leu Ile Trp Glu Ser Val Ser
    50                  55                  60

Val Thr Val Val Ala Ala Val Glu Ala Met Asn Trp Leu Lys
65                  70                  75

<210> SEQ ID NO 23
<211> LENGTH: 78
<212> TYPE: PRT
<213> ORGANISM: Artificial Sequence
<220> FEATURE:
<223> OTHER INFORMATION: Description of Artificial Sequence: mutated
      sites of T7 RNA

<400> SEQUENCE: 23

Tyr Gly Val Thr Arg Ser Val Thr Lys Arg Ser Val Met Thr Leu Ala
 1               5                  10                  15

Tyr Gly Ser Lys Glu Phe Gly Tyr Arg Gln Gln Val Leu Glu Asp Thr
            20                  25                  30

Ile Gln Pro Ala Ile Asp Ser Gly Lys Gly Leu Met Phe Thr Gln Pro
        35                  40                  45

Asn Gln Ala Ala Gly Tyr Met Ala Lys Leu Ile Trp Glu Ser Val Ser
    50                  55                  60

Val Thr Val Val Ala Ala Val Glu Ala Met Asn Trp Leu Lys
65                  70                  75

<210> SEQ ID NO 24
<211> LENGTH: 78
<212> TYPE: PRT
<213> ORGANISM: Artificial Sequence
<220> FEATURE:
<223> OTHER INFORMATION: Description of Artificial Sequence: mutated
      sites of T7 RNA

<400> SEQUENCE: 24

Tyr Gly Val Thr Arg Ser Val Thr Lys Arg Ser Val Met Thr Leu Ala
 1               5                  10                  15

Tyr Gly Ser Lys Glu Phe Gly Phe Arg Gln Gln Val Leu Glu Asp Thr
            20                  25                  30

Ile Gln Pro Ala Ile Asp Ser Gly Lys Gly Pro Met Tyr Thr Gln Pro
        35                  40                  45

Asn Gln Ala Ala Gly Tyr Met Ala Lys Leu Ile Trp Glu Ser Val Ser
    50                  55                  60

Val Thr Val Val Ala Ala Val Glu Ala Met Asn Trp Leu Lys
65                  70                  75

<210> SEQ ID NO 25
<211> LENGTH: 73
<212> TYPE: PRT
<213> ORGANISM: Artificial Sequence
<220> FEATURE:
<223> OTHER INFORMATION: Description of Artificial Sequence: residues
      of T7 RNA polymerase

<400> SEQUENCE: 25

Ala Gly Gln Trp Leu Ala Tyr Gly Val Thr Arg Ser Val Thr Lys Arg
 1               5                  10                  15

Ser Val Met Thr Leu Ala Tyr Gly Ser Lys Glu Phe Gly Phe Arg Gln
            20                  25                  30

Gln Val Leu Glu Asp Thr Ile Gln Pro Ala Ile Asp Ser Gly Lys Gly
        35                  40                  45

Leu Met Phe Thr Gln Pro Asn Gln Ala Ala Gly Tyr Met Ala Lys Leu
    50                  55                  60

Ile Trp Glu Ser Val Ser Val Thr Val
65                  70

<210> SEQ ID NO 26
<211> LENGTH: 73
<212> TYPE: PRT
<213> ORGANISM: Artificial Sequence
<220> FEATURE:
<223> OTHER INFORMATION: Description of Artificial Sequence: residues
      of T7 RNA polymerase

<400> SEQUENCE: 26

Ala Gly Gln Trp Leu Ala Tyr Gly Val Thr Arg Ser Val Thr Lys Arg
 1               5                  10                  15

Ser Val Met Thr Leu Ala Tyr Gly Ser Lys Glu Tyr Gly Phe Arg Gln
            20                  25                  30

Gln Val Leu Glu Asp Thr Ile Gln Pro Ala Ile Asp Ser Gly Lys Gly
        35                  40                  45

Leu Met Phe Thr Gln Pro Asn Gln Ala Ala Gly Tyr Met Ala Lys Leu
    50                  55                  60

Ile Trp Glu Ser Val Ser Val Thr Val
65                  70

<210> SEQ ID NO 27
<211> LENGTH: 73
<212> TYPE: PRT
<213> ORGANISM: Artificial Sequence
<220> FEATURE:
<223> OTHER INFORMATION: Description of Artificial Sequence: residues
      of T7 RNA polymerase -continued

<400> SEQUENCE: 27

Ala Gly Gln Trp Leu Ala Tyr Gly Val Thr Arg Ser Val Thr Lys Arg
 1               5                  10                  15

Ser Val Met Thr Leu Ala Tyr Gly Ser Lys Glu Phe Gly Phe Arg Gln
             20                  25                  30

Gln Val Leu Glu Asp Thr Ile Gln Pro Ala Ile Asp Ser Gly Lys Gly
         35                  40                  45

Pro Met Tyr Thr Gln Pro Asn Gln Ala Ala Gly Tyr Met Ala Lys Leu
     50                  55                  60

Ile Trp Glu Ser Val Ser Val Thr Val
 65                  70

<210> SEQ ID NO 28
<211> LENGTH: 73
<212> TYPE: PRT
<213> ORGANISM: Artificial Sequence
<220> FEATURE:
<223> OTHER INFORMATION: Description of Artificial Sequence:
      corresponding regions of T7 RNA polymerase

<400> SEQUENCE: 28

Ala Gln Gln Trp Leu Ala Tyr Gly Val Thr Arg Ser Val Thr Lys Arg
 1               5                  10                  15

Ser Val Met Thr Leu Ala Tyr Gly Ser Lys Glu Phe Gly Phe Arg Gln
             20                  25                  30

Gln Val Leu Asp Asp Thr Ile Gln Pro Ala Ile Asp Ser Gly Lys Gly
         35                  40                  45

Leu Met Phe Thr Gln Pro Asn Gln Ala Ala Gly Tyr Met Ala Lys Leu
     50                  55                  60

Ile Trp Asp Ala Val Ser Val Thr Val
 65                  70

<210> SEQ ID NO 29
<211> LENGTH: 73
<212> TYPE: PRT
<213> ORGANISM: Artificial Sequence
<220> FEATURE:
<223> OTHER INFORMATION: Description of Artificial Sequence:
      K11 RNA polymerase

<400> SEQUENCE: 29

Ala Ala Gln Trp Leu Gln Tyr Gly Val Thr Arg Lys Val Thr Lys Arg
 1               5                  10                  15

Ser Val Met Thr Leu Ala Tyr Gly Ser Lys Glu Ser Leu Val Arg Gln
             20                  25                  30

Gln Val Leu Glu Asp Thr Ile Gln Pro Ala Ile Asp Asn Gly Glu Gly
         35                  40                  45

Leu Met Phe Thr His Pro Asn Gln Ala Ala Gly Tyr Met Ala Lys Leu
     50                  55                  60

Ile Trp Asp Ala Val Thr Val Thr Val
 65                  70

<210> SEQ ID NO 30
<211> LENGTH: 75
<212> TYPE: PRT
<213> ORGANISM: Artificial Sequence
<220> FEATURE:
<223> OTHER INFORMATION: Description of Artificial Sequence:
      SP6 RNA polymerase

<400> SEQUENCE: 30

```
Ala Ser Ala Trp Asp Ser Ile Gly Ile Thr Arg Ser Leu Thr Lys Lys
 1               5                  10                  15

Pro Val Met Thr Leu Pro Tyr Gly Ser Thr Arg Leu Thr Cys Arg Glu
            20                  25                  30

Ser Val Ile Asp Tyr Ile Val Asp Leu Glu Glu Lys Glu Ala Gln Lys
        35                  40                  45

Ala Val Ala Glu Gly Arg Thr Ala Asn Lys Val His Pro Phe Glu Asp
    50                  55                  60

Asp Arg Gln Asp Tyr Leu Thr Pro Gly Ala Ala
65                  70                  75
```

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence:
    T7 RNA polymerase (WT)
<221> NAME/KEY: misc_feature
<222> LOCATION: (25)
<223> OTHER INFORMATION: Nucleotide 25 is n wherein n = any nucleotide.

<400> SEQUENCE: 31 gggaggggg gggggggcc ccccngggcg t                              31

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: T7 RNA
    polymerase (WT)
<221> NAME/KEY: misc_feature
<222> LOCATION: (7)..(30)
<223> OTHER INFORMATION: Nucleotides 7-9, 18, 25 and 30 are n wherein
    n = any nucleotide.

<400> SEQUENCE: 32
gcgtcnnnaa aacgcacntt ttctntcgtn gg                           32

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: mutant T7
    RNA polymerase F644Y

<400> SEQUENCE: 33 cgagggggg ccggtaccc                                           19

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: T7 RNA
    polymerase (WT)
<221> NAME/KEY: misc_feature
<222> LOCATION: (6)
<223> OTHER INFORMATION: Nucleotide 6 is n wherein n = any nucleotide

<400> SEQUENCE: 34
cccctntttg ttcctttagt gaggt                                   25

-continued

```
<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: mutant T7
      RNA polymerase L665P/F667Y

<400> SEQUENCE: 35 gagggggggcc ggtaacgc                                                      18

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: T7 RNA
      polymerase (WT)

<400> SEQUENCE: 36 acgcctttg ttccctttag tg                                                   22

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: T7 RNA
      polymerase

<400> SEQUENCE: 37
ccctttagtg aggttaattg cgcgcttggg taatcatgg                                39

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: T7 RNA
      polymerase

<400> SEQUENCE: 38
ccctttagtg aggttaattg cgcgcttggg taatcatgg                                39

<210> SEQ ID NO 39
<211> LENGTH: 479
<212> TYPE: DNA
<213> ORGANISM: Artificial Sequence
<220> FEATURE:
<223> OTHER INFORMATION: Description of Artificial Sequence: vector
      having T7 promoter
<221> NAME/KEY: misc_feature
<222> LOCATION: (4)..(479)
<223> OTHER INFORMATION: Nucleotides 4, 7-9, 13, 60, 74, 201, 211,
      303-304, 314, 320, 324-394, 396-419, 421-435, 439-444, and 446-479
      are n wherein n = any nucleotide

<400> SEQUENCE: 39
acgnggngnc gtncttaaga agtagtggtc ccccggctgc aaggattcca tacaagcttn         60
acgttaacgt cganctcgag gggggggccgg ctacagggct tttgttccct ttagtgaggg       120
ttaattgcgc gcttgggtaa tcatggtcat agctgtttcc tgtgtgaaat tgttatccgc       180
tcacaattcc acacaacata ngagccggga ncataaagtg taaagcctgg ggggctaat        240 gagtgagcta actcacatta attgcgttgc ggtcactggc cgctttccag tcgggaaacc       300
tgnngtggtc cggnggttan taannnnnnn nnnnnnnnn nnnnnntnn nnnnnnnnn           360
```
nnnnnnnnnn nnnnnnnnnn nnnnnnnnnn nnnnannnnn nnnnnnnnnn nnnnnnnnng    420
nnnnnnnnnn nnnnnggcnn nnnntnnnnn nnnnnnnnnn nnnnnnnnnn nnnnnnnnn     479

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: PCR product
<221> NAME/KEY: misc_feature
<222> LOCATION: (2)..(49)
<223> OTHER INFORMATION: Nucleotides 2-7, 12, 19, 27, 30, 38, 41 and
      49 are n wherein n = any nucleotide

<400> SEQUENCE: 40
cnnnnnncgg gnctgggtnc cgatccnaan ggaacagngg ntaatgtgna aacataaata    60

<210> SEQ ID NO 41
<211> LENGTH: 428
<212> TYPE: DNA
<213> ORGANISM: Artificial Sequence
<220> FEATURE:
<223> OTHER INFORMATION: Description of Artificial Sequence: PCR product
<221> NAME/KEY: misc_feature
<222> LOCATION: (184)..(373)
<223> OTHER INFORMATION: Nucleotides 184, 191 and 373 are n wherein
      n = any nucleotide

<400> SEQUENCE: 41
atatttttat tagctttatt tcaggcaagc acatttaacc aaattgcaaa ttatatcact    60
attagacaga aaatcctcac caggataaga cttctggagg tttggtacag tagtttgtct   120
tggatggctt catgtatgca gtcactatag tcagtattgc attggcacac ttacagctta   180
aacnaacagg ntaggaaaaa tagggagcaa catggagtgg gcatcctggt atttctacag   240
tcctgtagat gaagtctcta tatgtgcaaa catcctggga cagagcatat ttgggaagaa   300
acaggtttgc cattgatatc ccgtgtcata caatatccag cacagatggt ggtgttgatg   360
gttaggcaat aancacactc tctcctttcg atgtgcattg tatactcagt tggaatacaa   420
aaagacat                                                            428

<210> SEQ ID NO 42
<211> LENGTH: 61
<212> TYPE: DNA
<213> ORGANISM: Artificial Sequence
<220> FEATURE:
<223> OTHER INFORMATION: Description of Artificial Sequence: T7 RNA
      polymerase
<221> NAME/KEY: misc_feature
<222> LOCATION: (9)..(19)
<223> OTHER INFORMATION: Nucleotides 9, 10 and 19 are n wherein
      n = any nucleotide

<400> SEQUENCE: 42
ttaggaatnn tggtccccng gctgcaggat tcgatacaag cttacgatac gtcggactcg    60
g                                                                   61

<210> SEQ ID NO 43
<211> LENGTH: 301
<212> TYPE: DNA
<213> ORGANISM: Artificial Sequence
<220> FEATURE:
<223> OTHER INFORMATION: Description of Artificial Sequence:
      T7 RNA polymerase
<221> NAME/KEY: misc_feature
<222> LOCATION: (20)..(300)

```
<223> OTHER INFORMATION: Nucleotides 20, 23, 71, 80, 104, 177, 189,
      190, 225, 227-229, 232-236, 238-239, 241-245, 247, 249-250,
      252-253, 255, 260, 268, 271, 283, 291, 293, 295 and 300
      are n wherein n = any nucleotide

<400> SEQUENCE: 43 cgggggggggg ccgggctaan gcnttttgtt ccctttatga ggttaattgc gcgcttggta    60
atcatggtca nagctgtttn ctgtgtggaa ttgttaccgc tcanaatcca cacacacaac   120
atagagccgg gagataaagt gtaaagcctg gggtggtaat gagtgagcta atcacantaa   180
ttgcgttgnn tcatgccgct ttccagtcgg gaaactgtcg tggcngnnnt tnnnnnanna   240
nnnnntncnn cnntntttn tctcactntt ncttttcttt ttntcccttc ntncntcctn    300
t                                                                   301

<210> SEQ ID NO 44
<211> LENGTH: 60
<212> TYPE: DNA
<213> ORGANISM: Artificial Sequence
<220> FEATURE:
<223> OTHER INFORMATION: Description of Artificial Sequence:
      T7 RNA polymerase
<221> NAME/KEY: misc_feature
<222> LOCATION: (1)..(23)
<223> OTHER INFORMATION: Nucleotides 1-3, 12, 21 and 23 are
      n wherein n = any nucleotide

<400> SEQUENCE: 44
nnnacggggc gncgtcttag nantagtggt ccccggctgg aggattcgat acaacttacg    60

<210> SEQ ID NO 45
<211> LENGTH: 301
<212> TYPE: DNA
<213> ORGANISM: Artificial Sequence
<220> FEATURE:
<223> OTHER INFORMATION: Description of Artificial Sequence:
      T7 RNA polymerase
<221> NAME/KEY: misc_feature
<222> LOCATION: (148)..(301)
<223> OTHER INFORMATION: Nucleotides 148, 237, 247, 249, 251-254,
      256-276, 278-280, 282-287, 289-290, 293, 295 and 297-301
      are n wherein n = any nucleotide

<400> SEQUENCE: 45
acgatacgtc gactcgaggg ggggccggct aaggcttttt gttcccttta gtgagggtta    60
attgcgcgct tgggtaatca tggtcatagc tgtttcctgt gtgaaattgt tatccgctca   120
caattccaca caacatacga gccggganca taaagtgtaa agcctggggg gctaatgagt   180
gagctaactc acattaattg ccttgcggtc actgccgctt tccagtcggg aaactgncgt   240
gggccgngng nnnnannnnn nnnnnnnnn nnnnntnnn tnnnnngnn ctngntnnnn      300 n                                                                  301

<210> SEQ ID NO 46
<211> LENGTH: 61
<212> TYPE: DNA
<213> ORGANISM: Artificial Sequence
<220> FEATURE:
<223> OTHER INFORMATION: Description of Artificial Sequence:
      T7 RNA polymerase
<221> NAME/KEY: misc_feature
<222> LOCATION: (1)..(21)
<223> OTHER INFORMATION: Nucleotides 1, 11, 13, 15 and 21 are
      n wherein n = any nucleotide

<400> SEQUENCE: 46
```

```
ngggggccgt ncntnaggaa ngagtggtcc ccggctgcag gattcgatat caagcttatc    60
g                                                                    61
```

<210> SEQ ID NO 47
<211> LENGTH: 294
<212> TYPE: DNA
<213> ORGANISM: Artificial Sequence
<220> FEATURE:
<223> OTHER INFORMATION: Description of Artificial Sequence:
      T7 RNA polymerase
<221> NAME/KEY: misc_feature
<222> LOCATION: (24)..(293)
<223> OTHER INFORMATION: Nucleotides 24, 147, 169, 208, 212, 243,
      250-251, 253, 255, 257-260, 264, 266, 271, 273-274, 277-281,
      283, 285 and 293 are n wherein n = any nucleotide

<400> SEQUENCE: 47

```
tcgatacgtc gactcgaggg gggncccgct acaggctttt tgttcccttt agtgaggtaa    60
ttgggcgctt gggtaatcat ggtcatagct gtttcctgtg tgaaattgtt atccgctcac   120
aattccacac aacatacgag ccgggancat aaagtgtaaa gcctggggng cctaatgagt   180
gagctaatcc acattaattg cgttgcgntc antggccgct ttccagtcgg gaaactgtcg   240
tgngccgagn ntncnannnn aaananaaac ncnnaannnn nananaaaaa aana         294
```

<210> SEQ ID NO 48
<211> LENGTH: 61
<212> TYPE: DNA
<213> ORGANISM: Artificial Sequence
<220> FEATURE:
<223> OTHER INFORMATION: Description of Artificial Sequence:
      T7 RNA polymerase
<221> NAME/KEY: misc_feature
<222> LOCATION: (4)..(60)
<223> OTHER INFORMATION: Nucleotides 4, 7, 9, 13 and 60
      are n wherein n = any nucleotide

<400> SEQUENCE: 48

```
acgnggngnc gtncttaaga agtagtggtc ccccggctgc aaggattcga tacaagcttn    60
a                                                                    61
```

<210> SEQ ID NO 49
<211> LENGTH: 305
<212> TYPE: DNA
<213> ORGANISM: Artificial Sequence
<220> FEATURE:
<223> OTHER INFORMATION: Description of Artificial Sequence:
      T7 RNA polymerase
<221> NAME/KEY: misc_feature
<222> LOCATION: (2)..(305)
<223> OTHER INFORMATION: Nucleotides 2, 16, 143, 153, 244-245, 255,
      261, 264-289, and 291-305 are n wherein n = any nucleotide

<400> SEQUENCE: 49

```
tnacgttaac gtcganctcg aggggggggcc ggctacaggg cttttgttcc ctttagtgag    60
ggttaattgc gcgcttgggt aatcatggtc atagctgttt cctgtgtgaa attgttatcc   120
gctcacaatt ccacacaaca tangagccgg gancataaag tgtaaagcct gggggctaa    180 tgagtgagct aactcacatt aattgcgttg cggtcactgg ccgctttcca gtcgggaaac   240
ctgnngtggt ccggngggtta ntaannnnnn nnnnnnnnnn nnnnnnnnnt nnnnnnnnnn   300 nnnnn                                                                305
```

<210> SEQ ID NO 50
<211> LENGTH: 44

```
<212> TYPE: DNA
<213> ORGANISM: Artificial Sequence
<220> FEATURE:
<223> OTHER INFORMATION: Description of Artificial Sequence: PCR product
<221> NAME/KEY: misc_feature
<222> LOCATION: (11)
<223> OTHER INFORMATION: Nucleotide 11 is n wherein n = any nucleotide

<400> SEQUENCE: 50
aggtaagact nctgaggttt ggtacagtag tttgtcttga tggc                44

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: PCR product
<221> NAME/KEY: misc_feature
<222> LOCATION: (17)
<223> OTHER INFORMATION: Nucleotide 17 is n wherein n = any nucleotide

<400> SEQUENCE: 51
ggcttcatgt atgcagncac tatagtcagt attgcacttg                     40

<210> SEQ ID NO 52
<211> LENGTH: 83
<212> TYPE: DNA
<213> ORGANISM: Artificial Sequence
<220> FEATURE:
<223> OTHER INFORMATION: Description of Artificial Sequence: PCR product

<400> SEQUENCE: 52
gataagactt ctggaggttt ggtacagata gtttgtcttg atggcttca tgtatgcagt    60 cactatagtc agtattgcac ttg                                           83

<210> SEQ ID NO 53
<211> LENGTH: 53
<212> TYPE: DNA
<213> ORGANISM: Artificial Sequence
<220> FEATURE:
<223> OTHER INFORMATION: Description of Artificial Sequence: sequencing
      of hTSH-beta cDNA without inorganic pyrophophatase
<221> NAME/KEY: misc_feature
<222> LOCATION: (1)..(31)
<223> OTHER INFORMATION: Nucleotides 1, 3, 5-7, 9, 15 and 31
      are n wherein n = any nucleotide

<400> SEQUENCE: 53
ngngnnngnc gttcnaatga cgagtatgtg nacataatat tttatagctt tat      53

<210> SEQ ID NO 54
<211> LENGTH: 492
<212> TYPE: DNA
<213> ORGANISM: Artificial Sequence
<220> FEATURE:
<223> OTHER INFORMATION: Description of Artificial Sequence: sequencing
      of hTSH-beta cDNA without inorganic pyrophophatase
<221> NAME/KEY: misc_feature
<222> LOCATION: (69)..(492)
<223> OTHER INFORMATION: Nucleotides 69, 116, 347, 389, 393, 407,
      446, 449, 463, 474, 476, 478 and 483-492
      are n wherein n = any nucleotide

<400> SEQUENCE: 54
tttattcagg cagcacatta acaattgcaa ttatatcact atgacaggaa accttaccag    60
gtaagactnc tgaggtttgg tacagtagtt tgtcttgatg gcttcatgta tgcagncact   120
atagtcagta ttgcacttgg cacacttaca gcttaaacca acaggatagg aaaaataggg   180
```

-continued

```
agcaacatgg agtgggcatc ctggtattct acagtcctgt agatgaagtc tctatagtgc    240
aaacatcctg ggacagagca tatttgggaa gaaacagttt gcccattggg aatttttacc    300
ggcaaatatc agcaagtggg tgtgtggtta gcaaaanaca tctctctttc gtggcatgta    360
aatcagtgga taaaaaagac acgctgccna agnaagccaa aaacagnaag aggcagccat    420
gtggcgtatt ggtcgactgc agcatnaant tttgtcctta agngtccccc cccncncncc    480
ccnnnnnnnn nn                                                       492
```

<210> SEQ ID NO 55
<211> LENGTH: 72
<212> TYPE: DNA
<213> ORGANISM: Artificial Sequence
<220> FEATURE:
<223> OTHER INFORMATION: Description of Artificial Sequence: sequencing of hTSH-beta cDNA with inorganic pyrophophatase
<221> NAME/KEY: misc_feature
<222> LOCATION: (3)..(42)
<223> OTHER INFORMATION: Nucleotides 3-4, 7, 13, 19, 25, 33-34 and 42 are n wherein n = any nucleotide

<400> SEQUENCE: 55

```
cgnngtngcg ttncgatcna aatgnaacgg ganntaatgt gnaaacataa tattttctt     60 agctttattt ca                                                        72
```

<210> SEQ ID NO 56
<211> LENGTH: 551
<212> TYPE: DNA
<213> ORGANISM: Artificial Sequence
<220> FEATURE:
<223> OTHER INFORMATION: Description of Artificial Sequence: sequencing of hTSH-beta cDNA with inorganic pyrophophatase
<221> NAME/KEY: misc_feature
<222> LOCATION: (18)..(551)
<223> OTHER INFORMATION: Nucleotides 18, 361, 522-524, 527, 529 and 532-551 are n wherein n = any nucleotide

<400> SEQUENCE: 56

```
ttcaggcaag cacatttnaa cccaaattgg caaattatat cactcattag acaggaaaat    60
ccttaccagg ataagacttc tggaggtttg gtacagatag tttgtcttgg atggcttcat    120
gtatgcagtc actatagtca gtattgcact tggcacactt acagcttaaa ccaacaggat    180
aggaaaaata gggagcaaca tggagtgggc atcctggtat ttctacagtc ctgtagatga    240
agtctcttat atgtgcaaac atcctgggac agagcatatt tgggagaaa cagtttgcca    300 ttgatatccc gtgtcataca atatccagca cagatggtgg tgttgatggt taggcaataa    360
ncacactctc tcctttcgat gtgcattgta tactcagttg gaatacaaaa agacatcgct    420
tggccacatg caaggccaaa aacatgggca tcagaaagag agcagtcatg tggggaattg    480
gtcgactgca ggcatggaac cttttgttcc ctttagtgag gnnnaancnc cnnnnnnnnn    540
nnnnnnnnnn n                                                        551
```

<210> SEQ ID NO 57
<211> LENGTH: 146
<212> TYPE: DNA
<213> ORGANISM: Artificial Sequence
<220> FEATURE:
<223> OTHER INFORMATION: Description of Artificial Sequence: mutant T7 RNA polymerase F644Y/L665P/F667Y
<221> NAME/KEY: misc_feature
<222> LOCATION: (1)..(141)
<223> OTHER INFORMATION: Nucleotides 1-14, 17-18, 21, 26, 29, 34, 38, 40, 49-50, 52, 57, 74-75, 84, 109, 116, 131 and 141 are n wherein n = any nucleotide

<400> SEQUENCE: 57
nnnnnnnnnn nnnnggnngt nggttncgna tccnaaangn aacagggggnn antgtgnaaa     60 catgaatatt tttnntaagc tttnattcca ggcaagaca ttttaaccna aattgncaaa      120
ttatatcact nattagacag naaaat                                          146

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: mutant T7
      RNA polymerase F644Y/L665P/F667Y

<400> SEQUENCE: 58
agctttattt caggcaagca catttaacca aattgcaaat tatat                      45

<210> SEQ ID NO 59
<211> LENGTH: 49
<212> TYPE: DNA
<213> ORGANISM: Artificial Sequence
<220> FEATURE:
<223> OTHER INFORMATION: Description of Artificial Sequence: mutant T7
      RNA polymerase F644Y/L665P/F667Y

<400> SEQUENCE: 59
atcactatta gacagaaaat cctaccagat aagacttctg aggtttggt                  49

<210> SEQ ID NO 60
<211> LENGTH: 277
<212> TYPE: DNA
<213> ORGANISM: Artificial Sequence
<220> FEATURE:
<223> OTHER INFORMATION: Description of Artificial Sequence: mutant T7
      RNA polymerase F644Y/L665P/F667Y
<221> NAME/KEY: misc_feature
<222> LOCATION: (107)..(180)
<223> OTHER INFORMATION: Nucleotides 107, 148 and 180
      are n wherein n = any nucleotide

<400> SEQUENCE: 60
catcctggta tttctacagt cctgtagatg aagtctctat atgtgcaaca tcctgggaca     60
gagcatattt gggaagaaac agtttgccat tgaatcccgt gtcatanaat atccagcaca    120
gatggtggtg ttgatggtta gcaataanca cactctctcc tttcgatgtg cattgtatan    180
tcaggtggat acaaaaagac atcgcttggc ccacatgcaa ggccaaaaag cagacatcag    240
aaagagagca gtcatgtggg ggaattggtc cgactgc                             277

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence:
      termination pattern

<400> SEQUENCE: 61
agctttattt caggcaagca catttaacca aattgcaaat tatat                      45

<210> SEQ ID NO 62
<211> LENGTH: 44
<212> TYPE: DNA
<213> ORGANISM: Artificial Sequence

```
<220> FEATURE:
<223> OTHER INFORMATION: Description of Artificial Sequence:
      termination pattern

<400> SEQUENCE: 62
atcactatta gacagaaaat cctaccagat aagacttctg aggt                       44

<210> SEQ ID NO 63
<211> LENGTH: 45
<212> TYPE: DNA
<213> ORGANISM: Artificial Sequence
<220> FEATURE:
<223> OTHER INFORMATION: Description of Artificial Sequence:
      termination pattern

<400> SEQUENCE: 63
agctttattt caggcaagca catttaacca aattgcaaat tatat                      45

<210> SEQ ID NO 64
<211> LENGTH: 49
<212> TYPE: DNA
<213> ORGANISM: Artificial Sequence
<220> FEATURE:
<223> OTHER INFORMATION: Description of Artificial Sequence:
      termination pattern

<400> SEQUENCE: 64
atcactatta gacagaaaat cctaccagat aagacttctg aggtttggt                  49
```

METHOD OF DNA SEQUENCING

CROSS-REFERENCE TO RELATED APPLICATIONS

This application is a 371 of PCT/JP98/03039, filed Jul. 6, 1998, which claims priority from Japanese application 101155847, filed Jun. 4, 1998, and Japanese application 91196478, filed Jul. 7, 1997.

TECHNICAL FIELD

The present invention relates to methods for determining DNA sequences. In particular, the present invention relates to methods for determining DNA sequence utilizing mutant RNA polymerases. The present invention further relates to methods for determining DNA sequences utilizing novel 3'-deoxyribonucleotide derivatives as fluorescence-labeled terminators. The present invention still further relates to methods for determining DNA sequences wherein nucleic acid transcription reaction is performed in the presence of inorganic pyrophosphatase.

BACKGROUND ART

The polymerase chain reaction (PCR) method is an excellent method, and its utilization has expanded year by year [Randall K. Saiki et al. (1988) Science 239, 487–491]. In the PCR method, even one molecule of DNA fragment can be amplified. The method for sequencing PCR amplified products without cloning them (the direct sequencing method) is also a useful method [Corinne Wong et al. (1988) Nature, 330, 384–386]. This technique does not require construction of libraries and screening of such libraries, and is a quick method capable of simultaneously obtaining sequence information of many samples.

However, the above direct sequencing method suffers from two major problems.

One is that primers and 2'-deoxyribonucleoside 5'-triphosphates (2'-dNTPs) not incorporated remain in a reaction system, and the remained substances inhibit sequencing reactions. Therefore, in conventional methods, such primers and 2'-dNTPs must be removed from PCR products before sequencing. There are many methods for purification of PCR products and examples include purification by electrophoresis, ethanol precipitation, gel filtration and HPLC purification [see, for example, Dorit R. L. et al. (1991) Current Protocols in Molecular Biology, Vol. 11, John Wiley and Sons, New York, 15.2.1–15.2.11]. However, these methods are complicated without exception.

The second problem is quick renaturation of PCR products. When the PCR products are renatured into a double-stranded DNA, they are no longer single-stranded templates, and annealing between primers and single-stranded templates is inhibited. As methods for minimizing the renaturation, quenching after denaturation, biotilation of one primer and absorption of PCR products onto streptavidin-coated articles, use of exonuclease, asymmetric PCR and the like have been reported. See, for example, Barbara Bachmann et al., 1990, Nucleic Acid Res., 18, 1309-. However, most of these methods are time-consuming and very laborious.

Therefore, the present inventors proposed an absolutely novel method for determining nucleotide sequence of DNA for solving these problems. Which does not require removal of unreacted primers and 2'-deoxyribonucleoside 5'-triphosphates (2'-dNTPs) remaining in the PCR reaction system, and does not require denaturation at all. This method enables to eliminate the problem of quick renaturation of PCR reaction products [WO96/14434]. This method is a direct transcriptional sequencing method utilizing an RNA polymerase such as T7 RNA polymerase and a terminator for RNA transcription reaction (for example, 3'-deoxyribonucleoside 5'-triphosphates, 3'-dNTPs). According to this method, nucleotide sequences of DNA products amplified by the polymerase chain reaction can be used as they are for sequencing without removing primers and 2'-deoxyribonucleoside 5'-triphosphates (2'-dNTPs). In addition, because it does not require denaturation itself at all, it can avoid the problem of quick renaturation of PCR products, and hence is an extremely excellent method.

However, the present inventors further studied the above method, and found that it has a problem to be solved in order to obtain more accurate nucleotide sequence data.

In the above nucleotide sequence determination method, an RNA polymerase such as T7 RNA polymerase is used for the reaction in a mixture comprising ribonucleoside 5'-triphosphates including ATP, GTP, CTP, UTP and derivatives thereof, and at least one 3'-deoxyribonucleotide such as 3'-dATP, 3'-dGTP, 3'-dCTP, 3'-dUTP and derivatives thereof. In this reaction, polyribonucleotides are synthesized by sequential incorporation of ribonucleotides and deoxyribonucleotides into a ribonucleotide sequence in a manner corresponding to the sequence of templates.

However, it was found that 3'-deoxyribonucleotides and derivative thereof are unlikely to be incorporated into the sequence rather than corresponding ribonucleotides, and the occurrence of the incorporation may also vary among the ribonucleotides and the 3'-deoxyribonucleotides depending on a base group each nucleotide has. Such biased incorporation between ribonucleotides and 3'-deoxyribonucleotides, as well as among ribonucleotides having different base groups and among deoxyribonucleotides having different base groups may result in short transcription products and fluctuation of signals from labeled ribonucleotides. Therefore, it is difficult to obtain accurate sequence data even though transcription products can be obtained.

Therefore, an object of the present invention is to provide a method for determining DNA sequences which utilizes an RNA polymerase exhibiting incorporation ability with no or little bias resulting from differences in nucleotides, and is capable of producing a transcription product of a long chain and affording more accurate sequence data where fluctuation of signals from labeled deoxyribonucleotides is reduced.

In the description of the present invention, amino acid residues are represented by the conventionally used one-letter codes. For clarification, they are specifically mentioned for only those amino acids appeared in this text as follows: phenylalanine (F), tyrosine (Y), proline (P), leucine (L), and histidine (H). A numeral accompanied by the codes is a number counted from N-terminus of polymerase. For example, "F667" means that the 667th amino acid residue of this polymerase is F, and "F667Y" means that Y was substituted for F of the 667th residue.

By the way, DNA polymerases are also known to show biased incorporation resulting from difference in a base group each nucleotide has, and mutant DNA polymerases free from such biased incorporation have also been known [Japanese Patent Unexamined Publication (KOKAI) No. (Hei) 8-205874/1996; and Proc. Natl. Acid. Sci. USA, 92:6339–6345, (1995)].

In the aforementioned literatures, it is described as follows. In the sequencing reaction utilizing T7 DNA polymerase, the 526th amino acid in the polymerase contributes to equalize nucleotide incorporation. And due to homology between T7 DNA polymerase and other DNA polymerases, the bias of incorporation of the other DNA polymerases may be reduced by replacing an amino acid residue present in their region homologous to the 526th amino acid including region in the T7 DNA polymerase. That is, Y (tyrosine) 526 of T7 DNA polymerase results in the reduced bias of efficiency for incorporation of 2'-dNTPs and 2',3'-ddNTPs. F (phenylalanine) 762 of *E. coli* DNA polymerase I and F (phenylalanine) 667 of Thermus aquaticus DNA polymerase (generally called Taq DNA polymerase) are the amino acid residues corresponding to Y526 of T7 DNA polymerase and the bias of these polymerases may be reduced by substituting F762Y (tyrosine) and F667Y (tyrosine) respectively for these residues.

Further, it is also described that it was suggested that modification of a region of T7 RNA polymerase corresponding to the region discussed for DNA polymerases, i.e., the residues 631–640, may change its specificity for dNTPs.

However, RNA polymerases have not been used for sequencing methods so far, and therefore the different efficiency of ribonucleotide incorporation itself has not become a problem. Under such circumstances, any mutant RNA polymerases free from the biased incorporation have of course not been known. In fact, the aforementioned Japanese Patent Unexamined Publication (KOKAI) No. (Hei) 8-205874/1996 does not mention any specific examples of modification of T7 RNA polymerase.

The region of T7 RNA polymerase mentioned above is considered to correspond to the region consisting of 9–10 amino acid residues between amino acids K and YG in the motif B mentioned in Protein Engineering, 3:461–467, 1990, which region is particularly conserved in DNA polymerase α and I, and DNA-dependent RNA polymerases (T7 RNA polymerase is classified in these polymerases). F (phenylalanine) of the amino acid residue 762 in *E. coli* DNA polymerase and the amino acid residue 667 in Taq DNA polymerase, previously discussed for DNA polymerases, are observed in many of DNA polymerases classified in the type I. However, it was surprisingly found that T7 RNA polymerase does not have F (phenylalanine) in the residues 631–640 corresponding to the aforementioned region, though T7 RNA polymerase is highly homologous to DNA polymerases. Therefore, the teachings of the aforementioned literatures could not be realized as described.

Further, the present inventors attempted modification of amino acids of T7 RNA polymerase in the region corresponding to the helix O of the finger subdomain of *E. coli* DNA polymerase I, in which F762 of *E. coli* DNA polymerase I presents. However, F (phenylalanine) was not found also in the helix Z in T7 RNA polymerase, which is indicated in the steric structure reported in the literature of Sousa et al. (Nature, 364:593–599, 1993) and corresponds to the helix O of *E. coli* DNA polymerase I.

Under the circumstances, the present inventors originally searched for a novel RNA polymerase in order to provide an RNA polymerase which exhibits little or no bias for the incorporating ability due to the kind of ribonucleotides and 3'-deoxyribonucleotides. As a result, the method for determining DNA sequences of the present invention was completed based on the finding that an RNA polymerase having an increased ability of incorporating 3'-deoxyribonucleotides and derivatives thereof can be obtained by partially modifying amino acids in a wild type RNA polymerase.

While it will be apparent from the descriptions hereinafter, the RNA polymerase of the present invention, or in particular the location of the amino acid modification thereof is not suggested nor taught at all in Japanese Patent Unexamined Publication (KOKAI) No. (Hei) 8-205874/1996, and it was absolutely originally found by the present inventors.

Further, as a result of the present inventors' examination, it was found that the bias of the incorporation of ribonucleotides may be eliminated to some extent by using a mutant RNA polymerase, but the bias of the incorporation would still remain to a certain extent when a fluorescence-labeled 3'-deoxyribonucleotide is used as a terminator for nucleic acid extension reaction.

Therefore, a further object of the present invention is, from the viewpoint of obtaining a more practically useful method, to provide a method capable of eliminating the bias of the incorporation and more accurately determining nucleotide sequences even when a fluorescence-labeled 3'-deoxyribonucleotide is used.

SUMMARY OF THE INVENTION

The present invention relates to a method for determining DNA nucleotide sequences comprising reacting ribonucleoside 5'-triphosphates including ATP, GTP, CTP and UTP or derivatives thereof, and one or more kinds of 3'-deoxyribonucleoside 5'-triphosphates including 3'-dATP, 3'-dGTP, 3'-dCTP, 3'-dUTP and derivatives thereof (referred to as 3'-dNTP derivatives hereinafter) in the presence of an RNA polymerase and a DNA fragment containing a promoter sequence for the RNA polymerase to obtain a nucleic acid transcription product, separating the resulting transcription product, and determining a nucleic acid sequence from the resulting separated fraction, wherein the RNA polymerase is a mutant RNA polymerase consisting of a wild type RNA polymerase provided that at least one of amino acids in the wild type RNA polymerase was modified so as to enhance its ability for incorporating the 3'-dNTP derivatives in comparison with the corresponding wild type RNA polymerase.

The present invention further relates to the aforementioned method for determining DNA nucleotide sequences wherein the 3'-dNTP derivatives are 3'-deoxyribonucleotide derivatives represented by the following general formula [I]:

$$Q-V-(CH_2)_n-NH-R \qquad [I]$$

In the formula, Q represents a 3'-deoxyribonucleotide residue, n represents an integer not less than 1, preferably not less than 4, V represents —C≡C— or —CH=CH—, and R represents a fluorescent group.

The present invention further relates to the a aforementioned method for determining DNA nucleotide sequences wherein the nucleic acid transcription reaction is performed in the presence of an inorganic pyrophosphatase.

BRIEF DESCRIPTION OF THE DRAWINGS

FIG. 7 shows alignment of amino acid sequences continuation of [SEQ ID NOS.: 17–18] of T7 RNA polymerase and T3 RNA polymerase (latter half). The T7 RNA polymerase at the top is used as a standard, and the symbols . (dot) indicate the same amino acid residues as the T7 RNA polymerase, – indicates absence, and * at the bottom indicates amino acid residues common to the both polymerases.

FIG. 8 shows the sequences [SEQ ID NOS.: 25–27] around the residues 641–667 of T7 RNA polymerase, and amino acid sequences of the corresponding regions of T3 RNA polymerase [SEQ ID NO.:28], K11 RNA polymerase [SEQ ID NO.:29] and SP6 RNA polymerase [SEQ ID NO.:30]. While all of the residues are shown for T7RNA polymerase, the corresponding residues are indicated with . (dot) for T3, k11, and SP6 when they are the same as those of T7.

FIG. 22 shows the result of UV-visible region spectrophotometry of the carboxyrhodamine-6G-labeled 3'-deoxycytidine-5'-triphosphate (a compound of the general formula [I] where V is —C≡C— and n=4) obtained in Synthesis Example 54.

FIG. 23 shows the result of UV-visible region spectrophotometry of the carboxyrhodamine-X-labeled 7-deaza-3'-deoxyadenosine-5'-triphosphate (a compound of the general formula [I] where V is —C≡C— and n=4) obtained in Synthesis Example 55.

FIG. 34 (A-1 to A-5) and (B-1 to B-5) represent the result of sequencing utilizing a vector having T7 promoter as a template.

FIG. 35 A-1 to A-2, B-1 to B-2, C-1 to C-2, and D-1 to D-2 represents the result of sequencing utilizing a PCR product as a template.

FIG. 36 A-1 to A-6 and B-1 to B-6 represent the results of sequencing which indicate effect of addition of inorganic pyrophosphatase on the sequencing reaction utilizing a mutant T7 RNA polymerase (no addition and addition of 0.425 units).

FIG. 37 A-1 to A-6 and B-1 to B-6 represent the results of sequencing which indicate effect of addition of inorganic pyrophosphatase on the sequencing reaction utilizing a mutant T7 RNA polymerase (addition of 0.0425 units and 0.00425 units).

FIG. 41 A-1 to A-3, B-1 B-2, C-1 to C-3, D-1 to D-3 represent the results of improvement of incorporation rate of dye terminators by the mutant T7 RNA polymerase F644Y/L665P/F667Y as electrogram.

FIG. 42 A-1 to A-2 and B-1 to B-2 represents the termination pattern obtained by using TMR-3'-dUTP(n4) as the terminator (A), and the termination pattern obtained by using TMR-Allyl-3'-dUTP(n4) as the terminator (B) obtained in Reference Example 8.

EMBODIMENTS FOR CARRYING OUT THE INVENTION

Figure 5:
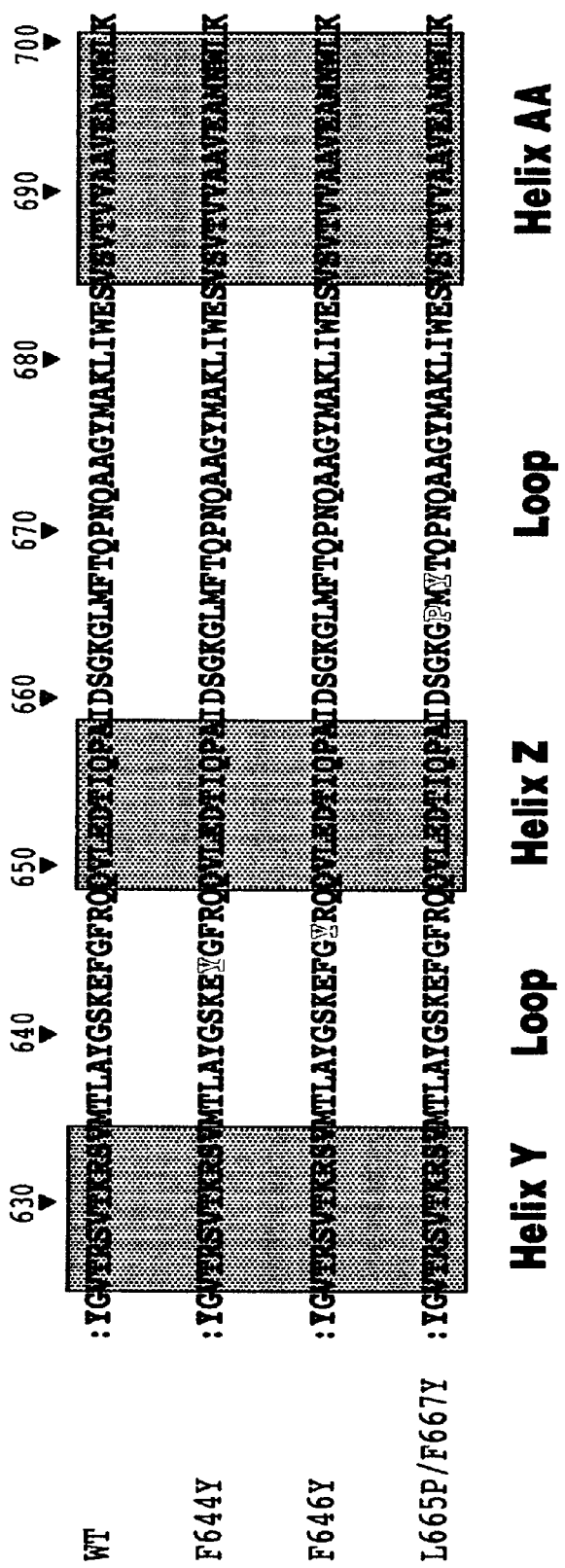
FIG. 5 shows details of mutated sites of T7 RNA polymerase. The outline characters indicate mutated amino acids [SEQ ID NOS.: 21–24].

The method for determining DNA sequences of the present invention comprises reacting ribonucleotides (NTPs) and 3'-deoxyribonucleotide (3'-dNTP) derivatives, in particular, 3'-dNTP derivatives wherein a linker is inserted between a fluorescent substance and 3'-deoxyribonucleotide, in the presence of an RNA polymerase and a DNA fragment containing a promoter sequence for the RNA polymerase, and determining a nucleic acid sequence from patterns of the resulting separated fraction of transcription product, characterized in that it utilizes a mutant RNA polymerase as an RNA polymerase.

Mutant RNA Polymerase

The mutant RNA polymerase used for the present invention consists of a wild type RNA polymerase, wherein at least one of amino acids of the polymerase is modified so that its ability for incorporating 3'dNTP derivatives should be enhanced compared with the corresponding wild type RNA polymerase.

According to the present invention, the "wild type RNA polymerase" include any naturally occurring RNA polymerases. In addition, the "wild type RNA polymerase" may be a wild type RNA polymerase having substitution, insertion and/or deletion of amino acids which are not the modification for obtaining increased ability for incorporating 3'-deoxyribonucleotide and derivatives thereof in comparison with the corresponding wild type RNA polymerase. That is, wild type RNA polymerases artificially modified with a purpose other than that described above are included in the above "wild type RNA polymerase". However, it is suitable to make such substitution, insertion and/or deletion of amino acids to the extent that the activity of RNA polymerase is maintained.

Examples of the "wild type RNA polymerase" include RNA polymerases derived from T7 phage, T3 phage, SP6 phage, K11 phage and the like. However, it is not limited to these RNA polymerases.

The "wild type RNA polymerase" according to the present invention include naturally occurring thermostable RNA polymerases, and naturally occurring RNA polymerases artificially modified (i.e. having substitution, insertion and/or deletion of amino acids) in order to impart thermostablity. However, it is suitable to make the modification for imparting thermostablity to the extent that the activity of RNA polymerase is maintained. The mutant RNA polymerase of the present invention prepared by using a thermostable RNA polymerase as the "wild type RNA polymerase" shall be thermostable. As a result, for example, it can be used in PCR to synthesize RNA fragments for sequencing in situ, i.e., during PCR, by using the PCR product as a template.

T7 RNA polymerase has been known to be a promoter specific RNA polymerase with an extremely high specificity.

The nucleotide sequence and production method of T7 RNA polymerase are reported in Davanloo et al., Proc. Natl. Acad. Sci. USA., 81:2035–2039 (1984). Its large scale production has been already described in Zawadzki et al., Nucl. Acids Res., 19:1948 (1991). This phage-derived RNA polymerase can pursue the transcription reaction with a single polypeptide, unlike RNA polymerases of E. coli and higher organisms (Chamberlin et al., Nature, 228:227–231,1970). Therefore, it is a particularly excellent material for analyzing the mechanism of transcription, and many mutants have been isolated and reported. Further, the results of its crystallographic analysis are mentioned in Sousa et al., Nature, 364:593–599, 1993.

As other promoter specific RNA polymerases of high specificity, 3 kinds of RNA polymerases derived from T3 phage which infects E. coli, SP6 phage which infects Salmonella, and K11 phage which infects Klebsiella pneumoniae have been well known.

The 4 kinds of RNA polymerases mentioned above are quite similar to one another in their primary structure of amino acids, sequence of promoter and the like as described hereinafter.

The RNA polymerase of the present invention has an increased ability of incorporating 3'-deoxyribonucleotides and derivatives thereof in comparison with the ability of a corresponding wild type RNA polymerase. As described above, wild type RNA polymerases poorly incorporate 3'-deoxyribonucleotides in comparison with ribonucleotides, which has obstructed their use in nucleotide sequencing. In contrast, the RNA polymerase of the present invention is modified so as to have the ability of incorporating 3'-deoxyribonucleotides and derivatives thereof at least twice higher than that of wild type. The incorporation of 3'-deoxyribonucleotides tends to be decreased especially when 3'-deoxyribonucleotide derivatives are labeled with a fluorescent tag. The RNA polymerase of the present invention can also improve incorporation of such 3'-deoxyribonucleotide derivatives.

The term ribonucleotide herein used means ribonucleoside 5'-triphosphates including ATP, GTP, CTP, UTP and derivative thereof, and 3'-deoxyribonucleotide means 3'-dATP, 3'-dGTP, 3'-dCTP and 3'-dUTP, and the derivative thereof means, for example, compounds composed of these 3'-deoxyribonucleotides which have a fluorescent label.

The RNA polymerase of the present invention is that at least one of amino acids in a corresponding wild type RNA polymerase is modified. This will be explained in detail hereinafter.

On the basis of the aforementioned various reports about T7 RNA polymerase, the present inventors tried to construct a mutant RNA polymerase which has little or no bias for incorporation efficiency valuable depending on the kind of ribonucleotides observed for T7 RNA polymerase. Various mutants were actually prepared to determine, in particular, which amino acids on wild type RNA polymerases should be mutated, and what kind of amino acids should be used for substitution when substitution is used as mutation. Then, it was found that the ability of incorporating 3'-deoxyribonucleotides and derivatives thereof can be improved by modifying at least one amino acid of wild type RNA polymerases, and completed the mutant RNA polymerase of the present invention.

The present inventors first constructed an expression plasmid pT7R inserted with the T7 RNA polymerase gene, and then mutants of T7 RNA polymerase were constructed based on the expression plasmid pT7R. That is, mutant T7 RNA polymerases, F644Y, F646Y, F667Y, F733Y, F782Y, and F882Y were constructed in which F (phenylalanine) residue of T7 RNA polymerase was replaced with Y (tyrosine) residue, and the ability of incorporation of these mutants was compared. Properties of Y639F mutant of the T7 RNA polymerase, which is a mutant at a location corresponding to Y526 of T7 DNA polymerase, are described in the literature (Sousa., EMBO J., 14:4609–4621 (1995)). Y639F mutant was also constructed, which has a mutation within the residue 631–640, those suggested to change their specificity for dNTP in Japanese Patent Unexamined Publication (KOKAI) No. (Hei) 8-205874/1996.

Figure 2:
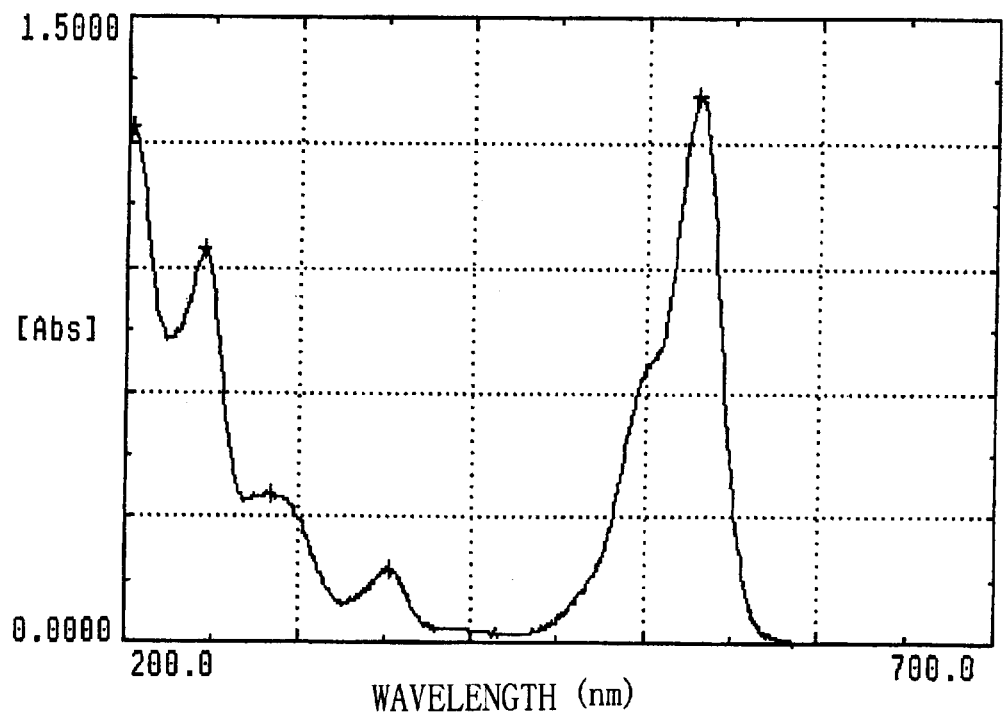
FIG. 2 shows T7 RNA polymerase gene on the T7 phage genome and the amino acid sequence of the encoded T7 RNA polymerase (latter half). The nucleotide sequence continuation of [SEQ ID NO.: 15] is shown in the upper sections, and the corresponding amino acid sequence continuation of [SEQ ID NO.: 16] is in the lower sections. The numerals for the nucleotide sequence at the right end indicate numbers of T7 phage genome registered at the DNA sequence database GeneBank (Locus T7CG, 39,937 base pairs), and the numerals of amino acids are appended from the first M (methionine) of T7 RNA polymerase starting with 1, and indicate that the full length is composed of 883 amino acid residues.
Figure 2:
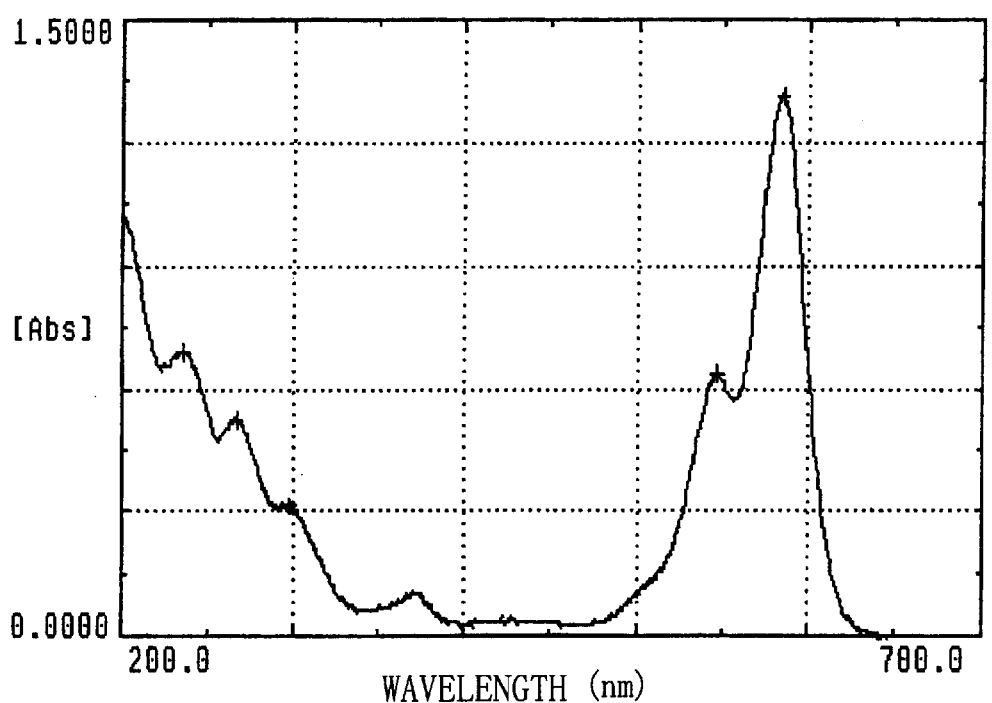
Figures 1, 34A:
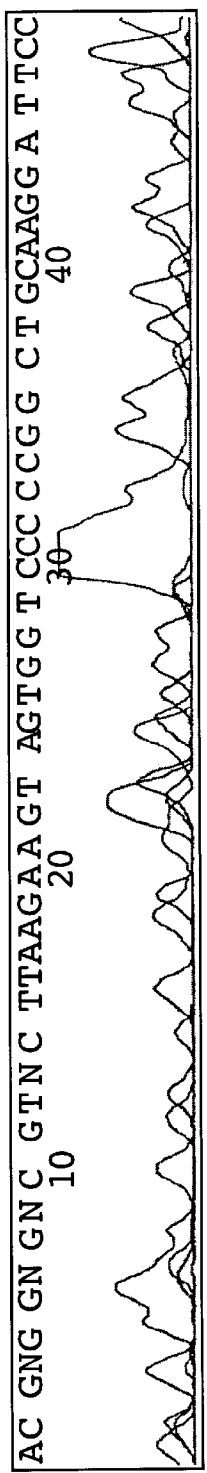
FIG. 1 shows T7 RNA polymerase gene on the T7 phage genome and the amino acid sequence of the encoded T7 RNA polymerase (first half). The nucleotide sequence is shown in the upper sections [SEQ ID NO.:15], and the corresponding amino acid sequence [SEQ ID NO.:16] is in the lower sections. The numerals for the nucleotide sequence at the right end indicate numbers of T7 phage genome registered at the DNA sequence database GeneBank (Locus T7CG, 39,937 base pairs), and the numerals of amino acids are appended from the first M (methionine) of T7 RNA polymerase starting with 1, and indicate that the full length is composed of 883 amino acid residues.
Figures 2, 34A:
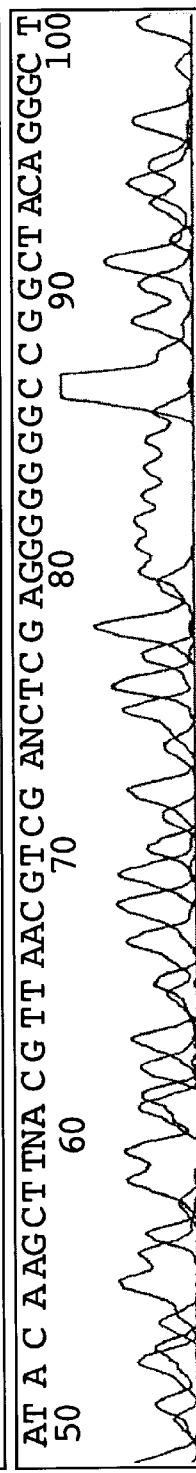

The amino acid sequence of wild type T7 RNA polymerase mentioned in this specification is based on the sequence encoded by nucleotides 3171–5822 of the T7 phage RNA sequence from the gene sequence database GeneBank, accession No. V01148 J02518 X00411 (39,937 base pairs) (cf. FIGS. 1 and 2). The upper sequences represented in FIGS. 1 and 2 are nucleotide sequences, and the lower sequences are amino acid sequences corresponding to the nucleotide sequences. For the nucleotide sequences, the numerals at the right ends are numbers of T7 phage genome registered at GeneBank (Locus T7CG, 39,937 base pairs), and the numerals at the right ends for the amino acids are appended from the first M (methionine) of T7 RNA polymerase starting with 1 and indicate that the full length consists of 883 amino acid residues.

This amino acid sequence is identical to the amino acid sequence reported in Moffatt et al., J. Mol. Biol., 173(2): 265–269, 1984 mentioned above.

Accordingly, the amino acid sequence and the numerals appended to each of the amino acids of wild type T7 RNA polymerase gene in this specification are basically the sequence and numbers represented in FIGS. 1 and 2. However, as described above, the aforementioned wild type T7 RNA polymerase may contain substitution, insertion and/or deletion which is not the modification intended by the present invention. Therefore, in the case that the wild type RNA polymerase, to which mutation should be introduced for the purpose of the present invention, is a wild type T7 RNA polymerase with other mutation, especially that such mutation is insertion or deletion of amino acids, numbers appended to amino acids are changed due to such insertion and deletion. A wild type T7 RNA polymerase having such insertion and deletion is a member of the wild type T7 RNA polymerase, to which a mutation intended by the present invention should be introduced, so long as it maintains T7 RNA polymerase activity even though its amino acid numbers are different from the numbers represented in FIGS. 1 and 2.

Figures 3, 34A:
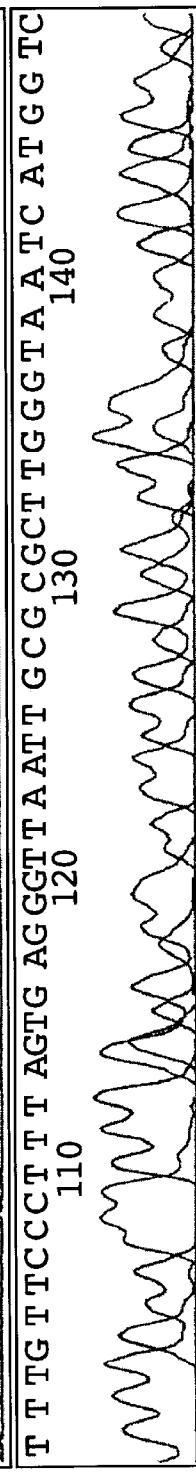
FIG. 3 shows alignment of amino acid sequences [SEQ ID NOS.:17–20] of the currently reported phage-derived RNA polymerases (first half). The T7 RNA polymerase at the top is used as a standard, and the symbols . (dot) indicate the same amino acid residues as the T7 RNA polymerase, – indicates absence, and * at the bottom indicates an amino acid residue common to all of the polymerases.
Figures 4, 34A:
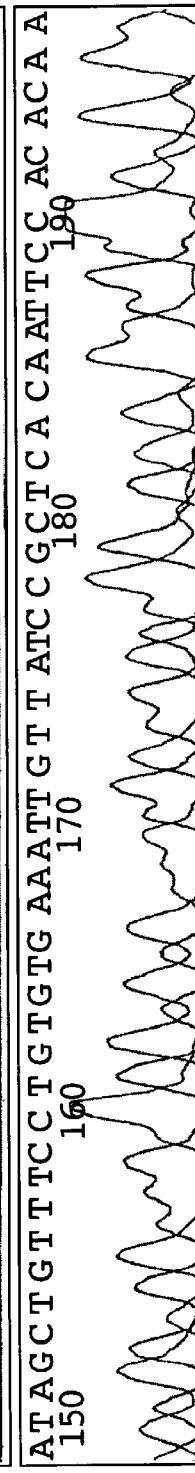
FIG. 4 shows alignment of amino acid sequences continuation of [SEQ ID NOS.: 17–20] of the currently reported phage-derived RNA polymerases (latter half). The T7 RNA polymerase at the top is used as a standard, and the symbols . (dot) indicate the same amino acid residues as the T7 RNA polymerase, – indicates absence, and * at the bottom indicates an amino acid residue common to all of the polymerases.
Figures 5, 34A:
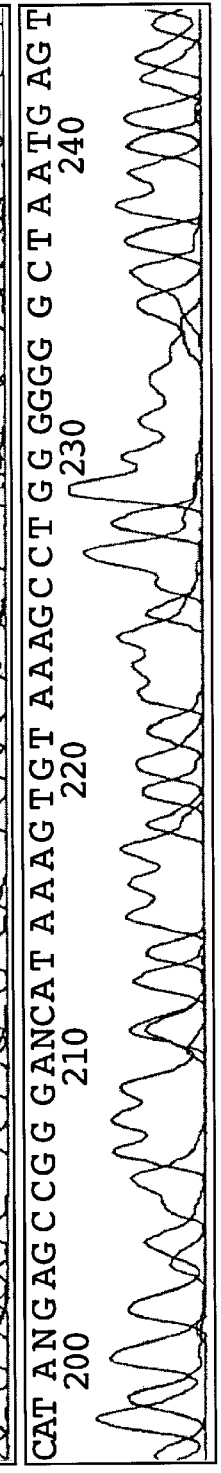
Figures 1, 34B:
Figures 2, 34B:
Figures 3, 34B:
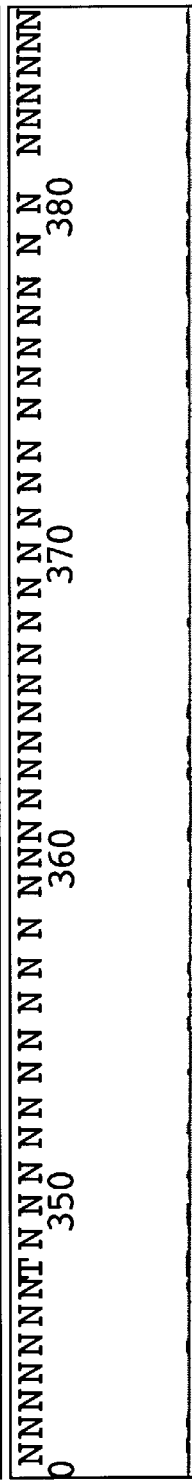
Figures 4, 34B:
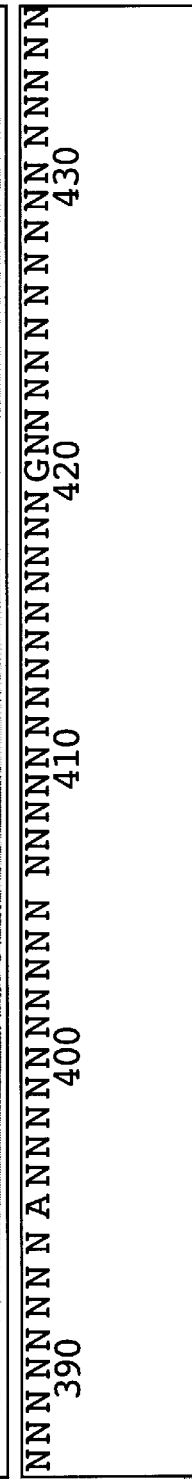
Figures 5, 34B:
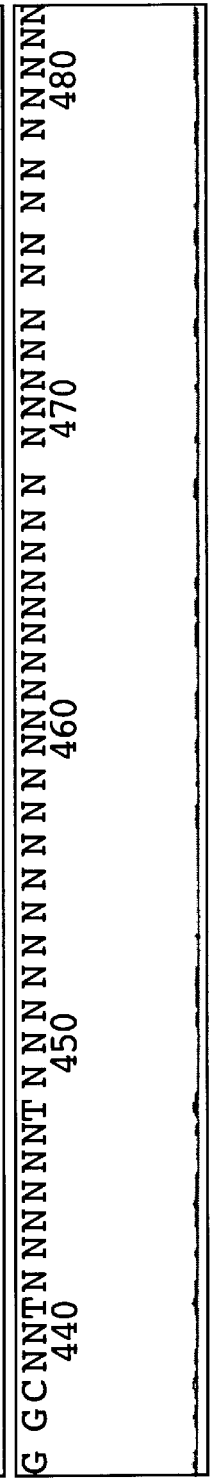
Figures 1, 35A:
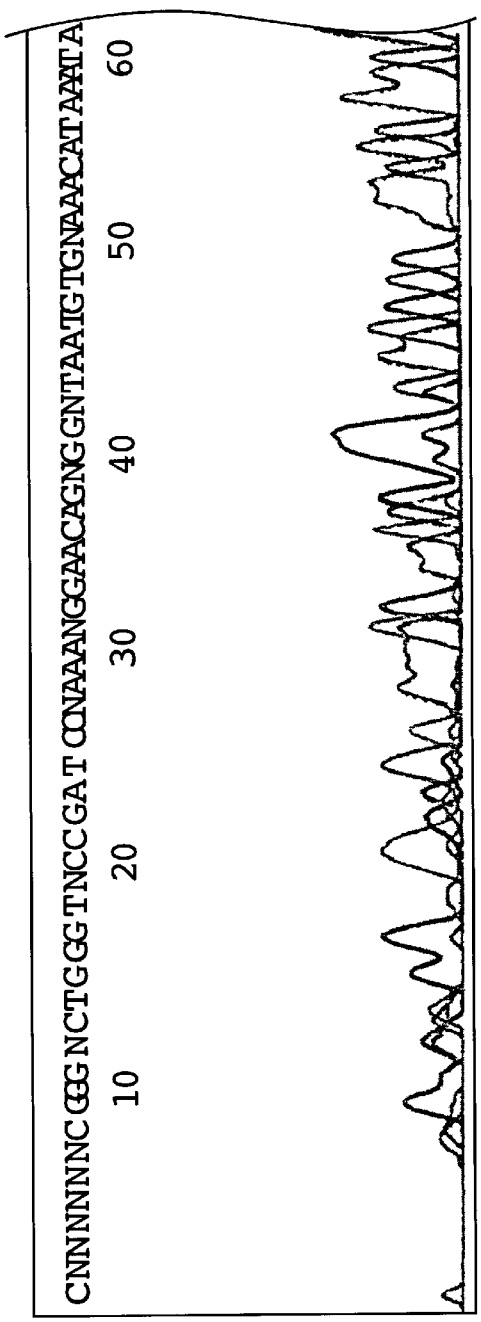
Figures 2, 35A:
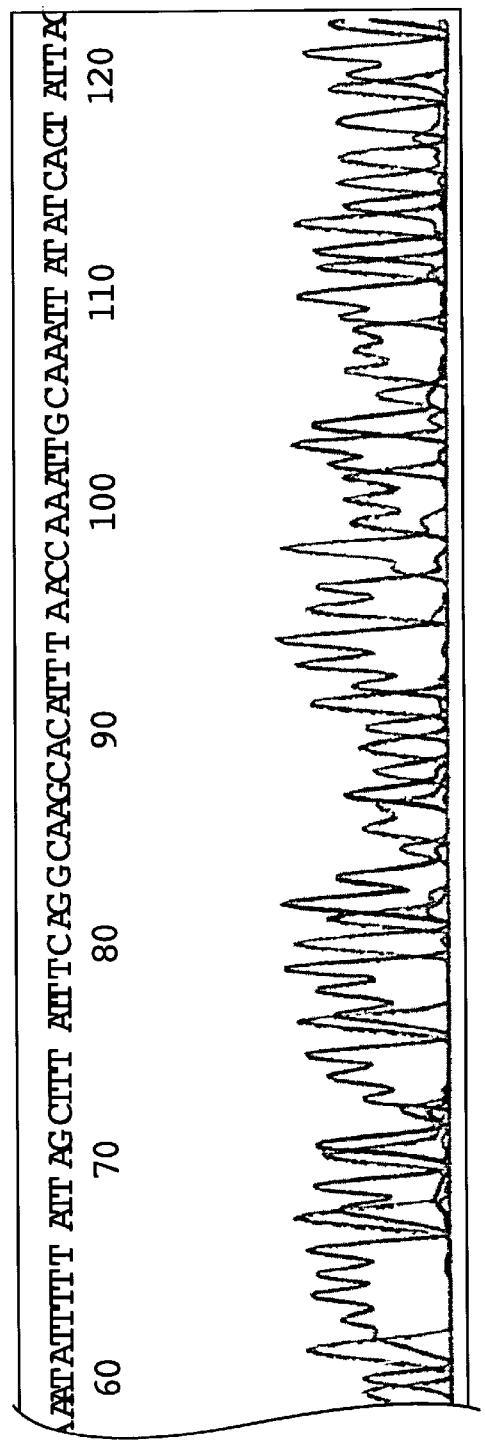
Figures 1, 35B:
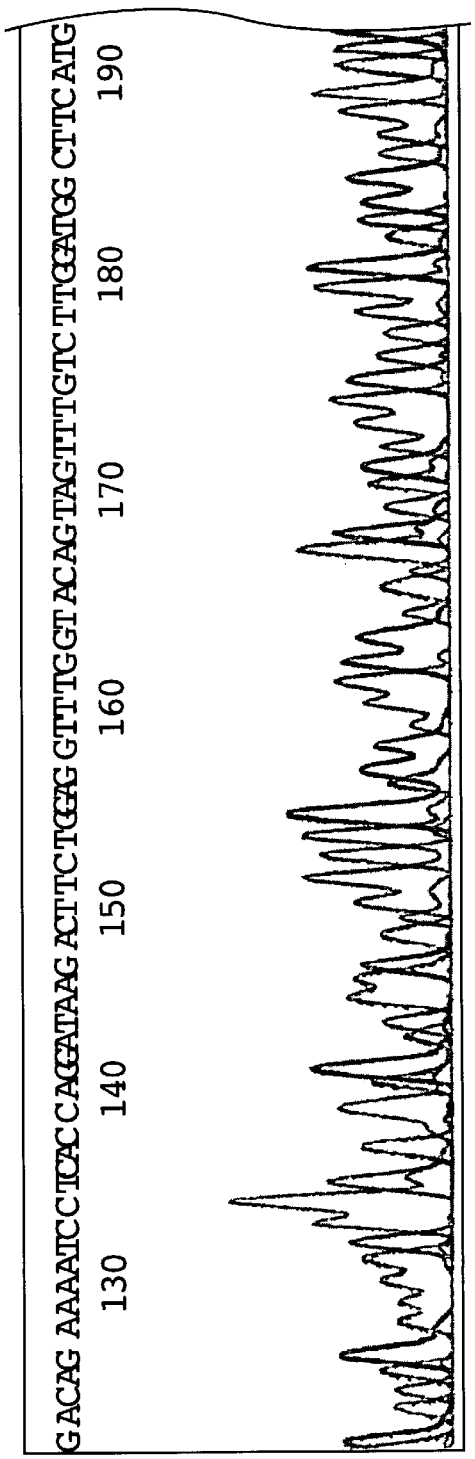
Figures 2, 35B:
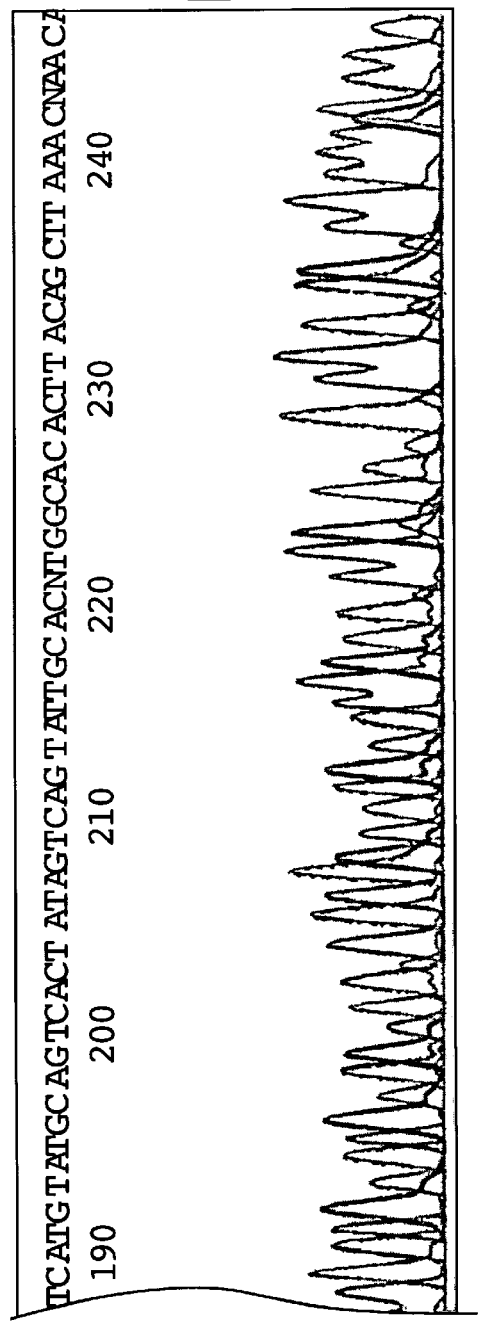
Figures 1, 35C:
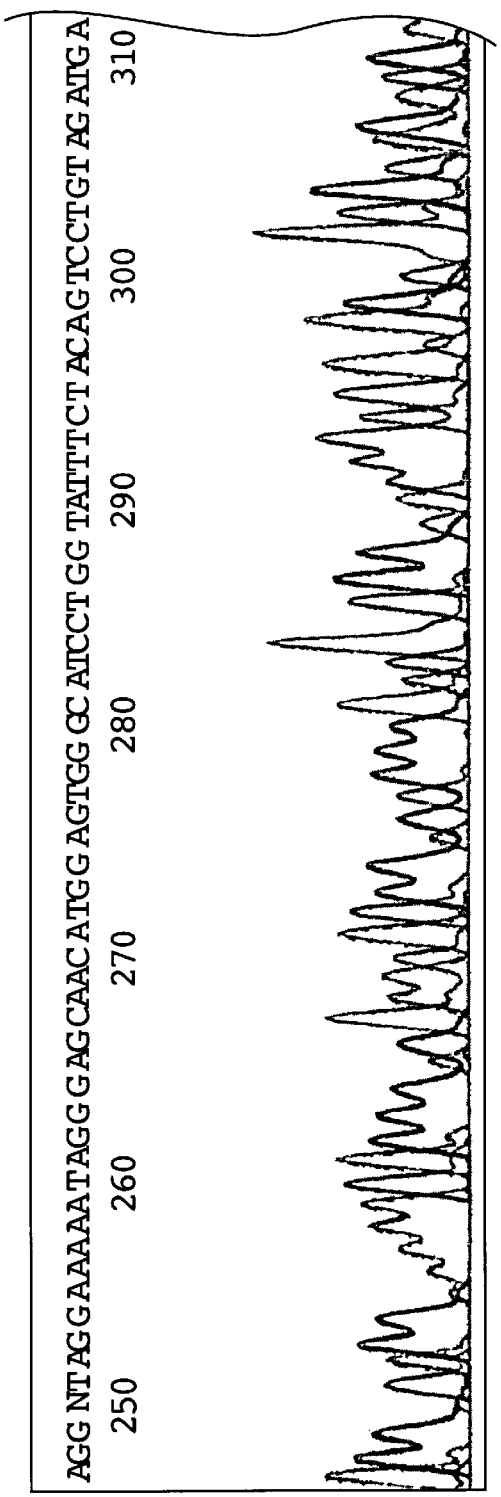
Figures 2, 35C:
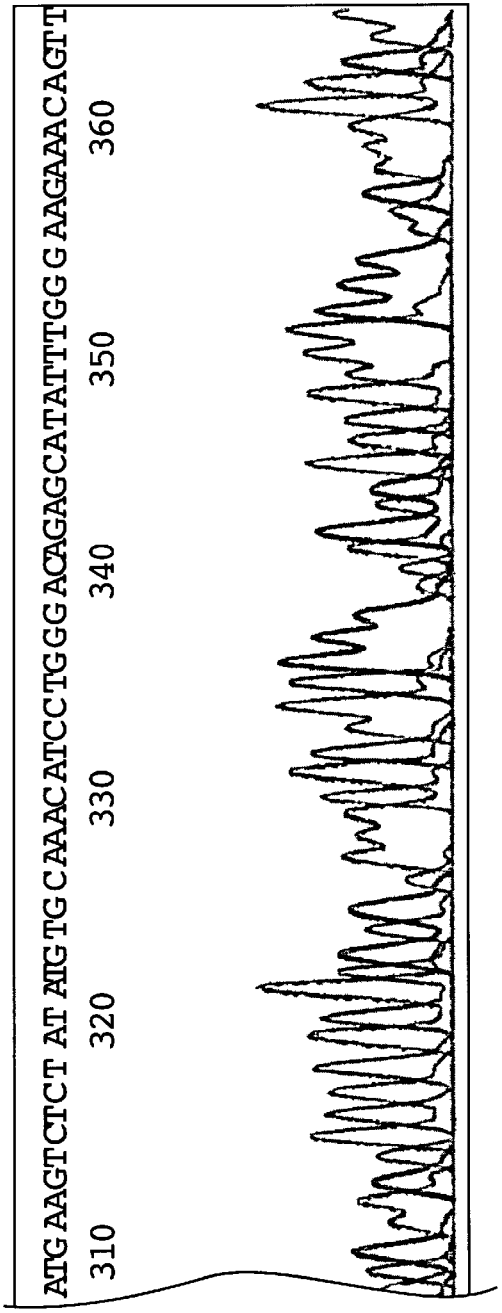
Figures 1, 35D:
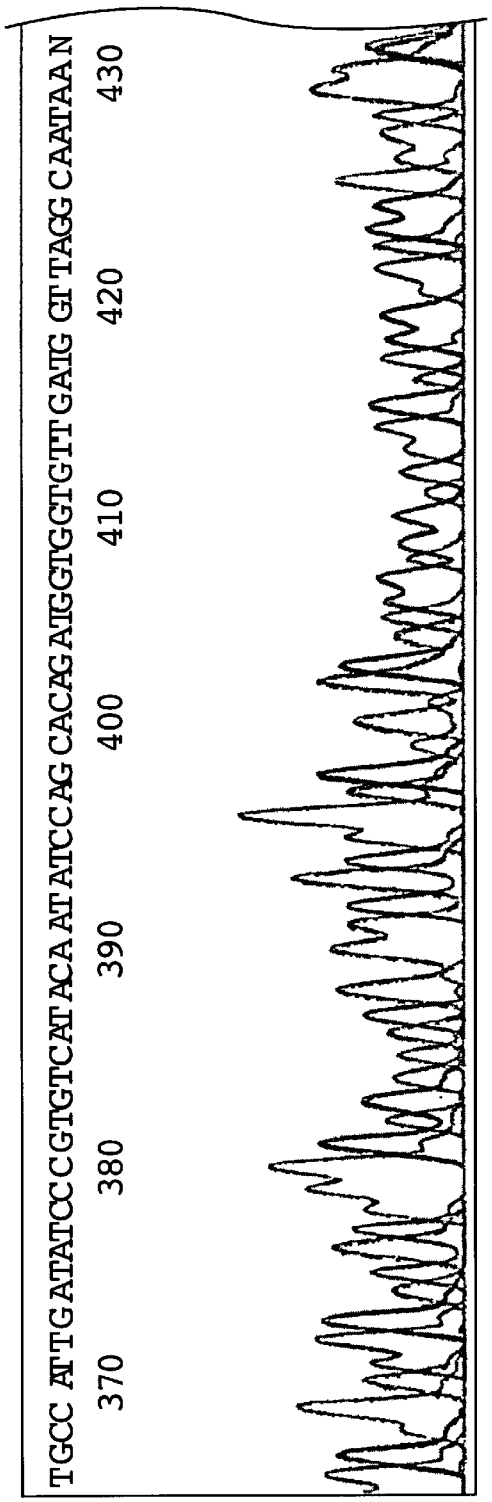
Figures 2, 35D:
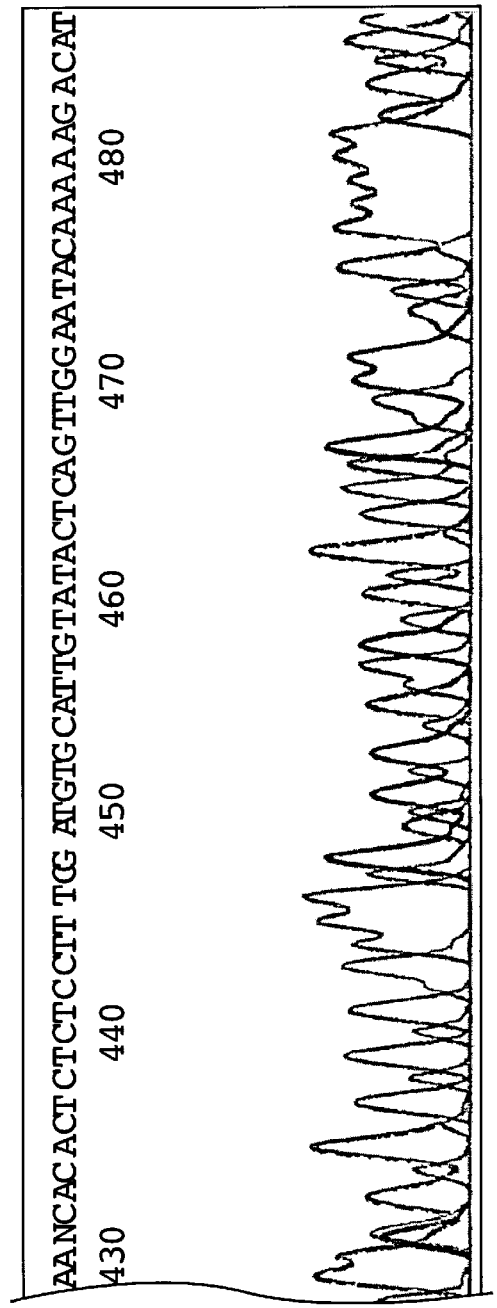

The amino acid numbers in sequences of RNA polymerases other than T7 RNA polymerase are decided as shown in the sequences listed in FIGS. 3 and 4. Those may also have substitution, insertion and/or deletion other than the modification intended by the present invention. Accordingly, like the amino acid sequence and the numbers appended to T7 RNA polymerase, when they have such a mutation by insertion or deletion of amino acids, the amino acid numbers are changed due to such insertion and deletion, and a wild type T7 RNA polymerase having such insertion and deletion is a member of the wild type T7 RNA polymerase to which a mutation intended by the present invention should be introduced.

The T7 RNA polymerase gene is prepared as follows: T7 phage DNA is purified. Separately, a primer specific for upstream of N-terminus amino acid region of the T7 RNA polymerase gene [SEQ ID NO: 1] (T7Rpol-N: 5'-ATA TTT TAG CCA TGG AGG ATT GAT ATA TGA ACA CGA TTA ACA TCG CTA AG-3') and a primer specific for downstream of C-terminus amino acid region of the same [SEQ ID NO: 2] (T7Rpol-C: 5'-ATA TTT TAG CCA RGG TAT AGT GAG TCG TAT TGA TTT GGC G-3') are synthesized. The phage DNA is used as a template for PCR, and thus an expression vector can be transformed into *E. coli* DH5α, and the transformed cells express a large amount of T7 RNA polymerase protein when ispropyl-β-D-galactopyranoside (IPTG) is added.

When the sequence of this T7 RNA polymerase gene prepared as described above was compared with the amino acid sequence shown in FIGS. 1 and 2, the both sequences completely confirmed to each other. The amino acid sequence shown in FIGS. 1 and 2 and the amino acid sequence reported in Grachev et al., Bioorg. Kim., 10:824–843, 1984 are different in that the 623rd Y and the 665th L in the amino acid sequence represented in FIGS. 1 and 2 are replaced with H (623rd) and P (665th) respectively in the amino acid sequence reported by Grachev et al. As described above, wild type RNA polymerases, which are the basis of the mutant RNA polymerase of the present invention, may contain substitution, insertion, and/or deletion of amino acids with respect to the sequence shown in FIGS. 1 and 2, which is not the modification intended by the present invention, and the amino acid sequence reported by Grachev et al. where the 623rd and the 665th residues are H and P respectively is included in a member of the wild type RNA polymerases to be a basis of the mutant RNA polymerase of the present invention.

The T7 RNA polymerase purified from *E. coli* harboring the expression vector pT7R exhibited sufficient RNA synthesis activity in vitro in the presence of DNA containing T7 promoter. Based on this expression plasmid pT7R, the above-mentioned Y639F, F644Y, F646Y, F667Y, F733Y, F782Y, and F882Y were constructed as mutant T7 RNA polymerases, and incorporation ability of these mutants was compared.

For the mutant T7 RNA polymerase having F644Y mutation, another mutation for replacing L665, which is adjacent to F664, with P was introduced in addition to the mutation of F644 according to the report of Grachev et al. mentioned above. That is, mutations of F644Y/L665P were introduced to examine the influence of L665P. Also for the mutant T7 RNA polymerase having F667Y mutation, another mutation for replacing L665, which is adjacent to F667, with P was introduced in addition to the mutation of F667 according to the report of Grachev et al. mentioned above. That is, mutations of F665P/F667Y were introduced.

A mutant T7 RNA polymerase which is introduced with F644Y/L665P/F667Y mutations was also constructed. Comparison of incorporation ability of these mutants was also performed.

The T7 RNA polymerases introduced with mutations were purified, and their abilities of promoter sequence specific RNA synthesis and incorporation of ribonucleoside 5'-triphosphates including ATP, GTP, CTP, UTP and derivatives thereof, as well as 3'-DATP, 3'-dGTP, 3'-dCTP, 3'-dUTP and derivatives thereof were compared with those of wild type T7 RNA polymerase. The results are shown in Table 1 hereinafter.

As a result, as shown in Table 1, F644Y, F644Y/L665P, L665P/F667Y and F644Y/L665P/F667Y maintained sufficient RNA synthesis activity, and showed marked improvement of incorporation of 3'-dATP, 3'-dGTP, 3'-dCTP, 3'-dUTP and derivatives thereof. The incorporation ability of the F644Y/L665P mutant was comparable to that of the F644Y mutant. From these results, it can be seen that the substitution of proline for leucine at 665 do not affect on the incorporation of 3'-dATP, 3'-dGTP, 3'-dCTP, 3'-dUTP and derivatives thereof. While the results are shown only for the L665P/F667Y mutant in Table 1, the F667Y mutant also showed the incorporation ability comparable to that of the L665P/F667Y mutant. The incorporation ability of the F644Y/L665P/F667Y mutant was the highest. While not shown in Table 1, the incorporation ability of the F644Y/F667Y mutant was almost equal to that of the F644Y/L665P/F667Y mutant.

The F782Y mutant maintained RNA synthesis activity, and showed slightly improved ability for incorporating 3'-dATP, 3'-dGTP, 3'-dCTP, 3'-dUTP and derivatives thereof. The F733Y mutant showed slightly decreased RNA synthesis activity, but showed slightly improved ability for incorporating 3'-dATP, 3'-dGTP, 3'-dCTP, 3'-dUTP and derivatives thereof. The F646Y mutant maintained RNA synthesis activity, but showed no improvement of ability for incorporating 3'-dATP, 3'-dGTP, 3'-dCTP, 3'-dUTP and derivatives thereof. The F882Y mutant is not mentioned in Table 1, because it showed markedly decreased RNA synthesis activity.

The Y639F mutant of the T7 RNA polymerase, which has the mutation at a location corresponding to Y526 of T7 DNA polymerase, maintained RNA synthesis activity, but showed no improvement of ability for incorporating 3'-dATP, 3'-dGTP, 3'-dCTP, 3'-dUTP and derivatives thereof.

The results mentioned above suggest that the RNA polymerase of the present invention is particularly an RNA polymerase having modification of at least one of amino acids present in the "nucleotide binding site" of the polymerase and that such a modification can enhance the ability for incorporating 3'-deoxyribonucleotides and other ribonucleotide analogues in comparison with the ability for corresponding ribonucleotides.

The amino acids present in the above "nucleotide binding site" can be, for example, amino acids in a loop between the helix Y and the helix Z and/or amino acids in a loop between the helix Z and the helix AA of wild type RNA polymerase.

From the steric structure shown in the literature of Sousa et al. (Nature, 364:593–599, 1993), the loop (corresponding to amino acid residues 635 to 647 of T7 RNA polymerase) between the helix Y (corresponding to amino acid residues 625 to 634 of the same) and the helix Z (corresponding to amino acid residues 649 to 658 of the same) and/or the loop (corresponding to amino acid residues 659 to 684 of the same) between the helix Z and the helix AA (corresponding to amino acid residues 685 to 699 of the same), which face the inside of the crafts in the polymerase molecule enclosing template DNA, are considered to constitute a part of the ribonucleotide binding site, which locates quite near the nucleotides. In the present invention, the F residues present at 644, 646 and 667 in a region corresponding to the loops were actually replaced with Y residues (see FIG. 5).

The F residues of 733, 782 and 882 are present in a region other than that corresponding to the loop, and considered to face the inside of the crafts in the polymerase molecule. These F residues were also actually replaced with Y residues.

The present invention further relates to an RNA polymerase which has modification at an amino acid selected from those in a region corresponding to the amino acid residues 641–667 of the RNA polymerase derived from T7 phage. The region corresponding to the amino acid residues 641–667 of the RNA polymerase derived from T7 phage correspond to the above-mentioned "nucleotide binding site".

Figures 1, 36A:
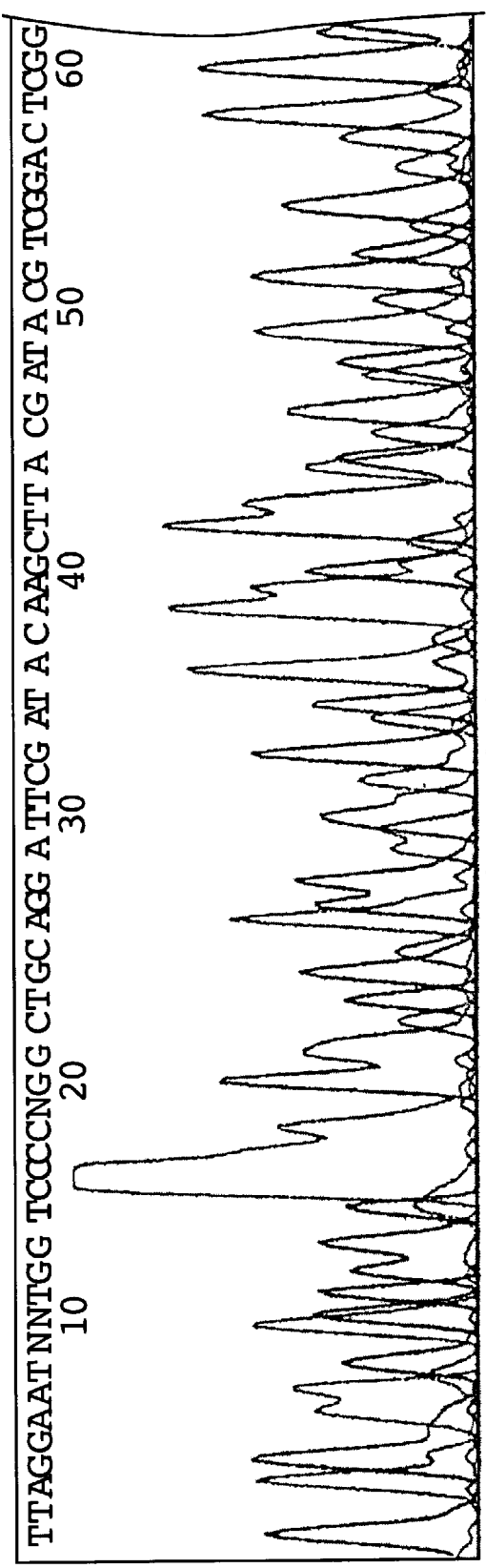
Figures 2, 36A:
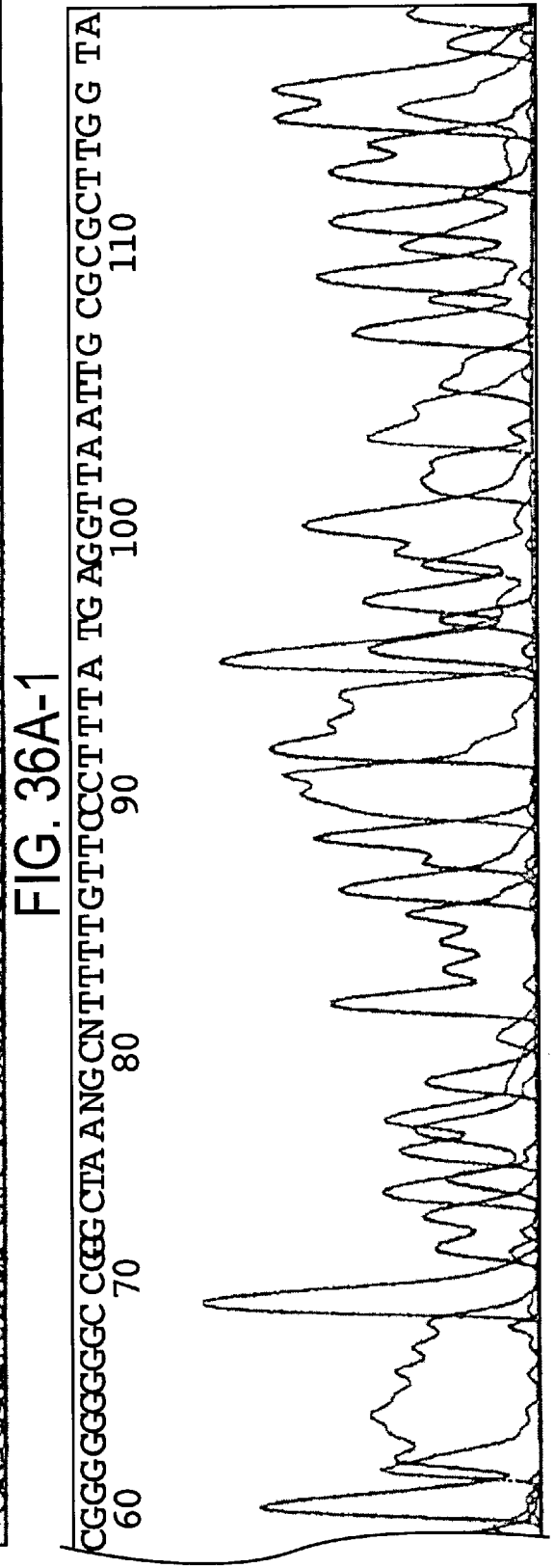
Figures 3, 36A:
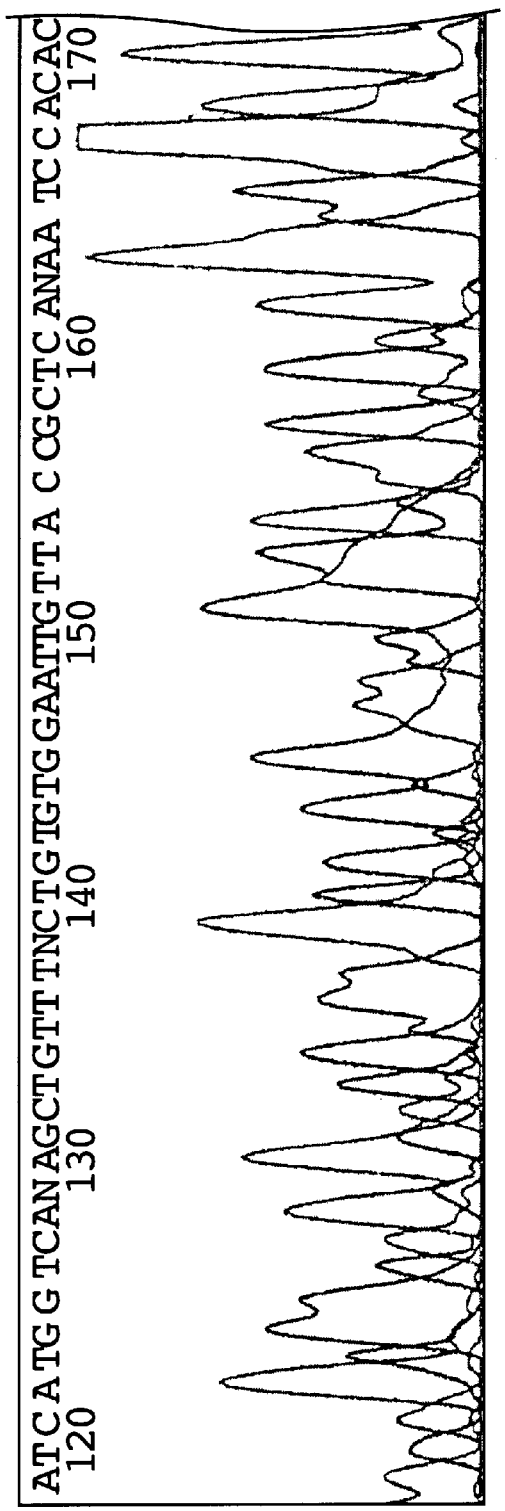
Figures 4, 36A:
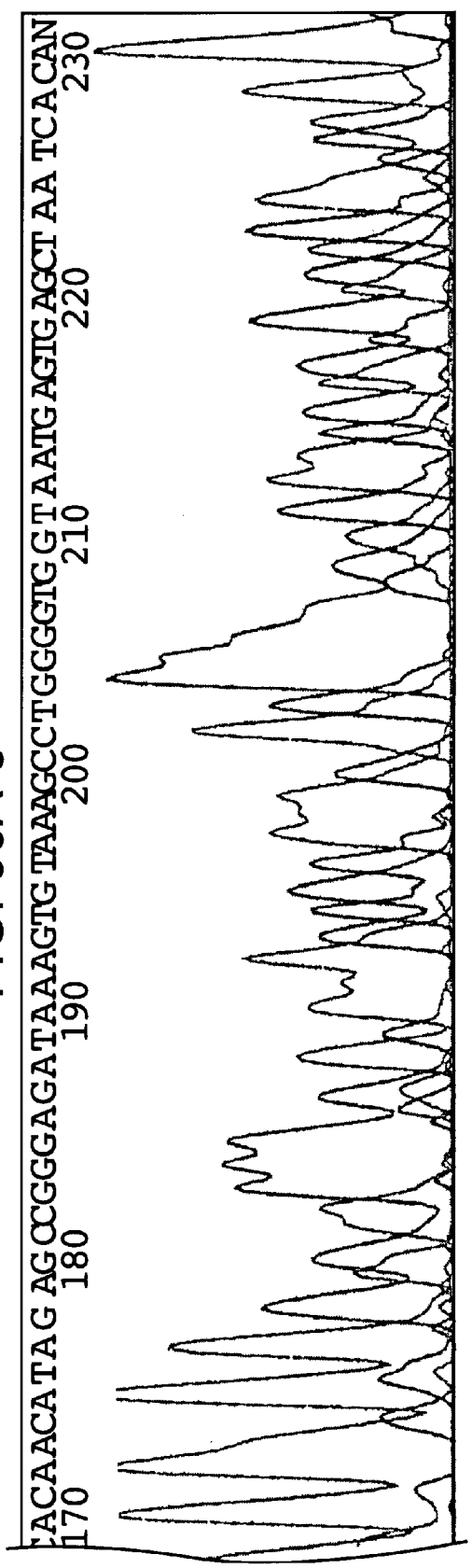
Figures 5, 36A:
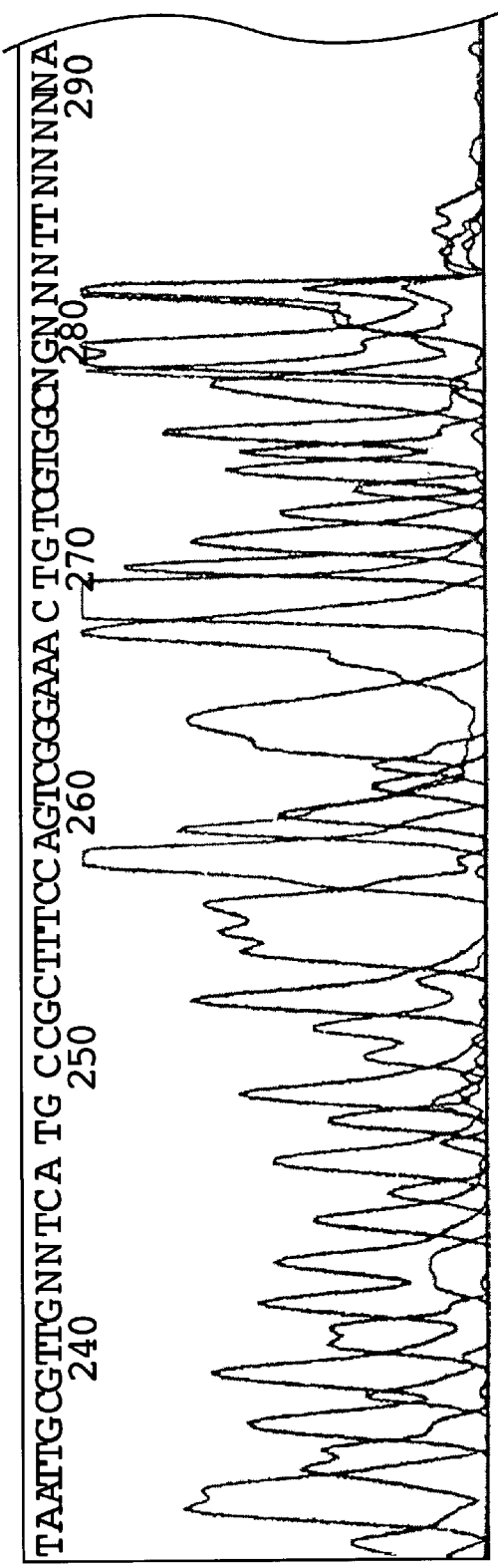
Figures 6, 36A:
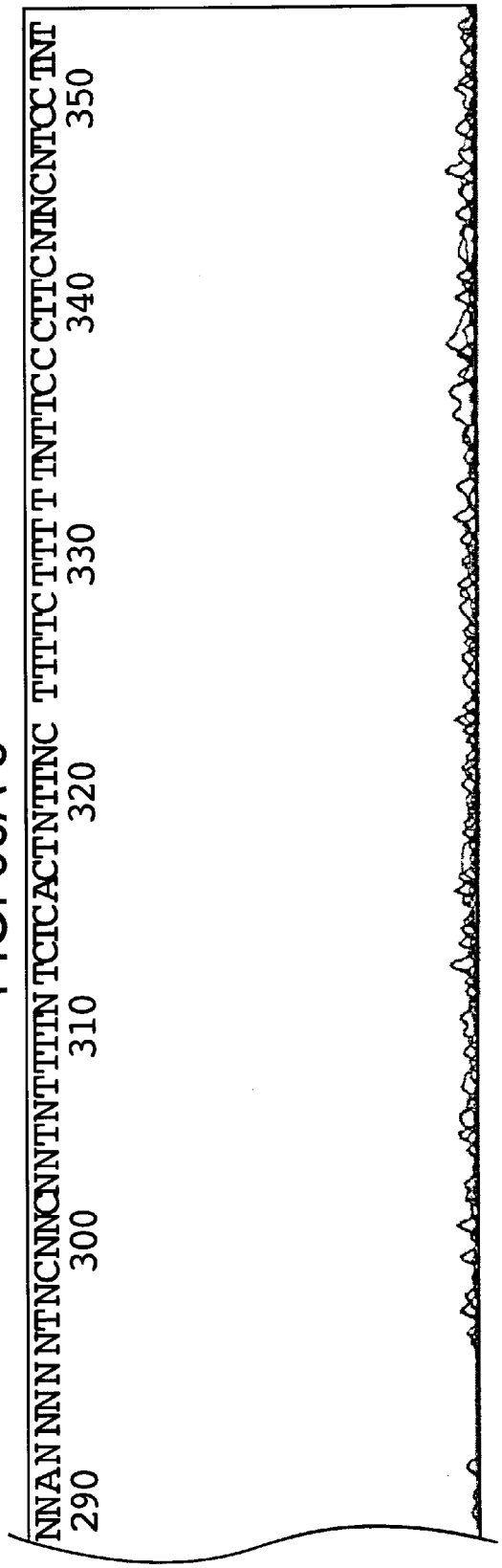
FIG. 6 shows alignment of amino acid sequences SEQ ID NOS.:17–18 of T7 RNA polymerase and T3 RNA polymerase (first half). The T7 RNA polymerase at the top is used as a standard, and the symbols . (dot) indicate the same amino acid residues as the T7 RNA polymerase, – indicates absence, and * at the bottom indicates amino acid residues common to the both polymerases.
Figures 3, 36B:
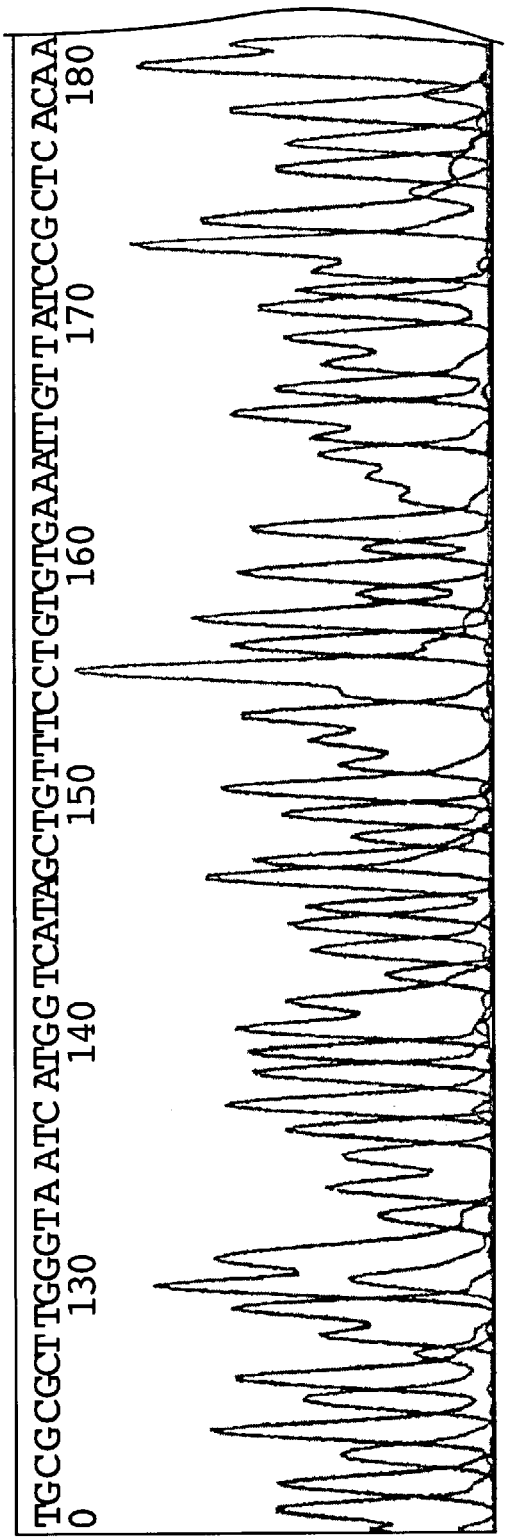
Figures 4, 36B:
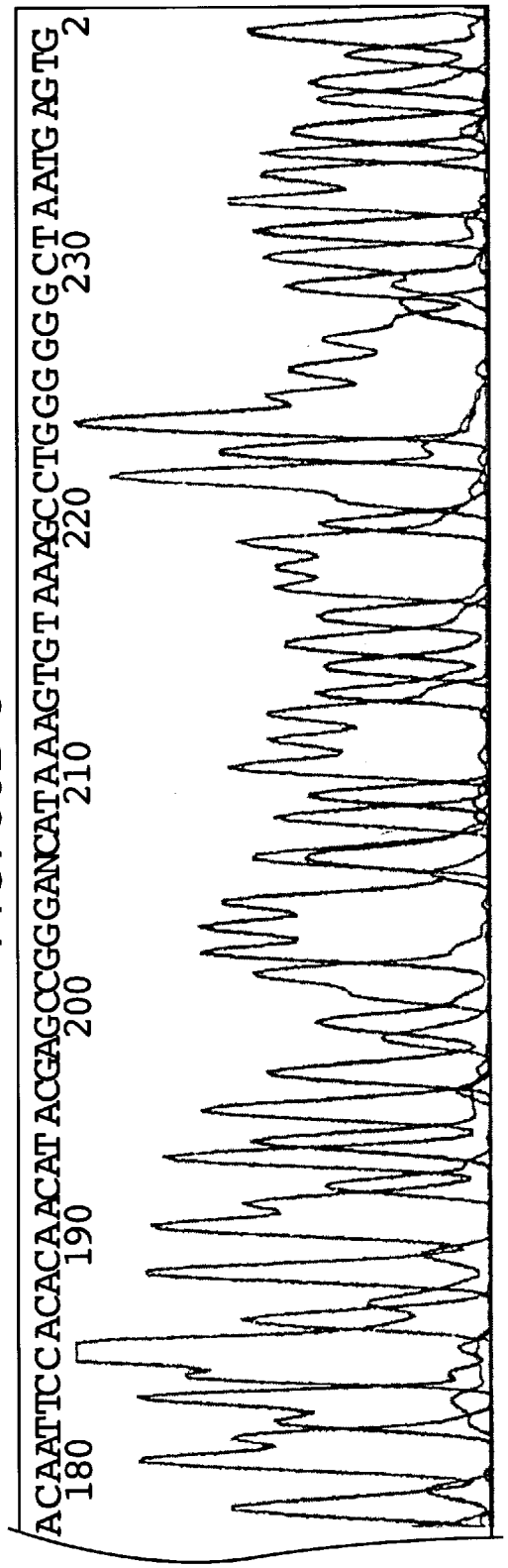
Figures 5, 36B:
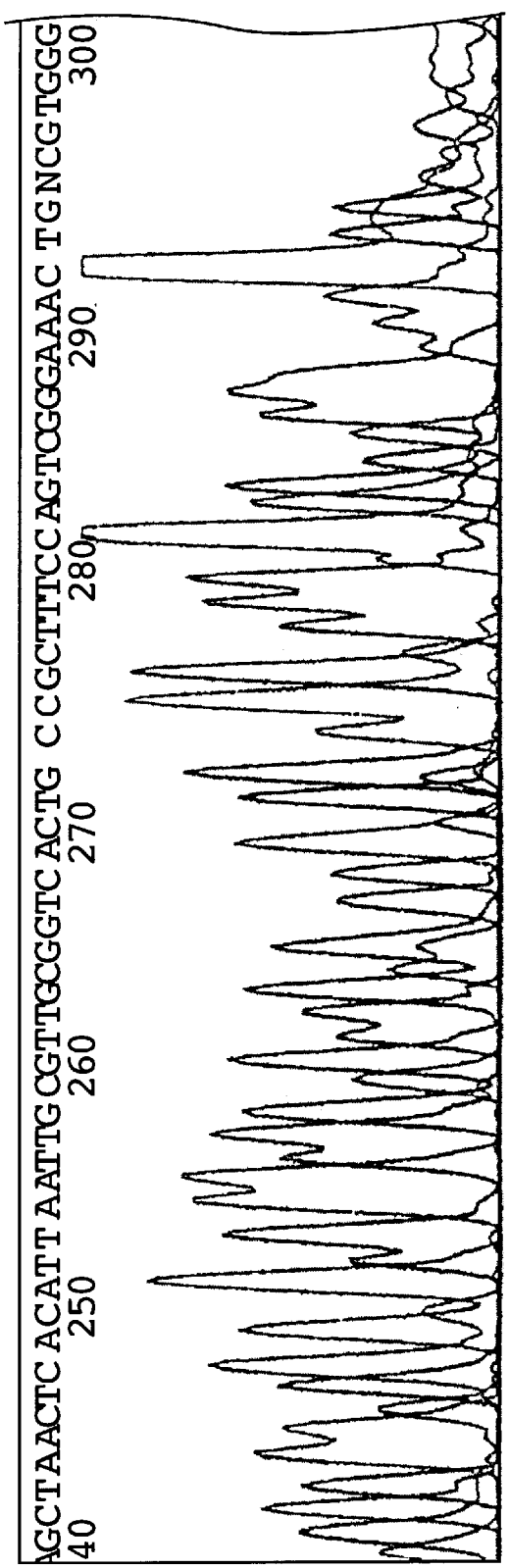
Figures 6, 36B:
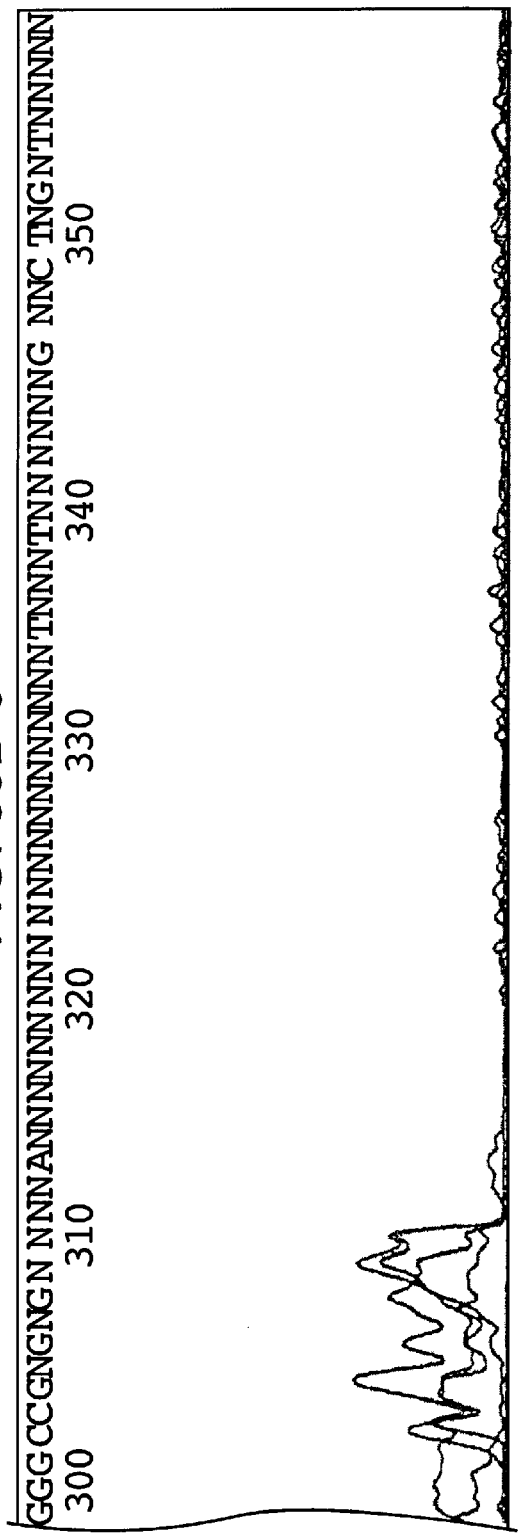
Figures 3, 37A:
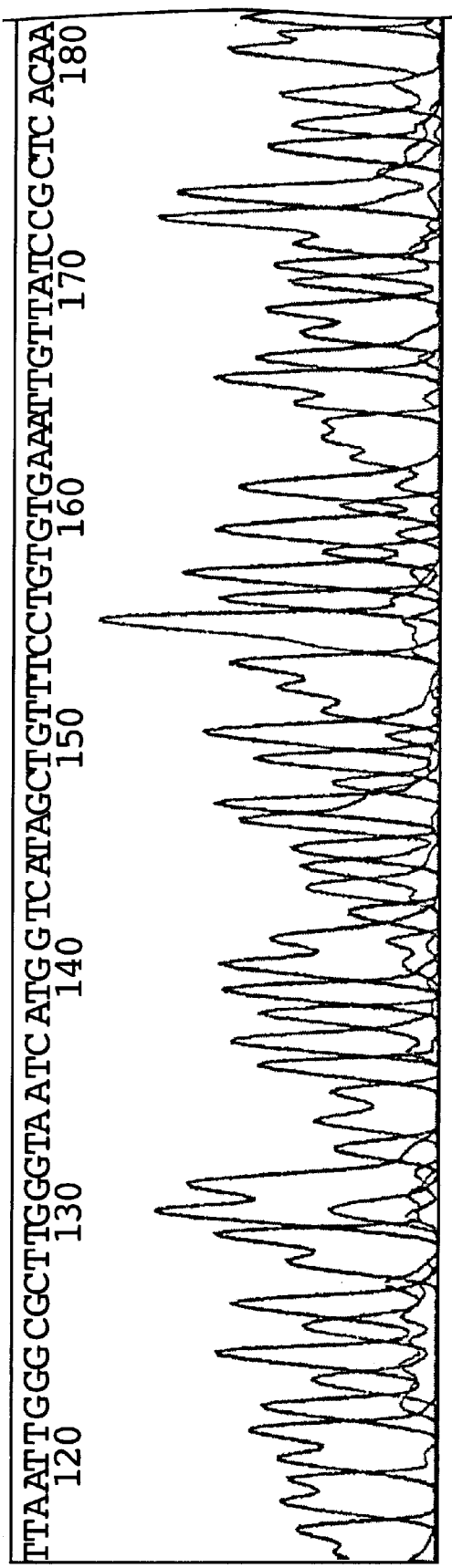
Figures 4, 37A:
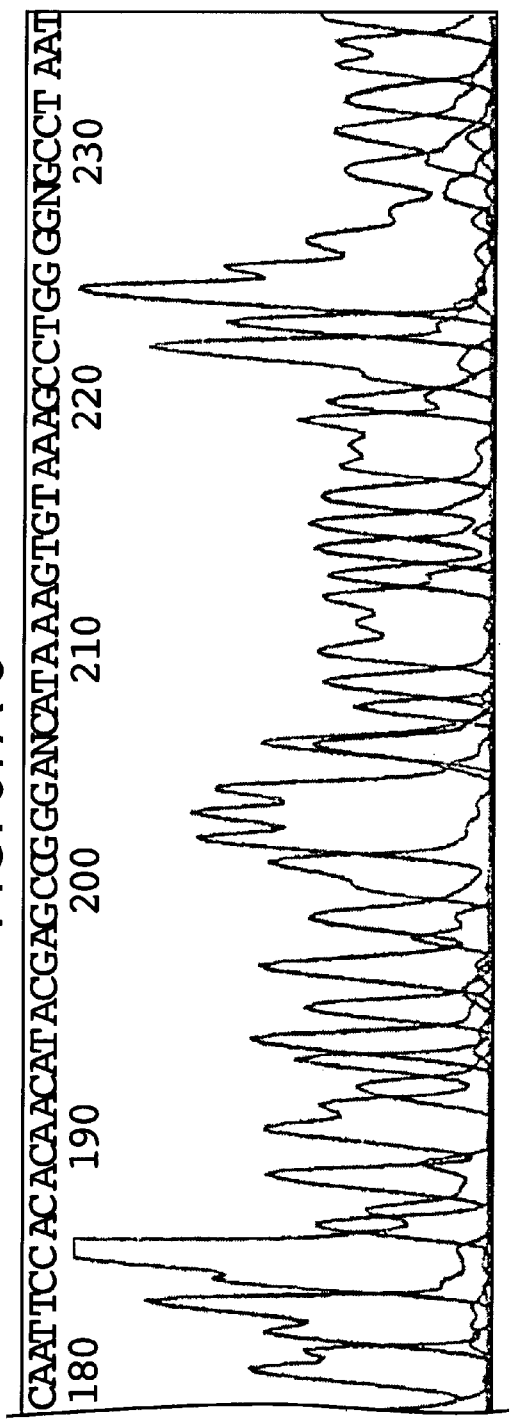
Figures 5, 37A:
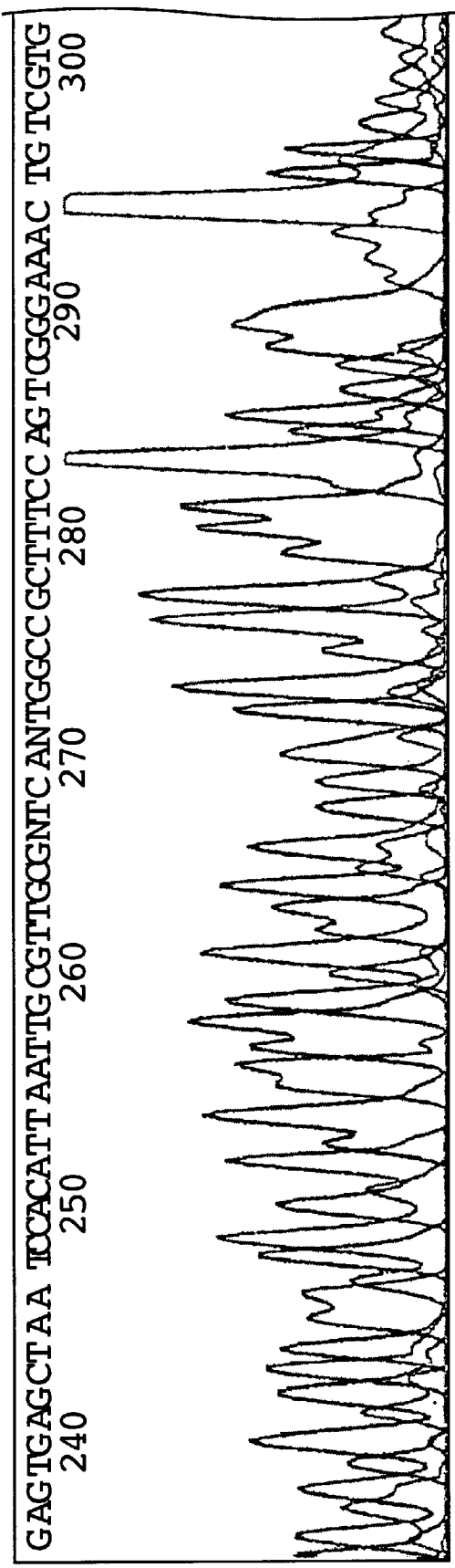
Figures 6, 37A:
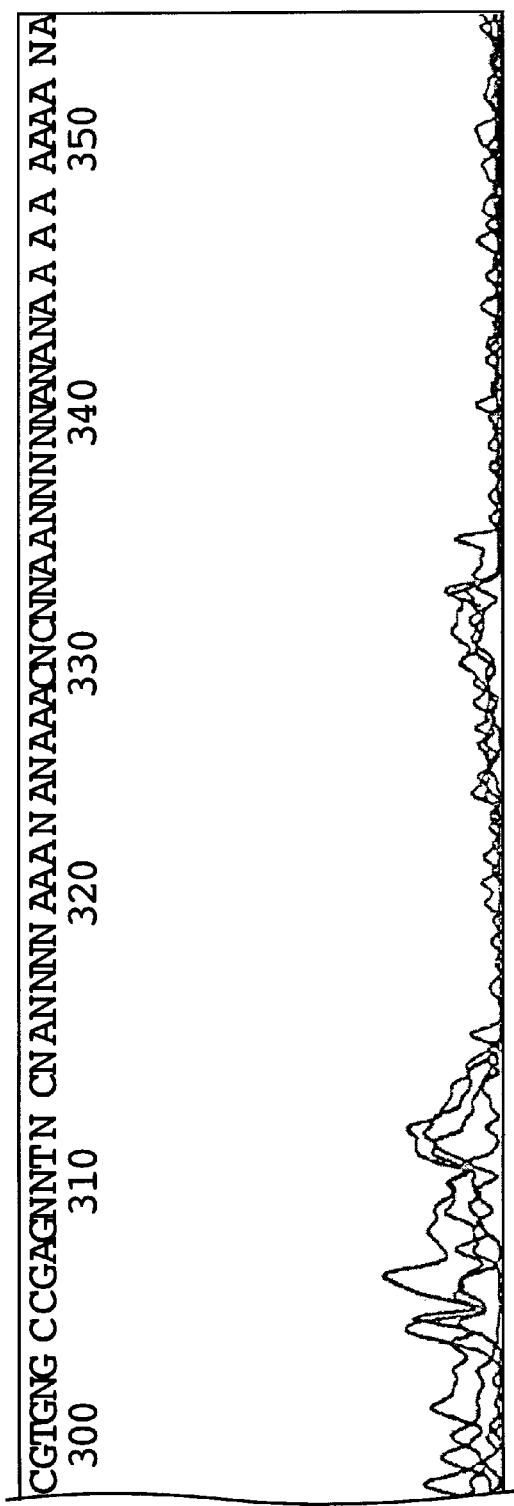
Figures 1, 37B:
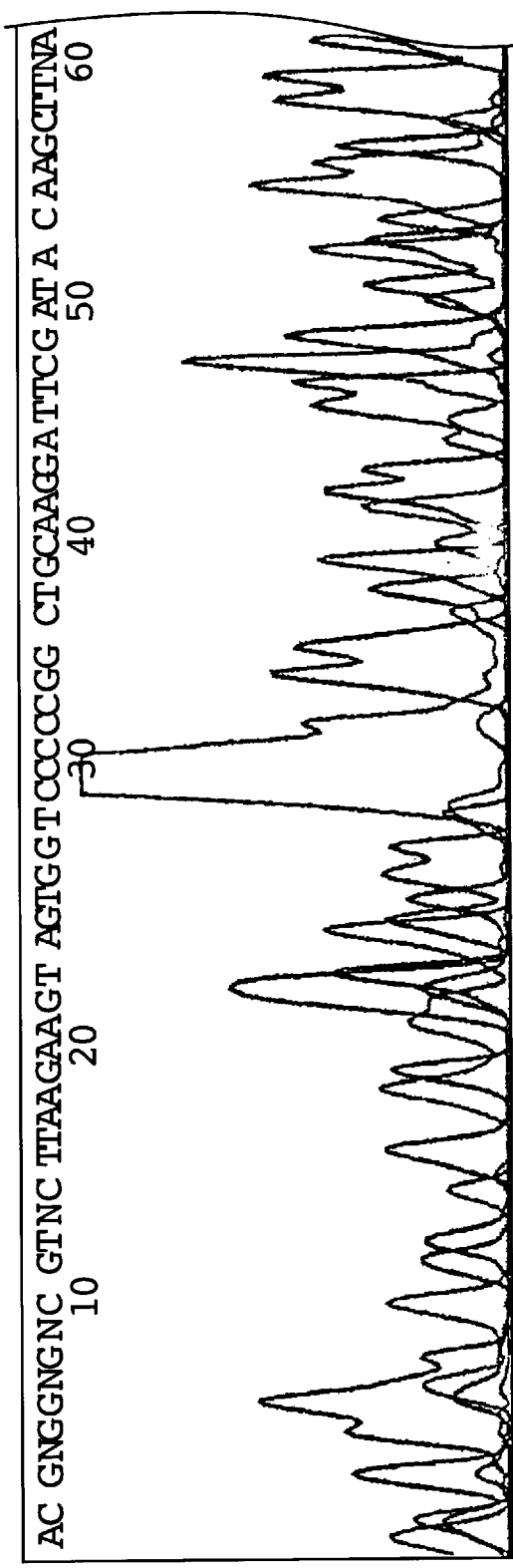
Figures 2, 37B:
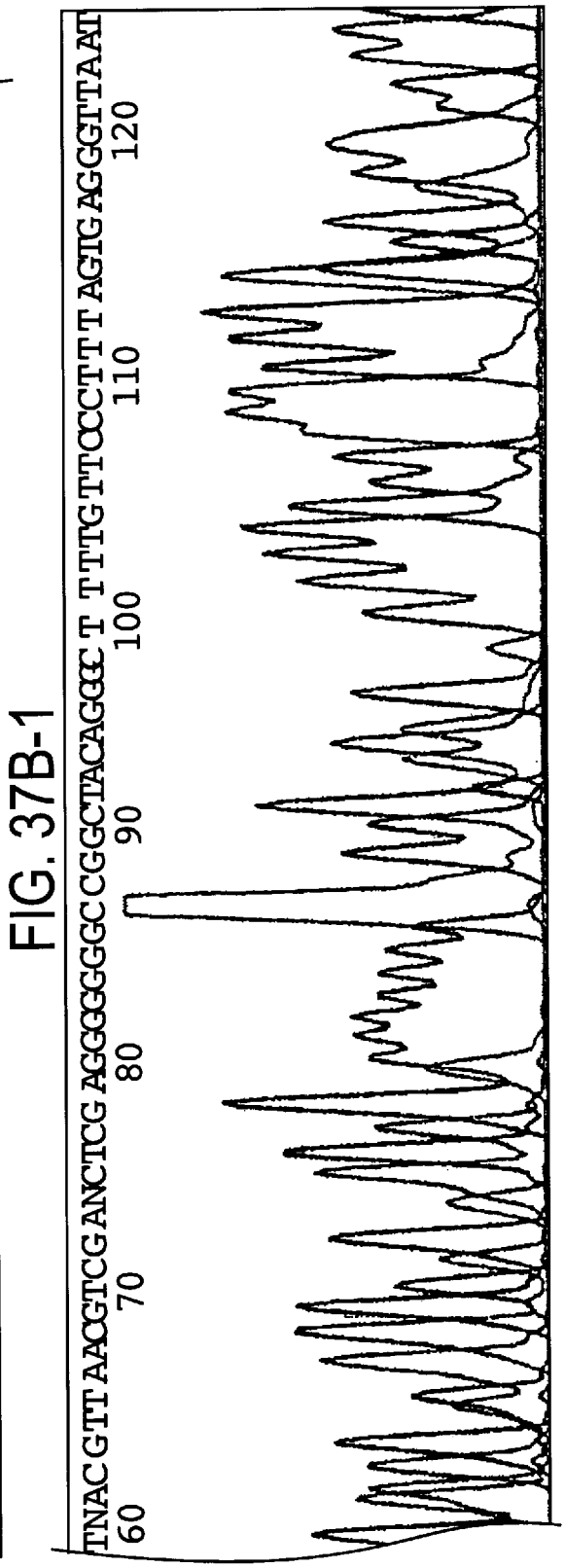
Figures 3, 37B:
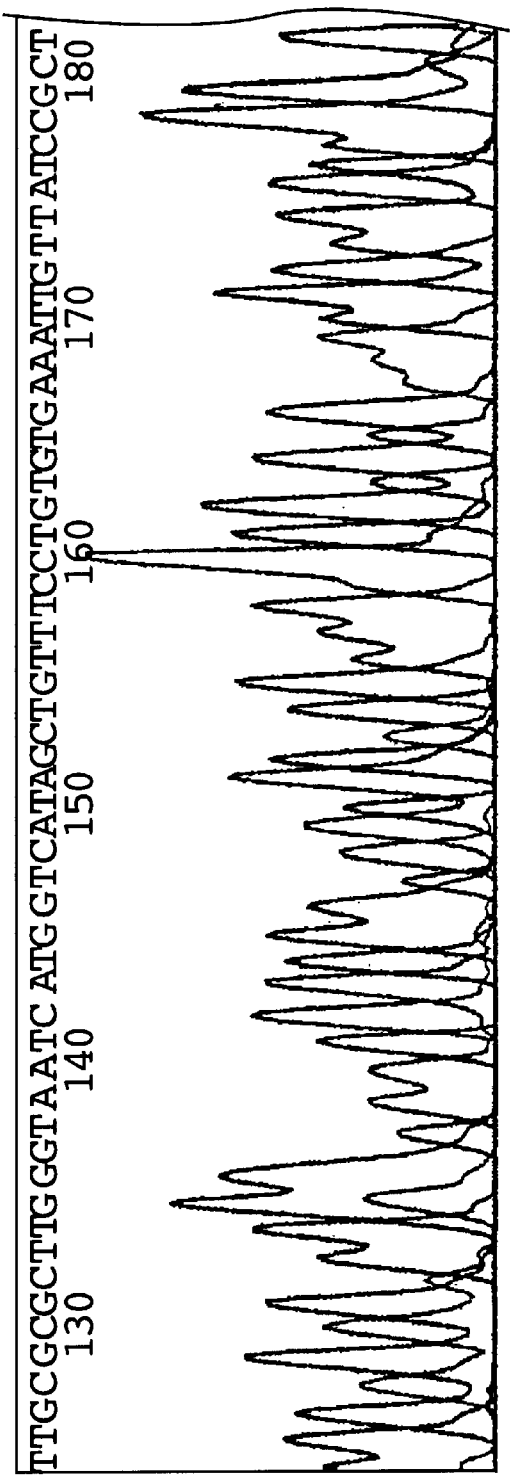
Figures 4, 37B:
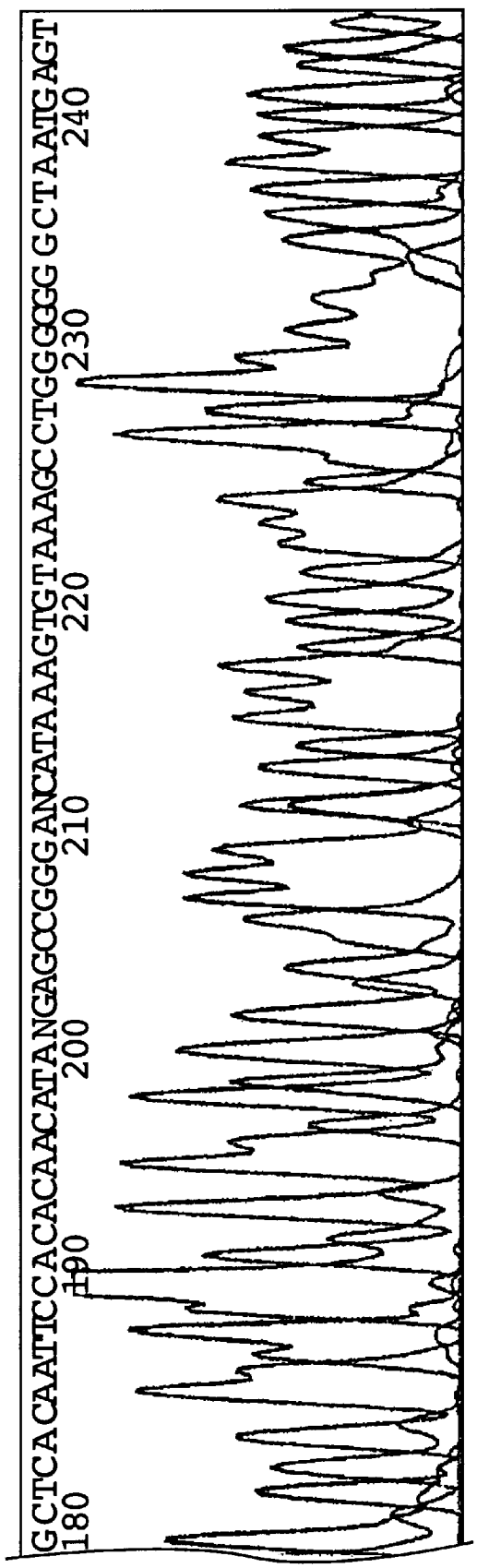
Figures 5, 37B:
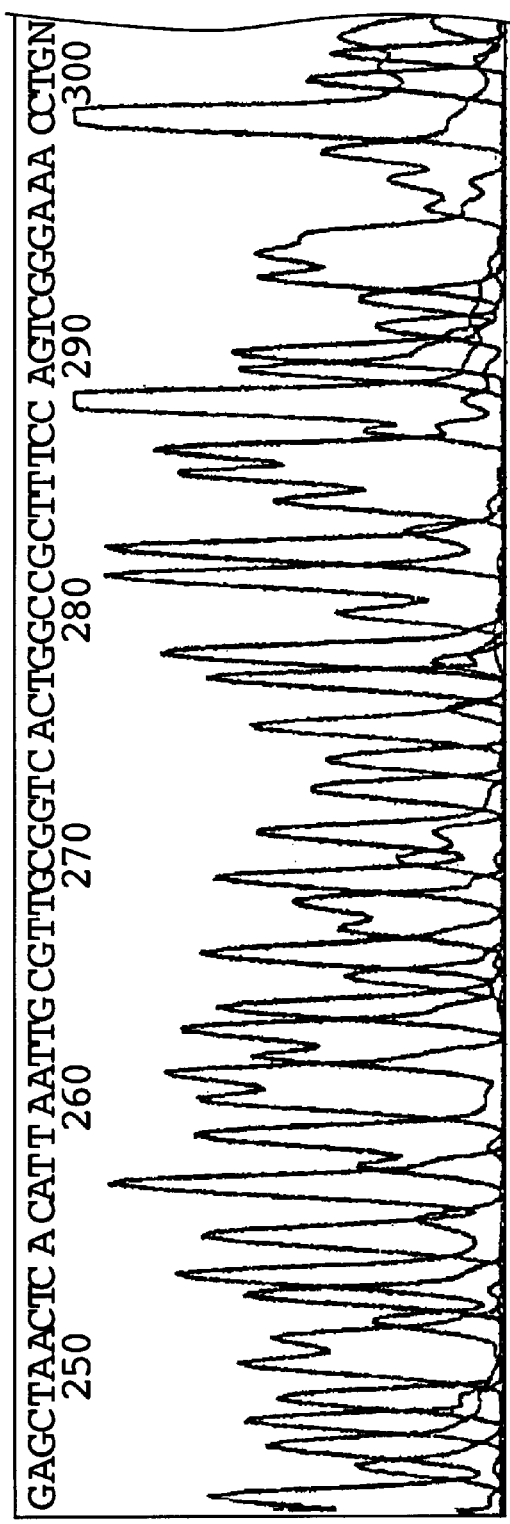
Figures 6, 37B:
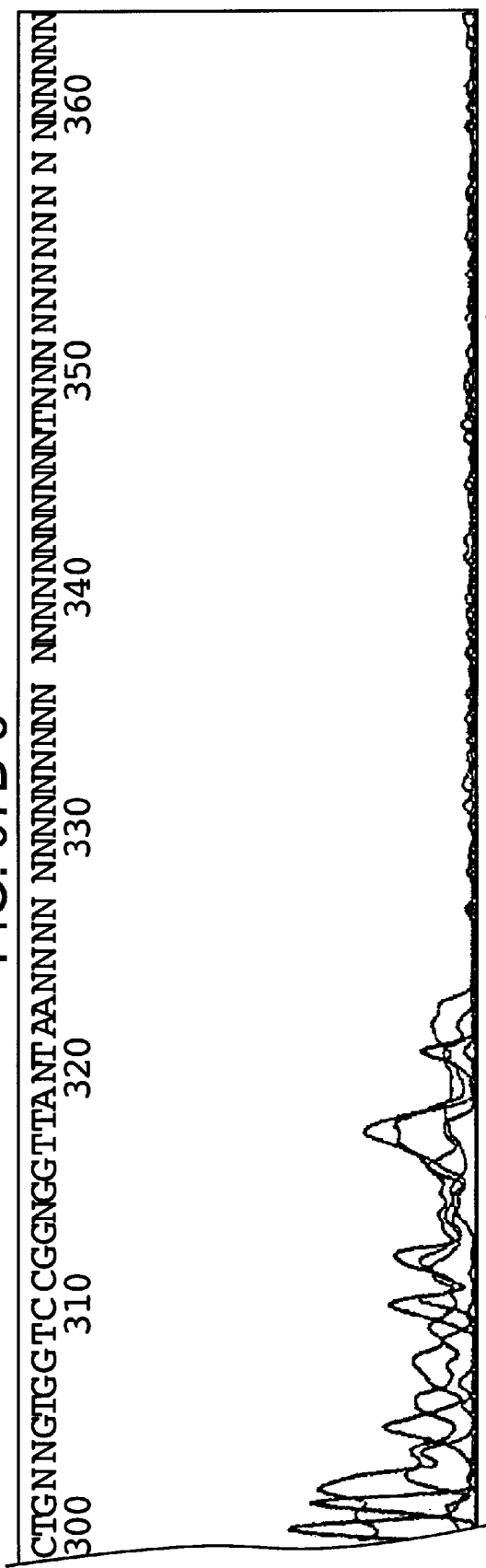
Figure 38A:
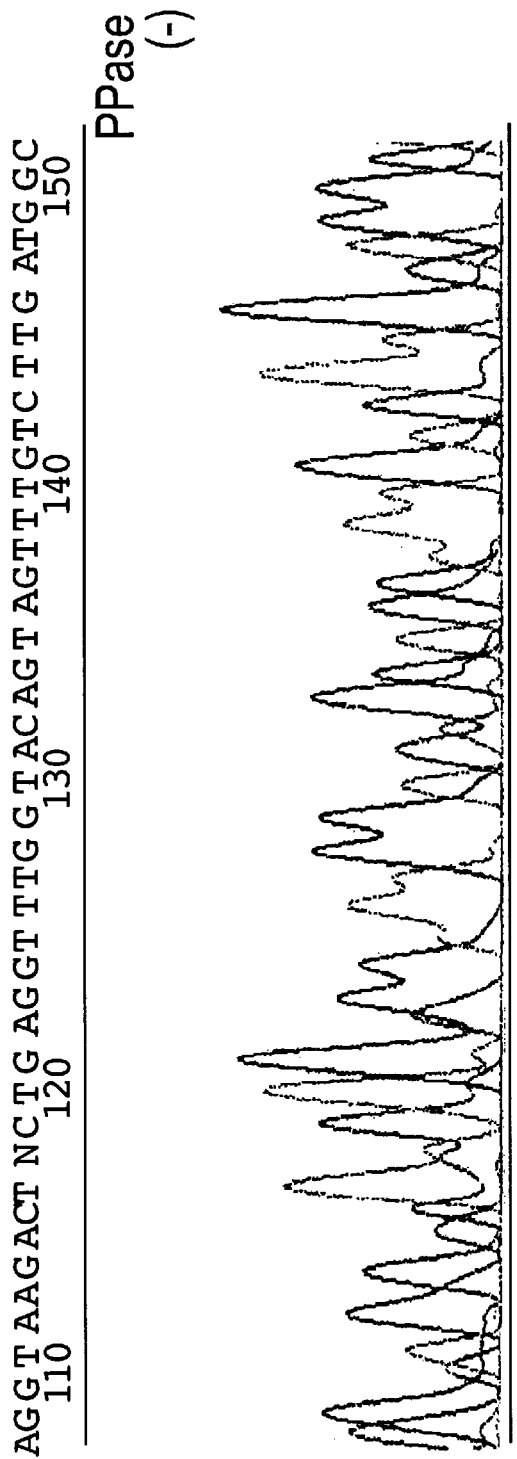
FIG. 38 A–D represents the results of sequencing which indicate effect of addition of inorganic pyrophosphatase on the sequencing reaction utilizing a PCR product as a template.
Figure 38B:
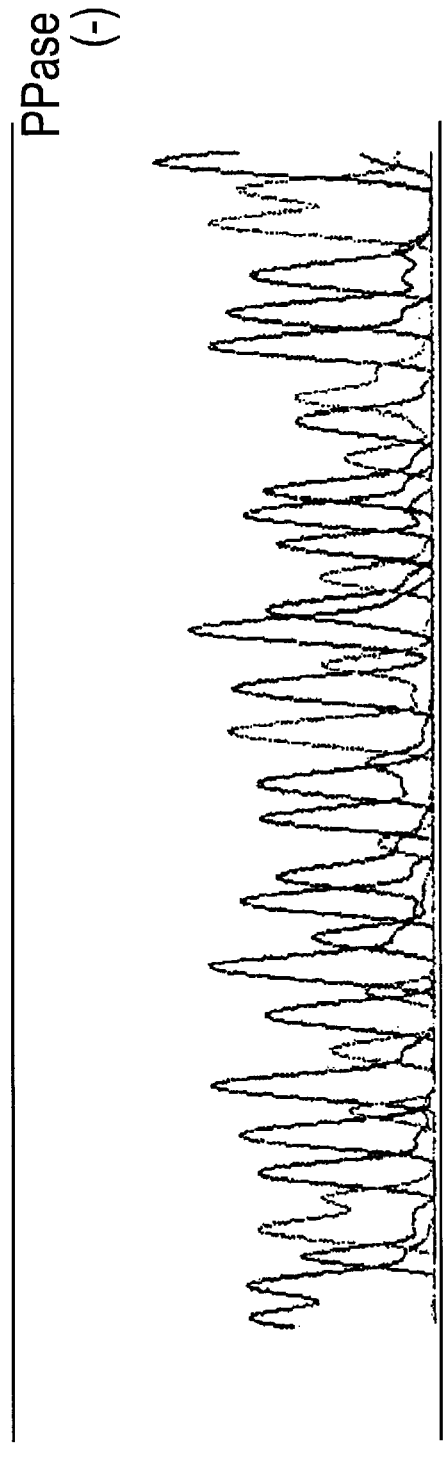
Figure 38C:
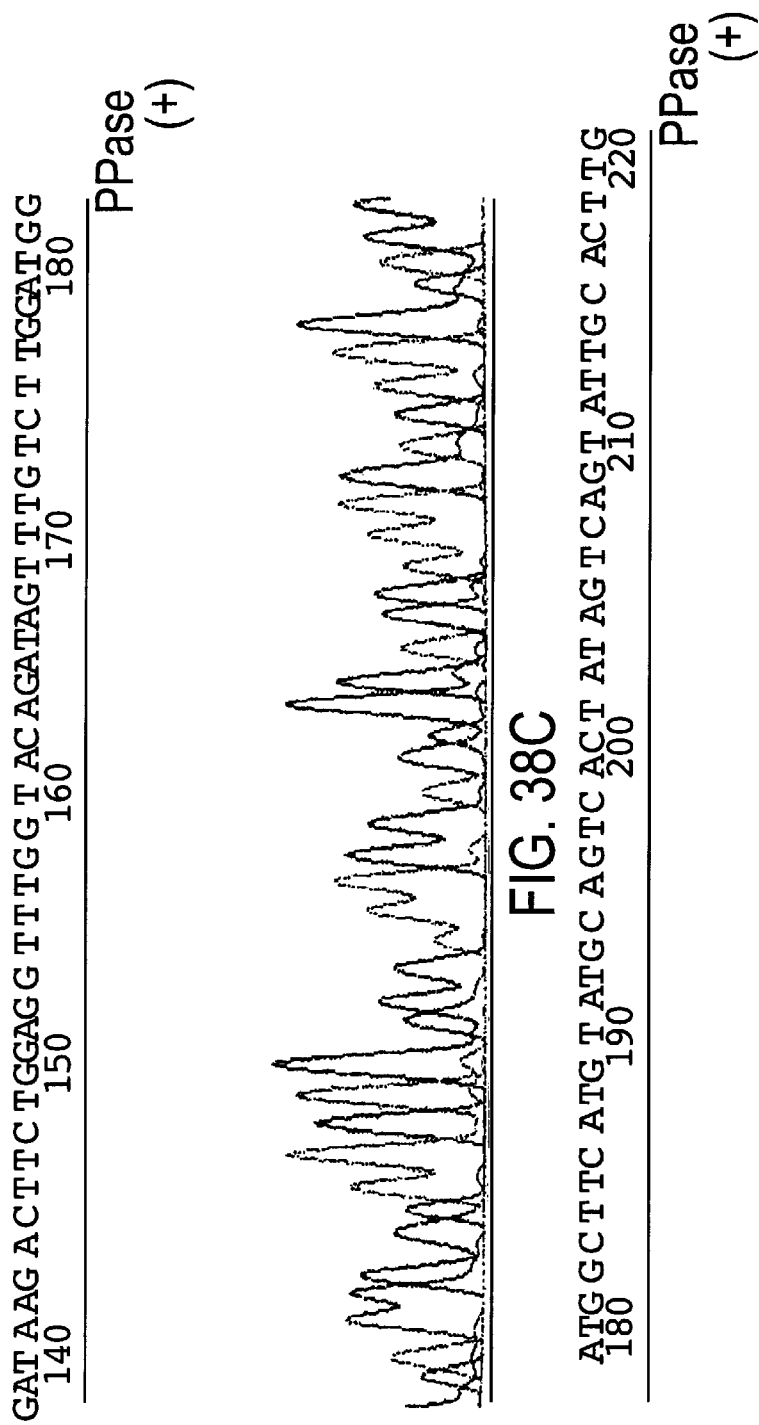
Figure 38D:
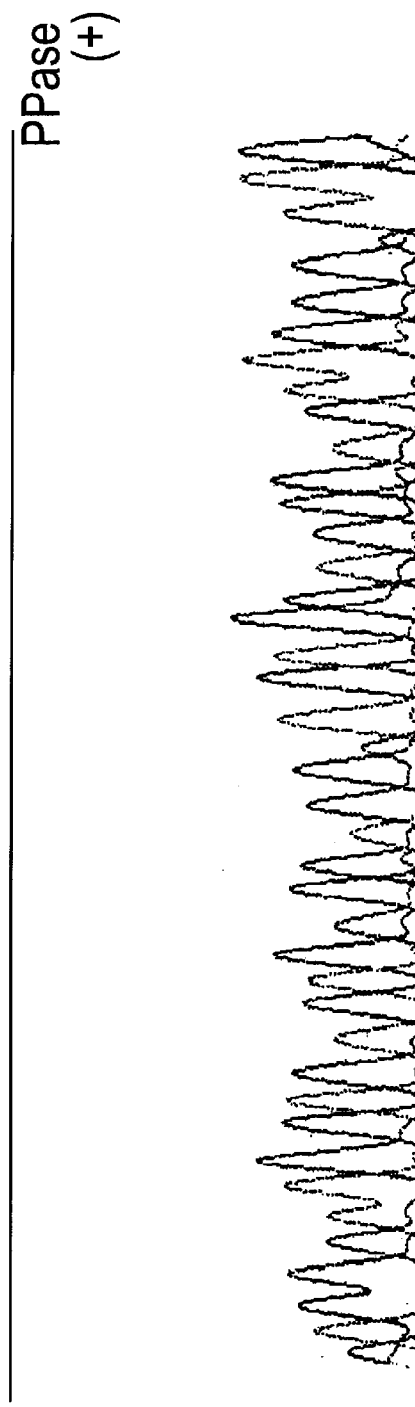
Figure 39A:
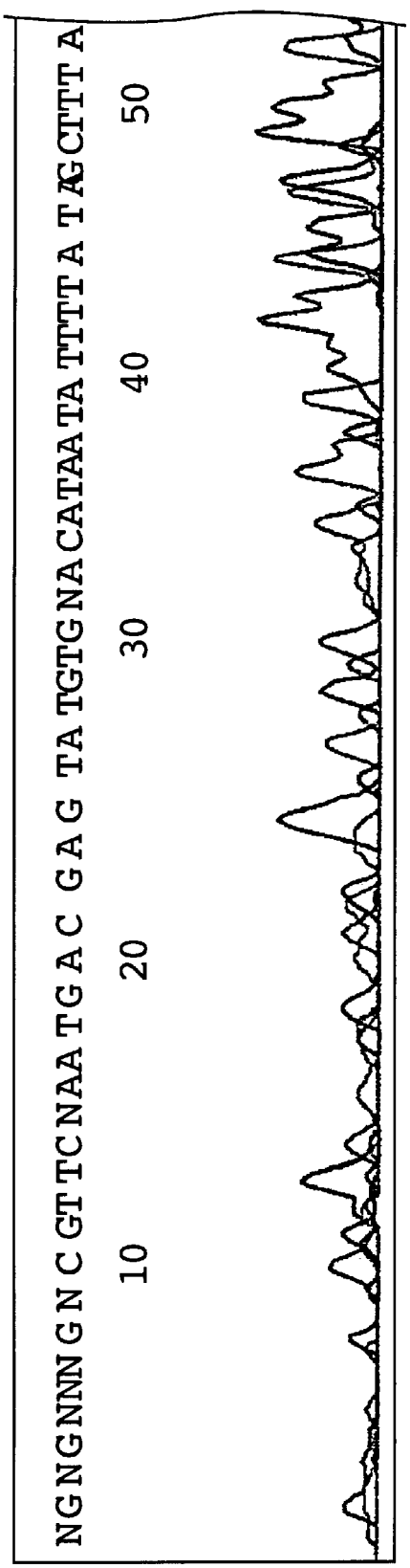
FIG. 39 A–I represents the results of sequencing of hTSH-β cDNA without addition of inorganic pyrophosphatase. The determined nucleotide sequence is compared with the already reported hTSH-β cDNA.
Figure 39B:
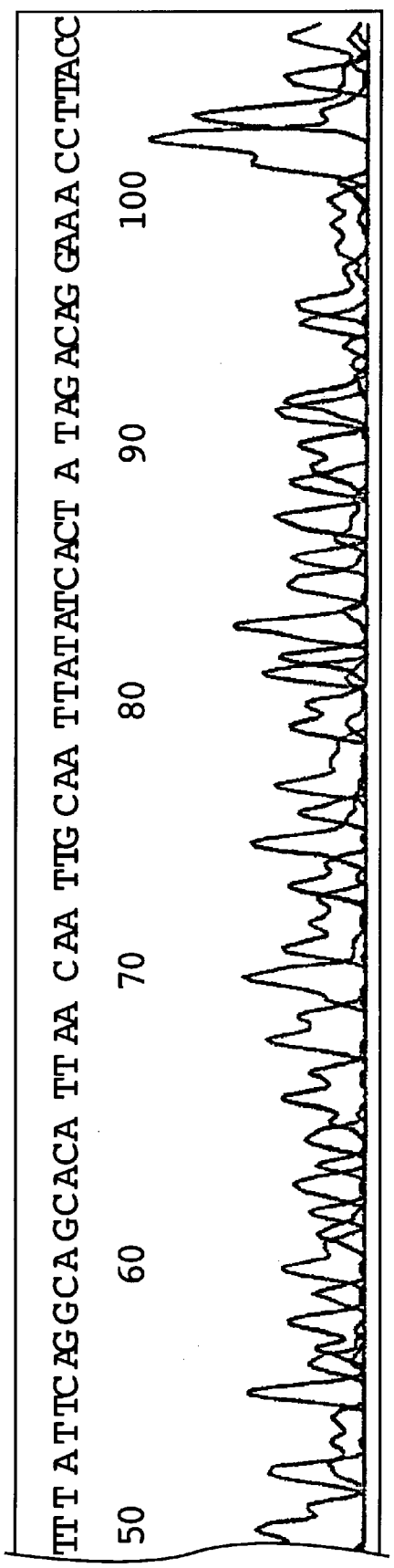
Figure 39C:
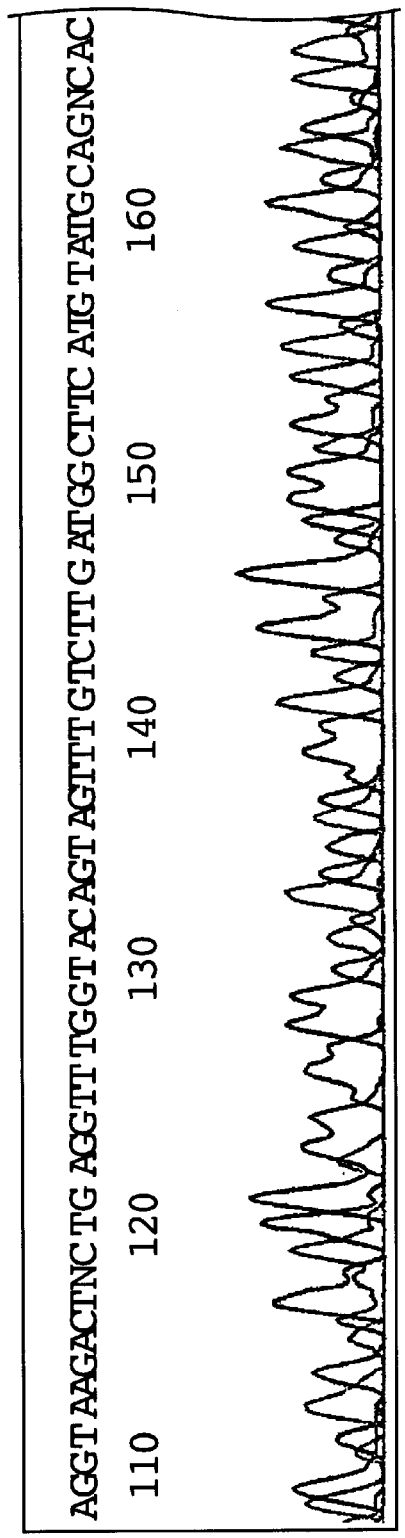
Figure 39D:
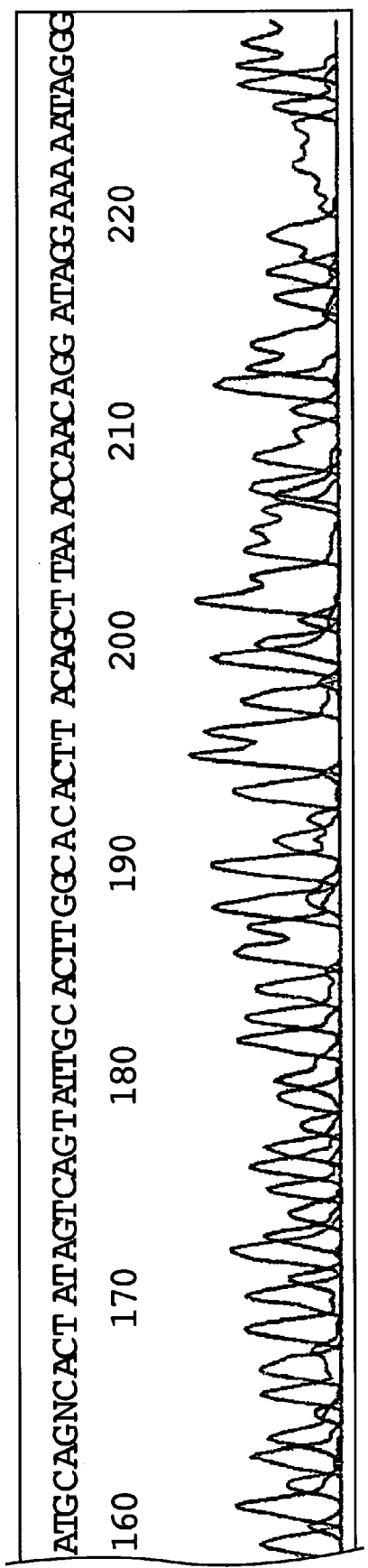
Figure 39E:
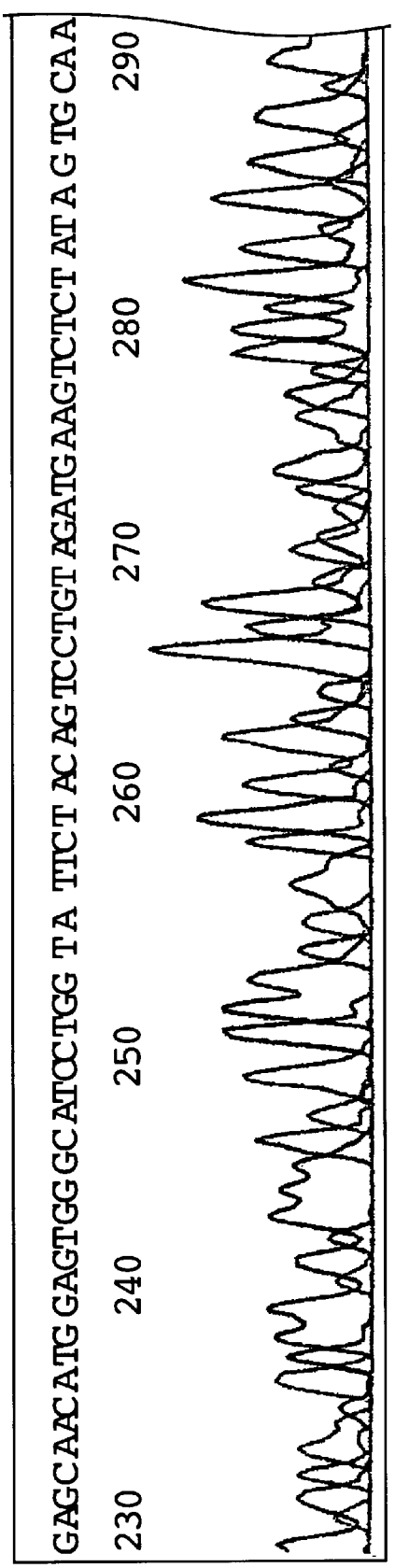
Figure 39F:
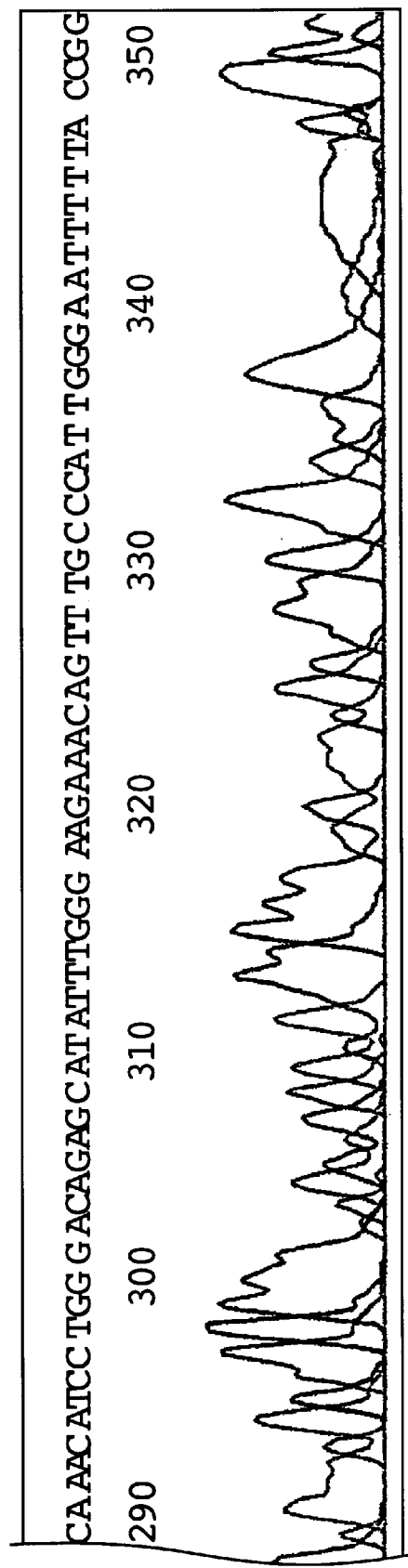
Figure 39I:
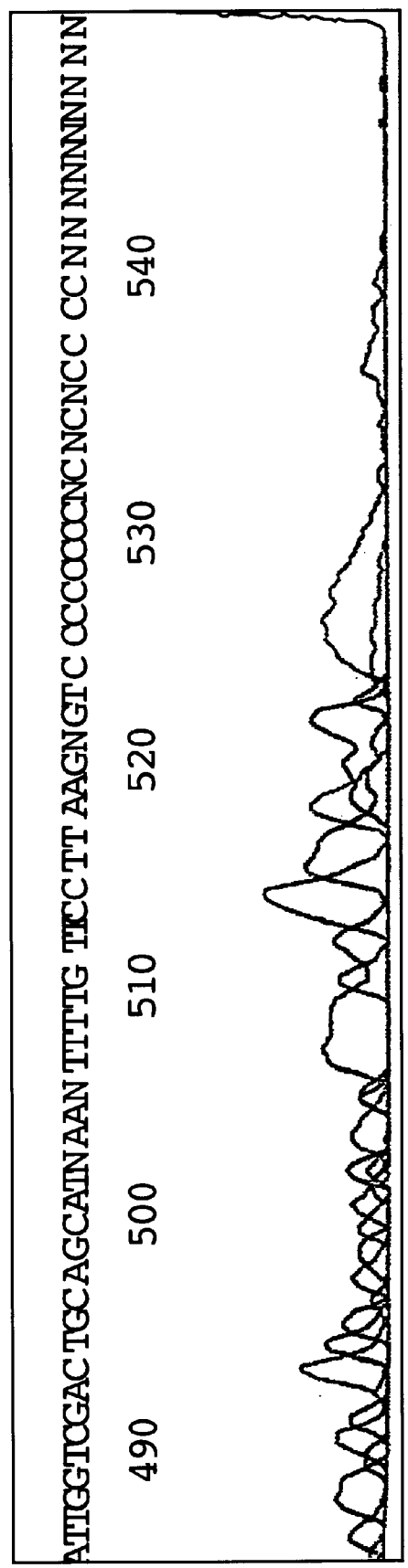
Figure 40C:
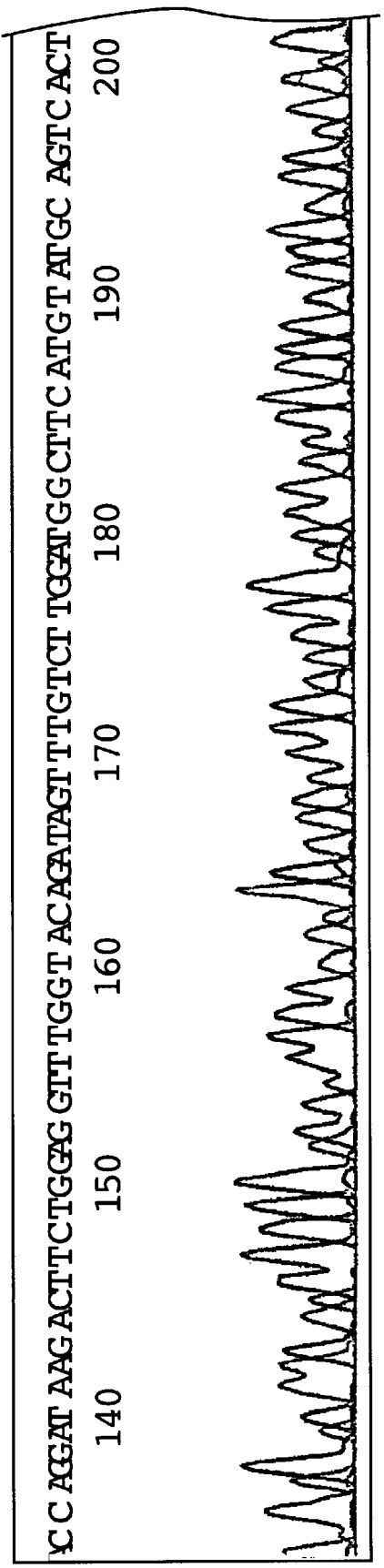
FIG. 40 A–J represents the results of sequencing of hTSH-β cDNA with addition of inorganic pyrophosphatase. The determined nucleotide sequence is compared with the previously reported hTSH-β cDNA.
Figure 40D:
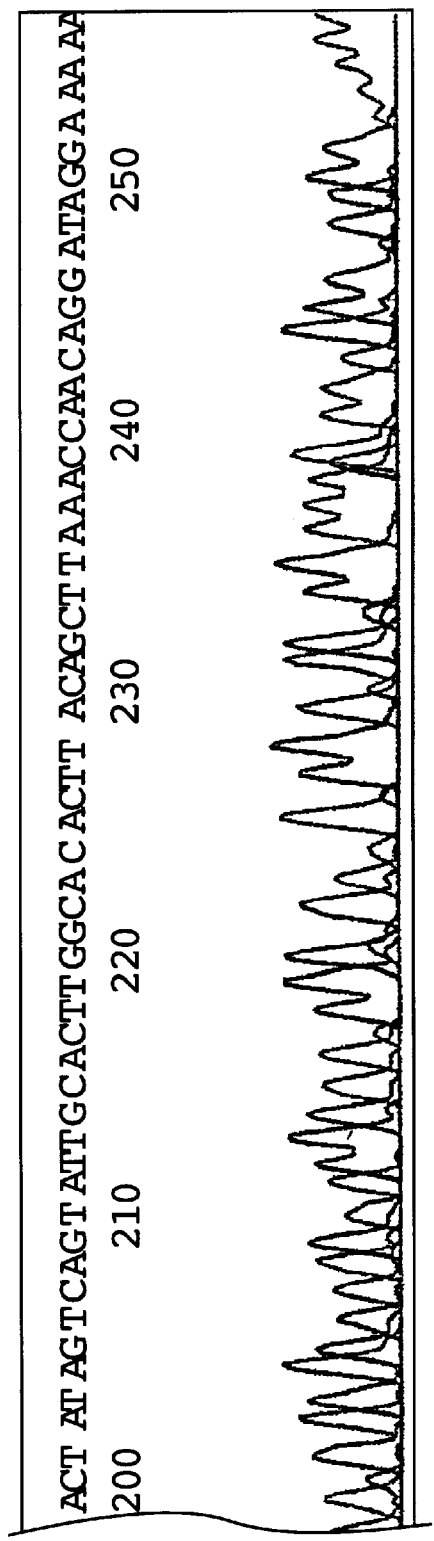
Figure 40E:
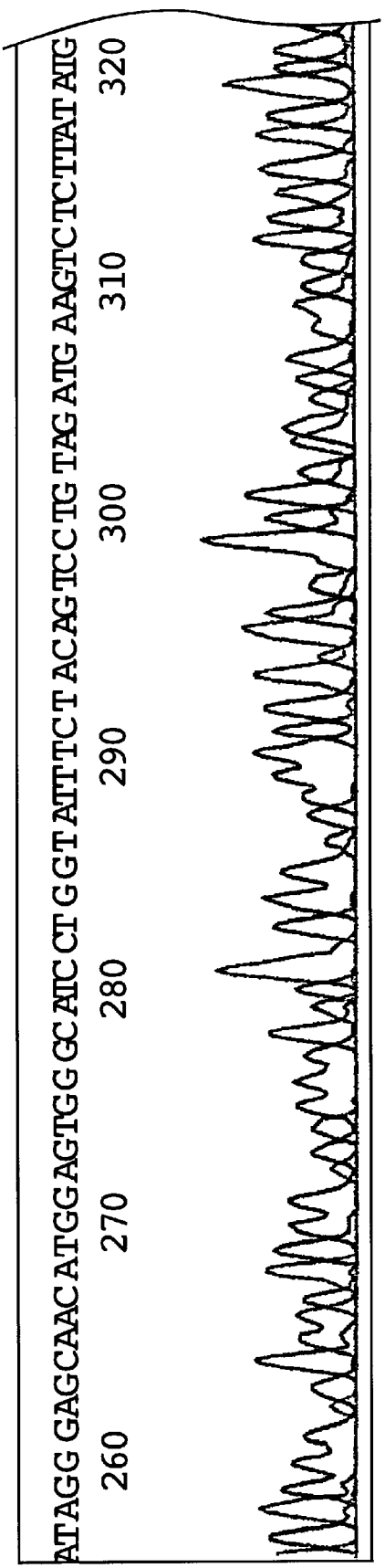
Figure 40F:
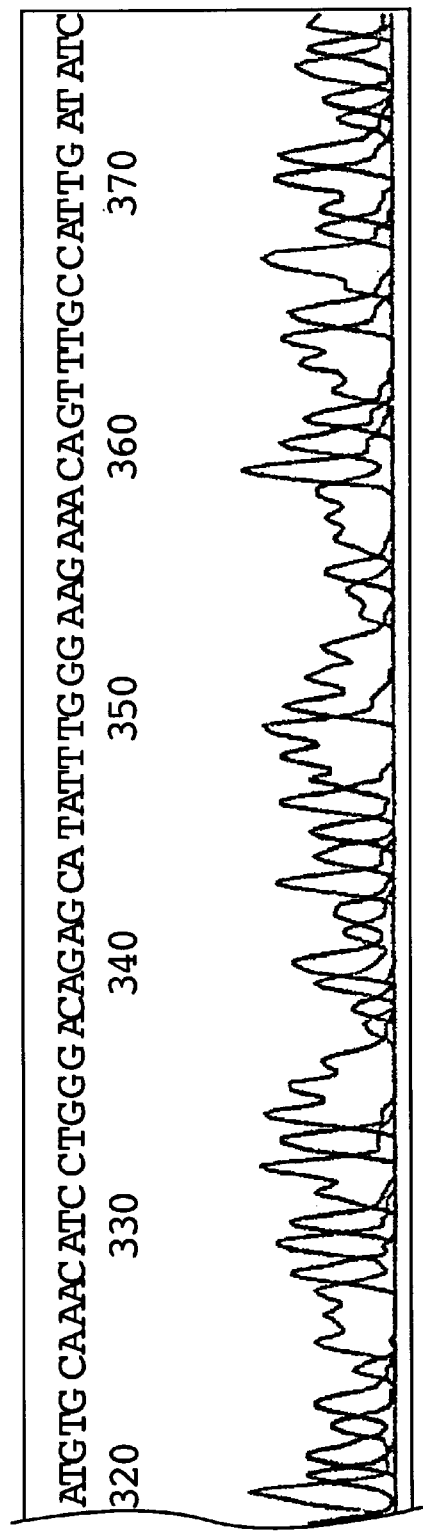
Figure 40G:
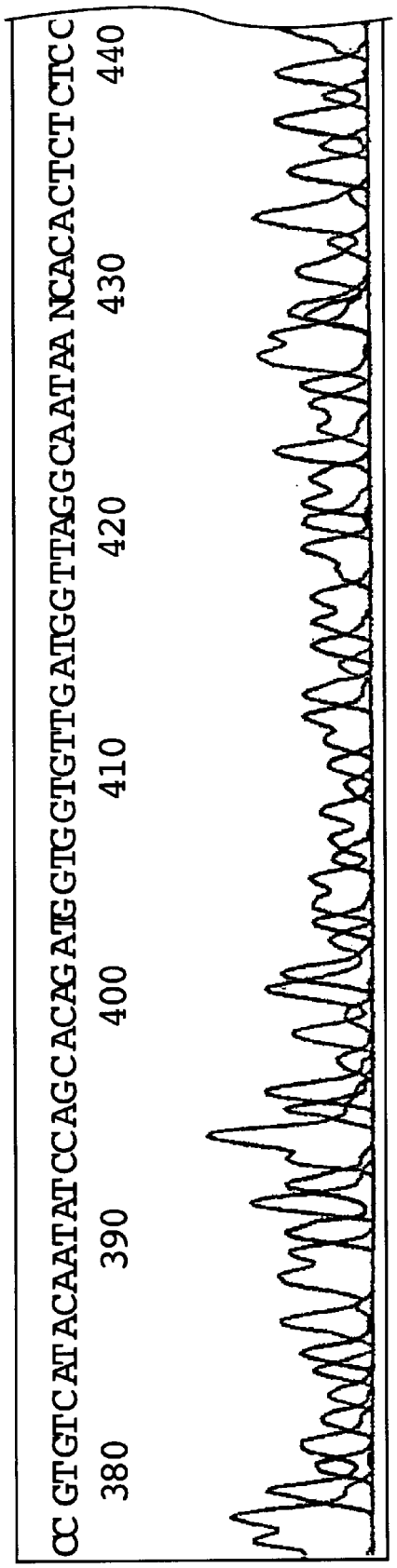
Figure 40H:
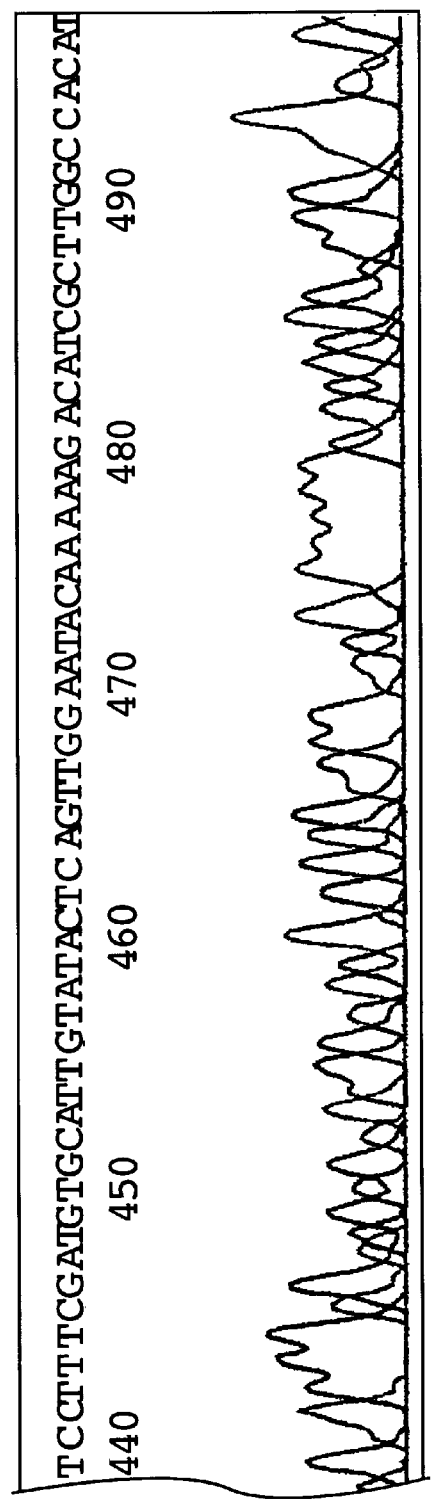
Figure 40I:
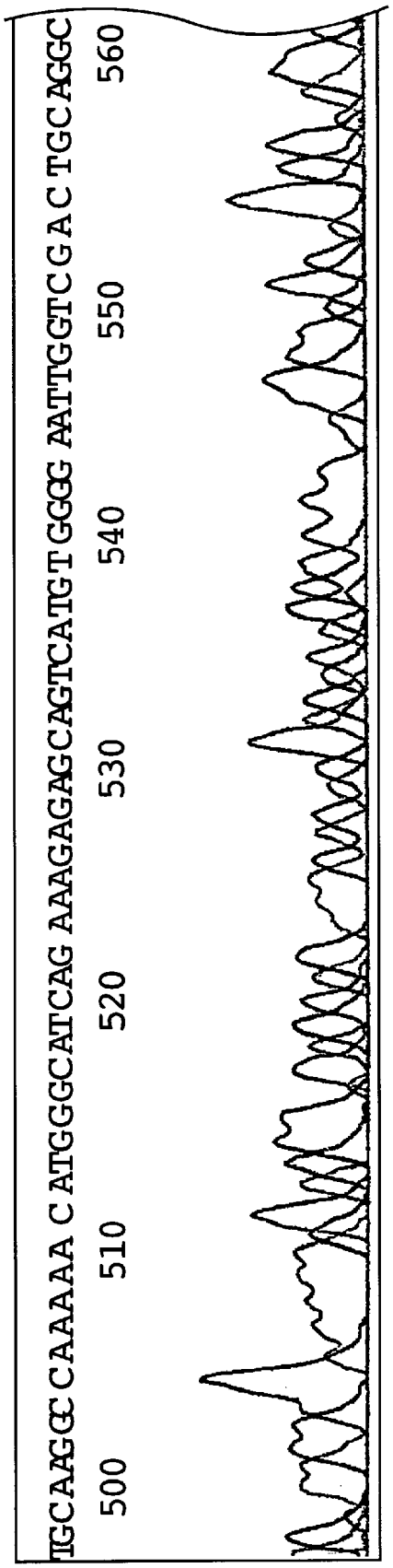
Figure 40J:
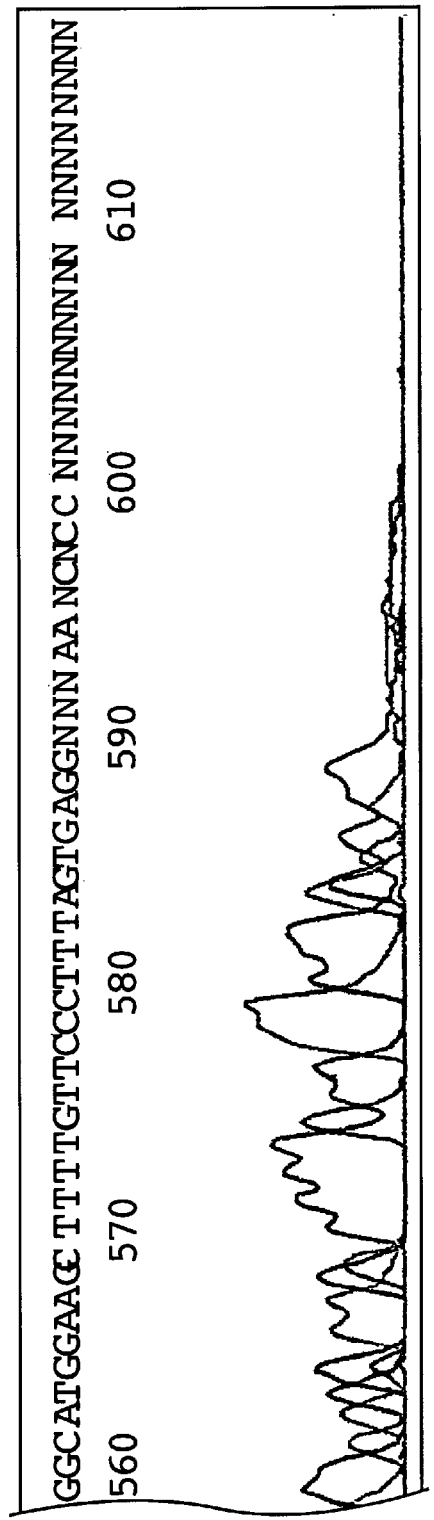
Figures 1, 41B:
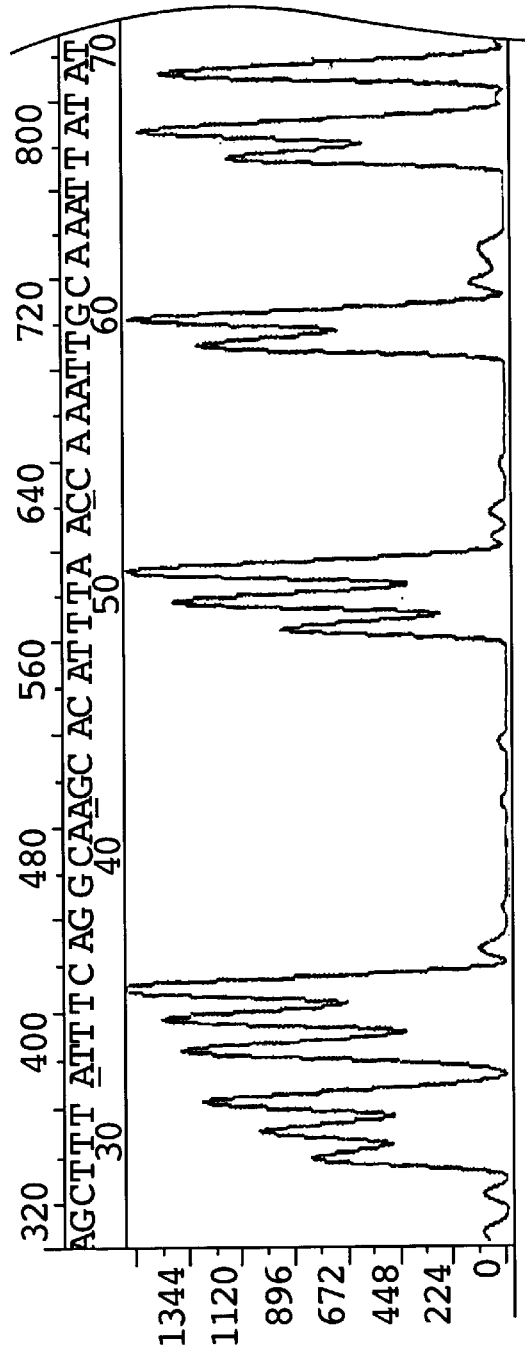
Figures 2, 41B:
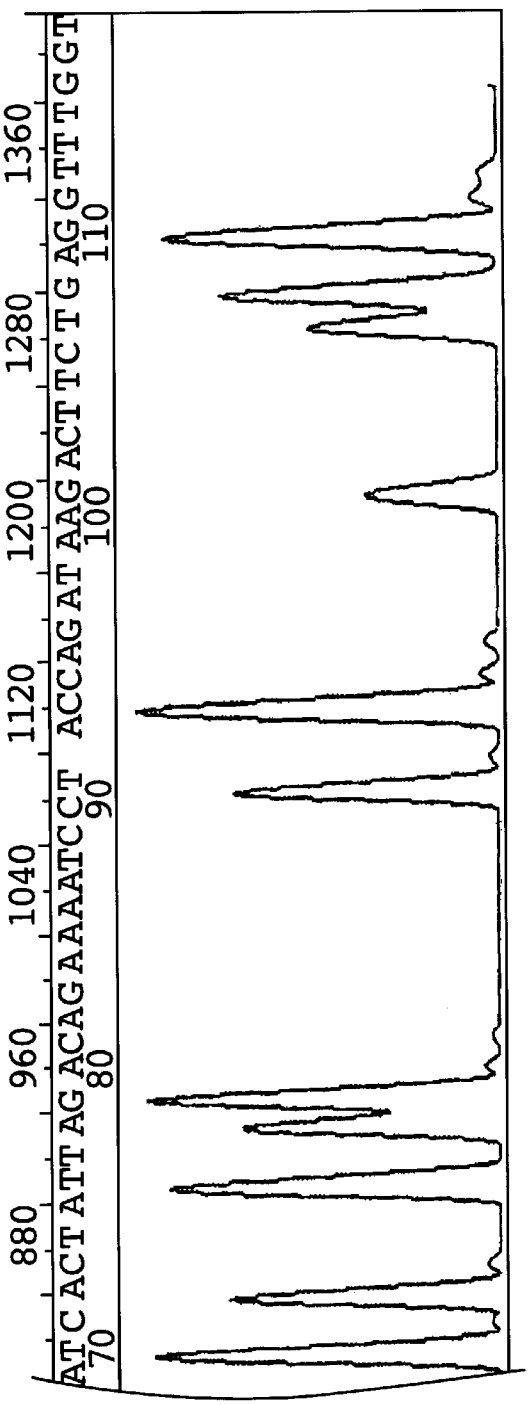
Figures 1, 41C:
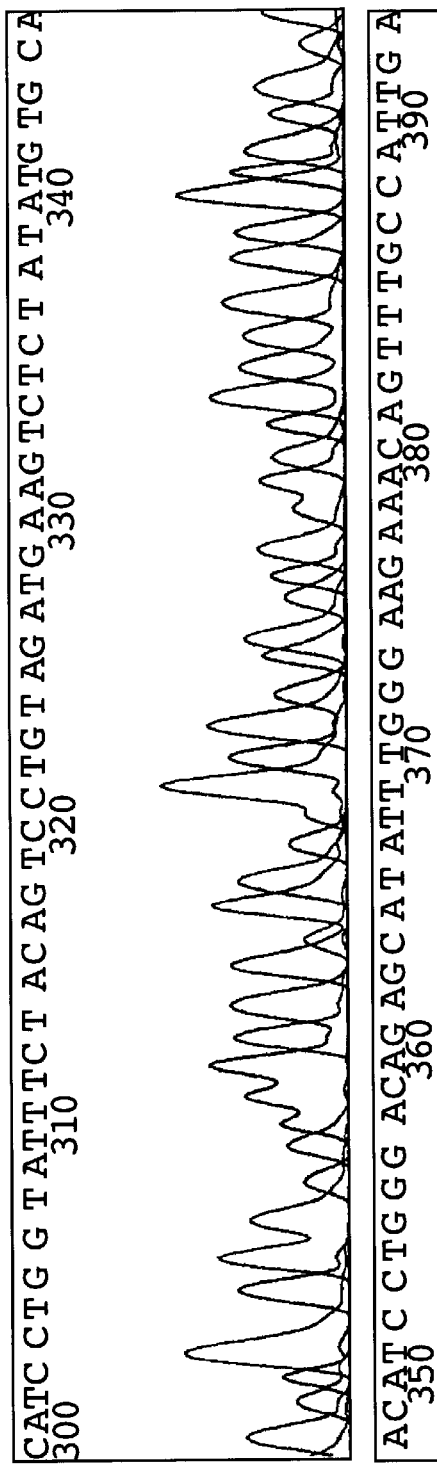
Figures 2, 41C:
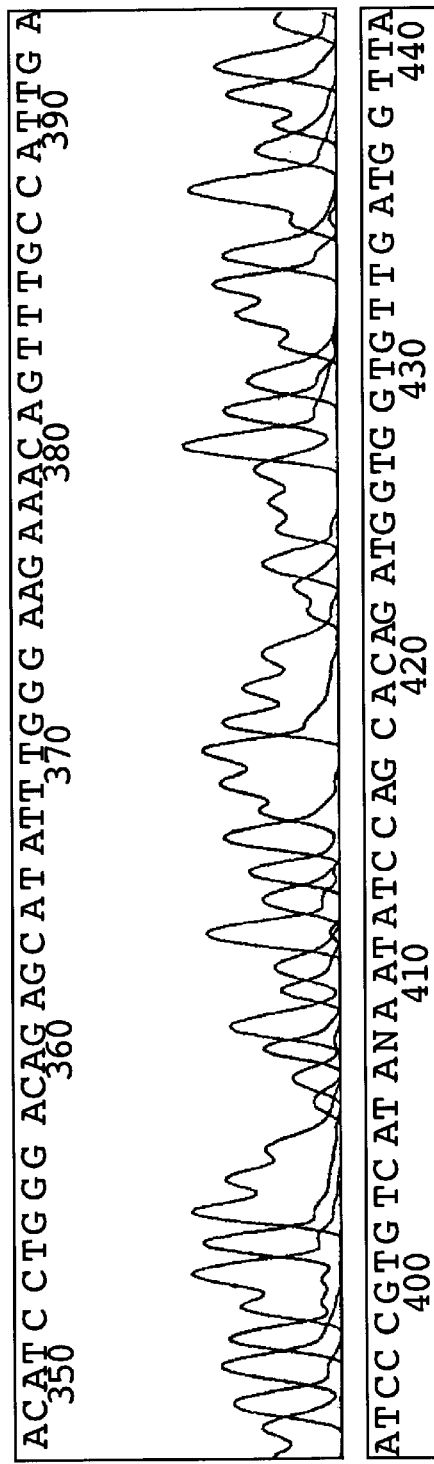
Figures 3, 41C:
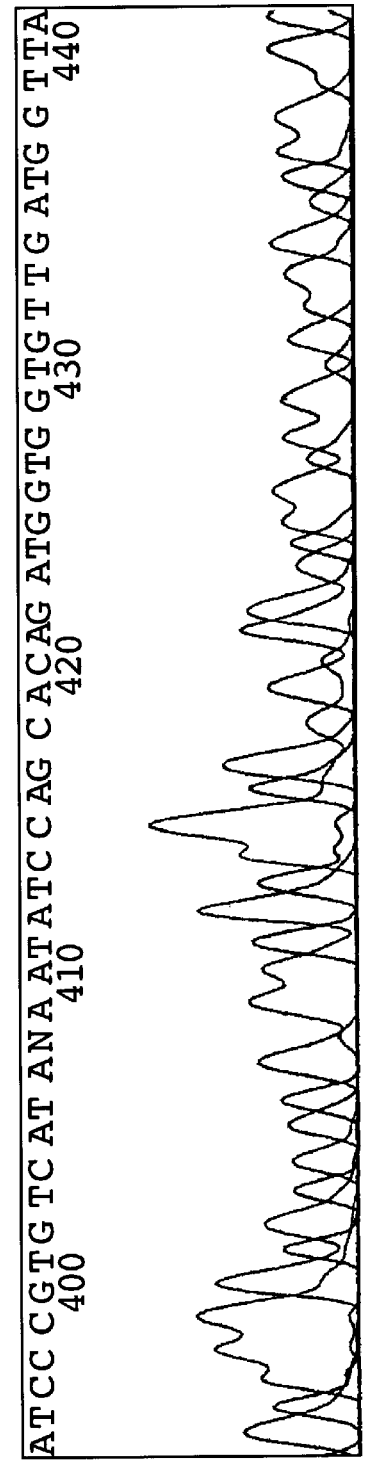
Figures 1, 41D:
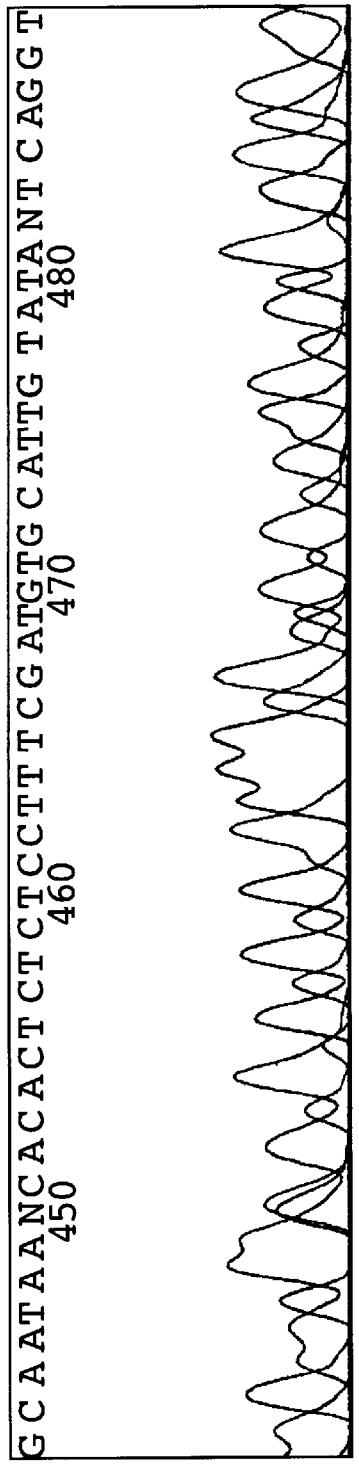
Figures 2, 41D:
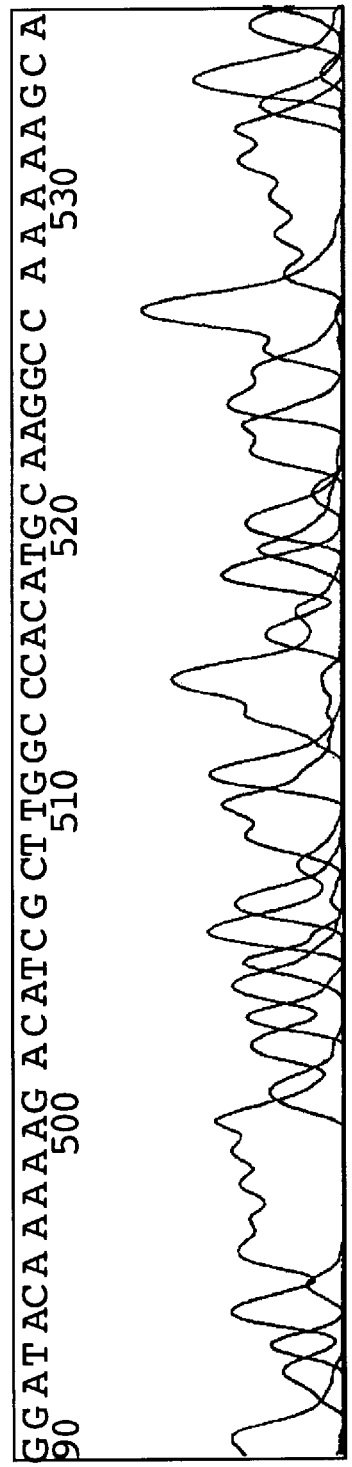
Figures 3, 41D:
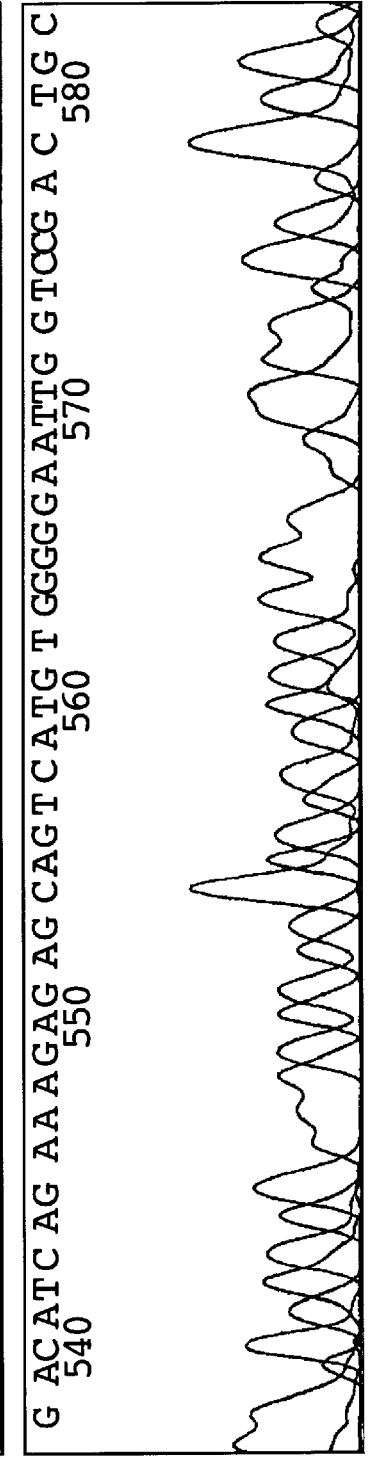

The above-mentioned four RNA polymerases extremely resemble one another in their primary structures of amino acids, sequence of promoter and the like. In FIGS. 3 and 4, alignment of amino acid sequences of the aforementioned four RNA polymerases derived from the phages is represented. From this alignment, it can be seen that the RNA polymerases derived from T7, T3, and K11 highly resemble one another. In particular, the amino acid sequences of RNA polymerases derived from T7 and T3 phages show extremely high similarity as shown in FIGS. 6 and 7. It is conformable to the fact that both of T7 and T3 phages are those infecting E. coli, and that they also resemble each other in their properties. Further, the promoter sequences recognizing these two RNA polymerases also resemble each other, and they have known to have extremely high recognition specificity. Thus, the results obtained in T7 RNA polymerase are relatively readily applied to other RNA polymerases having similar amino acid sequences.

From these high homologies, it can be concluded that a region corresponding to the amino acid residues 644–667 of the RNA polymerase derived from T7 phage in RNA polymerases other than the RNA polymerase derived from T7 phage is the amino acid residues 642–668 for the RNA polymerase derived from T3 phage, the amino acid residues 664–690 for the RNA polymerase derived from K11 phage, and the amino acid residues 633–670 for the RNA polymerase derived from SP6 phage. The RNA polymerases derived from T7, T3, and K11 phages extremely resemble one another as described above, and the results obtained for T7 RNA polymerase can be applied for other RNA polymerases having a similar amino acid sequence (see FIG. 8).

As an example of such other RNA polymerases, RNA polymerase derived from K11 phage having tyrosine at the amino acid residue 644 or 667 can be mentioned. RNA polymerase derived from T3 phage having tyrosine at the amino acid residue 645 or 668 can also be exemplified. RNA polymerase derived from K11 phage having tyrosine at one or more of the amino acid residues 664–669 and 690 can further be exemplified. RNA polymerase derived from SP6 phage having tyrosine at one or more of the amino acid residues 633–638 and 670 can still further be exemplified.

The modification of such an amino acid may be not only substitution of amino acid but also insertion or deletion of amino acid. The mutation of amino acid is, for example, substitution of tyrosine for at least one amino acid residue in a naturally occurring amino acid sequence. The amino acid to be replaced may be, for example, phenylalanine. However, the amino acid to be replaced is not limited to phenylalanine, and any amino acid may be replaced so long as it can enhance the ability for incorporating 3'-deoxyribonucleotides and other ribonucleotide analogues relative to ability for the corresponding ribonucleotides.

Among the mutant RNA polymerases of the present invention, the mutant T7 RNA polymerases F644Y, L665P/F667Y and F644Y/L665P/F667Y maintained sufficient RNA synthesis activity, and showed markedly improved ability for incorporating 3'-dNTPs, and the strong bias observed in the wild type is markedly reduced in these polymerases. Use of T7 RNA polymerase F644Y, L665P/F667Y or F644Y/L665P/F667Y having such characteristics enables a nucleotide sequence determination method utilizing transcription products, which is of more excellent practical applicability in comparison with a nucleotide sequence determination method utilizing a DNA polymerase.

E. coli strains pT7RF644Y (DH5 α) and pT7RL665P/F667Y (DH5 α), which produce the mutant T7 RNA polymerases F644Y and L665P/F667Y respectively, were already deposited at the National Institute of Bioscience and Human-Technology (Higashi 1-1-3 Tsukuba-shi Ibaraki-ken, Japan, 〒 305-0046) with international deposition numbers of 5998 (FERM-BP-5998) and 5999 (FERM-BP-5999) respectively on Jul. 2, 1997. An E. coli strain pT7RF644Y/L665P/F667Y (DH5 α), which produces the mutant T7 RNA polymerase F644Y/L665P/F667Y, was already deposited at the National Institute of Bioscience and Human-Technology with an international deposition number of 6364 (FERM-BP-6364) on May 20, 1998.

The aforementioned mutant RNA polymerases can be produced by preparing a nucleic acid molecule encoding an RNA polymerase, introducing a mutation into the nucleic acid molecule so that one or more nucleotides in one or more regions should be mutated, and collecting a modified RNA polymerase expressed by the mutated nucleic acid molecule. The preparation of the nucleic acid molecule encoding RNA polymerase, introduction of mutation into the nucleic acid molecule, and collection of the modified RNA polymerase can be performed by using conventional methods.

For example, a mutant T7 RNA polymerase can be constructed by the following method. By using an expression vector inserted with a T7 RNA polymerase gene as template, an expression plasmid comprising a region between the HpaI, and NcoI restriction sites in the C-terminus side of T7 RNA polymerase gene which is introduced with a mutation by PCR is constructed. Subsequently, this expression plasmid can be transformed into E. coli DH5 α, which can then produce a large amount of a mutant T7 RNA polymerase protein upon addition of isopropyl-β-D-thiogalactopyranoside (IPTG).

Method for Determining Nucleotide Sequence of DNA

The method for enzymatically synthesizing a nucleic acid transcription product using an RNA polymerase and a DNA fragment containing a promoter sequence for the RNA polymerase as a template, the method for separating nucleic acid transcription products, and the method for determining nucleic acid sequences from separated fractions have already been known. Therefore, concerning these methods, any known techniques, conditions, apparatuses and the like can be suitably used.

The DNA fragment to be a template is not particularly limited except that it should contain a promoter sequence for RNA polymerase. For example, the DNA fragment containing a promoter sequence may be a DNA product amplified by polymerase chain reaction. Further, the nucleic acid transcription reaction in the method of the present invention can be performed with an amplified DNA product without removing the primers and/or 2'-deoxyribonucleoside 5'-triphosphate and/or derivatives thereof used for the polymerase chain reaction. As the polymerase chain reaction for the above DNA amplification, any methods widely used as PCR can be used as they are. The DNA fragment containing a promoter sequence can be a DNA fragment obtained by ligating the promoter sequence and a DNA fragment to be amplified, and cloning the ligated fragment using a suitable host. That is, in the present invention, DNA sequences to be amplified, primers, conditions for amplification and the like are not particularly limited.

For example, the polymerase chain reaction for the amplification of DNA fragment containing a promoter sequence can be performed, for example, in a reaction system of 20 μl volume containing 10–50 ng of genomic DNA or 1 pg of cloned DNA, 10 μM each of primers, and 200 μM each of 2'-deoxyribonucleoside 5'-triphosphate (dATP, dGTP, dCTP, dTTP) by using Taq polymerase as the DNA polymerase.

However, either one of the primers for the polymerase chain reaction or an amplified inserted DNA (insert) should contain a promoter sequence for RNA polymerase, which will be explained hereinafter. In the direct transcriptional sequencing method, by using two kinds of primers one of which contains a phage promoter sequence, or an amplified inserted DNA containing a phage promoter sequence for PCR, the resulting PCR product can undergo in vitro transcription using an RNA polymerase driven by the promoter.

The promoter sequence for the RNA polymerase can be suitably selected depending on the kind of RNA polymerase to be used.

In the method of the present invention, nucleic acid transcripts such as RNA transcripts are synthesized from a DNA fragment containing a promoter sequence. Because the DNA fragment contains a promoter sequence for the RNA polymerase, go the above-mentioned mutant RNA polymerase is promoted by this promoter sequence, and thus nucleic acid transcripts such as RNA transcripts are synthesized.

In the synthesis of nucleic acid transcripts such as RNA transcripts, ribonucleoside 5'-triphosphates (NTPs) including ATP, GTP, CTP and UTP or derivatives thereof and one or more kinds of the 3'-dNTP derivatives are reacted in the presence of the mutant RNA polymerase mentioned above. The term 3'-dNTP derivatives is used in this specification as a generic term for collectively referring to 3'-dATP, 3'-dGTP, 3'-dCTP, 3'-dUTP and derivative thereof. As the ribonucleoside 5'-triphosphates (NTPs), at least four kinds of compounds different in their bases are necessary for the synthesis of transcripts including a case where a part of them is consisting of their derivatives such as ATP derivatives. However, two or more kinds of compounds carrying the same base may be used.

The 3'-hydroxy group at the 3' end of the transcription product, RNA or nucleic acid, is eliminated when a 3'-dNTP derivative is incorporated, and thus the synthesis of the RNA or nucleic acid is inhibited. As a result, RNA or nucleic acid fragments having a 3'-dNTP derivative at the 3' end with various sizes can be obtained. Such ribonucleoside analogues are obtained for each of the four kinds of 3'-dNTP derivatives different in their bases. These provided four kinds of ribonucleoside analogues can be used for the determination of RNA or nucleic acid sequence [Vladimir D. Axelred et al. (1985) Biochemistry Vol. 24, 5716–5723].

As for the 3'-dNTP derivatives, one or more kinds of them can be used for one transcription reaction. When one nucleic acid transcription reaction is performed by using one kind of 3'-dNTP derivative, the four kinds of transcription products with different 3'-dNTP derivatives at the 3' ends can be obtained by performing nucleic acid transcription reaction four times. One nucleic acid transcription reaction affords a transcription product which is a mixture of various RNA or nucleic acid fragments having the same 3'-dNTP derivative at the 3' ends with various molecular weights. The obtained four kinds of transcription products can independently subjected to separation and sequence determination explained hereinafter. Two or more of the four kinds of transcription products can also be mixed and subjected to the separation and sequence determination.

When two or more kinds of the 3'-dNTP derivatives are simultaneously used for one nucleic acid transcription reaction, two or more kinds of transcription products having different bases of 3'-dNTP derivatives at the 3' ends will be contained in the reaction product. This can be subjected to the separation and sequence determination explained hereinafter. It is preferred that two or more kinds of the 3'-dNTP derivatives are simultaneously used, because it reduced the number of nucleic acid transcription reactions.

Further, the transcription of nucleic acid such as RNA is achieved by an RNA polymerase in the presence of four kinds of ribonucleoside 5'-triphosphates different in their bases, and terminated by 3'-dNTP derivatives. As a result, for each base, an RNA or nucleic acid ladder for sequencing is formed. According to the present invention, the nucleic acid transcription is preferably performed in the presence of, in particular, different four kinds of ribonucleoside 5'-triphosphates, of which products are then separated to determine nucleotide sequences for the four kinds of bases at one time (simultaneously).

In the method of the present invention, the RNA or nucleic acid transcription products are separated. This separation can appropriately be performed by a method capable of separating a plurality of kinds of molecules with different molecular weights contained in the transcription product according to the molecular weights. As an example of such a separation method, electrophoresis can be mentioned. The HPLC can also be used.

As for the electrophoresis, conditions and the like are not particularly limited, and it can be performed by conventional manner. From bands (RNA or nucleic acid ladder) obtained by subjecting the transcription products to electrophoresis, sequences of RNA or nucleic acid can be determined.

The reading of the RNA or nucleic acid ladder can be performed by labeling the terminators for the transcription reaction, i.e., the ribonucleoside 5'-triphosphates (NTPs). The reading of the RNA or nucleic acid ladder also becomes possible by labeling the 3'-dNTP derivatives used for the transcription reaction. Examples of the label are radioactive or stable isotopes, fluorescent labels and the like. The sequences of the transcription products can also be determined by measuring mass of each transcription reaction product separated by electrophoresis by means of a mass spectrometer without using a label such as those mentioned above.

Specifically, the sequences of transcription products can be determined by, for example, using 3'-dNTP derivatives, more specifically, labeled 3'-dATP, 3'-dGTP, 3'-dCTP and 3'-dUTP, and detecting radioactive or stable isotopes, fluorescent labels and the like of the bands obtained by electrophoresis of the transcription products. Thus, the labeling of the 3'-dNTP derivatives reduces the fluctuation of radioactivity intensity or fluorescence intensity among the bands obtained, and makes the measurement easy. The detection of radioactive or stable isotopes or ladders emitting fluorescence can be performed by suitably using, for example, an apparatus used for DNA sequencing.

The sequences of transcription products can also be determined by using ATP, GTP, CTP and UTP labeled with radioactive or stable isotopes or fluorescence, and detecting the radioactive or stable isotopes or fluorescence of the band obtained by electrophoresis of the products.

The sequences of RNA or nucleic acid can also be determined by using differently fluorescence-labeled 3'-dATP, 3'-dGTP, 3'-dCTP and 3'-dUTP, and detecting four kinds of fluorescence of the bands obtained by electrophoresis of a mixture of various transcription product fragments having 3'-dATP, 3'-dGTP, 3'-dCTP or 3'-dUTP at their ends and differently labeled.

In the above method, the four kinds of 3'-dNTPs are labeled with different kinds of fluorescence. This makes it possible to afford bands emitting fluorescence corresponding to each of the four kinds of 3'-dNTPs different at their 3' ends by subjecting a mixture of four kinds of transcription products different in their 3' ends, and thereby it becomes possible to simultaneously determine four kinds of RNA or nucleic acid sequences by differentiating the different kinds of fluorescence.

As the fluorescence-labeled 3'-dNTPs, it is preferred to use the 3'-deoxyribonucleotide derivatives mentioned below.

3'-Deoxyribonucleotide Derivative (Terminator)

As the 3'-dNTP derivatives used for the method of determining DNA sequence of the present invention, 3'-deoxyribonucleotide derivatives represented by the following general formula [I] are preferably used, because the 3'-deoxyribonucleotide derivatives represented by the general formula [I] are easily incorporated into a sequence in a polymerase chain reaction by an RNA polymerase.

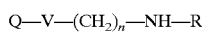   [I]

In the formula, Q represents a 3'-deoxyribonucleotide residue, n represents an integer not less than 4, V represents —C≡C— or —CH=CH—, and R represents a fluorescent group. n in the general formula [I] preferably represents an integer of 4–10. R in the general formula [I] is preferably represented by following general formula [VII]:

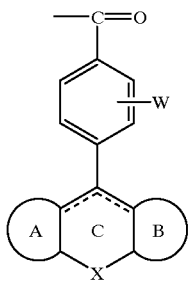   [VII]

The 3'-deoxyribonucleotide derivatives represented by the general formula [I] of the present invention are composed of three structural components:

(a) 3'-deoxyribonucleotide residue: Q, (b) linker of the general formula [VI]:

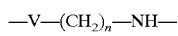   [VI]

wherein V and n have the same meanings as defined above, and (c) fluorescent group.

As the 3'-deoxyribonucleotide residue represented by Q, 7-deazapurine nucleotide residues represented by the following general formulae [II] and [III], and pyrimidine nucleotide residues represented by the following general formulae [IV] and [V] can be mentioned.

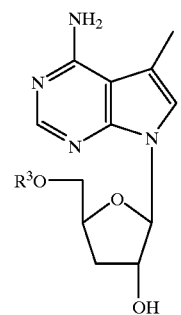   [II]

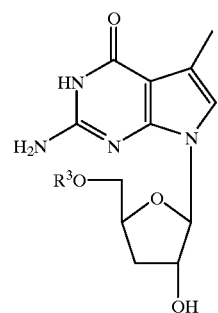   [III]

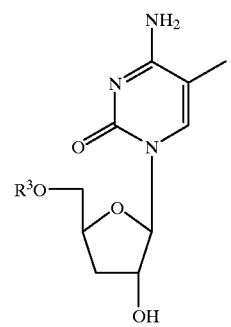   [IV]

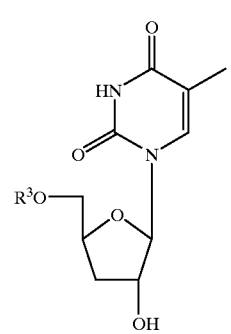   [V]

In above general formulae [II]–[V], $R_3$ represents —$PO_3H_2$, —$P_2O_6H_3$, —$P_3O_9H_4$ or a salt thereof. Preferred examples of the salt include alkali metal salts such as sodium salts, potassium salts and lithium salts, alkaline earth metal salts such as barium salts, ammonium salts such as triethylammonium salts, organic amine salts such as pyridine salts and the like.

The linker represented by the above general formula [VI] is a linker for binding the 3'-deoxyribonucleotide residue represented by Q and the fluorescent group.

That is, one of the carbon atoms forming double bond or triple bond in the linker is bonded to any of the 3'-deoxyribonucleotide residues represented by Q at 5-position for the pyrimidine nucleotide residues, or at 7-position for the 7-deazapurine nucleotide residues, respectively, and the —NH— group of the linker is bonded to a carboxyl group of the fluorescent dye group, so that a compound which have the 3'-deoxyribonucleotide residue and the fluorescent dye group is formed.

In the linker represented by the general formula [VI], examples of the methylene chain where n is not less than 4 include the methylene chain where n is 4–15, more specifically, a tetramethylene group, a pentamethylene group, a hexamethylene group, a heptamethylene group, an octamethylene group, a nonamethylene group, a decamethylene group and the like. From the viewpoint of improvement of incorporation rate by RNA polymerases, n should be an integer not less than 4, preferably n is an integer of 4–10, more preferably n is an integer of 4–8, particularly preferably n is 4 or 6.

The fluorescent group represented by R may be directly bound to the —NH— group, or bound to the —NH— group through a linker. The fluorescent group is not particularly limited, and may be suitably selected in view of fluorescence intensity, wavelength of fluorescence, easiness of incorporation by RNA polymerases and the like. However, the fluorescent group is preferably a fluorescent dye generating detectable luminescence emission subsequent to stimulation by energy absorption from a suitable energy source such as argon laser.

Examples of the fluorescent group R include groups represented by the following general formula [VII]. The fluorescent groups represented by the general formula [VII] are fluorescent dye groups generating detectable luminescence emission subsequent to stimulation by energy absorption from a suitable energy source such as argon laser.

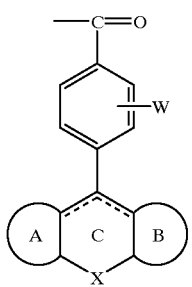

[VII]

In the formula, W represents carboxyl group, X represents —O—, —S—, —NR'— where R' represents hydrogen atom, a lower alkyl group, an aralkyl group or an aryl group, or —CH$_2$—, one of the ring A and the ring B represents

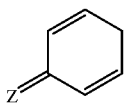

and the other one represents

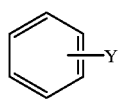

where Z represents O or =N$^+$R$_1$R$_2$, and Y represents OH or —NR$_1$R$_2$ where R$_1$ and R$_2$ each independently represent hydrogen atom or a lower alkyl group, or both of R$_1$ and R$_2$ represent a trimethylene group (i.e., R$_1$ and R$_2$ represent two trimethylene groups, of which other end is bonded to either one of the carbon atoms next to the nitrogen atom to which the trimethylene group is bonded), the broken line ------ in the ring C:

represents a bond present at a position decided by the structures of the ring A and the ring B, and the rings A, B and C and the benzene ring having W may optionally have one or more additional substituents.

The lower alkyl group represented by R' in —NR'— for X in the general formula [VII] may be linear, branched or cyclic, and examples thereof include alkyl groups having 1–6 carbon atoms such as, specifically, a methyl group, an ethyl group, an n-propyl group, an isopropyl group, an n-butyl group, an isobutyl group, a sec-butyl group, a pentyl group, an isopentyl group, a tert-pentyl group, a 1-methylpentyl group, an n-hexyl group, an isohexyl group, a cyclopropyl group, a cyclopentyl group, a cyclohexyl group and the like. Examples of the aralkyl group represented by R' include aralkyl groups having 7–20 carbon atoms such as, specifically, a benzyl group, a phenethyl group, a phenylpropyl group, a methylbenzyl group, a methylphenethyl group, an ethylbenzyl group, a naphthylmethyl group, a naphthylethyl group and the like, and examples of the aryl group represented by the same include a phenyl group, a tolyl group, a xylyl group, a naphthyl group and the like.

The lower alkyl group represented by R$_1$ or R$_2$ in =N$^{+R}$$_1$R$_2$ represented by Z or in —NR$_1$R$_2$ represented by Y in the general formula [VII] may be linear, branched or cyclic, and examples thereof include alkyl groups having 1–6 carbon atoms such as, specifically, a methyl group, an ethyl group, an n-propyl group, an isopropyl group, an n-butyl group, an isobutyl group, a sec-butyl group, a pentyl group, an isopentyl group, a tert-pentyl group, a 1-methylpentyl group, an n-hexyl group, an isohexyl group, a cyclopropyl group, a cyclopentyl group, a cyclohexyl group and the like.

In the above general formula [VII], when the carboxyl group represented by W is bound at such a position as represented in the following general formula [VIII]:

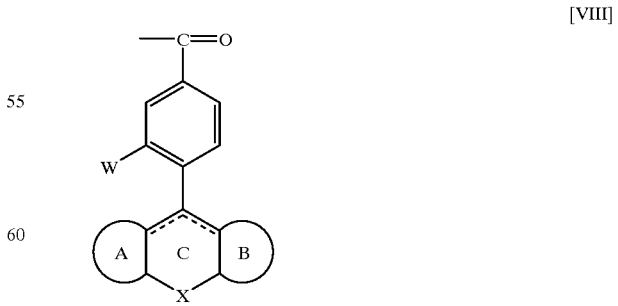

[VIII]

the portion of the fluorescent dye group in the 3'-deoxyribonucleotide derivatives of the present invention can take either of the following structures:

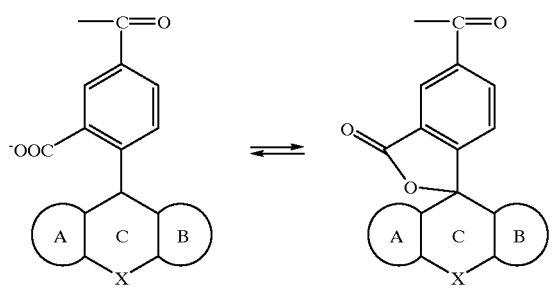

The carboxyl group may form a salt, for example, an alkali metal salt such as a sodium salt, a potassium salt and a lithium salt, an alkaline earth metal salt such as a barium salt, an ammonium salt such as a triethylammonium salt, an organic amine salt such as a pyridine salt or the like.

As an example of the compounds of the above general formula [VII] where, in the rings A and B, Z represents $=N^+R_1R_2$, and Y represents $—NR_1R_2$ where both of $R_1$ and $R_2$ represent a trimethylene group of which other end is bonded to either one of the carbon atoms next to the nitrogen atom to which the trimethylene group is bonded, a compound represented by the following formula can be mentioned:

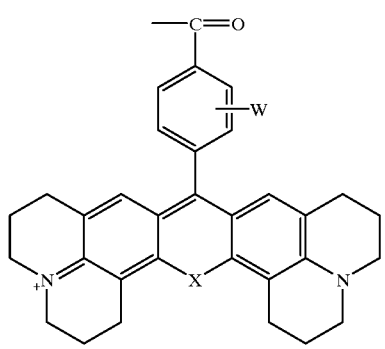

In above general formula [VII], the broken line ------ in the ring C:

represents a bond present at a position decided by the structures of the ring A and the ring B. More specifically, it can be exemplified as follows.

That is, when the ring A is

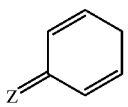

the bonding configuration of the ring C will be as follows:

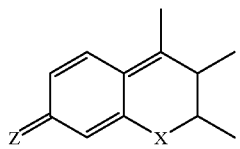

When the ring B is

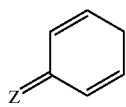

the bonding configuration of the ring C will be as follows:

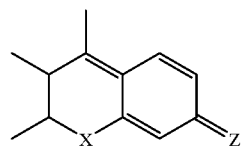

Further, when X is —NH—, the ring A (or the ring B) and the ring C can take either of the following configurations:

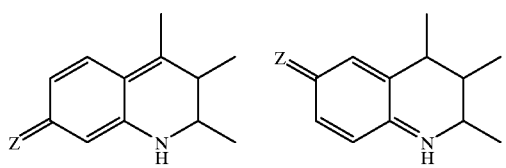

The rings A, B and C and the benzene ring having W may optionally have one or more additional substituents, and examples of such substituents include alkyl groups, alkoxy groups, halogen atoms and the like.

The alkyl groups may be linear, branched or cyclic, and may have a double bond, and examples thereof include alkyl groups having 1–20 carbon atoms, preferably alkyl groups having 1–6 carbon atoms. Specific examples thereof include a methyl group, an ethyl group, an n-propyl group, an isopropyl group, an n-butyl group, an isobutyl group, a sec-butyl group, a pentyl group, an isopentyl group, a tert-pentyl group, a 1-methylpentyl group, an n-hexyl group, an isohexyl group, a cyclopropyl group, a cyclopentyl group, a cyclohexyl group and the like. The alkoxy groups are preferably, for example, lower alkoxy groups having 1–6 carbon atoms. Specific examples thereof are, for example, a methoxy group, an ethoxy group, an n-propoxy group, an isopropoxy group, an n-butoxy group, a pentyloxy group, an isopentyloxy group, a tert-pentyloxy group, a 1-methylpentyloxy group, an n-hexyloxy group, an isohexyloxy group and the like. Examples of the halogen atoms include fluorine, chlorine, bromine, iodine and the like.

Preferred specific examples of the fluorescent dye group represented by the above general formula [VII] include those derived from fluorescent dyes such as 5- or 6-carboxytetramethylrhodamine (abbreviated as TMR hereinafter), 5- or 6-carboxyrhodamine-X (abbreviated as XR hereinafter), 5- or 6-carboxyrhodamine-6G (abbreviated as R6G hereinafter), 5- or 6-carboxyrhodamine-110 (abbreviated as R110 hereinafter), 5- or 6-carboxyfluorescein, 5- or 6-carboxy-2',7'- dichlorofluorescein, 5- or 6-carboxy-2',4',5',7'-tetrachlorofluorescein, 5- or 6-carboxy-4,7-dichloro-2',7'-dimethoxyfluorescein, 5- or 6-carboxy-4,7,4',5'-tetrachloro-2',7'-dimethoxyfluorescein, 5- or 6-carboxy-4',5'-dichloro-2',7'-dimethoxyfluorescein, 5- or 6-carboxy-4, A7-dichloro-1',2',7',8'-dibenzofluorescein, 5- or 6-carboxy-4,7-dichloro-1',2',7',8'-dibenzofluorescein and the like.

The 3'-deoxyribonucleotide derivatives of the present invention represented by general formula [I] can be synthesized easily, for example, according to the following synthesis schemes.

In the following synthesis schemes, $R_4$ represents a fluorescent dye group such as those mentioned above. Authorized nomenclatures for the abbreviations used in the following synthesis schemes are as follows.

CAN: cerium (IV) diammonium nitrate,

AcOH: acetic acid,

NPETFA: 5-trifluoroacetamido-1-pentyne,

NHETFA: 6-trifluoroacetamido-1-hexyne,

NOTFA: 8-trifluoroacetamido-1-octyne, $Et_3N$: triethylamine, $(Ph_3P)_4Pd$: tetrakis(triphenylphosphine) palladium (0), DMF: N, N-dimethylformamide, NHTfa: trifluoroacetamide $(EtO)_3PO$: triethyl phosphate, Tris(TBA)PP: tris(tri-n-butylammonium)pyrophosphate, TEAB: triethylammonium hydrogencarbonate buffer, TBDMSCl: tert-butyldimethylsilyl chloride, THF: tetrahydrofuran, TCDI: 1,1'-thiocarbonyldiimidazole, n-$Bu_3SnH$: tri-n-butyltin hydride, AIBN: 2,2'-azobis(isobutyronitrile), pyr.: pyridine, n-$BU_4NF$: tetrabutylammonium fluoride, $Ac_2O$: acetic anhydride, MeOH: methanol, NIS: N-iodosuccinimide, STC: 4-thiocresol, HMPA: hexamethylphosphoramide, MCPBA: m-chloroperbenzoic acid, $R_4$-OSU: succinimidyl ester of fluorescent dye group.

(1) Synthesis of fluorescence-labeled 3'-deoxyuridine 5'-triphosphates (compounds of the general formula [I] where V is —C≡C— and n=4)

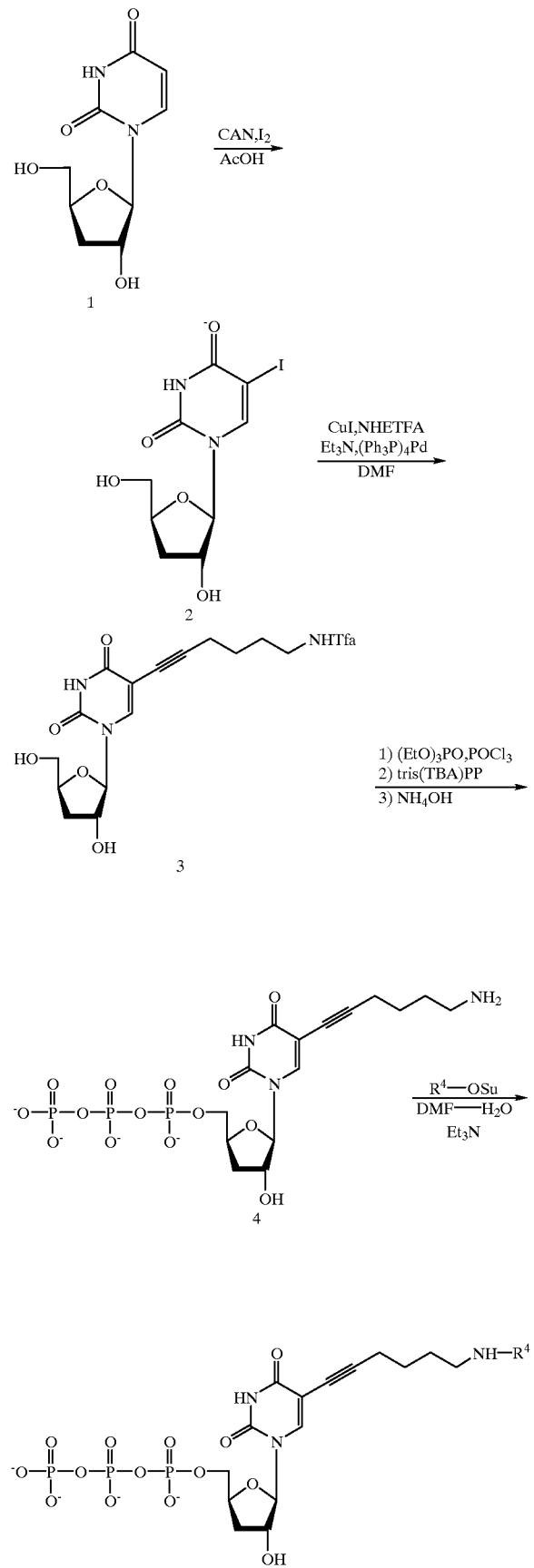

(2) Synthesis of fluorescence-labeled 3'-deoxycytidine 5'-triphosphates (compounds of the general formula [I] where V is —C≡C— and n=4)
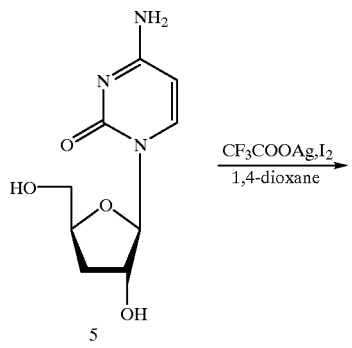
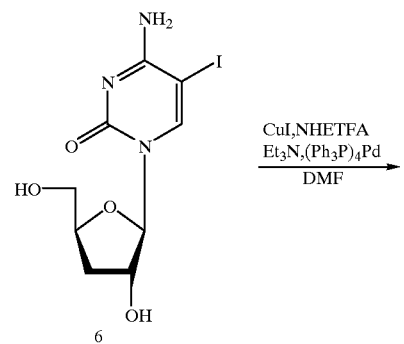
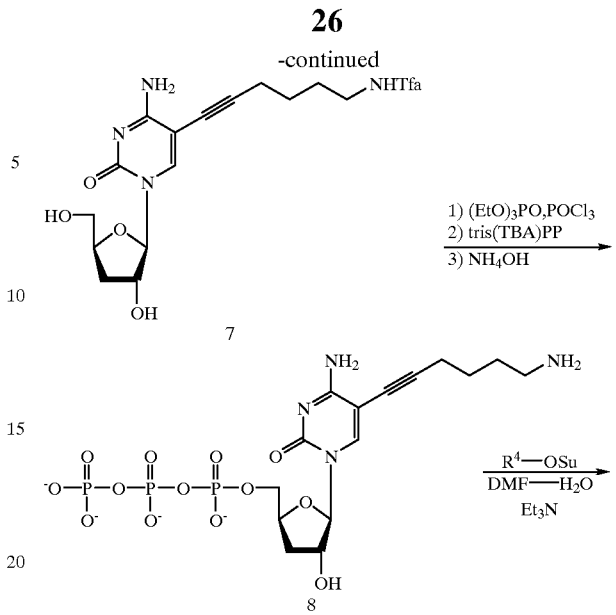
(3) Synthesis of fluorescence-labeled 3'-deoxycytidine 5'-triphosphates (compounds of the general formula [I] where V is —C≡C— and n=6)
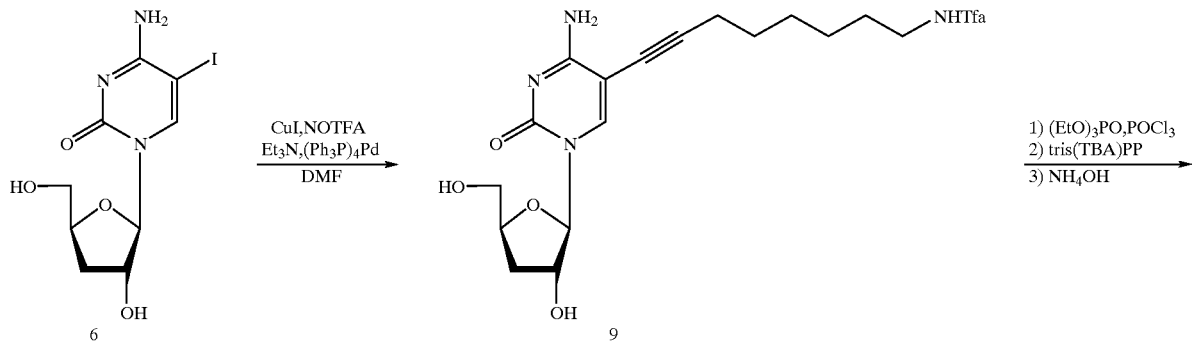

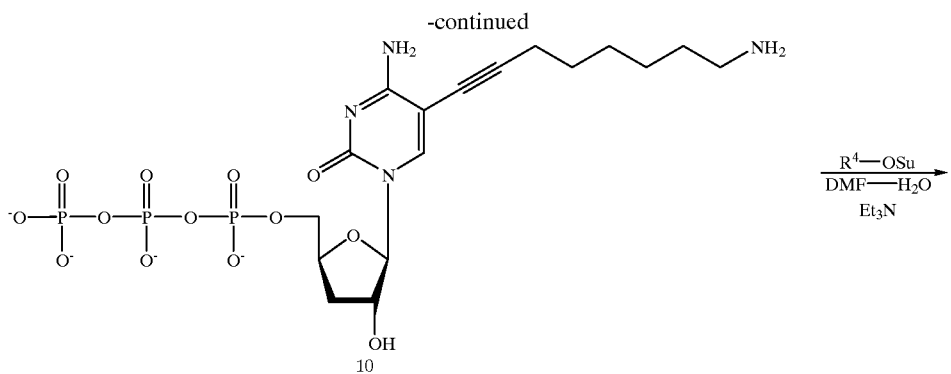
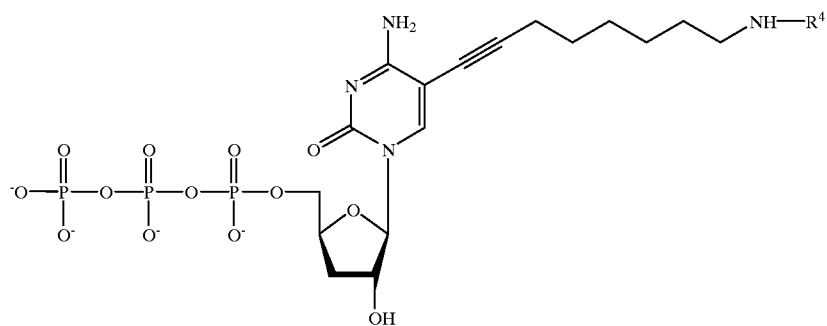
(4) Synthesis of fluorescence-labeled 7-deaza-3'-deoxyadenosine 5'-triphosphates (compounds of the general formula [1] where V is —C≡C— and n=4)
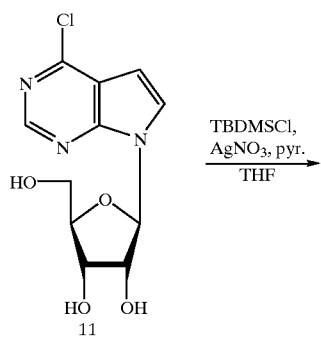
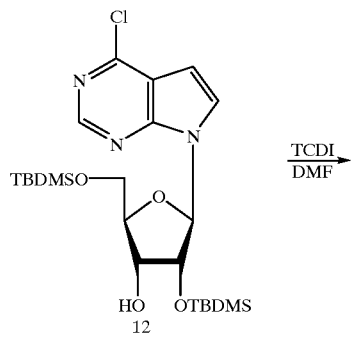
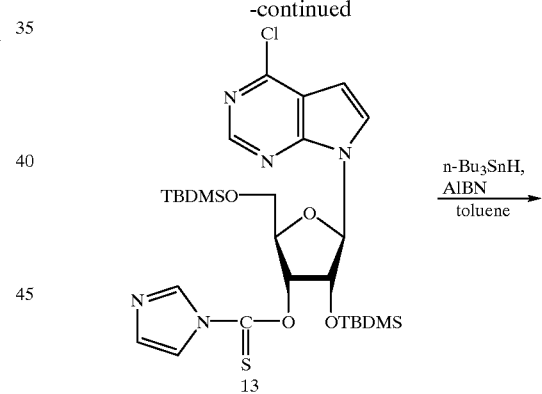
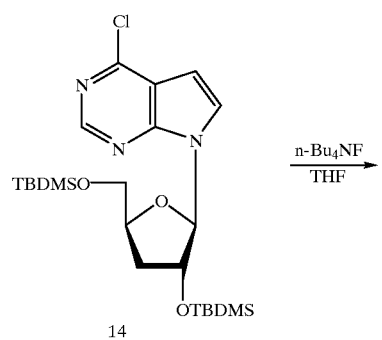

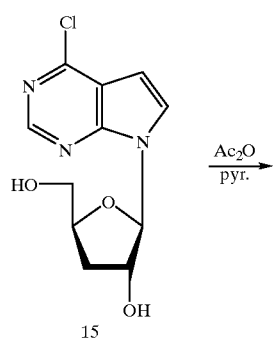
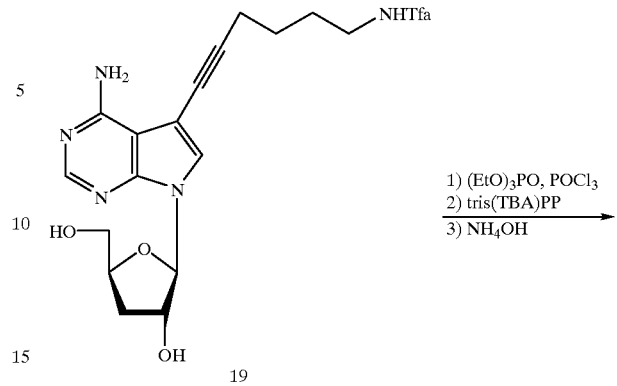
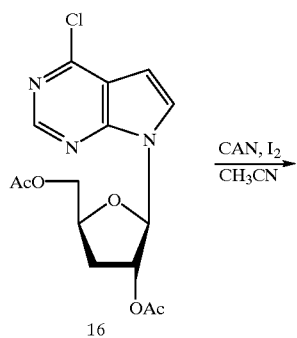
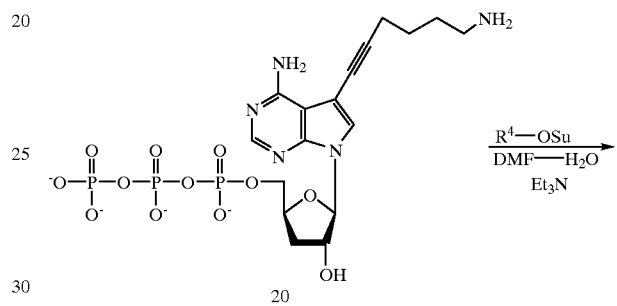
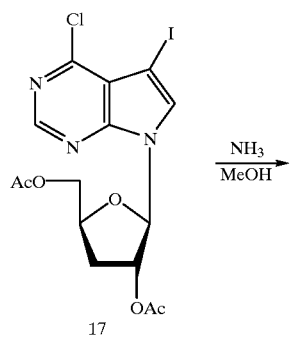
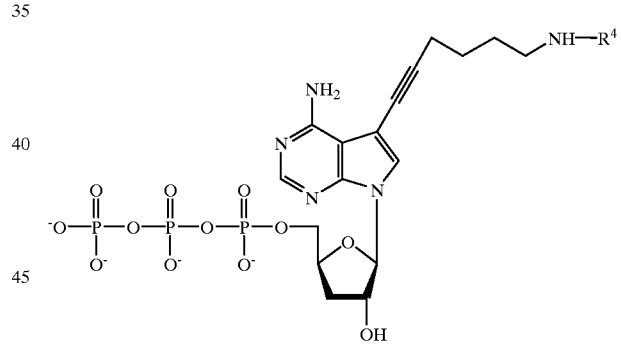
(5) Synthesis of fluorescence-labeled 7-deaza-3'-deoxyadenosine 5'-triphosphates (compounds of the general formula [I] where V is —C≡C— and n=6)
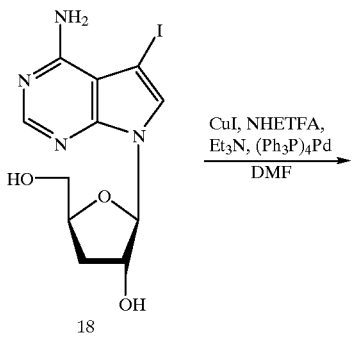
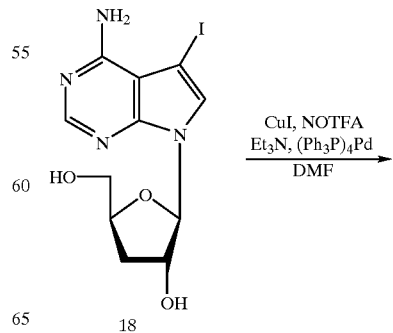

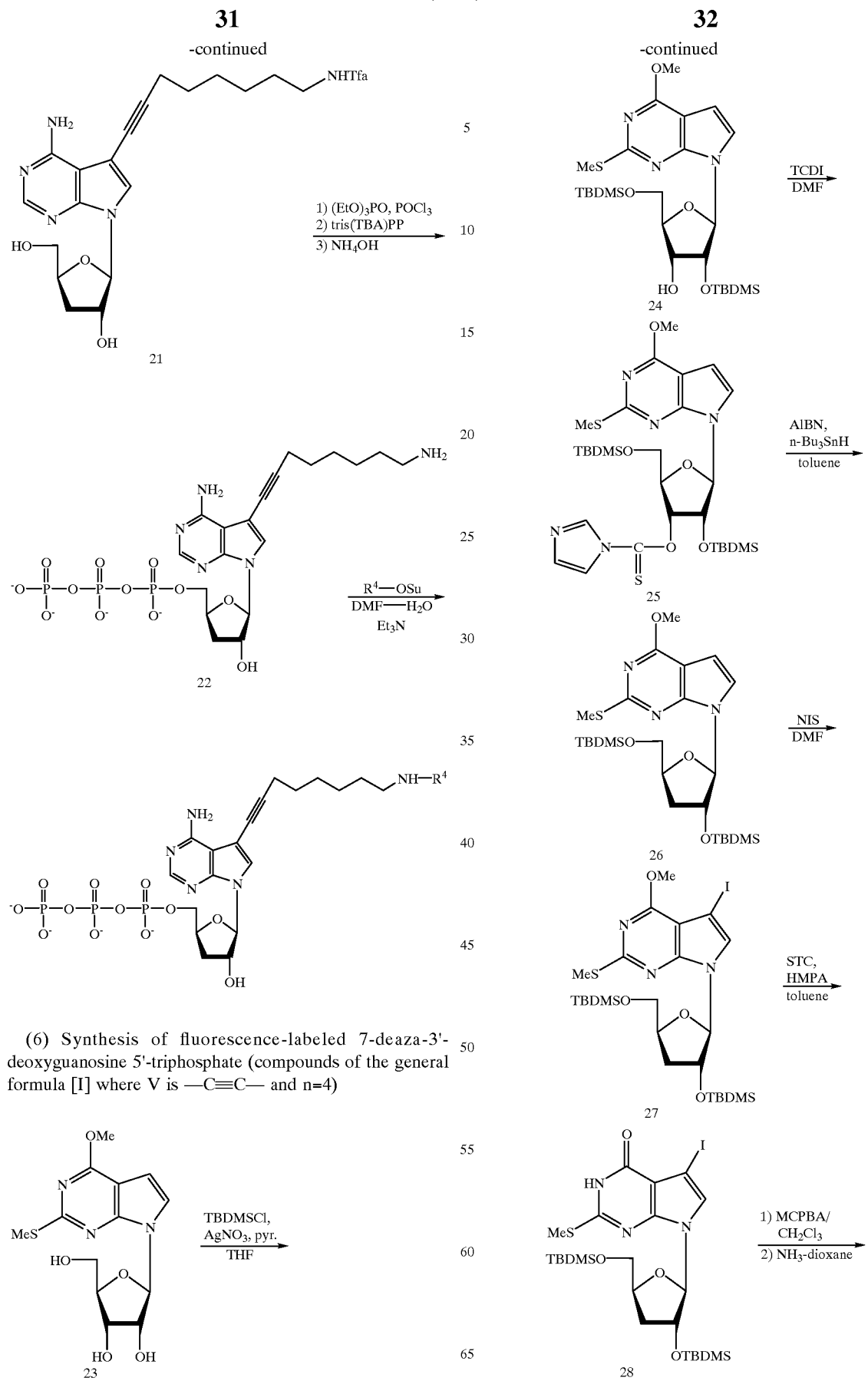
(6) Synthesis of fluorescence-labeled 7-deaza-3'-deoxyguanosine 5'-triphosphate (compounds of the general formula [I] where V is —C≡C— and n=4)

33
-continued
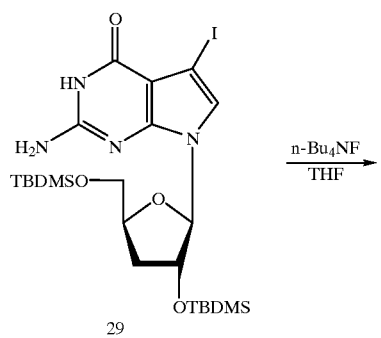
34
-continued
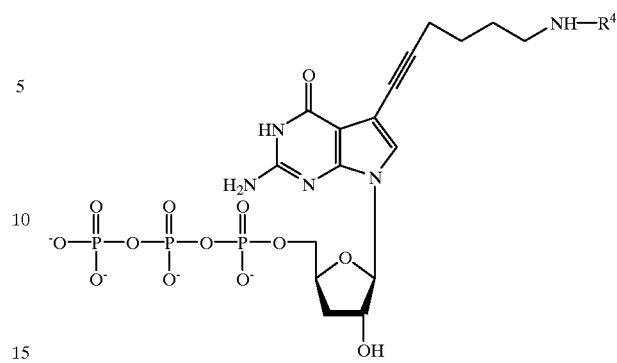
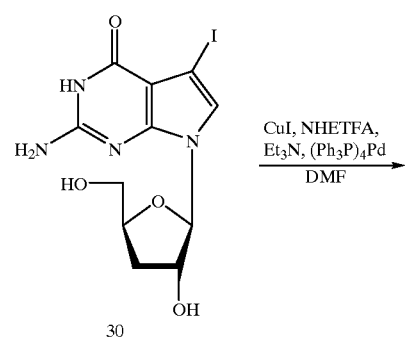
(7) Synthesis of fluorescence-labeled 3'-deoxyuridine 5'-triphosphates (comounds of the general formula [I] where V is —CH=CH— and n=4)
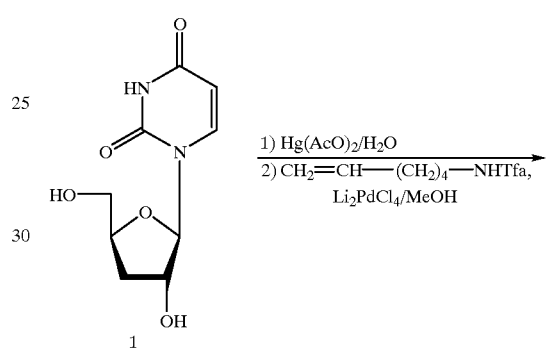
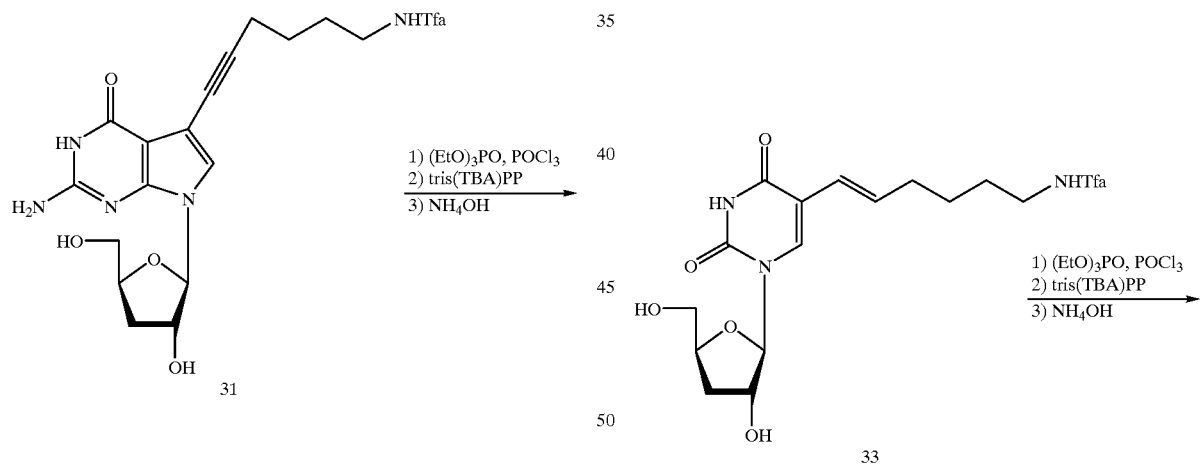
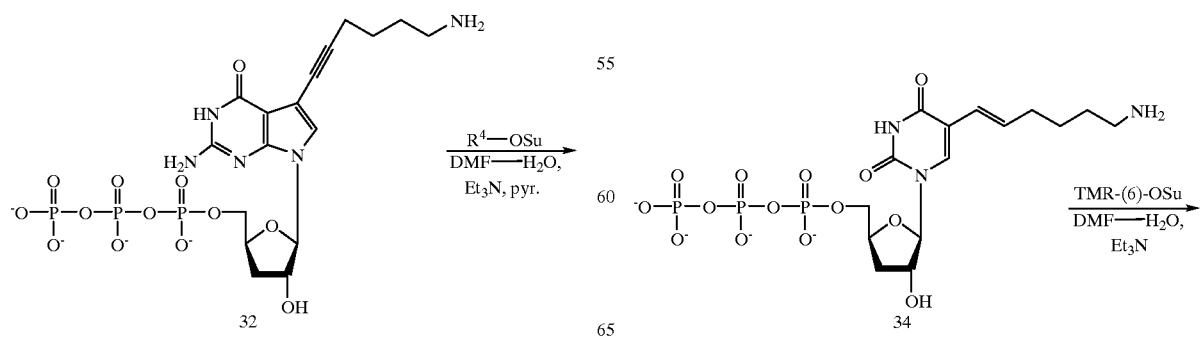

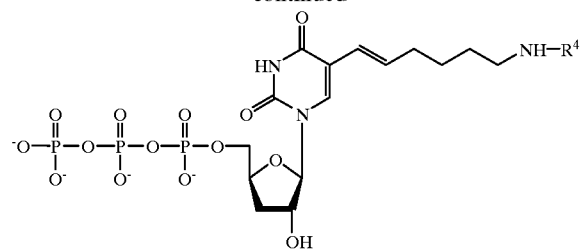

(8) Synthesis of fluorescence-labeled 3'-deoxyuridine 5'-triphosphates (compounds of the general formula [I] where V is —CH=CH— and n=4)

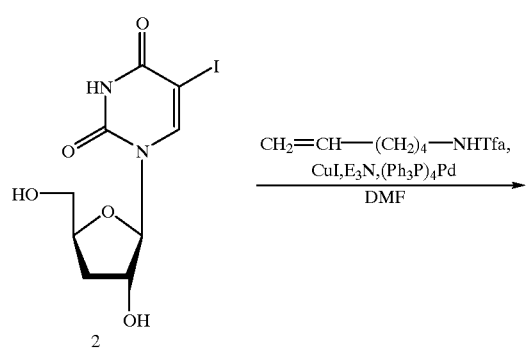

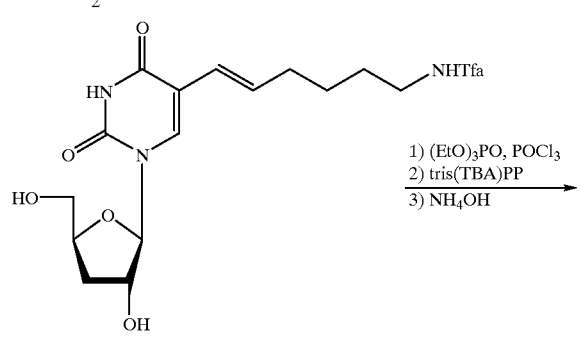

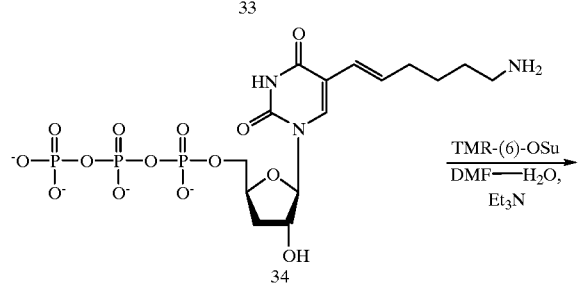

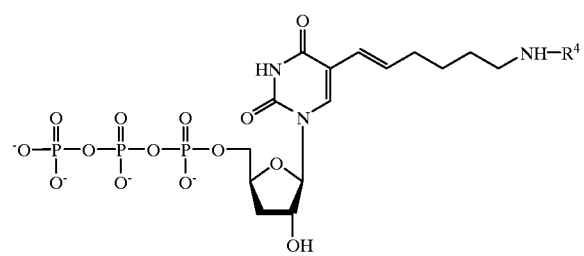

(9) Synthesis of fluorescence-labeled 7-deaza-3'-deoxycytidine 5'-triphosphates (compounds of the general formula [I] where V is —CH=CH— and n=4)

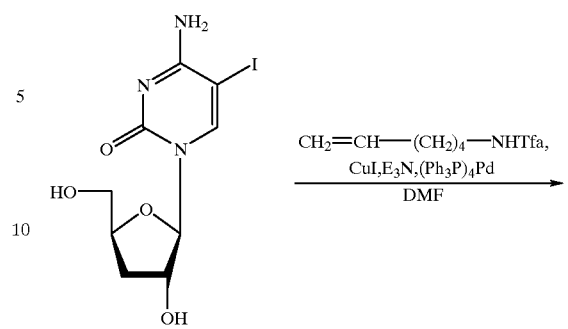

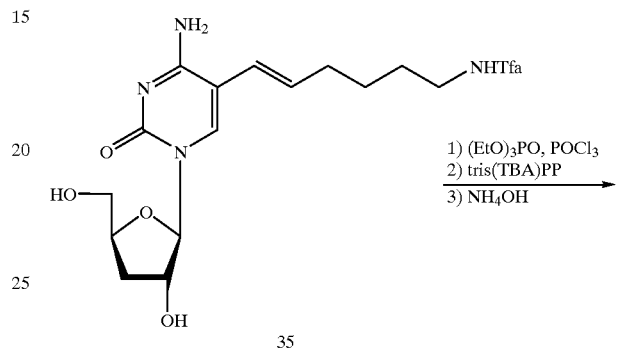

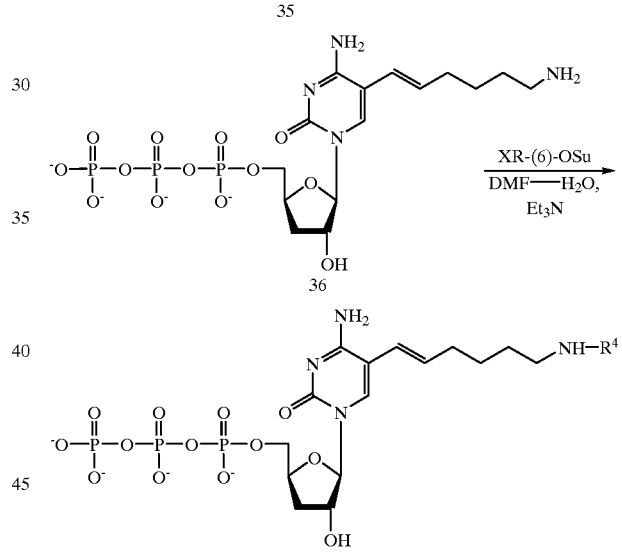

(10) Synthesis of fluorescence-labeled 7-deaza-3'-deoxyadenosine 5'-triphosphates (compounds of the general formula [I] where V is —CH=CH— and n=4)

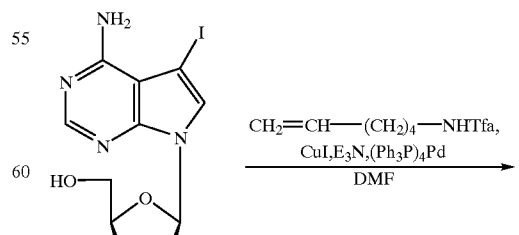

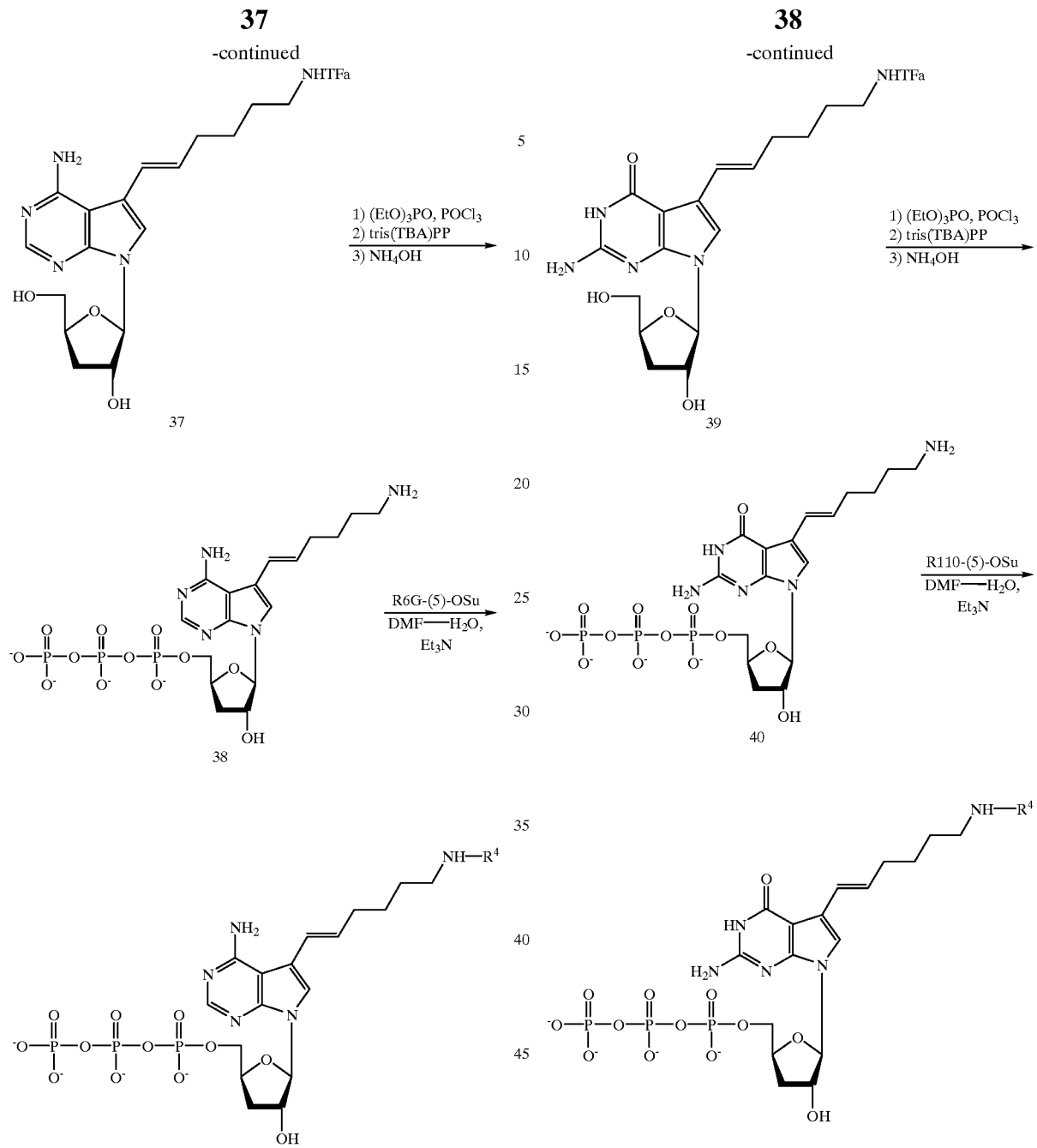

(11) Synthesis of fluorescence-labeled 7-deaza-3'-deoxyguanosine 5'-triphosphates (compounds of the general formula [I] where V is —CH=CH— and n=4)

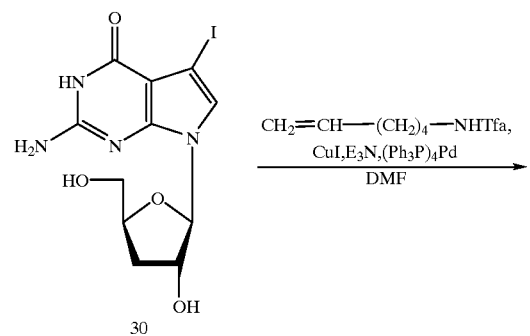

The 3'-deoxyribonucleotide derivatives of the present invention are extremely effective as RNA extension terminators for the DNA sequencing methods utilizing RNA polymerases and nucleotide sequences of DNA can be more surely determined by using them.

For example, a template DNA to be sequenced can be ligated to downstream of a promoter of an RNA polymerase, extension and termination reaction can be performed with the DNA in the presence of four ribonucleotides of adenine (A), guanine (G), cytosine (C), and uracil (U), and four 3'-deoxyribonucleotide derivatives modified with fluorescent dyes of the present invention, which correspond to the ribonucleotides, then the reaction products can be mixed and subjected to electrophoresis in one lane, and the fluorescence wavelength exited by laser can be spectrophotometrically detected to sequentially determine the DNA sequence.

The combination of a fluorescent dye and the four kinds of 3'-deoxyribonucleotide should be suitably selected, particularly when four kinds of sequences are determined in parallel in one lane, by considering difference of luminescence intensity of fluorescent dyes and difference of incorporation rate by an RNA polymerase due to the difference of the kind of bases of 3'-deoxyribonucleotides. That is, it is preferred to select such a combination that uniform intensity of fluorescence signals from each transcription product should be obtained for stable reading and highly accurate DNA sequencing.

The fluorescence intensities of the four kinds of fluorescent dyes used in the examples of the present invention, 5-carboxy-X-rhodamine succinimide ester (XR), 5-carboxyrhodamine 6G succinimide ester (R6G), 5-carboxytetramethylrhodamine succinimide ester (TMR), and 5-carboxyrhodamine 110-bis-trifluoroacetate succinimide ester (R110), when excited by argon laser at 488 nm and 514 nm, are in the order of R110, R6G>TMR>XR. The detection sensitivity is about 40 amol for R110 and R6G, about 400 amol for TMR, and about 800 amol for XR.

Further, incorporation rate of 3'-deoxyribonucleotides is different depending on the kind of RNA polymerase, and this should be considered for the selection of the combination. The incorporation rate of 3'-dNTP by T7 RNA polymerase was measured by using radioactive [$\alpha$-$^{32}$p]3'-dNTPs. As a result, it was in the order of 3'-dGTP>3'-dATP, 3'-dUTP>3'-dCTP.

Considering luminescence intensities of the above fluorescent dyes and incorporation rates by T7 RNA polymerase, the following combination and amounts of the fluorescent terminators were used in the examples of the present invention.

R6G-3'-dATP 1 $\mu$M
R110-3'-dGTP 1 $\mu$M
XR-3'-dCTP 50 $\mu$M
TMR-3'-dUTP 12.5 $\mu$M

Further, a combination of R6G-3'-dATP, R110-3'-dCTP, XR-3'-dGTP, and TMR-3'-dUTP in the following amounts affords uniform peak outputs.

R6G-3'-dATP 1 $\mu$M
R110-3'-dCTP 10 $\mu$M
XR-3'-dGTP 5 $\mu$M
TMR-3'-dUTP 12.5 $\mu$M

Preferred examples of the combinations of fluorescent dyes and the four kinds of 3'-deoxyribonucleotides for utilizing T7 RNA polymerase and mutants thereof are shown below. However, these are only for exemplification, and preferred combinations may be changed when the fluorescent dyes are changed.

Examples of combination of fluorescent dyes and bases
R6G-3'-dCTP, R110-3'-dATP, XR-3'-dUTP, and TMR-3'-dGTP;
R6G-3'-dATP, R110-3'-dCTP, XR-3'-dUTP, and TMR-3'-dGTP;
R6G-3'-dCTP, R110-3'-dUTP, XR-3'-dATP, and TMR-3'-dGTP;
R6G-3'-dUTP, R110-3'-dCTP, XR-3'-dATP, and TMR-3'-dGTP.

Nucleic Acid Transcription Reaction in the Presence of Inorganic Pyrophosphatase In the method of the present invention, it is preferred that the nucleic acid transcription reaction is performed in the presence of inorganic pyrophosphatase, because, by doing so, the difference of peak altitudes (intensities of signals) corresponding to each labeled ribonucleotide is reduced, thereby precision of sequence determination is improved and it becomes possible to obtain more accurate sequence data.

Pyrophosphorolysis occurs due to increase of pyrophosphate produced by DNA synthesis, and it acts to promote the reaction so that the resulting DNA product should be decomposed. As a consequence, the pyrophosphorolysis inhibits the sequencing in the dideoxy sequencing method utilizing a DNA polymerase. As for this fact, it has been known that, when an inorganic pyrophosphatase is used in the dideoxy sequencing method utilizing a DNA polymerase, it inhibits the pyrophosphorolysis and thus affords stable sequencing data [Japanese Patent Unexamined Publication (KOKAI) No. Hei 4-506002/1992].

However, it has not been known what kind of effect is exerted by the pyrophosphorolysis in the sequencing method utilizing an RNA polymerase. As a result of the present inventors' investigation, it was found that more stable sequence data can be obtained by performing the nucleic acid transcription reaction in the presence of inorganic pyrophosphatase in the aforementioned method of the present invention.

Inorganic pyrophosphatase (EC.3.6.1.1) is commercially available, and for example, it is sold by Sigma as INORGANIC PYROPHOSPHATASE and by Boehringer as Pyrophosphatase. While the amount of inorganic pyrophosphatase to be used may depends on the degrees of activities of inorganic pyrophosphatase and RNA polymerase, it is suitably in the range of $10^{-6}$ to $10^{-2}$ units for 1 unit of RNA polymerase.

A DNA sequence used as a template of the transcription can be determined from an RNA or nucleic acid sequence determined as described above. When a ladder is formed for each nucleotide, RNA or nucleic acid sequence information provided from four kinds of ladders can be integrated to determine the DNA sequence used as a template of transcription. When ladders are simultaneously formed for two or more kinds of nucleotides (when bands for two or more kinds of nucleotides are present in the same ladder), RNA or nucleic acid sequence information provided from the ladders can be integrated to determine the DNA sequence used as a template of transcription. In particular, when a ladder is formed simultaneously for four kinds of nucleotides (when bands for four kinds of nucleotides are present in the same ladder), the DNA sequence used as a template of transcription can be determined from RNA or nucleic acid sequence information provided from one ladder.

The sequencing method of the present invention can be utilized in various kits.

According to the present invention, the bias of incorporation abilities for ribonucleotides and the like, for example, the fact that 3'-deoxyribonucleotides are more unlikely to be incorporated into a polyribonucleotide sequence compared with corresponding ribonucleotides, and the fact that incorporation is fluctuated among ribonucleotides and among 3'-deoxyribonucleotides depending on the kind of the base groups, can be eliminated and thereby a method for determining DNA nucleotide sequences capable of affording more stable sequence data can be provided.

Considering the high processibility of RNA polymerases, the sequence determination method of the present invention would allow nucleotide sequence determination superior to that obtained by a nucleotide sequence determination method utilizing a DNA polymerase.

In particular, according to the method of the present invention, a DNA sequence of PCR product as it is can be determined without purifying the PCR product. This can be realized by the characteristic of RNA polymerases that remaining 2'-dNTPs in a reaction mixture is not consumed as a reactant in the presence of 3'-dNTP for sequencing.

Further, because the method of the present invention utilizes transcription reaction of RNA, it does not require use of a single-stranded template DNA nor primers as usual DNA sequencing methods, and it also does not require any denaturation step for hybridization of sequencing primers. Therefore, it is not affected by the renaturation of the PCR product, and DNA sequences can be easily determined.

Moreover, by using a thermostable mutant RNA polymerase as RNA polymerase, the method for determining DNA sequence of the present invention can be used for a step utilizing PCR, and as a result, it makes it possible to more rapidly determine DNA sequences.

EXAMPLES

The present invention will be explained more in detail with reference to the following examples.

Reference Example 1
Cloning of Wild Type T7 RNA Polymerase Gene and Construction of Expression Plasmid T7 phage harbored in *E. coli* was prepared as follows. *E. coli* strain C600 was inoculated in 200 ml of LB culture medium (culture medium prepared by dissolving Bacto tryptone 10 g, Bacto yeast extract 5 g, and NaCl 5 g in 1 liter of water, which was adjusted to pH 7.5, and sterilized in an autoclave). When the cell density reached OD (600 nm)=1.0, the cells were infected with the phage at a multiplicity of infection of about 2. The OD was determined periodically, and when the OD was sharply decreased, the cell residue was removed by centrifugation. The medium was added with NaCl and polyethylene glycol 6000 to final concentrations of 0.5 M and 10% respectively, stirred sufficiently, and left stand overnight to form precipitates. The precipitates were collected by centrifugation, and suspended in SM buffer (10 mM Tris-HCl, pH 7.5, 10 mM $MgSO_4$, 50 mM NaCl, 0.01% gelatin). This T7 phage concentrate was overlaid on CsCl solution layers carefully overlaid in a centrifugation tube (CsCl solutions having concentrations of 1.267 g/ml, 0.817 g/ml, and 0.705 g/ml from the bottom layer), and centrifuged at 22,000 rpm for 2 hours to form a phage layer. A white band of the phage was carefully separated, and dialyzed against TE buffer (10 mM Tris-HCl, pH 7.5, 1 mM EDTA) to remove the CsCl. This phage solution was treated with phenol to denature phage protein to purify genomic DNA of T7 phage.

Figure 9:
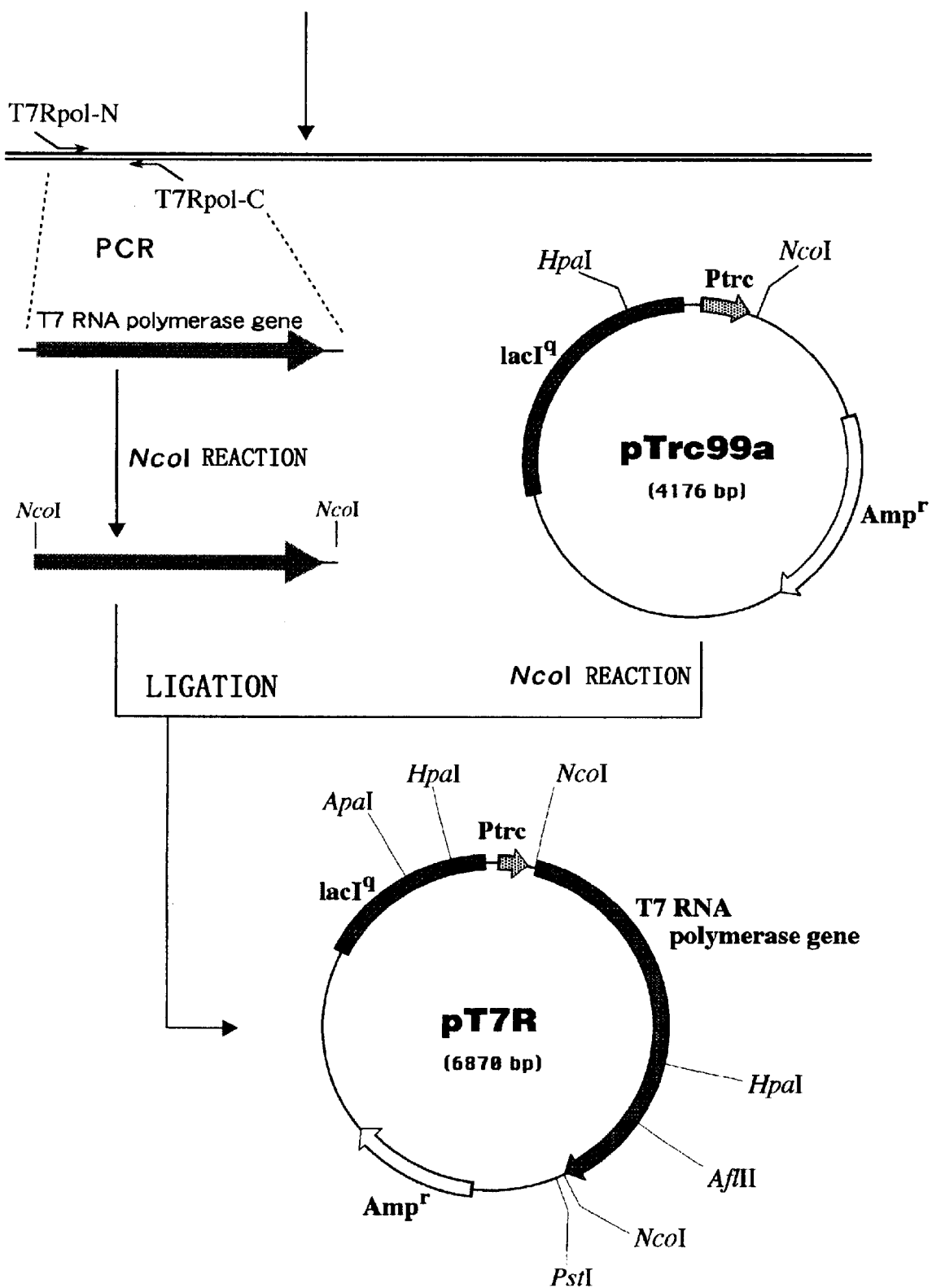
FIG. 9 shows a construction map of pT7R, a plasmid expressing wild type T7 RNA polymerase.

The T7 RNA polymerase gene corresponds to the 3171st–5822nd base pairs in the 39,937 base pairs of the genome DNA [the total nucleotide sequence of T7 genomic gene had already been reported by Dunn et al. (1983, J. Mol. Biol., 166(4):477–535), but it was slightly corrected (see T7 phage DNA sequence of GeneBank, accession No. V01148 J02518 X00411)]. This genomic DNA was used for PCR as a template, and cloned into an expression vector as follows (see FIG. 9). That is, the gene encoding the enzyme was amplified by PCR by using a primer specific for upstream of the N-terminus amino acid region of T7 RNA polymerase gene [SEQ ID NO: 1] (T7Rpol-N 5'-ATA TTT TAG CCA TGG AGG ATT GAT ATA TGA ACA CGA TTA ACA TCG CTA AG-3') and a primer specific for downstream of the C-terminus amino acid region of T7 RNA polymerase gene [SEQ ID NO: 2] (T7Rpol-C 5'-ATA TTT TAG CCA TGG TAT AGT GAG TCG TAT TGA TTT GGC G-3'), each containing NcoI restriction site at the 5'-end. This DNA fragment was digested with NcoI, and separated by electrophoresis on 1% agarose gel, and the band of the objective DNA fragment was cut out from the agarose, and purified by using Gene Pure Kit (Nippon Gene). The DNA fragment was ligated to an expression vector pTrc99a (Pharmacia Biotech) which had been digested with NcoI and dephosphorylated to construct pT7R which expressed T7 RNA polymerase at high level. The plasmid pT7R expressing wild type T7 RNA polymerase was transformed into *E. coli* DH5, and the cells resistant to antibiotic ampicillin was cultured. The Trc promoter contained in the expression vector pT7R was driven by adding IPTG to the culture medium. Two hours after the addition of IPTG, the *E. coli* cells were collected, and the total protein was analyzed by SDS-polyacrylamide gel electrophoresis. As a result, a protein band was detected at a location corresponding to about 99 kDa, which is the molecular weight of T7 RNA polymerase, only when IPTG was added. This protein was further purified by a partially modified version of the previously described method of Zawadzki, V et al. 1991, Nucl. Acids Res., 19:1948 (details may be substantially the same as those of the method for purifying mutant T7 RNA polymerase exemplified in Reference Example 3), and found to have RNA polymerase activity which was exerted in a T7 promoter specific manner.

Figure 10:
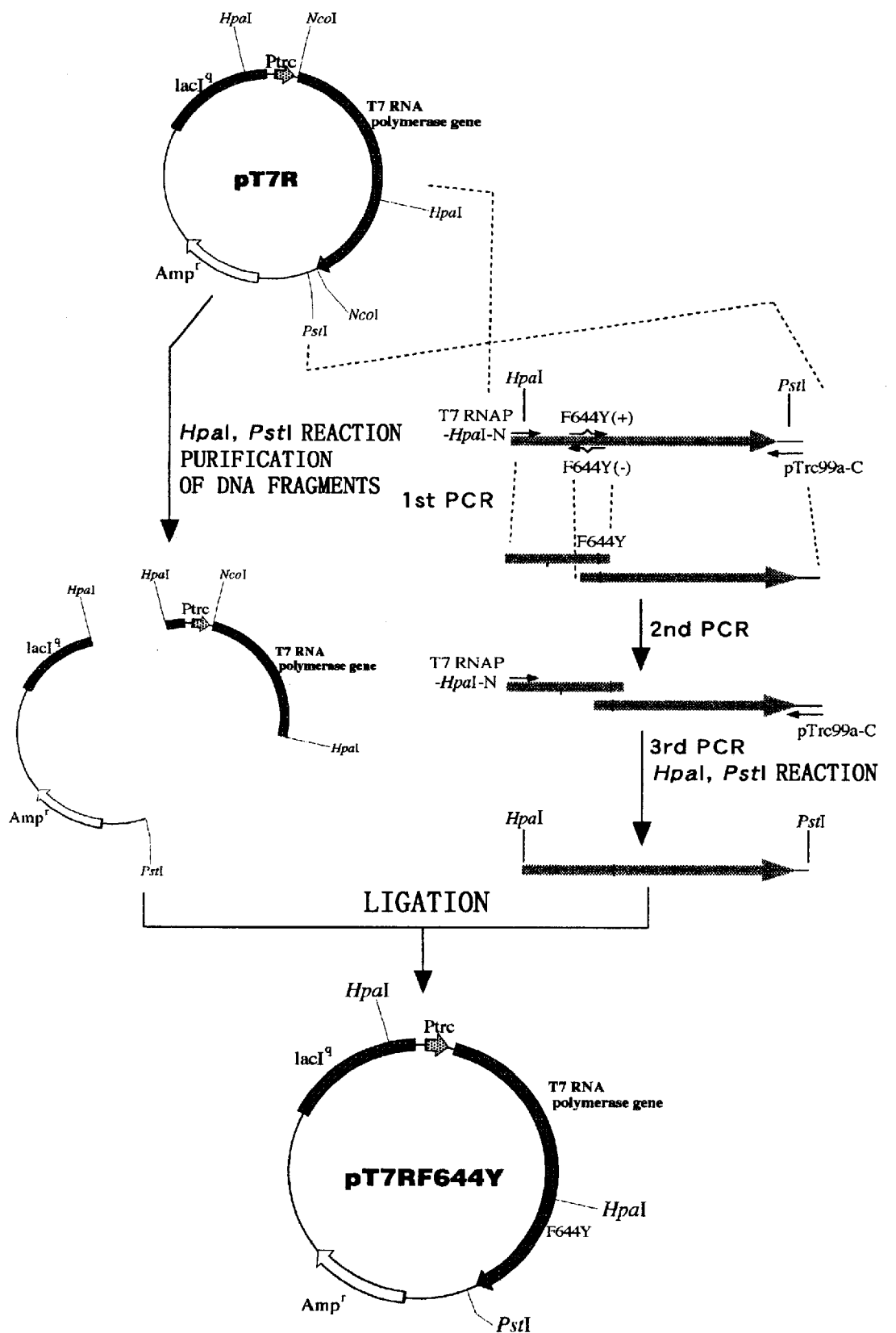
FIG. 10 shows a construction map of pT7RF644Y, a plasmid expressing a mutant T7 RNA polymerase F644Y.

Reference Example 2
Construction of Expression Plasmid for Producing Mutant T7 RNA Polymerases
(1) Construction of Expression Plasmid for Producing Mutant T7 RNA Polymerase F644Y (See FIG. 10)

By using pT7R inserted with the wild type T7 RNA polymerase gene as a template, mutation was introduced by PCR into the region between the HpaI and NcoI restriction sites corresponding to the C-terminus side of the T7 RNA polymerase gene. More precisely, the region was divided into two fragments on the left side and right side of the nucleotide to be mutated, and these DNA fragments were amplified by PCR using primers F646Y(+) (5'-GTT GAC GGA AGC CGT ACT CTT TGG AC-3') introduced with a mutation and F646Y(−) (5'-GTC CAA AGA GTA CGG CTT CCG TCA AC-3'), and primers [SEQ ID NOS.:5–6] T7RNAP-HpaI-N (5'-CGC GCG GTT AAC TTG CTT CCT AG-3') and pTrc99a-PstI-C (5'-GCA TGC CTG CAG GTC GAC TCT AG-3'), each containing a restriction cleavage site at the 5'-end. These DNA fragments had complementary regions, and denaturation, annealing and extension reactions of the regions were repeated to prepare a DNA fragment introduced with the desired mutation. This DNA fragment was purified by collecting only a DNA fragment of a desired size through agarose gel electrophoresis, and this was re-amplified by using it as a template together with the primers T7RNAP-HpaI-N and pTrc99a-PstI-C, and cleaved with restriction endonuclease HpaI and PstI. This DNA fragment was separated by 1% agarose gel electrophoresis, and the band of the desired DNA fragment was cut out, and purified. The HpaI-PstI DNA fragment of pT7R was replaced with this DNA fragment to introduce a mutation. The resulting pT7R was transformed into *E. coli* DH5 α, and cells harboring the plasmid introduced with the mutation were selected. Finally, the nucleotide sequence was determined to confirm whether the mutation was introduced into the desired site. Thus, the expression plasmid pT7RF644Y for producing mutant T7 RNA polymerase F644Y was obtained. For the production of the mutant T7 RNA polymerase F644Y from this plasmid, expression could be induced by adding IPTG to the cultured *E. coli* cells harboring the plasmid, like the production of wild type T7 RNA polymerase.

Figure 11:
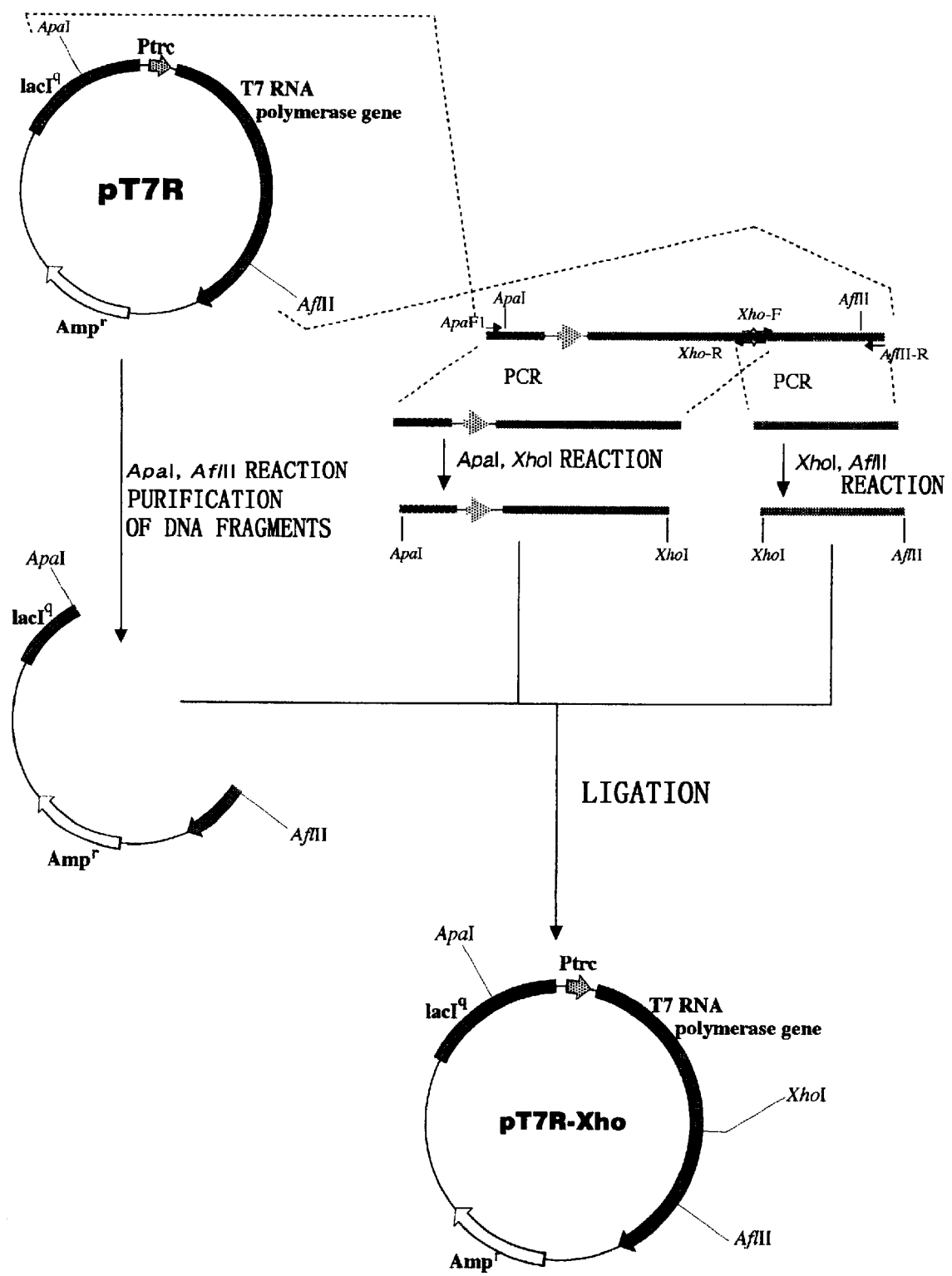
FIG. 11 shows a construction map of an improved version of plasmid pT7R, pT7R-Xho, having a restriction endonuclease XhoI site in the T7 RNA polymerase gene.
Figure 12:
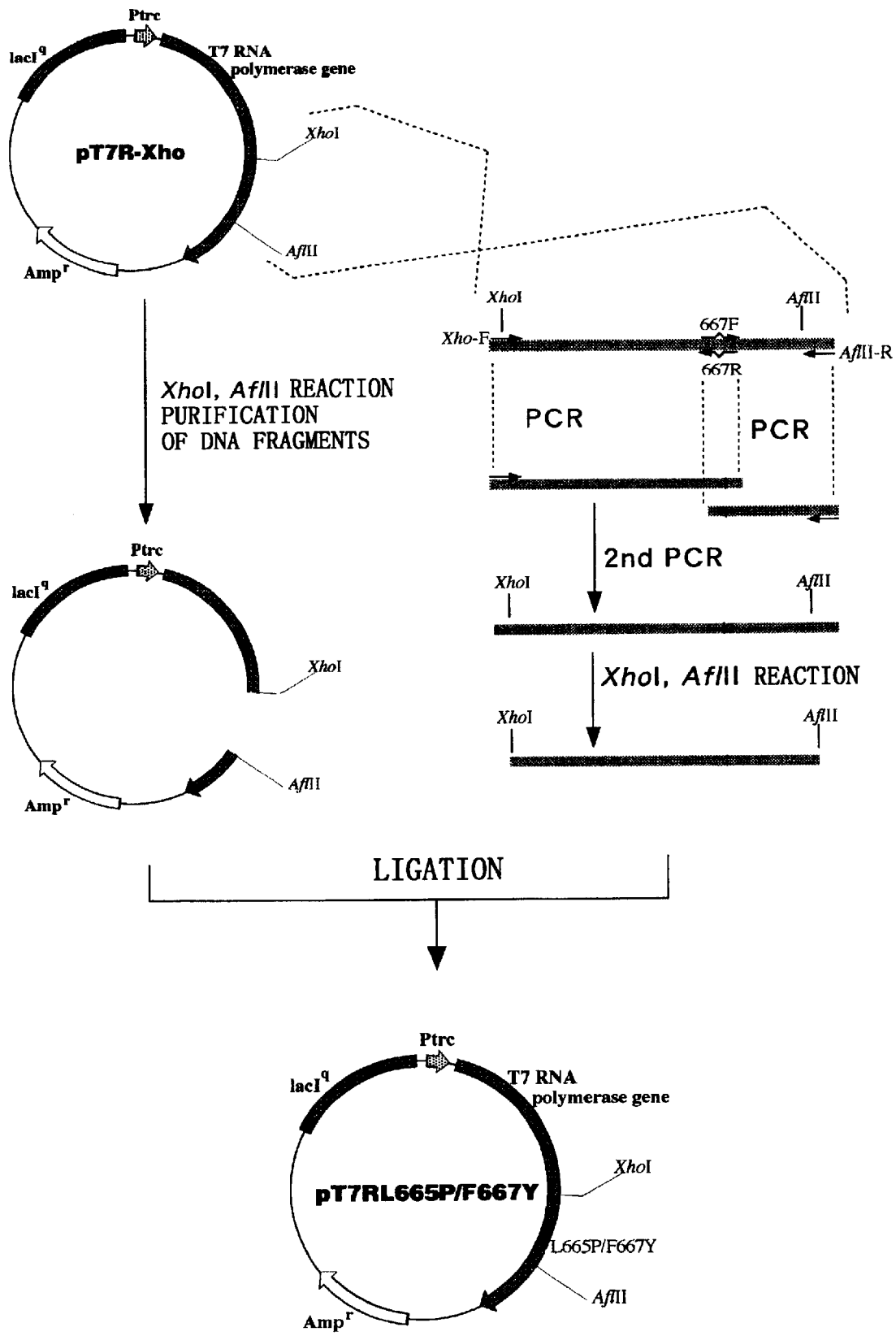
FIG. 12 shows a construction map of pT7RL665P/F667Y, a plasmid expressing a mutant T7RNA polymerase L665P/F667Y.

(2) Construction of Expression Plasmid for Producing Mutant T7 RNA Polymerase L665P/F677Y (See FIGS. 11 and 12)

The construction of mutant T7 RNA polymerase L665P/F667Y was performed as follows based on PCR technique as in the construction of the F644Y mentioned above.

First, a XhoI restriction site (CTCGAG) was introduced into the T7 RNA polymerase gene region of the expression vector pT7R having the wild type T7 RNA polymerase gene to facilitate the introduction of mutation. More specifically, the expression vector pT7R used as template was amplified by using a primer [SEQ ID NO.: 7] pair of primer ApaF1 (5'-CAT CTG GTC GCA TTG GGT CAC-3') and primer [SEQ ID NO.: 8] Xho-R (5'-CCA AGT GTT CTC GAG TGG AGA-3'), and a primer pair of a primer [SEQ ID NO.: 9] Xho-F (5'-CTA AGT CTC CAC TCGAGA ACA CTT GG-3') and a primer [SEQ ID NO.: 10] AflII-R (5'-CAG CCA GCA GCT TAG CAG CAG-3'), respectively. The former amplified DNA fragment was digested with restriction endonucleases ApaI and XhoI, and the latter amplified DNA fragment with restriction endonucleases AflII and XhoI, and they were ligated to the expression vector pT7R preliminarily treated with ApaI and AflII by using T4 DNA ligase. This reaction product was transformed into *E. coli* DH5 α, and several colonies grown on an agar plate containing antibiotic ampicillin were obtained. Some of these colonies were selected and cultured, and plasmid DNA was extracted from the cultured cells to obtain plasmid pT7R-Xho in which a XhoI restriction site was introduced in the T7 RNA polymerase gene region (see FIG. 11). Presence of this XhoI site can be confirmed by cleavage by a treatment with the restriction endonuclease XhoI, and nucleotide sequencing of the DNA. Using this plasmid pT7R-Xho as a template, PCR was performed with a primer pair of primer Xho-R and primer 667R (5'-GCT GAG TGT ACA TCG GAC CCT-3'), and a primer pair of a primer 667F (5'of -GCT GAG TGT ACA TCG GAC CCT-3') and a primer AflIIR. The PCR products were directly used as templates for the nucleotide sequencing of the DNA to determine the sequences of the primers 667R and 667F. Then, they were subjected to electrophoresis on 2% agarose gel (Agarose X from Nippon Gene was used as the agarose) respectively, and bands corresponding to DNA fragments of the desired sizes were cut out to purify the DNA fragments by using Gene Pure Kit. The purified two kinds of DNA fragments were mixed, and used as templates for PCR using the primers XhoF and AflIIR. After confirming that the amplified DNA fragment was the desired fragment by restriction mapping and DNA sequencing, the fragment was digested with restriction endonucleases XhoI and AflII, and the resulting fragment was ligated to the plasmid pT7R-Xho preliminarily treated with restriction endonucleases XhoI and AflII by using T4 DNA ligase. This reaction product was transformed into *E. coli* DH5 α, and several colonies of the cells grown on an agar plate containing antibiotic ampicillin were obtained. Some of these colonies were selected and cultured, and plasmid DNA was extracted from the cultured cells. The plasmid DNA was confirmed if it was introduced with the desired mutation by DNA sequencing to finally construct an expression plasmid pT7RL665P/F667Y for producing the mutant T7 RNA polymerase L665P/F667Y (see FIG. 12). For the production of the mutant T7 RNA polymerase L665P/F667Y from this plasmid, expression could be induced by adding IPTG to the cultured *E. coli* cells harboring the plasmid, like the production of wild type T7 RNA polymerase.

Reference Example 3
Purification of Mutant T7 RNA Polymerases

Mutant T7 RNA polymerase proteins introduced into *E. coli* were purified.

Wild types of this protein have already been described in Chamberlin, M et al. Nature, 228:227–231(1970), Davanloo et al., Proc. Natl. Acad. Sci. USA., 81:2035–2039 (1984). Its large scale production has also been reported by Zawadzki, V et al., Nucl. Acids Res., 19:1948 (1991).

All of the mutant T7 RNA polymerases can be purified by principally the same method. The difference of mutation site may cause some difference in the expression level, and behavior in column chromatography. The purification method of mutant T7 RNA polymerase F644Y is exemplified hereinafter. The expression vector pT7RF644Y for F644Y was introduced into *E. coli* DH5 α, and the cells were cultured in a test tube containing LB culture medium containing antibiotic ampicillin. When the OD (600 nm) of the medium reached 0.4–0.6, isopropyl-β-thiogalactopyranoside (IPTG) was added to the culture to a final concentration of 0.4 mM, and the cultivation was further continued for additional 8 hours. Then, the *E. coli* cells were collected by centrifugation. Typically, 2 liters of culture medium affords 10 g of *E. coli* cells in wet weight. If the *E. coli* cells are not used immediately, they can be stored in a refrigerator at –20° C. or lower.

Subsequent steps for purification of enzyme should be performed at a temperature lower than room temperature, preferably 0–5° C. unless otherwise indicated. The *E. coli* cells were washed with 10 times relative to the cell weight of a washing buffer (20 mM Tris-HCl, pH 8.1, 130 mM NaCl, 2 mM EDTANa$_2$ at 25° C.), centrifuged again (5,000× g, 4° C., 10 minutes), suspended in 10 times in volume of a sonication buffer [50 mM Tris-HCl, pH 8.1, 100 mM NaCl, 0.1 mM EDTANa$_2$, 5 mM dithiothreitol (DTT), 0.1 mM benzamidine, 30 μg/ml phenylmethylsulfonyl fluoride (PMSF), 10 μg/ml bacitracin], and sonicated by using Sonifier 450 (Branson) at 80W for more than 15 minutes to destroy the cells and reduce the viscosity of the cells. Then, the cell suspension is centrifuged at 12,000×g and 4° C. for ten minutes to remove the cell debris. 10% streptomycin sulfate was slowly added dropwise to the resulting supernatant to a final concentration of 2.0% with stirring, and stirring was further continued for 30 minutes. The supernatant was centrifuged at 12,000×g and 4° C. for ten minutes to remove precipitates, and slowly added with ammonium sulfate powder with stirring to form precipitates. In this case, precipitates were first collected by 30% saturation of ammonium sulfate (30% ammonium sulfate precipitation), and the resulting supernatant was further added with ammonium sulfate to 60% saturation with stirring to form precipitates again (30–60% ammonium sulfate precipitation). The supernatant was added again with ammonium sulfate powder to 90% ammonium sulfate saturation, and stirred at 4° C. for 1 hour, and the precipitates were collected by centrifugation. Aliquots of these three ammonium sulfate fractions were analyzed for proteins by SDS-acrylamide gel electrophoresis, and it was found that most of the objective mutant T7 RNA polymerase was present in the 30–60% ammonium sulfate fraction. Therefore, purification was performed hereafter by using this fraction. The.30'60% ammonium sulfate fraction was suspended in a small amount of column buffer (20 mM KPO$_4$, pH 7.7, 100 mM NaCl, 1 mM DTT, 30 μg/ml PMSF), and desalted by dialysis against 500 ml of the same buffer for 16hours. The dialysate was applied on a heparin-Sepharose column of 5 ml volume (Pharmacia Biotech). Subsequently, the column was washed with the same buffer until any material absorbing ultraviolet ray at 280 nm disappeared, and eluted with a linear gradient of 0.1

M to 0.64 M NaCl in the same buffer of about 40 times volume of the column volume. The eluent was collected in test tubes as fractions of a suitable volume, and immediately subjected to SDS-acrylamide gel electrophoresis for protein analysis to identify fractions containing proteins around a molecular weight considered to be of the objective T7 RNA polymerase. In typical examples, it should be found around 0.4 M NaCl. The fractions containing the protein were collected, and desalted by dialysis against about 1 liter of the column buffer (20 mM $KPO_4$, pH 7.7, 100 mM NaCl, 1 mM DTT, 30 µg/ml PMSF) for 16 hours. The fractions desalted by dialysis were applied to a Q-Sepharose column (Pharmacia Biotech) of 5 ml volume that preliminarily equilibrated with the same buffer, and the column was washed with the same buffer until any material absorbing ultraviolet ray at 280 nm disappeared, and eluted with a linear gradient of 0.1 M to 0.64 M NaCl in the same buffer of about 40 times volume of the column volume. The eluent was collected in test tubes as fractions of a suitable volume, and immediately subjected to SDS-acrylamide gel electrophoresis for protein analysis to identify fractions containing proteins around a molecular weight considered to be of the objective T7 RNA polymerase. In typical examples, it should be found around 0.24 M NaCl. The fractions containing the protein were collected, dialyzed against 500 ml of storage buffer (50% glycerol, 20 mM $KPO_4$, pH 7.7, 100 mM NaCl, 1 mM DTT, 30 µg/ml PMSF) for 16 hours, and stored at −20° C. until use. In vitro RNA synthesis activity and activity of the contaminated ribonuclease of this sample were examined. The in vitro RNA synthesis activity was examined by, for example, performing RNA synthesis reaction according to the enzyme dilution method by using the plasmid containing T7 promoter as a template and a commercially available wild type T7 RNA polymerase (BRL, Gibco) as a standard, and subjecting the synthesized RNA to agarose gel electrophoresis to estimate approximate titer. In this case, because degree of decomposition of RNA is also determined, simple assay for contaminated ribonuclease can simultaneously be performed. As a typical example, 2,500,000 units of the mutant T7 RNA polymerase F644Y protein was purified from 1 liter of culture medium using the above-described steps, and this preparation was substantially free from RNase contamination.

Figure 13:
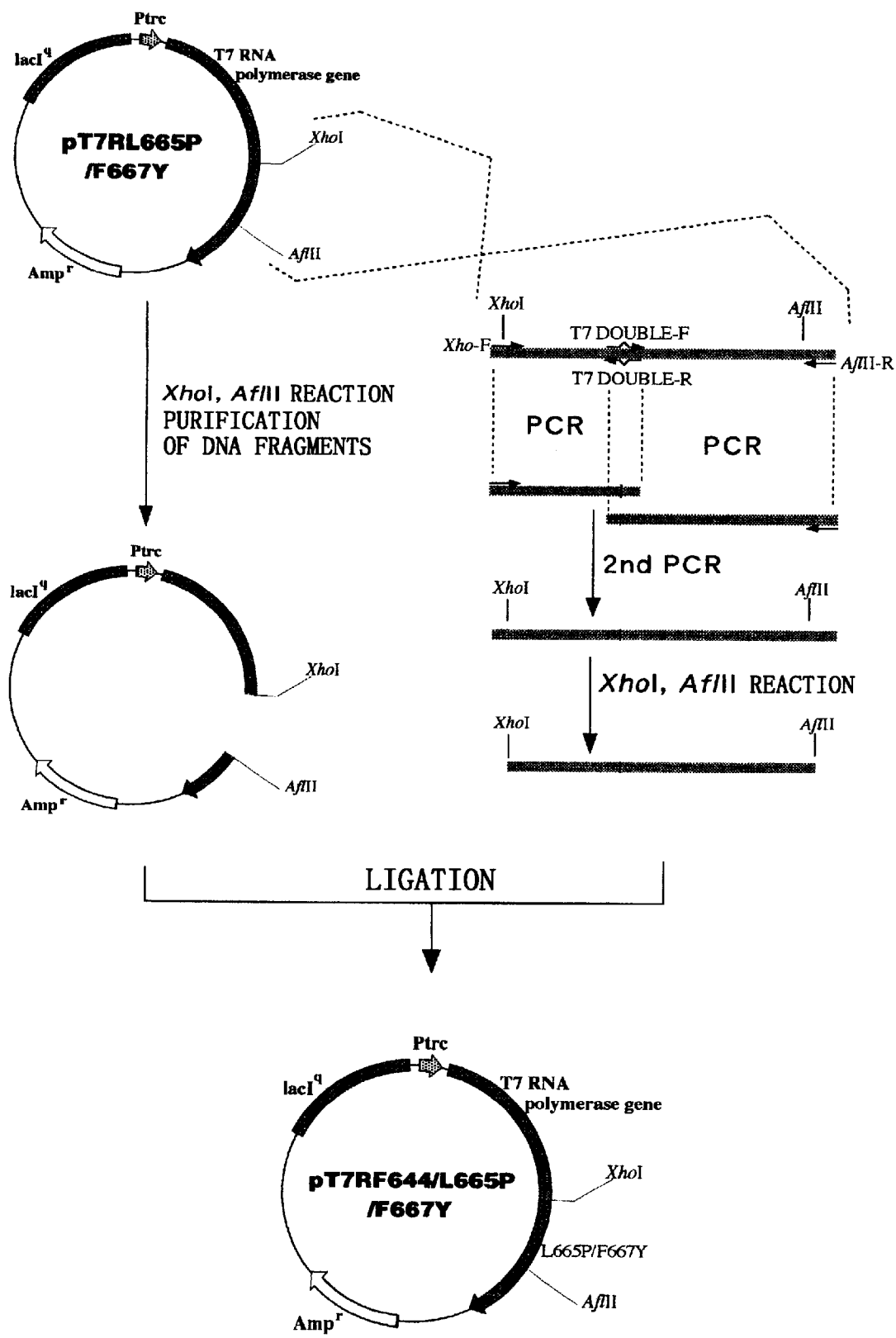
FIG. 13 shows a construction map of pT7R F644Y/ L665P/F667Y, a plasmid expressing a mutant T7RNA polymerase F644Y/L665P/F667Y.

Reference Example 4
Construction of Expression Plasmid for Producing Mutant T7 RNA Polymerase F644Y/L665P/F667Y (See FIG. 13)

Construction of the mutant T7 RNA polymerase F644Y/L665P/F667Y was performed based on PCR, as in the construction method of the expression plasmid for producing the mutant T7 RNA polymerase L665P/F667Y previously constructed (see Reference Example 2), as follows.

PCR was performed by using the expression plasmid producing the mutant T7 RNA polymerase L665P/F667Y as template together with a primer [SEQ ID NO.: 11] pair of the primer Xho-F and the primer T7-DOUBLE-R (21-mer: 5'-CTCTTTGGACCCGTAAGCCAG-3') or a primer [SEQ ID NO.: 12] pair of the primer T7-DOUBLE-F (29-mer: 5'-TTACGGGTCCAAAGAGTACGGCTTCCGTC-3') and the primer AflII-R. The PCR products were directly used as templates and determined for DNA sequences to confirm the sequences of the primers T7-DOUBLE-R and T7-DOUBLE-F. Each of the products was subjected to electrophoresis on 2% agarose gel to purify DNA fragment of the intended size. The purified two kinds of DNA fragments were mixed, and used as template for PCR using the primers XhoF and AflIIR. After confirming that the amplified DNA fragment was the desired fragments by restriction mapping and DNA sequencing, the fragment was digested with restriction endonucleases XhoI and AflII, and the resulting fragment was ligated to the plasmid pT7RL665P/F667Y preliminarily treated with restriction endonucleases XhoI and AflII by using T4 DNA ligase. This reaction product was transformed into E. coli DH5 α, and several colonies of the cells grown on an agar plate containing antibiotic ampicillin were obtained. Some of these colonies were selected and cultured, and plasmid DNA was extracted from the cultured cells. The nucleotide sequence of the plasmid DNA was sequenced to confirm that the desired mutation should be introduced, and thus an expression plasmid pT7RF644Y/L665P/F667Y for producing the mutant T7 RNA polymerase F644Y/L665P/F667Y was finally constructed (see FIG. 13). For the production of the mutant T7 RNA polymerase F644Y/L665P/F667Y from this plasmid, expression could be induced by adding IPTG to cultured E. coli cells harboring the plasmid, like the production of the wild type T7 RNA polymerase.

Reference Example 5
Purification of Mutant T7 RNA Polymerase F644Y/L665P/F667Y

The mutant T7 RNA polymerase F644Y/L665P/F667Y could be purified by the same method as in Reference Example 3. In a typical example, 1,000,000 units of the mutant T7 RNA polymerase F644Y/L665P/F667Y protein was purified from 1 liter of culture medium. The obtained RNA polymerase was detected substantially as a single band, and RNase was not detected in this specimen by SDS-polyacrylamide gel electrophoresis.

Synthesis Example 1
Synthesis of 3'-deoxy-5-iodocytidine (a Compound Corresponding to Compound 6 in the Above-mentioned Synthesis Scheme; Referred to as Compound 6 Hereinafter; the Compound Nos. Used Hereinafter Similarly Indicate Those in the Synthesis Schemes)

3'-Deoxycytidine (Compound 5, 3.0 g, 13.2 mmol) was suspended in a mixed solution of 1,4-dioxane (300 ml) and ethanol (30 ml), cooled to 10° C., added with silver trifluoroacetate (7.0 g, 31.7 mmol) and iodine (8.04 g, 31.7 mmol), and stirred at room temperature for two hours. After the reaction was completed, the precipitates were removed by filtration through celite, and washed with 1,4-dioxane, and the filtrate and the wash were combined, and concentrated to afford 3.84 g of 3'-deoxy-5-iodocytidine (Compound 6, yield; 82.4%). $^1$H-NMR (270 MHz, DMSO-$d_6$) δ ppm: 1.64–1.70 (m, 1H, 3'-Ha), 1.88–1.99 (m, 1H, 3'-Hb), 3.60–3.89 (m, 2H, 5'-Ha,b), 4.20–4.21 (m, 1H, 4'-H), 4.37–4.39 (m, 1H, 2'-H), 5.59 (s, 1H, 1'-H), 7.58 (brs, 1H, $NH_2$a), 8.41 (brs, 1H, $NH_2$b), 8.79 (brs, 1H, 6-H)

Synthesis Example 2
Synthesis of 5-trifluoroacetamido-1-pentyne

To a solution of sodium hydride (60% oil, 5.99 g, 0.15 mol) in DMF (340 ml), trifluoroacetamido (19.2 g, 0.17 mol) was added portionwise as 10 portions with ice cooling. Then, the solution was added with sodium iodide (20.4 g, 0.136 mol), then with a solution of 5-chloro-1-pentyne (13.97 g, 0.136 mol) in dimethylformamide (DMF, 50 ml), and allowed to react at room temperature for 4.5 hours and at 60° C. for 21 hours with stirring. After the reaction mixture was cooled, it was added with an aqueous solution (500 ml) of potassium dihydrogenphosphate (59.2 g), and extracted with ether (500 ml). The ether layer was washed with water, dried over magnesium sulfate and concentrated under reduced pressure, and the resulting residue was purified by silica gel column chromatography (eluent; hexane-ethyl acetate mixed solvent) to afford 17.6 g of 5-trifluoroacetamido-1-pentyne (yield; 67%).

$^1$H-NMR (270 MHz, CDCl$_3$) δ ppm: 1.83 (m, 2H, —CH$_2$CH$_2$CH$_2$—), 2.04 (t, 1H, J=2.7 Hz, H—CC—), 2.31 (dt, 2H, J=2.7, 6.6 Hz, —CCCH$_2$—), 3.52 (q, 2H, J=6.7 Hz, CH$_2$N), 6.88 (brs, 1H, NHTfa)

Synthesis Example 3

Synthesis of 3'-deoxy-5-(5"-trifluoroacetamido-1"-pentynyl)cytidine

To a solution of 3'-deoxy-5-iodocytidine (Compound 6, 777 mg, 2.20 mmol) in DMF (11 ml), the 5-trifluoroacetamido-1-pentyne (1.18 g, 6.60 mmol) obtained in Synthesis Example 2, cuprous (I) iodide (83.8 mg, 0.44 mmol), tetrakis(triphenylphosphine) palladium (0) (254 mg, 0.22 mmol), and triethylamine (0.613 ml, 4.4 mmol) were added under nitrogen gas flow, and allowed to reacted at room temperature for 30 minutes. The reaction mixture was diluted with a methylene chloride-methanol mixture (20 ml), added with ion exchange resin AG1X8 (BIO-RAD, HCO$_3^-$ type, 2.02 g), and stirred for 30 minutes. After filtration of the reaction mixture, the filtrate was concentrated, and the residue was purified by silica gel column chromatography (eluent; chloroform-methanol mixed solution), and crystallized from a methanol-ether mixture to afford 409 mg of a novel substance, 3'-deoxy-5-(5"-trifluoroacetamido-1"-pentynyl)cytidine (yield; 46.0%).

Melting point: 191–193° C.

$^1$H-NMR (270 MHz, DMSO-d$_6$) δ ppm: 1.63–1.78 (m, 3H, 3'-Ha and CH$_2$CH$_2$CH$_2$N), 1.86–1.96 (m, 1H, 3'-Hb), 2.39–2.44 (m, 2H, CH$_2$CH$_2$CH$_2$N), 3.27–3.31 (m, 2H, CH$_2$N), 3.51–3.82 (m, 2H, 5'-Ha, b), 4.12–4.31 (m, 2H, 2'-H and 4'-H), 5.15 (t, 1H, J=5.1 Hz, 5'-OH), 5.51 (d, 1H, J=4.1 Hz, 2'-OH), 5.62 (s, 1H, 1'-H), 6.69 (brs, 1H, 4-NHa), 7.64 (brs, 1H, 4-NHb), 8.30 (s, 1H, 6-H), 9.50 (brs, 1H, NHTfa)

Synthesis Example 4

Synthesis of tris(tri-n-butylammonium)pyrophosphate

Tetrasodium pyrophosphate decahydrate (2.23 g) was dissolved in water (50 ml), and loaded on an ion exchange resin column Dowex 50WX8 (Dowex, H$^+$ type, 45 ml). The column was eluted with water, and the eluent was collected until its pH became substantially neutral. The eluent was added with tri-n-butylamine (3.55 ml) and stirred sufficiently. The mixture was concentrated under reduced pressure, and the residue was further concentrated to dryness by azeotropy with ethanol, pyridine, and DMF. The resulting residue was dissolved in dry DMF to a total volume of 10 ml to afford 0.5 M concentration of tris(tri-n-butylammonium) pyrophosphate.

Synthesis Example 5

Synthesis of 5-(5"-amino-1"-pentynyl)-3'-deoxycytidine-5'-triphosphate

3'-Deoxy-5-(5"-trifluoroacetamido-1"-pentynyl)cytidine (121 mg, 0.3 mmol) was dissolved in triethyl phosphate (1.21 ml), cooled to −20° C., then added with phosphorus oxychloride (25 μl), and stirred at −20° C. After 30 minutes, the reaction mixture was added with further phosphorus oxychloride (22 μl), and stirred for further 5 hours. The reaction mixture was added to 0.5 M solution of the tris (tri-n-butylammonium) pyrophosphate obtained in Synthesis Example 4 in DMF (3.6 ml) cooled to −20° C., and stirred at room temperature for two hours. After the reaction was completed, the reaction mixture was added with a triethylamine-water mixture (5 ml), left stand overnight, then added with 25% aqueous ammonia (20 ml), and left stand for 4 hours. The reaction mixture was washed with ether, and concentrated to dryness, and the resulting residue was purified by DEAE-Toyopearl ion exchange column chromatography (Tosoh Corporation, 1.7×30 cm, eluent; triethylammonium hydrogencarbonate buffer (pH 7.5), 0 M→0.3 M linear gradient (total volume; 1 L)) to afford 105 mg of a novel substance, 5-(5"-amino-1"-pentynyl)-3'-deoxycytidine-5'-triphosphate (yield; 36.6%).

Synthesis Example 6

Synthesis of XR-labeled 3'-deoxycytidine-5'-triphosphate (A Compound of General Formula [I] where V is —C≡C— and n=3)

To 5-(5"-amino-1"-pentynyl)-3'-deoxycytidine-5'-triphosphate (8 μ mol) dissolved in a mixture of DMF (300 μl) and water (300 μl) was added with triethylamine (10 μl) and 5-carboxy-X-rhodamine succinimide ester (Molecular Probe, 26.9 μ mol), and stirred at room temperature overnight. The reaction mixture was diluted with water (30 ml), and purified by DEAE-Toyopearl ion exchange column chromatography (1.7×15 cm, eluent; triethylammoniumhydrogencarbonate buffer (pH 7.5), 0.1 M→0.7 M linear gradient (total volume; 2 L)) to afford 6.28 μ mol (yield; 78.5%) of XR-labeled 3'-deoxycytidine-5'-triphosphate represented by the following formula [a compound of the general formula [I] where V is —C≡C— and n=3, abbreviated as XR-3'dCTP(n3) hereinafter].

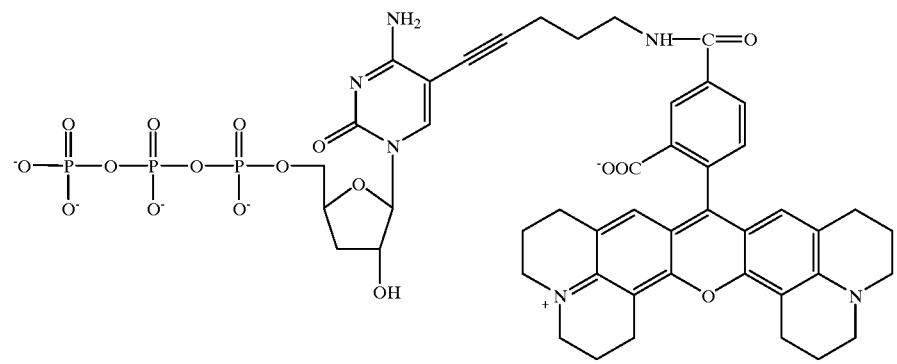

Figure 14:
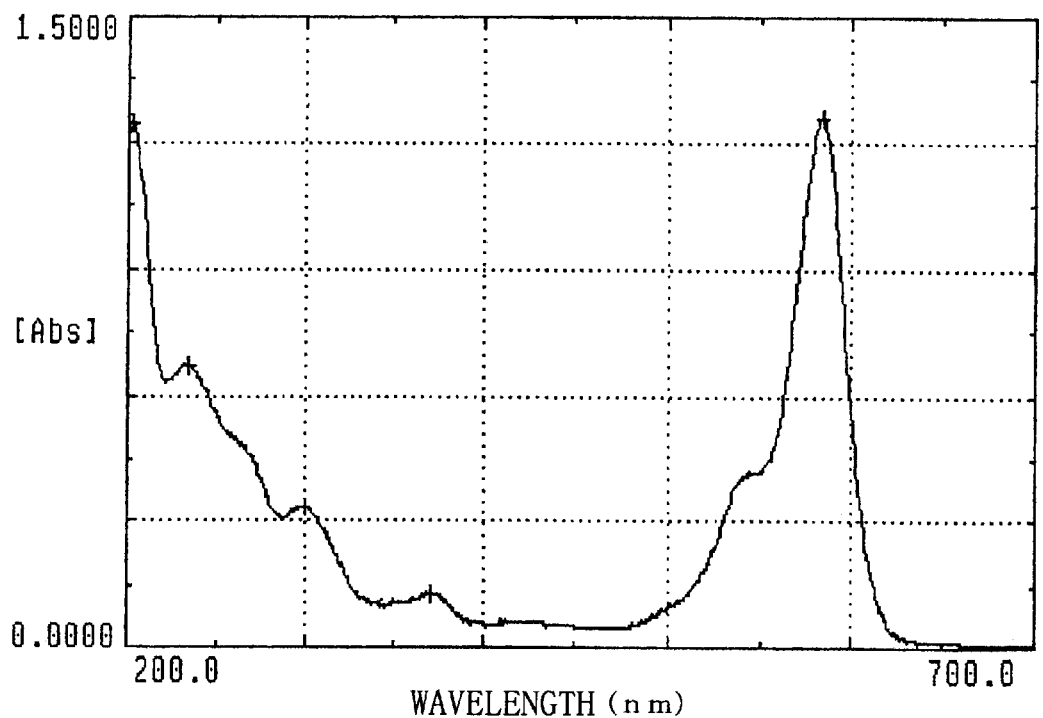
FIG. 14 shows the result of UV-visible region spectrophotometry of the carboxyrhodamine-X-labeled 3'-deoxycytidine-5'-triphosphate (a compound of the general formula [I] where V is —C≡C— and n=3) obtained in Synthesis Example 6.

The absorption spectrum for UV-visible region resulting from spectroscopy of the obtained XR-3'dCTP(n3) (measurement wavelength; 700 nm to 200 nm, reference; distilled water) performed by using DU640 UV-visible region spectrophotometer [Beckman] is shown in FIG. 14.

Synthesis Example 7

Synthesis of 6-trifluoroacetamido-1-hexyne
1) Synthesis of 5-hexynyl-p-toluenesulfonate To an ice-cooled solution of p-toluenesulfonyl chloride (20.11 g, 105.5 mmol) in pyridine (30 ml), 5-hexyn-1-ol (Tokyo Chemical Industry Co., Ltd., 10 ml, 91.7 mmol) was added dropwise, and stirred at room temperature for 20 hours. The reaction mixture was added with water (15 ml), stirred, and then poured into water (500 ml). This solution was extracted with ether (300 ml), and the ether layer was washed with cold 1N-hydrochloric acid, saturated aqueous sodium hydrogencarbonate and water, dried over magnesium sulfate, and concentrated under reduced pressure to afford 7.33 g of 5-hexynyl-p-toluenesulfonate (yield; 32%).

2) Synthesis of 6-iodo-1-hexyne

A mixture of 5-hexynyl-p-toluenesulfonate (7.33 g, 33.3 mmol), sodium iodide (4.99 g, 33.3 mmol) and acetone (37 ml) was allowed to react under reflux for one hour. After cooling, the precipitates were removed by filtration, and the filtrate was concentrated. The resulting residue was purified by silica gel column chromatography (eluent; hexane) to afford 3.31 g of 6-iodo-1-hexyne (yield; 54.8%).

3) Synthesis of 6-trifluoroacetamido-1-hexyne

To a solution of sodium hydride (60% oil, 2.55 g, 63.6 mol) in DMF (50 ml), trifluoroacetamide (8.99 g, 79.6 mmol) was added portionwise as about 10 portions with ice cooling. Subsequently, a solution of 6-iodo-1-hexyne (3.31 g, 15.9 mmol) in DMF (15 ml) was added to the reaction mixture. The reaction mixture was stirred at room temperature for four hours. The reaction mixture was added with saturated aqueous ammonium chloride (100 ml) and ether (100 ml) for extraction. The ether layer was dried over magnesium sulfate, and concentrated under reduced pressure, and the resulting residue was purified by silica gel column chromatography (eluent; hexane-ethyl acetate mixed solvent) to afford 2.0 g of 6-trifluoroacetamido-1-hexyne (yield; 65.4%).

Melting point: 41.0–42.5° C.

$^1$H-NMR (270 MHz, CDCl$_3$) δ ppm: 1.53–1.80 (m, 4H, —CH$_2$(CH$_2$)$_2$—), 1.98 (t, 1H, J=2.7 Hz, H—CC—), 2.26 (dt, 2H, J=2.5, 6.7 Hz, CC—CH$_2$—), 3.41 (q, 2H, J=6.8 Hz, CH$_2$—N), 6.48 (brs, 1H, NHTfa)

Synthesis Example 8

Synthesis of 3'-deoxy-5-(6"-trifluoroacetamido-1"-hexynyl)cytidine (Compound 7)

To a solution of 3'-deoxy-5-iodocytidine (Compound 6, 800 mg, 2.27 mmol) in DMF (11.4 ml), the 6-trifluoroacetamido-1-hexyne obtained in Synthesis Example 7 (1.31 g, 6.80 mmol), cuprous (I) iodide (86.3 mg, 0.453 mmol), tetrakis(triphenylphosphine)palladium (0) (262 mg, 0.227 mmol), and triethylamine (0.632 ml, 4.53 mmol) were added under nitrogen gas flow, and allowed to react at room temperature for 30 minutes. The reaction mixture was diluted with a methylene chloride-methanol mixture (20 ml), added with ion exchange resin AG1X8 (HCO$_3$$^-$ type, 2.02 g), and stirred for 30 minutes. After filtration of the reaction mixture, the filtrate was concentrated, and the resulting residue was purified by silica gel column chromatography (eluent, chloroform-methanol mixed solution), crystallized from a methanol-ether mixture to afford 399 mg of a novel substance, 3'-deoxy-5-(6"-trifluoroacetamido-1"-hexynyl)cytidine (Compound 7, yield; 42.1%).

Melting point: 195–197° C.

$^1$H-NMR (270 MHz, DMSO-d$_6$) δ ppm: 1.52–1.69 (m, 5H, 3'-Ha and CH$_2$CH$_2$CH$_2$CH$_2$N), 1.86–1.96 (m, 1H, 3'-Hb), 2.39–2.50 (m, 2H, CCH$_2$—), 3.18–3.28 (m, 2H, CH$_2$N), 3.50–3.83 (m, 2H, 5l'-Ha, b), 4.11–4.33 (m, 2H, 2—H and 4—H), 5.14 (t, 1H, J=4.9 Hz, 5'-OH), 5.50 (d, 1H, J=4.0 Hz, 2'-OH), 5.62 (s, 1H, 1'-H), 6.65 (brs, 1H, 4-NHa), 7.59 (brs, 1H, 4-NHb), 8.29 (s, 1H, 6-H), 9.41 (brs, 1H, NHTfa)

Synthesis Example 9

Synthesis of 5-(6"-amino-1"-hexynyl)-3'-deoxycytidine-5'-triphosphate (Compound 8)

3'-Deoxy-5-(6"-trifluoroacetamido-1"-hexynyl)cytidine (Compound 7, 125.5 mg, 0.3 mmol) was dissolved in triethyl phosphate (1.26 ml), cooled to −20° C., added with phosphorus oxychloride (25.11 μl), and stirred at −20° C. After 30 minutes, the reaction mixture was added with further phosphorus oxychloride (22.32 μl), and stirred for further 5 hours. This reaction mixture was added to 0.5 M solution of tris(tri-n-butylammonium) pyrophosphate in DMF (3.6 ml) cooled to −20° C., and stirred at room temperature for two hours. After the reaction was completed, the reaction mixture was added with a triethylamine-water mixture (4 ml), left stand overnight, added with 25% aqueous ammonia (20 ml), and left stand for four hours. The reaction mixture was washed with ether, and concentrated to dryness, and the obtained residue was purified by DEAE-Toyopearl ion exchange column chromatography (1.7×30 cm, eluent; triethylammonium hydrogencarbonate buffer (pH 7.5), 0 M→0.3 M linear gradient (total volume; 1 L)) to afford 200 mg of a novel substance, 5-(6"-amino-1"-hexynyl)-3'-deoxycytidine-5'-triphosphate (Compound 8, yield; 69.0%).

Synthesis Example 10

Synthesis of XR-labeled 3'-deoxycytidine-5'-triphosphate (A Compound of the General Formula [I] where V is —C≡C— and n=4)

To 5-(6"-amino-1"-hexynyl)-3'-deoxycytidine-5'-triphosphate (Compound 8, 10 μ mol) dissolved in a mixture of DMF (300 μl) and water (300 μl), triethylamine (10 μl), and 5-carboxy-X-rhodamine succinimide ester (Molecular Probe, 15 μmol) were added, and stirred at room temperature overnight. The reaction mixture was diluted with water (30 ml), and purified by DEAE-Toyopearl ion exchange column chromatography (1.7×15 cm, eluent; triethylammoniumhydrogencarbonate buffer (pH7.5), 0.1 M→0.7 M linear gradient (total volume; 2 L)) to afford 8.02 μmol (yield; 80.2%) of XR-labeled 3'-deoxycytidine-5'-triphosphate represented by the following formula where n of the methylene chain in the linker section is 4 [a compound of the general formula [I] where V is —C≡C—and n=4, abbreviated as XR-3'dCTP(n4) hereinafter].

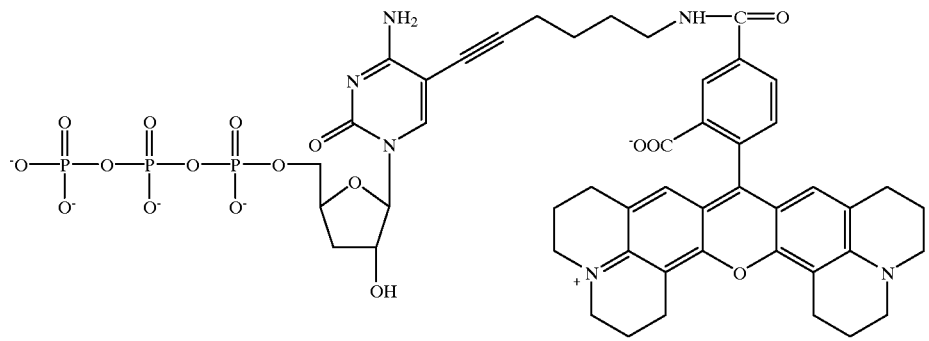

Figure 15:
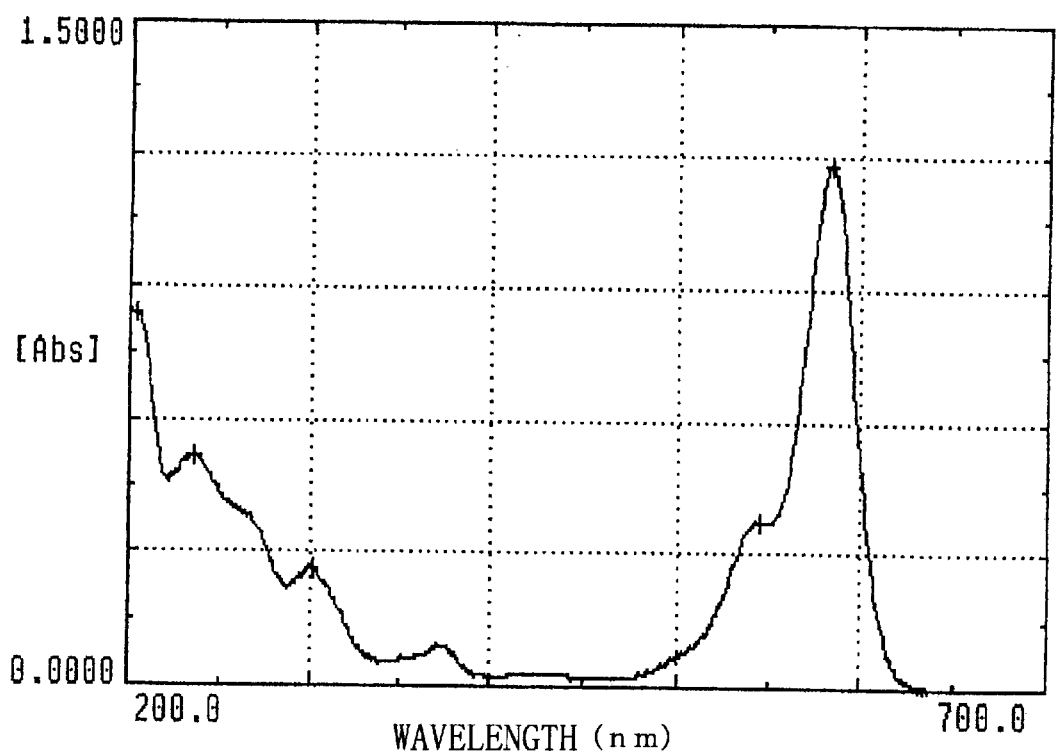
FIG. 15 shows the result of UV-visible region spectrophotometry of the carboxyrhodamine-X-labeled 3'-deoxycytidine-5'-triphosphate (a compound of the general formula [I] where V is —C≡C— and n=4) obtained in Synthesis Example 10.

The absorption spectrum for UV-visible region resulting from spectroscopy of the obtained XR-3'dCTP(n4) (measurement wavelength; 700 nm to 200 nm, reference; distilled water) performed by using DU640 UV-visible region spectrophotometer [Beckman] is shown in FIG. 15.

Synthesis Example 11
Synthesis of 8-trifluoroacetamido-1-octyne
1) Synthesis of 7-octyn-1-ol A suspension of lithium acetylide ethylenediamine complex (Aldrich, 11.3 g, 122.5 mmol) and dimethyl sulfoxide (50 ml) was cooled to 5–10° C., and added dropwise with 1-bromo-6-tetrahydropyranyloxyhexane (Sigma, 25 g, 94.3 mmol) over two hours. Then, the reaction mixture was stirred at room temperature for two hours. The reaction mixture was added with water (10 ml), stirred for ten minutes, then poured into water (150 ml), and extracted with ether (300 ml). The ether layer was washed with water, dried over magnesium sulfate, and concentrated under reduced pressure to afford 18.1 g of 8-(tetrahydropyranyloxy)-1-octyne as oil (yield; 91.2%). Dowex 50WX8 (H+ type, 18 g) was added to a mixture of 8-(tetrahydropyranyloxy)-1-octyne (18 g, 85.6 mmol), chloroform (40 ml) and methanol (140 ml), and heated for 1 hour under reflux. After the resin was separated by filtration, the filtrate was concentrated, and the resulting residue was purified by silica gel column chromatography (eluent; hexane-ethyl acetate mixed solvent) to afford 9.6 g of 7-octyn-1-ol (yield; 88.6%).

2) Synthesis of 7-octynyl-p-toluenesulfonate

To an ice-cooled solution of p-toluenesulfonyl chloride (17.4 g, 91.3 mmol) in pyridine (30 ml), 7-octyne-1-ol (9.6 g, 76.1 mmol) was added dropwise, and stirred at 5–10 ° C. for 20 hours. The reaction mixture was added with water (15 ml), stirred, then poured into water (500 ml), and extracted with ether (500 ml). The ether layer was washed with cold 1N-hydrochloric acid, saturated aqueous sodium hydrogencarbonate and water, dried over magnesium sulfate, and concentrated under reduced pressure to afford 18.3 g of 7-octynyl-p-toluenesulfonate (yield; 85.7%).

3) Synthesis of 8-iodo-1-octyne

A mixture of 7-octynyl-p-toluenesulfonate (18.3 g, 65.2 mmol), sodium iodide (9.77 g, 65.2 mmol) and acetone (91 ml) was allowed to react for four hours under reflux. After cooling, the precipitates were removed by filtration, and the filtrate was concentrated. The resulting residue was purified by silica gel column chromatography (eluent; hexane) to afford 14.5 g of 8-iodo-1-octyne (yield; 94.2%).

4) Synthesis of 8-trifluoroacetamido-1-octyne

To a solution of sodium hydride (60% oil, 9.82 g, 245 mmol) in DMF (200 ml), trifluoroacetamide (34.7 g, 307 mmol) divided into 10 portion was added portionwise with ice cooling. Then, the reaction mixture was added with a solution of 8-iodo-1-octyne (14.5 g, 61.4 mmol) in DMF (60 ml), and stirred at room temperature for two hours. The reaction mixture was added with saturated aqueous ammonium chloride (400 ml) and ether (400 ml) for extraction. The ether layer was dried over magnesium sulfate, and concentrated under reduced pressure, and the resulting residue was purified by silica gel column chromatography (eluent; hexane-ethyl acetate mixed solvent), and crystallized from hexane to afford 10.8 g of 8-trifluoroacetamido-1-octyne (yield; 79.3%).

Melting point: 29.5–30.0° C.

$^1$H-NMR (270 MHz, CDCl$_3$) δ ppm: 1.36–1.63 (m, 8H, —CH$_2$(CH$_2$)$_4$—), 1.94 (t, 1H, J=2.7 Hz, H—CC—), 2.20 (dt, 2H, J=2.5, 6.7 Hz, CC—CH$_2$—), 3.37 (q, 2H, J=6.8 Hz, CH$_2$—N), 6.28 (brs, 1H, NHTfa)

Synthesis Example 12
Synthesis of 3'-deoxy-5-(8''-trifluoroacetamido-1''-octynyl)cytidine (Compound 9)

To a solution of 3'-deoxy-5-iodocytidine (Compound 6, 450 mg, 1.27 mmol) in DMF (6.4 ml), the 8-trifluoroacetamido-1-octyne (846 mg, 3.82 mmol) obtained in Synthesis Example 11, cuprous (I) iodide (48.5 mg, 0.25 mmol), tetrakis(triphenylphosphine) palladium (0) (147 mg, 0.127 mmol), and triethylamine (0.355 ml, 2.55 mmol) were added under nitrogen gas flow, and allowed to react at room temperature for 30 minutes. The reaction mixture was diluted with a methylene chloride-methanol mixture (12 ml), added with ion exchange resin AG1X8 (HCO$_3^-$ type, 1.17 g), and stirred for 30 minutes. After filtration of the reaction mixture, the filtrate was concentrated, and the resulting residue was purified by silica gel column chromatography (eluent; chloroform-methanol mixed solution), and crystallized from a methanol-ether mixture to afford 219 mg of a novel substance, 3'-deoxy-5-(8''-trifluoroacetamido-1''-octynyl)cytidine (Compound 9, yield; 38.5%).

Melting point: 165–167° C.

$^1$H-NMR (270 MHz, DMSO-d$_6$) δ ppm: 1.27–1.54 (m, 8H, —(CH$_2$)$_4$—), 1.63–1.69 (m, 1H, 3'-Ha), 1.86–1.97 (m, 1H, 3'-Hb), 2.37 (t, 2H, J=7.0 Hz, CCCH$_2$), 3.14–3.21 (m, 2H, CH$_2$N), 3.49–3.56 (m, 1H, 5'-Ha), 3.75–3.81 (m, 1H, 5'-Hb), 4.08–4.31 (m, 2H, 2'-H and 4'-H), 5.13 (t, 1H, J=5.0 Hz, 5'-OH), 5.49 (d, 1H, J=4.1 Hz, 2'-OH), 5.62 (d, 1H, J=1.4 Hz, 1'-H), 6.62 (brs, 1H, 4-NHa), 7.58 (brs, 1H, 4-NHb), 8.28 (s, 1H, 6-H), 9.41 (brs, 1H, NHTfa)

Synthesis Example 13

Synthesis of 5-(8"-amino-1"-octynyl)-3'-deoxycytidine-5'-triphosphate (Compound 10)

3'-Deoxy-5-(8"-trifluoroacetamido-1"-octynyl)cytidine (Compound 9, 134 mg, 0.3 mmol) was dissolved in triethyl phosphate (1.34 ml), cooled to −20° C., added with phosphorus oxychloride (25.11 μl), and stirred at −20 °C. After 30 minutes, the mixture was added with further phosphorus oxychloride (22.32 μl), and stirred for further 3.5 hours. This reaction mixture was added to 0.5 M solution of tris(tri-n-butylammonium) pyrophosphate in DMF (3.6 ml) cooled to −20° C., and stirred at room temperature for two hours. After the reaction was completed, the reaction mixture was added with a triethylamine-water mixture (5 ml), left stand overnight, then added with 25% aqueous ammonia (20 ml), and left stand for four hours. The reaction mixture was washed with ether, and concentrated to dryness, and the obtained residue was purified by DEAE-Toyopearl ion exchange column chromatography (1.7×30 cm, eluent; triethylammonium hydrogencarbonate buffer (pH 7.5), 0 M →0.3 M linear gradient (total volume; 1 L)) to afford 262 mg of a novel substance, 5-(8"-amino-1"-octynyl)-3'-deoxycytidine-5'-triphosphate (Compound 10, yield; 50.0%).

Synthesis Example 14

Synthesis of XR-labeled 3'-deoxycytidine-5'-triphosphate (A Compound of the General Formula [I] Where V is —C≡C— and n=6)

To 5-(8"-amino-1"-octynyl)-3'-deoxycytidine-5'-triphosphate (Compound 10, 8 μmol) dissolved in a mixture of DMF (300 μl) and water (300 μl), triethylamine (10 μl) and 5-carboxy-X-rhodamine succinimide ester (Molecular Probe, 12 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.7 M linear gradient (total volume; 2 L)) to afford 5.34 μmol (yield; 66.7%) of XR-labeled 3'-deoxycytidine-5'-triphosphate represented by the following formula [a compound of the general formula [I] where V is —C≡C— and n=6, abbreviated as XR-3'dCTP(n6) hereinafter].

Synthesis Example 15

Synthesis of 6-chloro-9-{2',5'-bis(O-tert-butyldimethylsilyl)-3'-O-[(imidazol-1"-yl) thiocarbonyl]-β-D-ribofuranosyl}-7-deazapurine (Compound 13)

6-Chloro-9-(β-D-ribofuranosyl)-7-deazapurine (Compound 11, 3.58 g, 12.5 mmol) was dissolved in THF (160 ml), added with pyridine (5.1 ml, 62.7 mmol), silver nitrate (4.68 g, 27.6 mmol) and tert-butyldimethylsilyl chloride (4.16 g, 27.6 mmol), and stirred at room temperature overnight. After the reaction was completed, the precipitates were removed by filtration through celite, and the filtrate was concentrated, dissolved in chloroform, and washed with 0.2 N hydrochloric acid and saturated saline. The chloroform layer was dried over anhydrous magnesium sulfate, and the chloroform was evaporated to quantitatively afford 6.42 g of a novel substance, 6-chloro-9-[2,5-bis(O-tert-butyldimethylsilyl)-β-D-ribofuranosyl]-7-deazapurine (Compound 12). This compound was dissolved in DMF (120 ml) without further purification, added with 1,1'-thiocarbonyldiimidazole (13.36 g, 75.0 mmol), and stirred at room temperature overnight. After the reaction was completed, the reaction mixture was added with ethyl acetate and water, and the organic layer was washed with saturated saline. The ethyl acetate layer was dried over anhydrous magnesium sulfate, and concentrated under reduced pressure, and the resulting residue was purified by silica gel column chromatography (eluent; ethyl acetate-n-hexane mixed solvent) to afford 4.03 g of a novel substance, 6-chloro-9-{2',5'-bis(O-tert-butyldimethylsilyl)-3'-O-[(imidazol-1-yl) thiocarbonyl]-β-D-ribofuranosyl}-7-deazapurine (Compound13, yield; 51.5%).

Synthesis Example 16

Synthesis of 6-chloro-9-[2',5'-bis(O-tert-butyldimethylsilyl)-3'-deoxy-β-D-ribofuranosyl]-7-deazapurine (Compound 14)

6-Chloro-9-{2',5'-bis(O-tert-butyldimethylsilyl)-3'-O-[(imidazol-1-yl)thiocarbonyl]-β-D-ribofuranosyl}-7-deazapurine (Compound 13, 4.0 g, 6.41 mmol) was dissolved in toluene (200 ml), added with 2,2'-azobis (isobutyronitrile) (0.21 g, 1.3 mmol) and tri-n-butyltinhydride (3.45 ml, 13 mmol), and stirred under nitrogen gas flow at 80° C. for 30 minutes. After the reaction

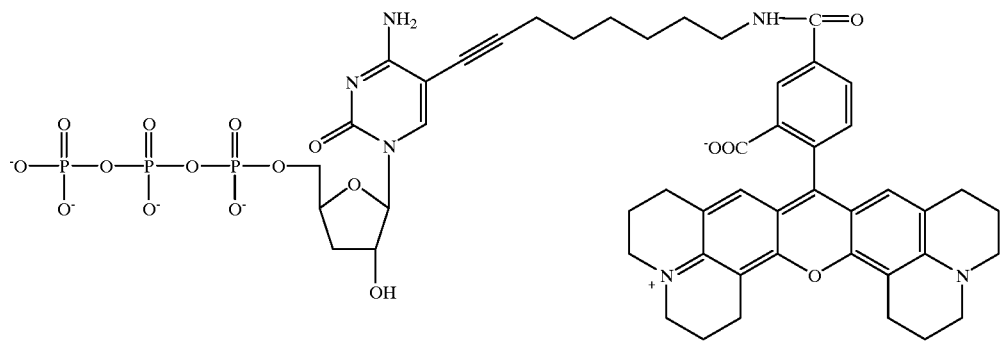

Figure 16:
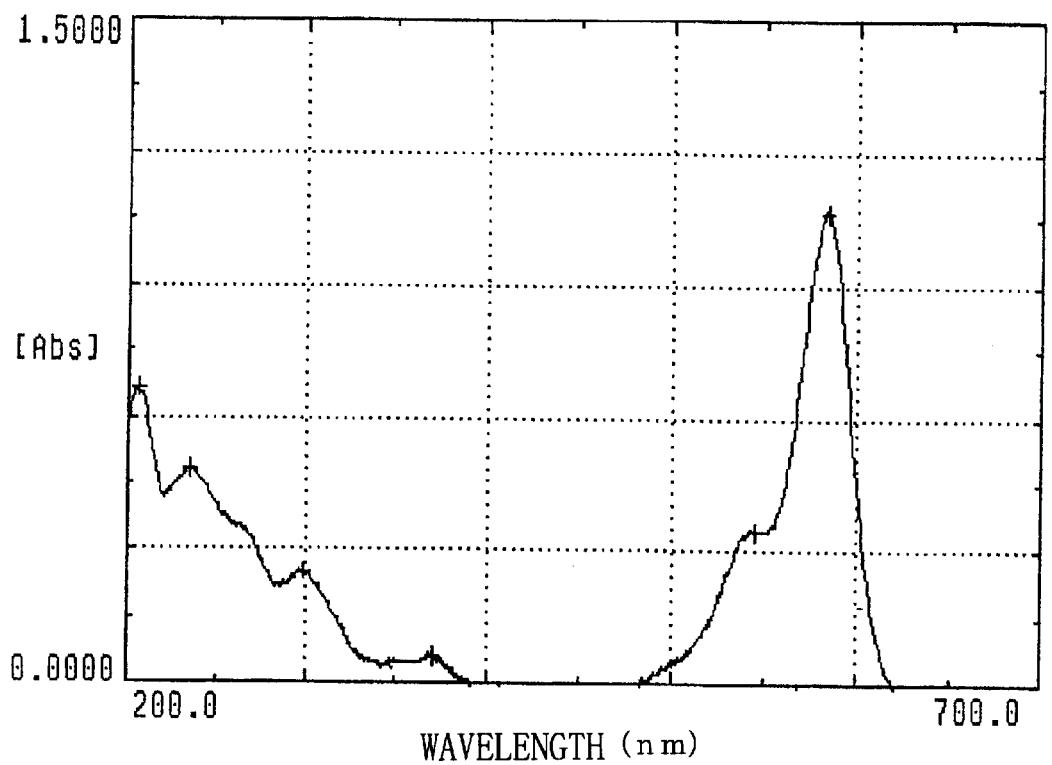
FIG. 16 shows the result of UV-visible region spectrophotometry of the carboxyrhodamine-X-labeled 3'-deoxycytidine-5'-triphosphate (a compound of the general formula [I] where V is —C≡C— and n=6) obtained in Synthesis Example 14.

The absorption spectrum for UV-visible region resulting from spectroscopy of the obtained XR-3'dCTP(n6) (measurement wavelength; 700 nm to 200 nm, reference; distilled water) performed by using DU640 UV-visible region spectrophotometer [Beckman] is shown in FIG. 16.

was completed, the toluene was evaporated, and the residue was purified by silica gel column chromatography (eluent; ethyl acetate-n-hexane mixed solvent) to afford 2.60 g of a novel substance, 6-chloro-9-[2',5'-bis(O-tert-butyldimethylsilyl)-3'-deoxy-β-D-ribofuranosyl]-7-deazapurine (Compound 14, yield; 81.5%).

Synthesis Example 17
Synthesis of 6-chloro-9-(3'-deoxy-β-D-ribofuranosyl)-7-deazapurine (Compound 15)

6-Chloro-9-[2',5'-bis(O-tert-butyldimethylsilyl)-3'-deoxy-β-D-ribofuranosyl]-7-deazapurine (Compound 14, 2.6 g, 5.2 mmol) was dissolved in THF (30 ml), added with 1 M tetrabutylammonium fluoride (12.5 ml, 12.5 mmol), and stirred at room temperature overnight. After the reaction was completed, the reaction mixture was concentrated under reduced pressure, and purified by silica gel column chromatography (eluent; chloroform-methanol mixed solvent) to quantitatively afford 1.47 g of a novel substance, 6-chloro-9-(3'-deoxy-β-D-ribofuranosyl)-7-deazapurine (Compound 15).

$^1$H-NMR (270 MHz, DMSO-d6) δ ppm: 1.93, 2.23 (m, 2H, 3'-Ha, b), 3.55, 3.71 (2dd, 2H, J=4.1, 11.9; 3.2, 11.6 Hz, 5'-Ha, b), 4.36 (m, 1H, 2'-H), 4.45 (m, 1H, 4'-H), 5.02 (brs, 1H, 5'-OH), 5.66 (brs, 1H, 2'-OH), 6.19 (d, 1H, J=2.4 Hz, 1'-H), 6.70 (d, 1H, J=3.8 Hz, 7-H), 8.02 (d, 1H, J=4.1 Hz, 8-H), 8.66 (s, 1H, 2-H)

Synthesis Example 18
Synthesis of 6-chloro-9-(3'-deoxy-2',5'-di-O-acetyl-β-D-ribofuranosyl)-7-deazapurine (Compound 16)

6-Chloro-9-(3'-deoxy-β-D-ribofuranosyl)-7-deazapurine (Compound 15, 1.47 g, 5.45 mmol) was dissolved in pyridine (15 ml), added with acetic anhydride (5 ml), and stirred at room temperature overnight. After the reaction was completed, the reaction mixture was cooled to 0° C., added with methanol (5 ml), and concentrated under reduced pressure. The residue was dissolved in chloroform, and washed with 0.5 N hydrochloric acid and saturated saline. The chloroform layer was dried over anhydrous magnesium sulfate, and the chloroform was evaporated to quantitatively afford 2.00 g of a novel substance, 6-chloro-9-(3'-deoxy-2',5'-di-O-acetyl-β-D-ribofuranosyl)-7-deazapurine (Compound 16).

Synthesis Example 19
Synthesis of 6-chloro-7-iodo-9-(3'-deoxy-2',5'-di-O-acetyl-β-D-ribofuranosyl)-7-deazapurine (Compound 17)

6-Chloro-9-(3'-deoxy-2',5'-di-O-acetyl-β-D-ribofuranosyl)-7-deazapurine (Compound 16, 1.44 g, 4.07 mmol) was dissolved in acetonitrile (67 ml), added with cerium (IV) diammonium nitrate (0.62 g, 2.44 mmol) and iodine (1.12 g, 2.03 mmol), and stirred at 80° C. for 30 minutes. After the reaction was completed, the acetonitrile was concentrated under reduced pressure, and the residue was dissolved in ethyl acetate, and washed with 5% sodium hydrogensulfite solution, saturated sodium hydrogencarbonate solution and saturated saline. The ethyl acetate layer was dried over anhydrous magnesium sulfate, and evaporated, and the residue was crystallized from methylene chloride-ether to afford 1.46 g of a novel substance, 6-chloro-7-iodo-9-(3'-deoxy-2',5'-di-O-acetyl-β-D-ribofuranosyl)-7-deazapurine (Compound 17, yield; 75.0%).

Melting point: 149–150° C.

$^1$H-NMR (270 MHz, DMSO-d$_6$) δ ppm: 2.14, 2.17 (2s, 6H, 2Ac), 2.23–2.49 (m, 2H, 3'-Ha, b), 4.25–4.48 (m, 2H, 5'-Ha, b), 4.58–4.68 (m, 1H, 4'-H), 5.52–5.54 (m, 1H, 2'-H), 6.33 (d, 1H, J=1.4 Hz, 1'-H), 7.64 (s, 1H, 8-H), 8.63 (s, 1H, 2-H)

Synthesis Example 20
Synthesis of 7-iodo-3'-deoxy-7-deazaadenosine (Compound 18)

6-Chloro-7-iodo-9-(3'-deoxy-2',5'-di-O-acetyl-β-D-ribofuranosyl)-7-deazapurine (Compound 17, 1.63 g, 3.40 mmol) and ammonia-methanol (70 ml) were allowed to react at 110° C. for 20 hours. After the reaction was completed, the reaction mixture was concentrated under reduced pressure, and crystallized from methanol to afford 1.00 g of a novel substance, 7-iodo-3'-deoxy-7-deazaadenosine (Compound 18, yield; 78.8%).

Melting point: 223–225° C. (decomposition)

Synthesis Example 21
Synthesis of 7-deaza-7-(6"-trifluoroacetamido-1"-hexynyl)-3'-deoxyadenosine (Compound 19)

To a solution of 7-iodo-3'-deoxy-7-deazaadenosine (Compound 18, 220 mg, 0.585 mmol) in DMF (3 ml), the 6-trifluoroacetamido-1-hexyne obtained in Synthesis Example 7 (339 mg, 1.75 mmol), cuprous (I) iodide (22.3 mg, 0.117 mmol), tetrakis(triphenylphosphine) palladium (0) (67.5 mg, 0.058 mmol), and triethylamine (0.163 ml, 1.17 mmol) were added under nitrogen gas flow, and allowed to react at room temperature for 30 minutes. The reaction mixture was diluted with a methylene chloride-methanol mixture (6 ml), added with ion exchange resin AG1X8 (HCO$_3^-$ type, 0.55 g), and stirred for 30 minutes. After filtration of the reaction mixture, the filtrate was concentrated, and the resulting residue was purified by silica gel column chromatography (eluent; chloroform-methanol mixed solution) to afford 210 mg of a novel substance, 7-deaza-7-(6"-trifluoroacetamido-1"-hexynyl)-3'-deoxyadenosine (Compound 19, yield; 81.6%).

$^1$H-NMR (270 MHz, DMSO-d$_6$) δ ppm: 1.55–1.63 (m, 4H, —(CH$_2$)$_2$—), 1.83–1.92 (m, 1H, 3'-Ha), 2.13–2.24 (m, 1H, 3'-Hb), 2.47–2.52 (m, 2H, CCCH$_2$—), 3.16–3.24 (m, 2H, CH$_2$N), 3.46–3.54 (m, 1H, 5'-Ha), 3.62–3.68 (m, 1H, 5'-Hb), 4.23–4.38 (m, 2H, 2'-H and 4'-H), 5.03 (t, 1H, J=5.5 Hz, 5'-OH), 5.56 (d, 1H, J=4.3 Hz, 2'-OH), 6.01 (d, 1H, J=2.2 Hz, 1'-H), 6.60 (brs, 2H, 6-NH$_2$), 7.65 (s, 1H, 8-H), 8.11 (s, 1H, 2-H), 9.44 (brs, 1H, NHTfa)

Synthesis Example 22
Synthesis of 7-deaza-7-(6"-amino-1"-hexynyl)-3'-deoxyadenosine-5'-triphosphate (Compound 20)

7-Deaza-7-(6"-trifluoroacetamido-1"-hexynyl)-3'-deoxyadenosine (Compound 19, 181 mg, 0.41 mmol) was dissolved in triethyl phosphate (1.81 ml), cooled to −20° C., then added with phosphorus oxychloride (34.32 µl), and stirred at −20° C. After 30 minutes, the reaction mixture was added with further phosphorus oxychloride (30.5 µl), and stirred for further four hours.

This reaction mixture was added to 0.5 M solution of tris (tri-n-butylammonium) pyrophosphate in DMF (4.9 ml) cooled to −20° C., and stirred at room temperature for three hours. After the reaction was completed, the reaction mixture was added with a triethylamine-water mixture (5 ml), left stand overnight, added with 25% aqueous ammonia (20 ml), and left stand for four hours. The reaction mixture was washed with ether, and concentrated to dryness, and the resulting residue was purified by DEAE-Toyopearl ion exchange column chromatography (1.2×30 cm, eluent; triethylammonium hydrogencarbonate buffer (pH$_{7.5}$), 0 M→0.3 M linear gradient (total volume; 1 L)) to afford 283 mg of a novel substance 7-deaza-7-(6"-amino-1"-hexynyl)-3'-deoxyadenosine-5'-triphosphate (Compound 20, yield; 69.6%).

Synthesis Example 23
Synthesis of R6G-labeled 7-deaza-3'-deoxyadenosine-5'-triphosphate (A Compound of the General Formula [I] Where V is —C≡C— and n=4)

To 7-deaza-7-(6"-amino-1"-hexynyl)-3'-deoxyadenosine-5'-triphosphate (Compound 20, 8 µmol) dissolved in a mixture of DMF (0.6 ml) and water (0.3 ml), triethylamine (10 µl) and a solution of 5-carboxyrhodamine-6G succinimide ester (Molecular Probe, 16 µmol) in DMF (1.3 ml) were added, and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH 7.5), 0.1 M→0.6 M linear gradient (total volume; 2 L)) to afford 5.33 µmol (yield; 66.7%) of R6G-labeled 7-deaza-3'-deoxyadenosine-5'-triphosphate represented by the following formula [a compound of the general formula [I] where V is —C|C— and n=4, abbreviated as R6G-3'dATP(n4) hereinafter].

Synthesis Example 25
Synthesis of 7-deaza-7-(8"-amino-1"-octynyl)-3'-deoxyadenosine-5'-triphosphate (Compound 22)

7-Deaza-7-(8"-trifluoroacetamido-1"-octynyl)-3'-deoxyadenosine (Compound 21, 189 mg, 0.403 mmol) was dissolved in triethyl phosphate (1.89 ml), cooled to −20° C., then added with phosphorus oxychloride (33.7 µl), and stirred at −20° C. After 30 minutes, the reaction mixture was added with further phosphorus oxychloride (30.0 µl), and stirred for further four hours.

This reaction mixture was added to 0.5 M solution of tris (tri-n-butylammonium) pyrophosphate in DMF (4.8 ml) cooled to −20° C., and stirred at room temperature for three

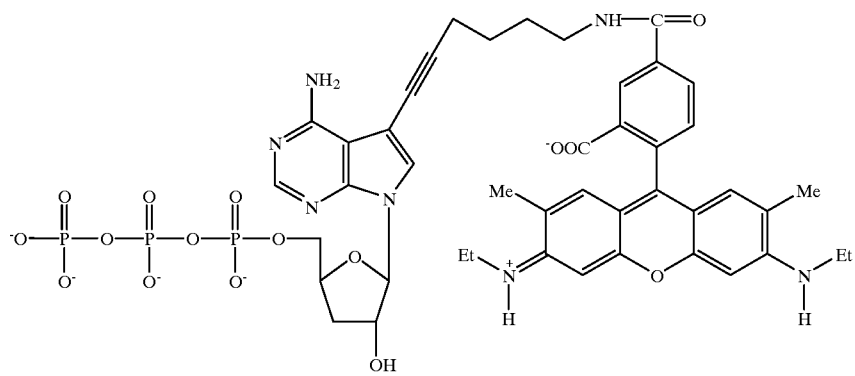

In the formula, Et represents an ethyl group, and Me represents a methyl group.

Figure 17:
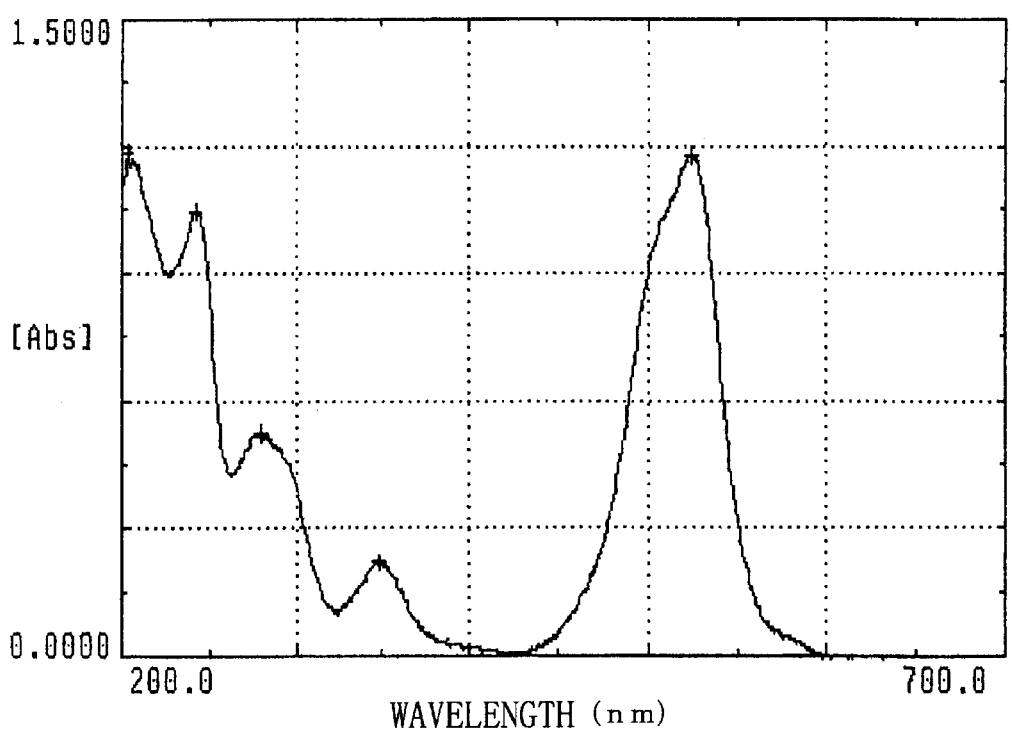
FIG. 17 shows the result of UV-visible region spectrophotometry of the carboxyrhodamine-6G-labeled 7-deaza-3'-deoxyadenosine-5'-triphosphate (a compound of the general formula [I] where V is —C≡C— and n=4) obtained in Synthesis Example 23.

The absorption spectrum for UV-visible region resulting from spectroscopy of the obtained R6G-3'dATP(n4) (measurement wavelength; 700 nm to 200 nm, reference; distilled water) performed by using DU640 UV-visible region spectrophotometer [Beckman] is shown in FIG. 17.

Synthesis Example 24
Synthesis of 7-deaza-7-(8"-trifluoroacetamido-1"-octynyl)-3'-deoxyadenosine (Compound 21)

To a solution of 7-iodo-3'-deoxy-7-deazaadenosine (Compound 18, 220 mg, 0.585 mmol) in DMF (3 ml), the 8-trifluoroacetamido-1-octyne obtained in Synthesis Example 11 (388 mg, 1.75 mmol), cuprous (I) iodide (22.3 mg, 0.117 mmol), tetrakis(triphenylphosphine) palladium (0) (67.5 mg, 0.058 mmol), and triethylamine (0.163 ml, 1.17 mmol) were added under nitrogen gas flow, and allowed to react at room temperature for 30 minutes. The reaction mixture was diluted with a methylene chloride-methanol mixture (6 ml), added with ion exchange resin AG1X8 ($HCO_3^-$ type, 0.55 g), and stirred for 30 minutes. After filtration of the reaction mixture, the filtrate was concentrated, and the resulting residue was purified by silica gel column chromatography (eluent; chloroform-methanol mixed solution) to afford 216 mg of a novel substance, 7-deaza-7-(8"-trifluoroacetamido-1"-octynyl)-3'-deoxyadenosine (Compound 21, yield; 78.7%).

$^1$H-NMR (270 MHz, DMSO-$d_6$) δ ppm: 1.29–1.58 (m, 8H, —$(CH_2)_4$—), 1.83–1.91 (m, 1H, 3'-Ha), 2.14–2.24 (m, 1H, 3'-Hb), 2.44–2.51 (m, 2H, $CCCH_2$), 3.15–3.22 (m, 2H, $CH_2N$), 3.46–3.54 (m, 1H, 5'-Ha), 3.62–3.70 (m, 1H, 5'-Hb), 4.26–4.36 (m, 2H, 2'-H and 4'-H), 5.04 (t, 1H, J=5.4 Hz, 5'-OH), 5.56 (d, 1H, J=4.6 Hz, 2'-OH), 6.01 (d, 1H, J=2.4 Hz, 1'-H), 6.60 (brs, 2H, 6-$NH_2$), 7.65 (s, 1H, 8-H), 8.11 (s, 1H, 2-H), 9.38 (brs, 1H, NHTfa)

hours. After the reaction was completed, the reaction mixture was added with a triethylamine-water mixture (15 ml), left stand overnight, added with 25% aqueous ammonia (20 ml), and left stand for four hours. The reaction mixture was washed with ether, and concentrated to dryness, and the resulting residue was purified by DEAE-Toyopearl ion exchange column chromatography (1.2×30 cm, eluent; triethylammonium hydrogencarbonate buffer (pH 7.5), 0 M→0.6 M linear gradient (total volume; 1 L)) to afford 143 mg of a novel substance, 7-deaza-7-(8"-amino-1"-octynyl)-3'-deoxyadenosine-5'-triphosphate (Compound 22, yield; 35%)).

Synthesis Example 26
Synthesis of R6G-labeled 7-deaza-3'-deoxyadenosine-5'-triphosphate (A Compound of the General Formula [I] Where V is —C≡C— and n=6)

To 7-deaza-7-(8"-amino-1"-octynyl)-3'-deoxyadenosine-5'-triphosphate (Compound 22, 8 µmol) dissolved in a mixture of DMF (0.6 ml) and water (0.3 ml), triethylamine (10 µl) and a solution of 5-carboxyrhodamine-6G succinimide ester (Molecular Probe, 16 µmol) in DMF (1.3 ml) were added, and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH 7.5), 0.1 M→0.6 M linear gradient (total volume; 2 L)) to afford 4.3 µmol (yield; 53.8%) of R6G-labeled 7-deaza-3'-deoxyadenosine-5'-triphosphate represented by the following formula [a compound of the general formula [I] where V is —C≡C— and n=6, abbreviated as R6G-3'dATP(n6) hereinafter].

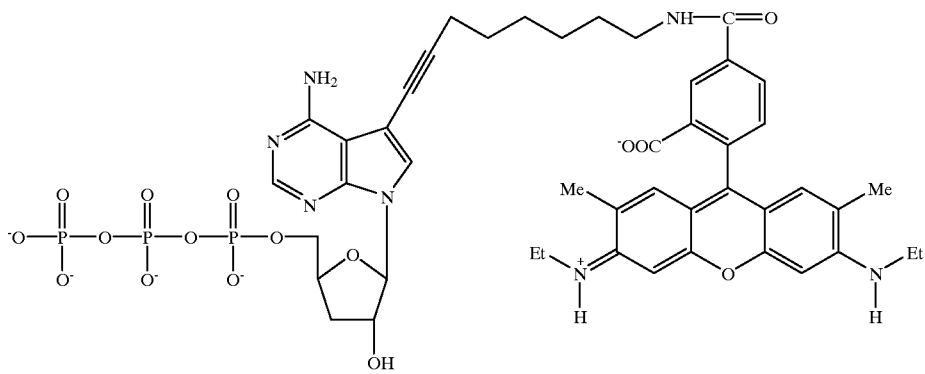

In the formula, Et represents an ethyl group, and Me represents a methyl group.

Figure 18:
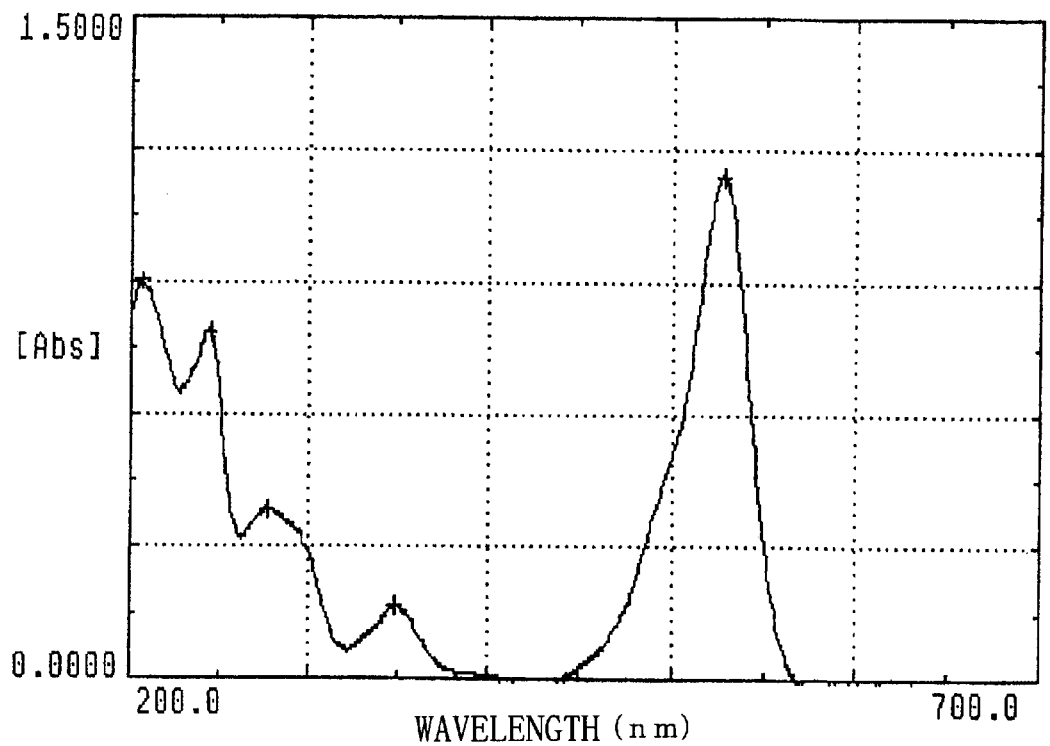
FIG. 18 shows the result of UV-visible region spectrophotometry of the carboxyrhodamine-6G-labeled 7-deaza-3'-deoxyadenosine-5'-triphosphate (a compound of the general formula [I] where V is —C≡C— and n=6) obtained in Synthesis Example 26.

The absorption spectrum for UV-visible region resulting from spectroscopy of the obtained R6G-3'dATP(n6) (measurement wavelength; 700 nm to 200 nm, reference; distilled water) performed by using DU640 UV-visible region spectrophotometer [Beckman] is shown in FIG. 18.

Synthesis Example 27
Synthesis of 3'-deoxy-5-iodouridine (Compound 2)

3'-Deoxyuridine (Compound 1, 2.08 g, 9.11 mmol) was dissolved in acetic acid (75 ml), added with cerium (IV) diammonium nitrate (2.50 g, 4.56 mmol) and iodine (1.39 g, 2.73 mmol), and stirred at 80° C. for 30 minutes. After the reaction was completed, the reaction mixture was concentrated under reduced pressure, and further concentrated by azeotropy three times with an ethanol-toluene mixture (1:2 v/v; 30 ml), and three times with a water-ethanol mixture (1:2 v/v; 30 ml) to afford an oily product. The resulting residue was purified by silica gel column chromatography (eluent; methylene chloride-methanol mixed solvent) to afford 1.78 g of 3'-deoxy-5-iodouridine (Compound 2, yield; 55.08%).

$^1$H-NMR (270 MHz, DMSO-$d_6$) δ ppm: 1.89–1.92 (m, 1H, 3'-Ha), 2.17–2.26 (m, 1H, 3'-Hb), 3.51–3.56 (m, 1H, 5'-Ha), 3.74–3.79 (m, 1H, 5'-Hb), 4.22–4.30 (m, 2H, 2'-H and 4'-H), 5.59 (s, 1H, 1'-H), 8.31 (s, 1H, 6-H), 11.72 (s, 1H, NH)

Synthesis Example 28
Synthesis of 3'-deoxy-5-(6"-trifluoroacetamido-1"-hexynyl) uridine (Compound 3)

To a solution of 3'-deoxy-5-iodouridine (Compound 2, 805 mg, 2.27 mmol) in DMF (12 ml), the 6-trifluoroacetamido-1-hexyne obtained in Synthesis Example 7 (1.31 g, 6.80 mmol), cuprous (I) iodide (86.3 mg, 0.453 mmol), tetrakis(triphenylphosphine) palladium (0) (262 mg, 0.227 mmol), and triethylamine (0.63 ml, 4.53 mmol) were added under nitrogen gas flow, and allowed to react at room temperature for four hours. The reaction mixture was concentrated under reduced pressure, and the resulting residue was dissolved in a methylene chloride-methanol mixture (20 ml), added with ion exchange resin AG1X8 (BIO-RAD, HCO$_3^-$ type, 2 g), and stirred for 30 minutes. After filtration of the reaction mixture, the filtrate was concentrated, and the resulting residue was purified by silica gel column chromatography (eluent; methylene chloride-methanol mixed solution) to afford 419 mg of a novel substance, 3'-deoxy-5-(6"-trifluoroacetamido-1"-hexynyl)uridine (Compound 3, yield; 45.5%).

$^1$H-NMR (270 MHz, DMSO-$d_6$) δ ppm: 1.49–1.64 (m, 4H, —(CH$_2$)$_2$—), 1.92–1.97 (m, 1H, 3'-Ha), 2.17–2.28 (m, 1H, 3'-Hb), 2.39 (t, 2H, J=6.9 Hz, —CCCH$_2$), 3.21 (q, 2H, J=6.3 Hz, CH$_2$N), 3.49–3.54 (m, 1H, 5'-Ha), 3.72–3.75 (m, 1H, 5'-Hb), 4.24–4.35 (m, 2H, 2'-H and 4'H), 5.20 (t, 1H, J=4.9 Hz, 5'-OH), 5.52 (d, 1H, J=3.8 Hz, 2'-OH), 5.75 (s, 1H, J=2.2 Hz, 1'-H), 8.23 (s, 1H, 6-H), 9.42 (brs, 1H, NHTfa), 11.57 (s, 1H, 3-NH)

Synthesis Example 29
Synthesis of 5-(6"-amino-1"-hexynyl)-3'-deoxyuridine-5'-triphosphate (Compound 4)

3'-Deoxy-5-(6"-trifluoroacetamido-1"-hexynyl)uridine (Compound 3, 122.5 mg, 0.3 mmol) was dissolved in triethyl phosphate (1.23 ml), cooled to −20° C., added with phosphorus oxychloride (25 μl), and stirred at −20° C. After 30 minutes, the reaction mixture was added with further phosphorus oxychloride (22 μl), and stirred for further five hours. This reaction mixture was added to 0.5 M solution of tris(tri-n-butylammonium) pyrophosphate in the DMF (3.6 ml) cooled to −20° C., and stirred at room temperature for four hours. After the reaction was completed, the reaction mixture was added with a triethylamine-water mixture (5 ml), left stand overnight, added with 25% aqueous ammonia (20 ml), and left stand for four hours. The reaction mixture was washed with ether, and concentrated to dryness, and the resulting residue was purified by DEAE-Toyopearl ion exchange column chromatography (Tosoh Corporation, 1.2× 30 cm, eluent; triethylammonium hydrogencarbonate buffer (pH 7.5), 0 M→0.3 M linear gradient (total volume; 1 L)) to afford 172 mg of a novel substance, 5-(6"-amino-1"-hexynyl)-3'-deoxyuridine-5'-triphosphate (Compound 4, yield; 60.0%).

Synthesis Example 30
Synthesis of TMR-labeled 3'-deoxyuridine-5'-triphosphate (A Compound of the General Formula [I] Where V is —C≡C— and n=4)

To 5-(6"-amino-1"-hexynyl)-3'-deoxyuridine-5'-triphosphate (Compound 4, 8 μmol) dissolved in a mixture of DMF (300 μl) and water (300 μl), triethylamine (10 μl) and 5-carboxytetramethylrhodamine succinimide ester (Molecular Probe, 13 μmol) were added, and stirred at room temperature overnight. The reaction mixture was diluted with water (30 ml), and purified by DEAE-Toyopearl ion exchange column chromatography (1.7×30 cm, eluent; triethylammonium hydrogencarbonate buffer (pH 7.5), 0.05 M→0.7 M linear gradient (total volume; 2 L)) to afford 5.9 μmol (yield; 73.8%) of TMR-labeled 3'-deoxyuridine-5'-triphosphate represented by the following formula [a compound of the general formula [I] where V is —C≡C— and n=4, abbreviated as TMR-3'dUTP(n4) hereinafter].

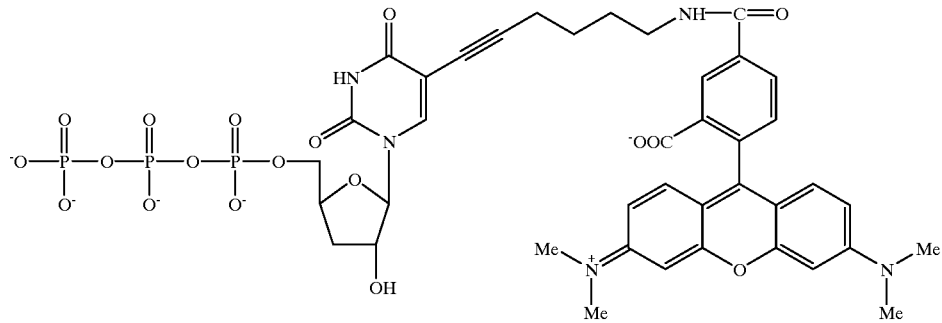

In the formula, Me represents a methyl group.

Figure 19:
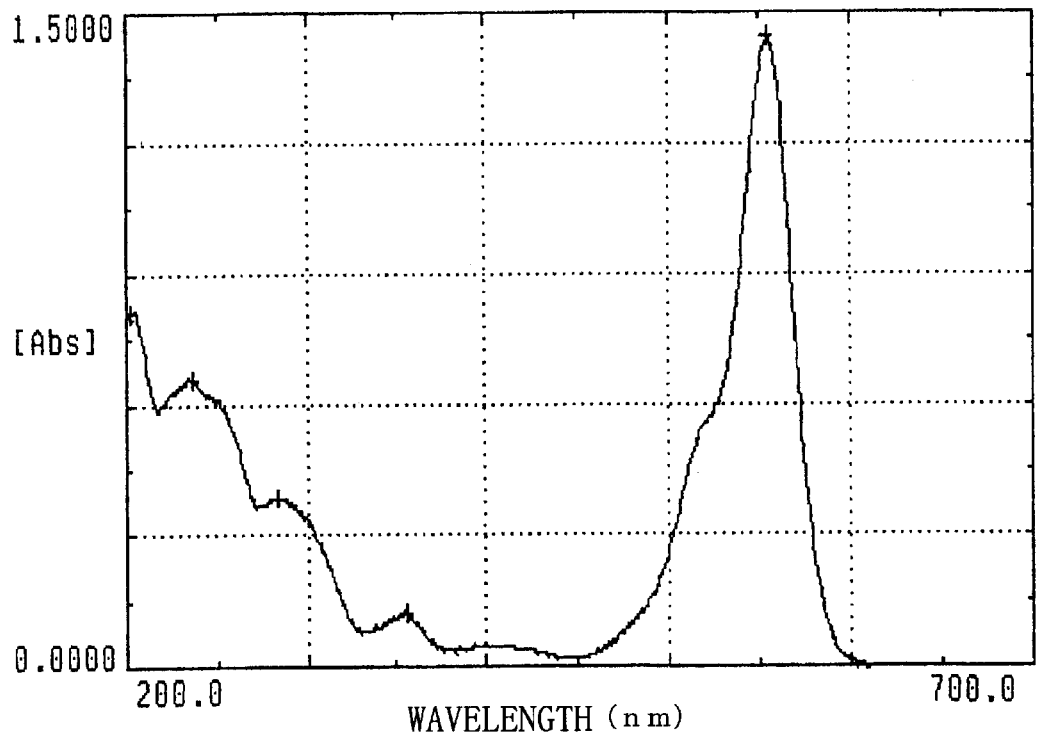
FIG. 19 shows the result of UV-visible region spectrophotometry of the carboxytetramethylrhodamine-labeled 3'-deoxyuridine-5'-triphosphate (a compound of the general formula [I] where V is —C≡C— and n=4) obtained in Synthesis Example 30.

The absorption spectrum for UV-visible region resulting from spectroscopy of the obtained TMR-3'dUTP(n4) (measurement wavelength; 700 nm to 200 nm, reference; distilled water) performed by using DU640 UV-visible region spectrophotometer [Beckman] is shown in FIG. 19.

Synthesis Example 31
Synthesis of 6-methoxy-2-methylthio-9-{2',5'-bis(O-tert-butyldimethylsilyl)-3'-O-[(imidazol-1-yl)thiocarbonyl]-β-D-ribofuranosyl}-7-deazapurine (Compound 25)

6-Methoxy-2-methylthio-9-(β-D-ribofuranosyl)-7-deazapurine (Compound 23, 12.86 g, 39.28 mmol) was dissolved in THF (580 ml), added with pyridine (16.8 ml, 208 mmol), silver nitrate (15.55 g, 91.5 mmol) and tert-butyldimethylsilyl chloride (13.80 g, 91.5 mmol), and stirred at room temperature overnight. After the reaction was completed, the precipitates were removed by filtration through celite, and the filtrate was concentrated, dissolved in chloroform, and washed with 0.2 N hydrochloric acid and saturated saline. The chloroform layer was dried over anhydrous magnesium sulfate, and the chloroform was evaporated to afford 24.0 g of crude 6-methoxy-2-methylthio-9-[2',5'-bis(O-tert-butyldimethylsilyl)-β-D-ribofuranosyl]-7-deazapurine (Compound 24). The resulting Compound 24 (24.0 g) was dissolved in DMF (400 ml), added with 1,1'-thiocarbonyldiimidazole (35.0 g, 196.5 mmol), and stirred at room temperature overnight. After the reaction was completed, the reaction mixture was added with ethyl acetate and water, and the organic layer was washed with saturated saline. The ethyl acetate layer was dried over anhydrous magnesium sulfate, and concentrated under reduced pressure, and the resulting residue was purified by silica gel column chromatography (eluent; ethyl acetate-chloroform mixed solvent) to afford 20.45 g of a novel substance, 6-methoxy-2-methylthio-9-{2',5'-bis(O-tert-butyldimethylsilyl)-3'-O-[(imidazol-1-yl)thiocarbonyl]-β-D-ribofuranosyl}-7-deazapurine (Compound 25, yield; 78.2%).

Synthesis Example 32
Synthesis of 6-methoxy-2-methylthio-9-[2',5'-bis(O-tert-butyldimethylsilyl)-3'-deoxy-β-D-ribofuranosyl]-7-deazapurine (Compound 26)

6-Methoxy-2-methylthio-9-{2',5'-bis(O-tert-butyldimethylsilyl)-3'-O-[(imidazol-1-yl)thiocarbonyl]-β-D-ribofuranosyl}-7-deazapurine (Compound 25, 20.45 g, 30.7 mmol) was dissolved in toluene (1 L), added with 2,2'-azobis(isobutyronitrile) (1.01 g, 6.1 mmol) and n-tributyltin hydride (16.5 ml, 61.4 mmol), and stirred at 80° C. under nitrogen gas flow for 30 minutes. After the reaction was completed, the toluene was evaporated, and the residue was purified by silica gel column chromatography (eluent; ethyl acetate-n-hexane mixed solvent) to afford 14.57 g of a novel substance, 6-methoxy-2-methylthio-9-[2',5'-bis(O-tert-butyldimethylsilyl)-3'-deoxy-β-D-ribofuranosyl]-7-deazapurine (Compound 26, yield; 87.9%).

Synthesis Example 33
Synthesis of 7-iodo-6-methoxy-2-methylthio-9-[2',5'-bis(O-tert-butyldimethylsilyl)-3'-deoxy-β-D-ribofuranosyl]-7-deazapurine (Compound 27)

6-Methoxy-2-methylthio-9-[2',5'-bis(O-tert-butyldimethylsilyl)-3'-deoxyβ-D-ribofuranosyl]-7-deazapurine (Compound 26, 15.57 g, 28.84 mmol) was dissolved in DMF, added with N-iodosuccinimide (7.79 g, 34.61 mmol), and stirred at room temperature for five hours under nitrogen gas flow while shielded from light. After the reaction was completed, the reaction mixture was cooled to 0° C., and added with ethyl acetate and water, and the organic layer was washed with 5% sodium thiosulfate solution, saturated sodium hydrogencarbonate solution, and saturated saline. The ethyl acetate layer was dried over anhydrous magnesium sulfate, and the ethyl acetate was evaporated. The residue was purified by silica gel column chromatography (eluent; chloroform-n-hexane mixed solvent) to afford 19.06 g of a novel substance, 7-iodo-6-methoxy-2-methylthio-9-[2',5'-bis(O-tert-butyldimethylsilyl)-3'-deoxy-β-D-ribofuranosyl]-7-deazapurine (Compound 27, yield; 99.3%).

1H-NMR (270 MHz, DMSO-$d_6$) δ ppm: –0.10, –0.06, 0.12, 0.13 (4s, 12H, 4 MeSi), 0.80, 0.93 (2s, 18H, 2t-Bu), 1.90–2.10 (m, 1H, 3'-Ha), 2.18–2.28 (m, 1H, 3'-Hb), 2.54 (s, 3H, SMe), 3.72 (dd, 1H, J=2.7, 11.6 Hz, 5'-Ha), 3.94 (dd, 1H, J=2.2, 11.6 Hz, 5'-Hb), 4.03 (s, 3H, OMe), 4.32–4.48 (m, 2H, 2'-H, 4'-H), 6.07 (d, 1H, J=3.0 Hz, 1'-H), 7.59 (s, 1H, 8-H)

Synthesis Example 34
Synthesis of 7-iodo-2-methylthio-9-[2',5'-bis(O-tert-butyldimethylsilyl)-3'-deoxy-β-D-ribofuranosyl]-7-deazapurin-6-one (Compound 28)

4-Thiocresol (3.36 g, 27.0 mmol) was dissolved in methanol, and added with sodium methoxide (1.61 g, 29.7 mmol), and the methanol was evaporated after stirring for five minutes. This residue was added with 7-iodo-6-methoxy-2-methylthio-9-[2',5'-bis(O-tert-butyldimethylsilyl)-3'-deoxyβ-D-ribofuranosyl]-7-deazapurine (Compound 27, 4.00 g, 6 mmol) dissolved in toluene (150 ml) and hexamethylphosphoramide (10 ml, 57.1 mmol), and refluxed under nitrogen gas flow for 4.5 hours. After the reaction was completed, ethyl acetate and water were added to the reaction mixture, and the organic layer was washed with saturated saline. The organic layer was dried anhydrous magnesium sulfate, and concentrated under reduced pressure, and the resulting residue was purified by silica gel column chromatography (eluent; methylene chloride-methanol mixed solvent) to afford 2.35 g of a novel substance, 7-iodo-2-methylthio-9-[2',5'-bis(O-tert-butyldimethylsilyl)-3'-deoxy-β-D-ribofuranosyl]-7-deazapurin-6-one (Compound28, yield; 59.9%).

$^1$H-NMR (270 MHz, DMSO-d$_6$) δ ppm: 0.06, 0.08, 0.20, 0.24 (4s, 12H, 4 MeSi), 0.92, 1.03 (2s, 18H, 2t-Bu), 2.07–2.13 (m, 1H, 3'-Ha), 2.34–2.38 (m, 1H, 3'-Hb), 2.63 (s, 3H, SMe), 3.81–4.05 (m, 2H, 5'-Ha,b), 4.46–4.57 (m, 2H, 2'-H, 4'-H), 6.12 (d, 1H, J=3.0 Hz, 1'-H), 7.47 (s, 1H, 8-H), 12.44 (s, 1H, 1-H)

Synthesis Example 35

Synthesis of 7-iodo-2',5'-bis(O-tert-butyldimethylsilyl)-3'-deoxy-7-deazaguanosine (Compound 29)

7-Iodo-2-methylthio-9-[2',5'-bis(O-tert-butyldimethylsilyl)-3'-deoxy-β-D-ribofuranosyl]-7-deazapurin-6-one (Compound 28, 2.30 g, 3.53 mmol) was dissolved in methylene chloride (90 ml), cooled to 0° C., added with m-chloroperbenzoic acid (0.96 g, 3.88 mmol), and stirred at 0° C. for 15 minutes and at room temperature for one hour. After the reaction was completed, the reaction mixture was washed with saturated sodium hydrogencarbonate solution and saturated saline, and dried over anhydrous magnesium sulfate, and the methylene chloride was evaporated. The resulting residue was purified by silica gel column chromatography (eluent; chloroform-methanol mixed solvent) to afford 2.02 g of a sulfoxide compound (yield; 83.9%). This compound was dissolved in 1,4-dioxane (20 ml), cooled to −78° C., added with aqueous ammonia (60 ml), and heated to 110° C. for six hours. After the reaction was completed, the reaction mixture was concentrated under reduced pressure, and the resulting residue was purified by silica gel column chromatography (eluent; methylene chloride-methanol mixed solvent) to afford 1.60 g of a novel substance, 7-iodo-2',5'-bis(O-tert-butyldimethylsilyl)-3'-deoxy-7-deazaguanosine (Compound 29, yield; 73.1%).

Synthesis Example 36

Synthesis of 3'-deoxy-7-iodo-7-deazaguanosine (Compound 30)

7-Iodo-2',5'-bis(O-tert-butyldimethylsilyl)-3'-deoxy-7-deazaguanosine (Compound 29, 1.6 g, 2.58 mmol) was dissolved in THF (50 ml), added with 1 M tetrabutylammonium fluoride (6.2 ml, 6.17 mmol), and stirred at room temperature overnight. After the reaction was completed, the reaction mixture was concentrated under reduced pressure, and the residue was purified by silica gel column chromatography (eluent; chloroform-methanol mixed solvent), and crystallized from methanol to afford 0.80 g of a novel substance, 3'-deoxy-7-iodo-7-deazaguanosine (Compound 30, yield; 79.1%).

Melting point: 176–178° C. (decomposition)

$^1$H-NMR (270 MHz, DMSO-d$_6$) δ ppm: 1.81–1.89 (m, 1H, 3'-Ha), 2.10–2.20 (m, 1H, 3'-Hb), 3.43–3.64 (m, 2H, 5'-Ha,b), 4.18–4.29 (m, 2H, 2'-H, 4'-H), 4.91 (t, 1H, J=5.5 Hz, 5'-OH), 5.46 (d, 1H, J=4.3 Hz, 2'-OH), 5.80 (d, 1H, J=2.4 Hz, 1'-H), 6.30 (brs, 2H, 2-NH$_2$), 7.10 (s, 1H, 8-H), 10.45 (brs, 1H, 1-H)

Synthesis Example 37

Synthesis of 3'-deoxy-7-(6"-trifluoroacetamido-1"-hexynyl)-7-deazaguanosine (Compound 31)

To a solution of 3'-deoxy-7-iodo-7-deazaguanosine (Compound 30, 765 mg, 2.0 mmol) in DMF (10 ml), the 6-trifluoroacetamido-1-hexyne obtained in Synthesis Example 7 (1.16 g, 6.0 mmol), cuprous (I) iodide (76.4 mg, 0.40 mmol), tetrakis(triphenylphosphine) palladium (0) (226mg, 0.20 mmol), and triethylamine (0.56 ml, 4.0 mmol) were added under nitrogen gas flow, and allowed to react at room temperature for one hour. The reaction mixture was diluted with methylene chloride-methanol mixture (20 ml), added with ion exchange resin AG1X8 (HCO$_3^-$ type, 2.0 g), and stirred for 30 minutes. After filtration of the reaction mixture, the filtrate was concentrated, and the resulting residue was purified by silica gel column chromatography (eluent; chloroform-methanol mixed solution) to afford 616 mg of a novel substance, 3'-deoxy-7-(6"-trifluoroacetamido-1"-hexynyl)-7-deazaguanosine (Compound 31, yield; 69.5%).

Melting point: 185–187° C.

$^1$H-NMR (270 MHz, DMSO-d$_6$) δ ppm: 1.47–1.68 (m, 4H, —(CH$_2$)$_2$—), 1.80–1.88 (m, 1H, 3'-Ha), 2.09–2.19 (m, 1H, 3'-Hb), 2.38 (t, 2H, J=6.9 Hz, CCCH$_2$), 3.25 (q, 2H, J=6.8 Hz, CH$_2$N), 3.42–3.62 (m, 2H, 5'-Ha,b), 4.17–4.30 (m, 2H, 2'-H, 4'-H), 4.90 (t, 1H, J=5.5 Hz, 5'-OH), 5.45 (d, 1H, J=4.3 Hz, 2'-OH), 5.80 (d, 1H, J=2.7 Hz, 1'-H), 6.28 (brs, 2H, 2-NH$_2$), 7.11 (s, 1H, 8-H), 9.42 (brs, 1H, NHTfa), 10.39 (s, 1H, 1-H)

Synthesis Example 38

Synthesis of 7-deaza-7-(6"-amino-1"-hexynyl)-3'-deoxyguanosine-5'-triphosphate (Compound 32)

3'-Deoxy-7-(6"-trifluoroacetamido-1"-hexynyl)-7-deazaguanosine (Compound 31, 133 mg, 0.3 mmol) was dissolved in triethyl phosphate (1.33 ml), cooled to −20° C., added with phosphorus oxychloride (25 μl), and stirred at −20° C. After 30 minutes, the reaction mixture was added with further phosphorus oxychloride (22 μl), and further stirred overnight. This reaction mixture was added to 0.5 M solution of tris (tri-n-butylammonium) pyrophosphate in DMF (3.6 ml) cooled to −20° C., and stirred at room temperature for three hours. After the reaction was completed, the reaction mixture was added with a triethylamine-water mixture (4 ml), washed with ether, and purified by DEAE-Toyopearl ion exchange column chromatography (1.7×30cm, eluent; triethylammonium hydrogencarbonate buffer (pH 7.5), 0 M→0.6 M linear gradient (total volume; 2 L)). The purified product was added with 25% aqueous ammonia (20 ml), left stand for one hour, and then concentrated under reduced pressure, and the obtained residue was purified again by DEAE-Toyopearl ion exchange column chromatography (1.7×30 cm, eluent; triethylammonium hydrogencarbonate buffer (pH 7.5), 0 M→0.3 M linear gradient (total volume; 1 L)) to afford 108 mg of a novel substance, 7-deaza-7-(6"-amino-1"-hexynyl)-3'-deoxyguanosine-5'-triphosphate (Compound 32, yield; 36.4%).

Synthesis Example 39

Synthesis of R110-labeled 7-deaza-3'-deoxyguanosine-5'-triphosphate (A Compound of General Formula [I] Where V is —C≡C— and n=4)

7-Deaza-7-(6"-amino-1"-hexynyl)-3'-deoxyguanosine-5'-triphosphate (Compound 32, 8 μmol) and 5-carboxyrhodamine-110-bis-trifluoroacetate succinimide ester (Molecular Probe, 15 μmol) were dissolved in DMF (500 μl) and water (250 μl), added with triethylamine (0.16 ml) and pyridine (0.29 ml), and stirred overnight. The reaction mixture was diluted with water (30 ml), and purified by DEAE-Toyopearl ion exchange column chromatography (1.7×30 cm, eluent; triethylammonium hydrogencarbonate buffer (pH$_{7.5}$), 0.1 M→0.8 M linear gradient (total volume; 1 L)) to afford 3.38 μmol (yield; 42.3%) of R110-labeled 7-deaza-3'-deoxyguanosine-5'-triphosphate represented by the following formula [a compound of the general formula [I] where V is —C≡C— and n=4, abbreviated as R110–3'dGTP(n4) hereinafter].

Synthesis Example 42
Synthesis of 5-(3"-amino-1"-propynyl)-3'-deoxyuridine-5'-triphosphate 3'-Deoxy-5-(3"-trifluoroacetamido-1"-propynyl)uridine (42 mg, 0.11 mmol) was dissolved in triethyl phosphate (1.13 ml), cooled to −20° C., then added with phosphorus oxychloride (25 μl), and stirred at −20° C. After 30 minutes,

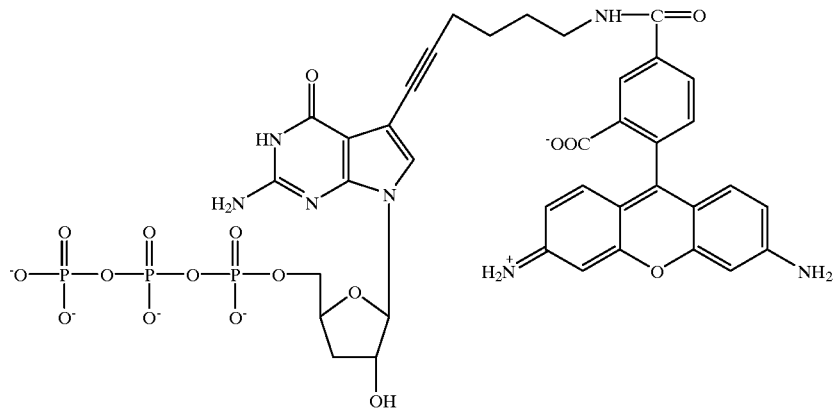

the reaction mixture was added with further phosphorus oxychloride (22 μl), and stirred for further five hours. This reaction mixture was added to 0.5 M solution of the tris(tri-n-butylammonium) pyrophosphate obtained in Synthesis Example 4 in DMF (3.6 ml) cooled to −20° C., and stirred at room temperature for two hours. After the reaction was completed, the reaction mixture was added with a triethylamine-water mixture (4 ml), left stand overnight, added with 25% aqueous ammonia (20 ml), and left stand for four hours. The reaction mixture was washed with ether, and concentrated to dryness, and the obtained residue was purified by DEAE-Toyopearl ion exchange column chromatography (Tosoh Corporation, 1.2×30 cm, eluent; triethylammonium hydrogencarbonate buffer (pH 7.5), 0 M→0.3 M linear gradient (total volume; 1 L)) to afford 115 mg of 5-(3"-amino-1"-propynyl)-3'-deoxyuridine-5'-triphosphate (yield; 41.3%).

Synthesis Example 43
Synthesis of TMR-labeled 3'-deoxyuridine-5'-triphosphate (A Compound of the General Formula [I] Where V is —C≡C— and n=1)

A solution of 5-carboxytetramethylrhodamine succinimide ester (Molecular Probe, 15 mg) in DMF (0.9 ml) was added to 5-(3"-amino-1"-propynyl)-3'-deoxyuridine-5'-triphosphate (10.5 μmol) in 1 M triethylammonium hydrogencarbonate buffer (pH 9.05, 1.2 ml), and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH$_{7.5}$), 0.05 M→0.7 M linear gradient (total volume; 2 L)) to afford 7.38 μmol (yield; 70.2%) of TMR-labeled 3'-deoxyuridine-5'-triphosphate [a compound of the general formula [I] where n=1, abbreviated as TMR-3'dUTP(n1) hereinafter].

Figure 20:
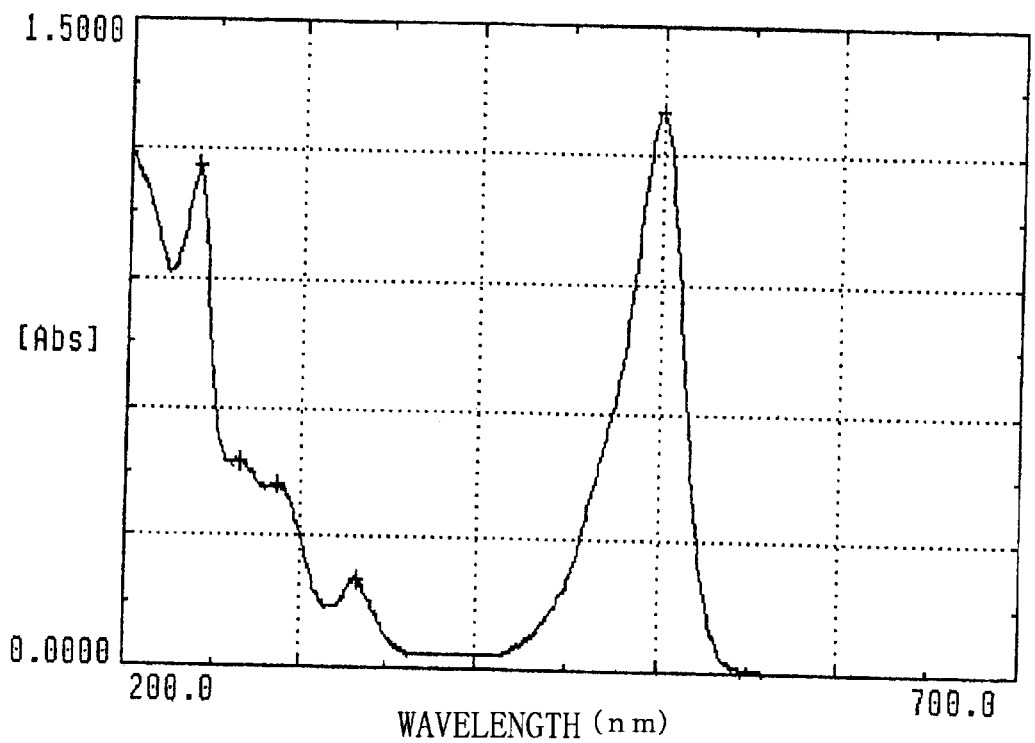
FIG. 20 shows the result of UV-visible region spectrophotometry of the carboxyrhodamine-110-labeled 7-deaza-3'-deoxyguanosine-5'-triphosphate (a compound of general formula [I] where V is —C≡C— and n=4) obtained in Synthesis Example 39.

Synthesis Example 44
Synthesis of 3'-deoxy-5-(3"-trifluoroacetamido-1"-propynyl)cytidine To a solution of 3'-deoxy-5-iodocytidine (Compound 6, 1.0 g, 2.83 mmol) in DMF (14 ml), the The absorption spectrum for UV-visible region resulting from spectroscopy of the obtained R110-3'dGTP (n4) (measurement wavelength; 700 nm to 200 nm, reference; distilled water) performed by using DU640 UV-visible region spectrophotometer [Beckman] is shown in FIG. 20.

Synthesis Example 40
Synthesis of N-propargyltrifluoroacetamide

Propargylamine (Aldrich, 25 g, 0.45 mol) was added dropwise to methyl trifluoroacetate (Tokyo Chemical Industry Co., Ltd., 69.2 g, 0.54 mol) cooled to 0° C. They were allowed to react at 0° C. for two hours to afford 43.8 g (86.0%) of N-propargyltrifluoroacetamide after purification by vacuum distillation (23 mmHg, boiling point; 77° C.).

Synthesis Example 41
Synthesis of 3'-deoxy-5-(3"-trifluoroacetamido-1"-propynyl)uridine To a solution of 3'-deoxy-5-iodouridine (Compound 2, 1.56 g, 4.4 mmol) in DMF (22 ml), the N-propargyltrifluoroacetamide obtained in Synthesis Example 40 (1.54 ml, 13.2 mmol), cuprous (I) iodide (168 mg, 0.88 mmol), tetrakis(triphenylphosphine) palladium (0) (508 mg, 0.44 mmol), and triethylamine (1.23 ml, 8.8 mmol) were added under nitrogen gas flow, and allowed to react at room temperature for four hours. The reaction mixture was concentrated under reduced pressure, and the resulting residue was dissolved in a methylene chloride-methanol mixture (40 ml), added with ion exchange resin AG1X8 (BIO-RAD, HCO$_3^-$ type, 4 g), and stirred for 30 minutes. After filtration of the reaction mixture, the filtrate was concentrated, and the resulting residue was purified by silica gel column chromatography (eluent; methylene chloride-methanol mixed solution) to afford 918 mg of 3'-deoxy-5-(3"-trifluoroacetamido-1"-propynyl)uridine (yield; 55.3%).

$^1$H-NMR (270 MHz, DMSO-d$_6$) δ ppm: 1.89–1.92 (m, 1H, 3'-Ha), 2.17–2.26 (m, 1H, 3'-Hb), 3.53, 3.76 (2dd, 2H, J=3.1, 11.9; 2.7, 12.1 Hz, 5'-Ha,b), 4.22–4.30 (m, 4H, 2'-H, 4'-H, —CH$_2$—), 5.20 (brs, 1H, 5'-OH), 5.52 (d, 1H, J=4.0 Hz, 2'-OH), 5.75 (d, 1H, J=1.9 Hz, 1'-H), 8.34 (s, 1H, 6-H), 10.06 (t, 1H, J=5.4 Hz, NHTfa), 11.67 (s, 1H, NH)

N-propargyltrifluoroacetamide obtained in Synthesis Example 2 (0.99 ml, 8.50 mmol), cuprous (I) iodide (108 mg, 0.566 mmol), tetrakis(triphenylphosphine) palladium (0) (327 mg, 0.283 mmol), and triethylamine (0.8 ml, 5.66 mmol) were added under nitrogen gas flow, and allowed to react at room temperature for 30 minutes. The reaction mixture was diluted with a methylene chloride-methanol mixture (25 ml), added with ion exchange resin AG1X8 ($HCO_3^-$ type, 2.6 g), and stirred for 30 minutes. After filtration of the reaction mixture, the filtrate was concentrated, and the resulting residue was purified by silica gel column chromatography (eluent; methylene chloride-methanol mixed solution) to afford 879 mg of 3'-deoxy-5-(3"-trifluoroacetamido-1"-propynyl)cytidine (yield; 82.5%).

$^1$H-NMR (270 MHz, DMSO-$d_6$) δ ppm: 1.64–1.71 (m, 1H, 3'-Ha), 1.86–1.96 (m, 1H, 3'-Hb), 3.52–3.57 (m, 1H, 5'-Ha), 3.79–3.83 (m, 1H, 5'-Hb), 4.14–4.28 (m, 4H, 2'-H, 4'-H, -CH$_2$—), 5.18 (t, 1H, J=5.0 Hz, 5'-OH), 5.53 (d, 1H, J=3.8 Hz, 2'-OH), 5.63 (s, 1H, 1'-H), 6.76 (brs, 1H, NH$_2$a), 7.74 (brs, 1H, NH$_2$b), 8.38 (s, 1H, 6-H), 9.93 (brs, 1H, NHTfa)

Synthesis Example 45

Synthesis of 5-(3"-amino-1'-propynyl)-3'-deoxycytidine-5'-triphosphate

3'-Deoxy-5-(3"-trifluoroacetamido-1"-propynyl)cytidine (113 mg, 0.3 mmol) was dissolved in triethyl phosphate (1.13 ml), cooled to −20° C., added with phosphorus oxychloride (25 μl), and stirred at −20° C. After 30 minutes, the reaction mixture was added with further phosphorus oxychloride (22 μl), and stirred for further five hours. This reaction mixture was added to 0.5 M solution of the tris (tri-n-butylammonium) pyrophosphate obtained in Synthesis Example 4 in DMF (3.6 ml) cooled to −20° C., and stirred at room temperature for two hours. After the reaction was completed, the reaction mixture was added with a triethylamine-water mixture (4 ml), left overnight, then added with 25% aqueous ammonia (20 ml), and left stand for four hours. The reaction mixture was washed with ether, and concentrated to dryness, and the resulting residue was purified by DEAE-Toyopearl ion exchange column chromatography (1.2×30 cm, eluent; triethylammonium hydrogencarbonate buffer (pH 7.5), 0 M→0.3 M linear gradient (total volume; 1 L)) to afford 115 mg of 5-(3"-amino-1"-propynyl)-3'-deoxycytidine-5'-triphosphate (yield; 41.3%).

Synthesis Example 46

Synthesis of XR-labeled 3'-deoxycytidine-5'-triphosphate (A Compound of the General Formula [I] Where V is —C≡C— and n=1)

To 5-(3"-amino-1"-propynyl)-3'-deoxycytidine-5'-triphosphate (8 μmol) dissolved in 1 M triethylammonium hydrogencarbonate buffer (pH 9.05, 0.4 ml), a solution of 5-carboxy-X-rhodamine succinimide ester (Molecular Probe, 15 mg) in DMF (0.9 ml) was added, and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH$_{7.5}$), 0.1 M→0.7 M linear gradient (total volume; 2 L)) to afford 2.93 μmol (yield; 36.6%) of XR-labeled 3'-deoxycytidine-5'-triphosphate [a compound of the general formula [I] where V is —C≡C— and n=1, abbreviated as XR-3'dCTP(n1) hereinafter].

Synthesis Example 47

Synthesis of 7-deaza-7-(3"-trifluoroacetamido-1"-propynyl)-3'-deoxyadenosine

To a solution of 7-iodo-3'-deoxy-7-deazaadenosine (Compound 18, 0.5 g, 1.33 mmol) in DMF (6.7 ml), the N-propargyltrifluoroacetamide obtained in Synthesis Example 40 (0.47 ml, 3.99 mmol), cuprous (I) iodide (51 mg, 0.266 mmol), tetrakis(triphenylphosphine) palladium (0) (154 mg, 0.133 mmol), and triethylamine (0.37 ml, 2.66 mmol) were added under nitrogen gas flow, and allowed to react at room temperature for 30 minutes. The reaction mixture was diluted with a methylene chloride-methanol mixture (12 ml), added with ion exchange resin AG1X8 ($HCO_3^-$ type, 1.22 g), and stirred for 30 minutes. After filtration of the reaction mixture, the filtrate was concentrated, and the resulting residue was purified by silica gel column chromatography (eluent; methylene chloride-methanol mixed solution) to afford 436 mg of 7-deaza-7-(3"-trifluoroacetamido-1"-propynyl)-3'-deoxyadenosine (yield; 82.3%).

$^1$H-NMR (270 MHz, DMSO-$d_6$) δ ppm: 1.83–1.91 (m, 1H, 3'-Ha), 2.14–2.24 (m, 1H, 3'-Hb), 3.48–3.56 (m, 1H, 5'-Ha), 3.66–3.73 (m, 1H, 5'-Hb), 4.30–4.35 (m, 4H, 2'-H, 4'-H, —CH$_2$—), 5.08 (t, 1H, J=5.5 Hz, 5'-OH), 5.59 (d, 1H, J=3.8 Hz, 2'-OH), 6.02 (d, 1H, J=2.2 Hz, 1'-H), 6.80 (brs, 2H, NH$_2$), 7.79 (s, 1H, 8-H), 8.12 (s, 1H, 2-H), 10.08 (brs, 1H, NHTfa)

Synthesis Example 48

Synthesis of 7-deaza-7-(3"-amino-1"-propynyl)-3'-deoxyadenosine-5'-triphosphate

7-Deaza-7-(3"-trifluoroacetamido-1"-propynyl)-3'-deoxyadenosine (120 mg, 0.3 mmol) was dissolved in triethyl phosphate (1.2 ml), cooled to −20° C., added with phosphorus oxychloride (25 μl), and stirred at −20° C. After 30 minutes, the reaction mixture was added with further phosphorus oxychloride (22 μl), and stirred for further four hours. This reaction mixture was added to 0.5 M solution of the tris (tri-n-butylammonium) pyrophosphate obtained in Synthesis Example 4 in DMF (3.6 ml) cooled to −20° C., and stirred at room temperature for three hours. After the reaction was completed, the reaction mixture was added with a triethylamine-water mixture (4 ml), left stand overnight, added with 25% aqueous ammonia (20 ml), and left stand for four hours. The reaction mixture was washed with ether, and concentrated to dryness, and the obtained residue was purified by DEAE-Toyopearl ion exchange column chromatography (1.2×30 cm, eluent; triethylammonium hydrogencarbonate buffer (pH 7.5), 0 M→0.3 M linear gradient (total volume; 1 L)) to afford 114 mg of 7-deaza-7-(3"-amino-1"-propynyl)-3'-deoxyadenosine-5'-triphosphate (yield; 39.9%).

Synthesis Example 49

Synthesis of R6G-labeled 7-deaza-3'-deoxyadenosine-5'-triphosphate (A compound of the General Formula [I] Where V is —C≡C— and n=1)

To 7-deaza-7-(3"-amino-1"-propynyl)-3'-deoxyadenosine-5'-triphosphate (8 μmol) dissolved in 1 M triethylammonium hydrogencarbonate buffer (pH 9.05, 0.4 ml), a solution of 5-carboxyrhodamine-6G succinimide ester (Molecular Probe, 14.5 mg) in DMF (0.8 ml) were added, and stirred at room temperature overnight. The reaction mixture was diluted with water (30 ml), and purified by DEAE-Toyopearl ion exchange column chromatography (1.2×30 cm, eluent; triethylammonium hydrogencarbonate buffer (pH 7.5), 0.1 M→0.6 M linear gradient (total volume; 2 L)) to afford 2.54 μl mol (yield; 31.7%) of R6G-labeled 7-deaza-3-deoxyadenosine-5'-triphosphate [a compound of the general formula [I] where V is —C≡C— and n=1, abbreviated as R6G-3'dATP(n1) hereinafter].

Synthesis Example 50
Synthesis of 3'-deoxy-7-(3"-trifluoroacetamido-1"-propynyl)-7-deazaguanosine To a solution of 3'-deoxy-7-iodo-7-deazaguanosine (Compound 30, 0.65 g, 1.7 mmol) in DMF (8.5 ml), the N-propargyltrifluoroacetamide obtained in Synthesis Example 40 (0.58 ml, 5.0 mmol), cuprous (I) iodide (63 mg, 0.33 mmol), tetrakis (triphenylphosphine) palladium (0) (192 mg, 0.17 mmol), and triethylamine (0.46 ml, 3.31 mmol) were added under nitrogen gas flow, and allowed to reacted at room temperature for one hour. The reaction mixture was diluted with a methylene chloride-methanol mixture (16 ml), added with ion exchange resin AG1X8 ($HCO_3^-$ type, 1.6 g), and stirred for 30 minutes. After filtration of the reaction mixture, the filtrate was concentrated, and the resulting residue was purified by silica gel column chromatography (eluent; chloroform-methanol mixed solution) to afford 485 mg of 3'-deoxy-7-(3"-trifluoroacetamido-1"-propynyl)-7-deazaguanosine (yield; 70.5%).

$^1$H-NMR (270 MHz, DMSO-$d_6$) δ ppm: 1.81–1.91 (m, 1H, 3'-Ha), 2.10–2.21 (m, 1H, 3'-Hb), 3.42–3.68 (m, 2H, 5'-Ha,b), 4.22–4.30 (m, 4H, 2'-H, 4'-H, —$CH_2$—), 4.94 (t, 1H, J=5.5 Hz, 5'-OH), 5.49 (d, 1H, J=4.3 Hz, 2'-OH), 5.81 (d, 1H, J=2.4 Hz, 1'-H), 6.32 (brs, 2H, 2-$NH_2$), 7.27 (s, 1H, 8-H), 10.05 (brs, 1H, NHTfa), 10.50 (brs, 1H, 1-H)

Synthesis Example 51
Synthesis of 7-deaza-7-(3"-amino-1"-propynyl)-3'-deoxyguanosine-5'-triphosphate 3'-Deoxy-7-(3"-trifluoroacetamido-1"-propynyl)-7-deazaguanosine (125 mg, 0.3 mmol) was dissolved in triethyl phosphate (1.25 ml), cooled to −20° C., added with phosphorus oxychloride (25 µl), and stirred at −20° C. After 30 minutes, the reaction mixture was added with further phosphorus oxychloride (22 µl), and further stirred overnight. This reaction mixture was added to 0.5 M solution of the tris (tri-n-butylammonium) pyrophosphate obtained in Synthesis Example 4 in DMF (3.6 ml) cooled to −20° C., and stirred at room temperature for three hours. After the reaction was completed, the reaction mixture was added with a triethylamine-water mixture (4 ml), washed with ether, and purified by DEAE-Toyopearl ion exchange column chromatography (1.2×30 cm, eluent; triethylammonium hydrogencarbonate buffer (pH 7.5), 0 M→0.6 M linear gradient (total volume; 2 L)). The purified product was added with 25% aqueous ammonia (15 ml), and left stand for one hour, and then concentrated under reduced pressure, and the obtained residue was purified again by DEAE-Toyopearl ion exchange column chromatography (1.2×30 cm, eluent; triethylammonium hydrogencarbonate buffer (pH 7.5), 0 M→0.3 M linear gradient (total volume; 1 L)) to afford 75 mg of 7-deaza-7-(3"-amino-1"-propynyl)-3'-deoxyguanosine-5'-triphosphate (yield; 25.9%).

Synthesis Example 52
Synthesis of R110-labeled 7-deaza-3'-deoxyguanosine-5'-triphosphate (a compound of the general formula [I] where V is —C≡C— and n=1)

7-Deaza-7-(3"-amino-1"-propynyl)-3'-deoxyguanosine-5'-triphosphate (10.5 µmol) and 5-carboxyrhodamine-110-bis-trifluoroacetate succinimide ester (Molecular Probe, 31.5 mg) were dissolved in DMF (0.49 ml) and water (0.23 ml), added with triethylamine (0.16 ml) and pyridine (0.29 ml), and stirred overnight. The reaction mixture was diluted with water (30 ml), and purified by DEAE-Toyopearl ion exchange column chromatography (1.2×30 cm, eluent; triethylammonium hydrogencarbonate buffer (pH 7.5), 0.1 M→0.8 M linear gradient (total volume; 1 L)) to afford 3.67 µmol (yield; 34.9%) of R110-labeled 7-deaza-3'-deoxyguanosine-5'-triphosphate [a compound of the general formula [I] where V is —C≡C— and n=1, abbreviated as R110-3'dGTP(n1) hereinafter].

Synthesis Example 53
Synthesis of R110-labeled 3'-deoxycytidine-5'-triphosphate (A Compound of the General Formula [I] Where V is —C≡C— and n=4)

To 5-(6"-amino-1"-hexynyl)-3'-deoxycytidine-5'-triphosphate (Compound 8, 8 µmol) dissolved in a mixture of DMF (400 µl) and water (200 µl), triethylamine (20 µl) and 5-carboxyrhodamine-110-bis-trifluoroacetate succinimide ester (Molecular Probe, 21 µmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.8 M linear gradient (total volume; 1 L)) to afford 5.83 µmol (yield; 72.9%) of R110-labeled 3'-deoxycytidine-5'-triphosphate represented by the following formula [a compound of the general formula [I] where V is —C≡C— and n=4, abbreviated as R110–3'dCTP(n4) hereinafter].

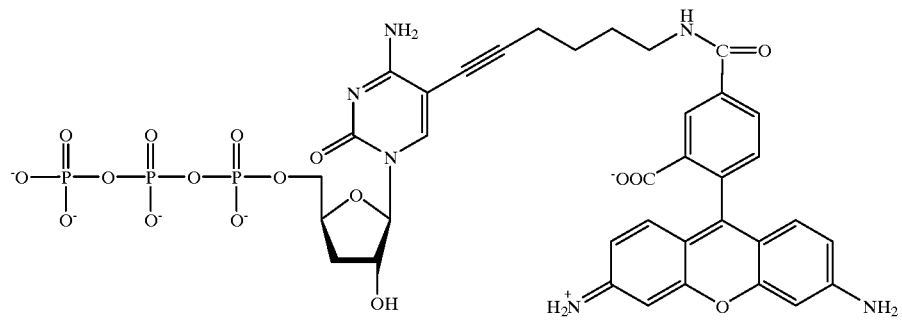

Figure 21:
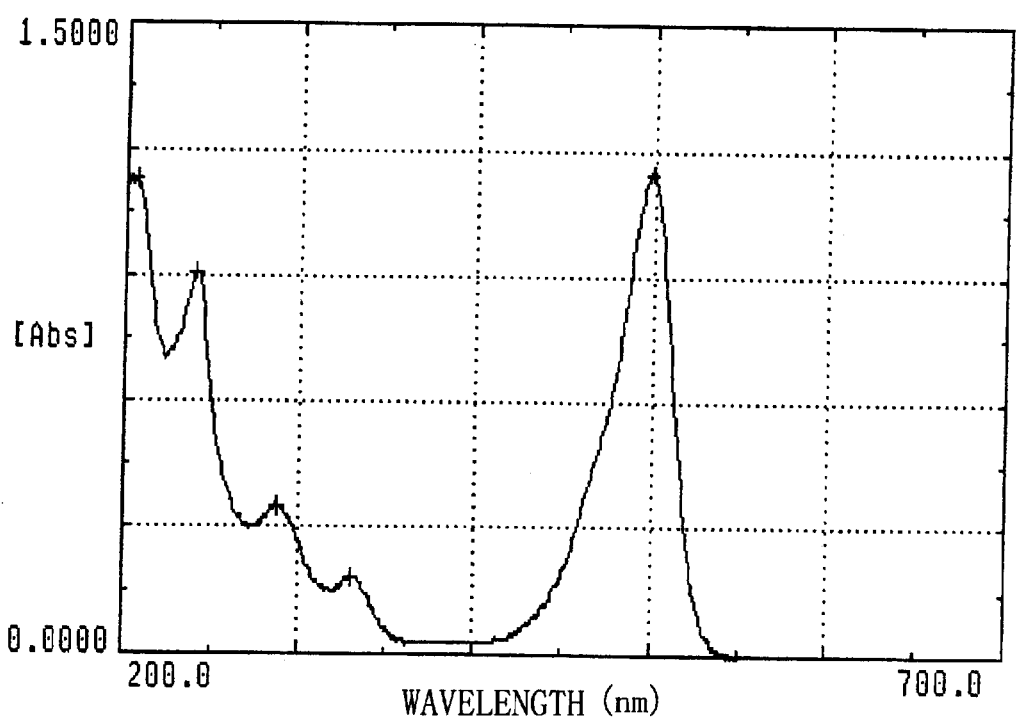
FIG. 21 shows the result of UV-visible region spectrophotometry of the carboxyrhodamine-110-labeled 3'-deoxycytidine-5'-triphosphate (a compound of the general formula [I] where V is —C≡C— and n=4) obtained in Synthesis Example 53.

The absorption spectrum for UV-visible region resulting from spectroscopy of the obtained R110-3'dCTP (n4) (measurement wavelength; 700 nm to 200 nm, reference; distilled water) performed by using DU640 UV-visible region spectrophotometer [Beckman] is shown in FIG. 21.

Synthesis Example 54
Synthesis of R6G-labeled 3'-deoxycytidine-5'-triphosphate (A Compound of the General Formula [I] Where V is —C≡C— and n=4)

To 5-(6"-amino-1"-hexynyl)-3'-deoxycytidine-5'-triphosphate (Compound 8, 8 µmol) dissolved in a mixture of DMF (2.9 ml) and water (0.9 ml), triethylamine (20 μl), and 6-carboxyrhodamine-6G succinimide ester (Molecular Probe, 16 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.7 M linear gradient (total volume; 1 L)) to afford 5.83 μmol (yield; 43.1%) of R6G-labeled 3'-deoxycytidine-5'-triphosphate represented by the following formula [a compound of the general formula [I] where n=4, abbreviated as R6G-3'dCTP(n4) hereinafter].

(Molecular Probe, 22 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.1 M→0.6 M linear gradient (total volume; 1 L)) to afford 4.39 μmol (yield; 54.8%) of XR-labeled 7-deaza-3'-deoxyadenosine-5'-triphosphate represented by the following formula [a compound of the general formula [I] where V is —C≡C— and n=4, abbreviated as XR-3'dATP(n4) hereinafter].

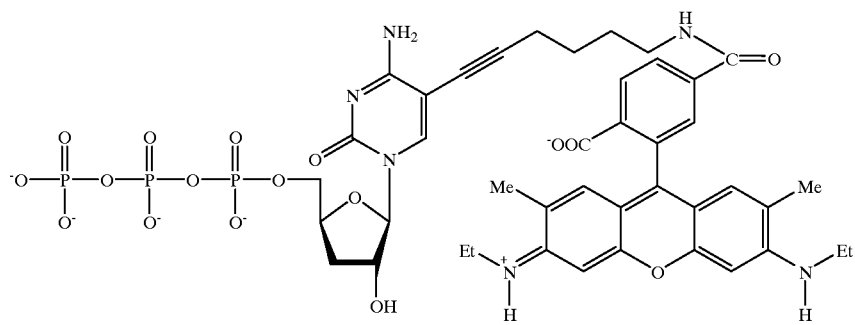

In the formula, Et represents an ethyl group, and Me represents a methyl group.

The absorption spectrum for UV-visible region resulting from spectroscopy of the obtained R6G-3'dCTP(n4) (measurement wavelength; 700 nm to 200 nm, reference;

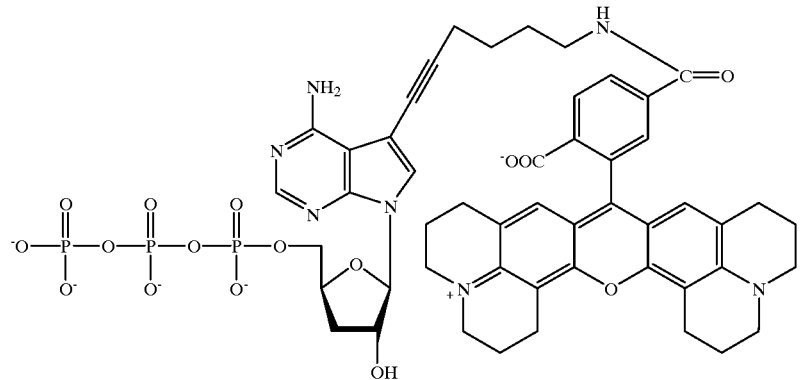

distilled water) performed by using DU640 UV-visible region spectrophotometer [Beckman] is shown in FIG. 22.

Synthesis Example 55

Synthesis of XR-labeled 7-deaza-3'-deoxyadenosine-5'-triphosphate (A Compound of the General Formula [I] Where V is —C≡C— and n=4)

To 7-deaza-7-(6"-amino-1"-hexynyl)-3'-deoxyadenosine-5'-triphosphate (Compound 20, 8 μmol) dissolved in a mixture of DMF (400 μl) and water (400 μl), triethylamine (20 μl) and 6-carboxy-X-rhodamine succinimide ester The absorption spectrum for UV-visible region resulting from spectroscopy of the obtained XR-3'dATP(n4) (measurement wavelength; 700 nm to 200 nm, reference; distilled water) performed by using DU640 UV-visible region spectrophotometer [Beckman] is shown in FIG. 23.

Synthesis Example 56

Synthesis of XR-labeled 7-deaza-3'-deoxyguanosine-5'-triphosphate (A Compound of the General Formula [I] Where V is —C≡C— and n=4)

7-Deaza-7-(6"-amino-1"-hexynyl)-3'-deoxyguanosine-5'-triphosphate (Compound 32, 8 μmol) and 5-carboxy-X- rhodamine succinimide ester (Molecular Probe, 19 μmol) were dissolved in DMF (400 μl) and water (200 μl), added with triethylamine (20 μl), and stirred overnight. The reaction mixture was diluted with water (30 ml), and purified by DEAE-Toyopearl ion exchange column chromatography (1.7×15 cm, eluent; triethylammonium hydrogencarbonate (pH 7.5), 0.1 M→0.8 M linear gradient (total volume; 1 L)) to afford 2.68 μmol (yield; 33.5%) of XR-labeled 7-deaza-3'-deoxyguanosine-5'-triphosphate represented by the following formula [a compound of the general formula [I] where V is —C≡C— and n=4, abbreviated as XR-3'dGTP (n4) hereinafter].

cooling. Subsequently, a solution of 6-iodo-1-hexene (31.27 g, 149 mmol) in DMF (130 ml) was added to the reaction mixture, and stirred at room temperature for three hours. The reaction mixture was added with saturated aqueous ammonium chloride (300 ml) and ether (300 ml) for extraction. The ether layer was washed twice with saturated saline (300 ml), dried over magnesium sulfate, and concentrated under reduced pressure, and the resulting residue was purified by silica gel column chromatography (eluent; hexane-ethyl acetate mixed solvent) to afford 24.36 g of 6-trifluoroacetamido-1-hexene (yield; 83.8%).

$^1$H-NMR (270 MHz, CDCl$_3$) δ ppm: 1.39–1.69 (m, 4H, —CH$_2$(CH$_2$)$_2$CH$_2$—), 2.04–2.14 (m, 2H, H$_2$C=C—), 3.37

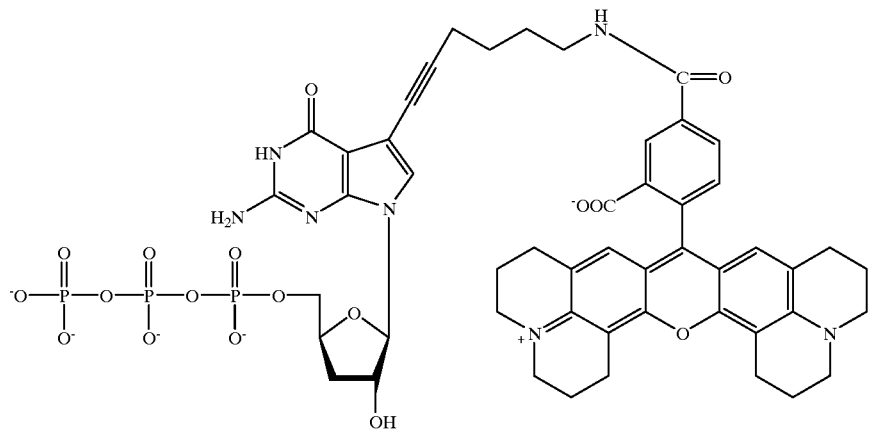

(dd, 2H, J=7.0, 13.8 Hz, CH$_2$N), 4.96–5.06 (m, 2H,=CH CH$_2$), 5.71–5.86 (m, 1H$_2$CH$_2$C=CH), 6.45 (brs, 1H, NHTfa)

Figure 24:
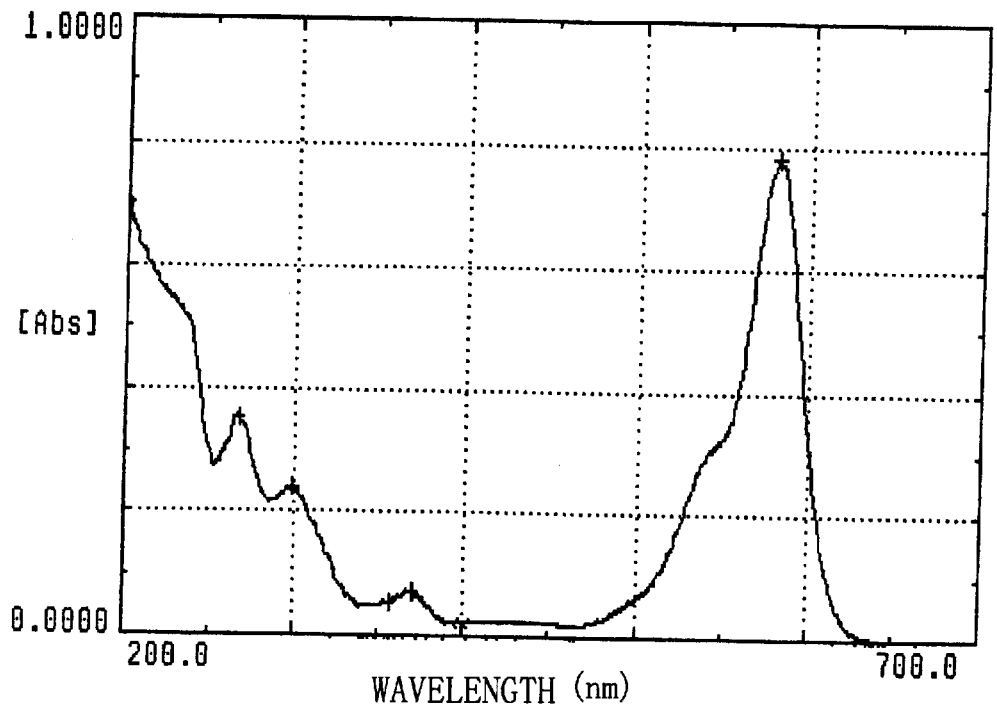
FIG. 24 shows the result of UV-visible region spectrophotometry of the carboxyrhodamine-X-labeled 7-deaza-3'-deoxyguanosine-5'-triphosphate (a compound of the general formula [I] where V is —C≡C— and n=4) obtained in Synthesis Example 56.

The absorption spectrum for UV-visible region resulting from spectroscopy of the obtained XR-3'dGTP(n4) (measurement wavelength; 700 nm to 200 nm, reference; distilled water) performed by using DU640 UV-visible region spectrophotometer [Beckman] is shown in FIG. 24.

Synthesis Example 57
Synthesis of 6-trifluoroacetamido-1-hexene
1) Synthesis of 5-hexenyl-p-toluenesulfonate To an ice-cooled solution of p-toluenesulfonyl chloride (54.78 g, 287 mmol) in pyridine (100 ml), 5-hexen-1-ol (Tokyo Chemical Industry Co., Ltd., 20 ml, 239 mmol) was added dropwise, and stirred at 5° C. for 16 hours. The reaction mixture was poured into iced water (500 ml), and extracted with ether (500 ml). The ether layer was washed with cold 1N-hydrochloric acid, saturated aqueous sodium hydrogencarbonate and saturated saline, dried over magnesium sulfate, and concentrated under reduced pressure to afford 44.37 g of 5-hexenyl-p-toluenesulfonate (yield; 72.9%).

2) Synthesis of 6-iodo-1-hexene

A mixture of 5-hexenyl-p-toluenesulfonate (44.3 g, 174 mmol), sodium iodide (31.3 g, 209 mmol) and acetone (250 ml) was allowed to react under reflux for three hours. After cooling, the precipitates were removed by filtration, and the filtrate was concentrated. The resulting residue was dissolved in ether (500 ml), washed with saturated aqueous sodium hydrogensulfite, saturated aqueous sodium hydrogencarbonate and saturated saline, dried over magnesium sulfate, and concentrated under reduced pressure to afford 31.27 g of 6-iodo-1-hexene (yield; 85.5%).

3) Synthesis of 6-trifluoroacetamido-1-hexene

To a solution of sodium hydride (60% oil, 14.89 g, 372 mmol) in DMF (370 ml), trifluoroacetamido (50.39 g, 446 mmol) was added portionwise as about 10 portions with ice Synthesis Example 58
Synthesis of 3'-deoxy-5-(6"-trifluoroacetamido-1"-hexenyl) uridine (Compound 33)

A solution of palladium chloride (1.77 g, 10 mmol) and lithium chloride (0.85 g, 20 mmol) in methanol (100 ml) was stirred overnight to prepare 0.1 M solution of lithium tetrachloropalladate. 3'-Deoxyuridine (Compound 1, 1.14 g, 5 mmol) and mercury (II) acetate (1.60 g, 5 mmol) were dissolved in water (50 ml), and stirred at 60° C. for five hours. The reaction mixture was concentrated under reduced pressure, and the residue was suspended in anhydrous methanol (55 ml), add with the 0.1 M solution of lithium tetrachloropalladate prepared above (55 ml) and the 6-trifluoroacetamido-1-hexene obtained in Synthesis Example 57 (3.42 g, 17.5 mmol), and allowed to react under reflux for 16 hours. The reaction mixture was saturated with hydrogen sulfide gas, then the precipitates were removed by filtration through celite, and the filtrate was concentrated. The resulting residue was purified by silica gel column chromatography (eluent; dichloromethane-methanol mixed solution), and HPLC (column; Wakosil II 5C18 RS Prep, 20.0×250 mm, eluent; acetonitrile-water mixed solution) to afford 454 mg of a novel substance, 3'-deoxy-5-(6"-trifluoroacetamido-1"-hexenyl)uridine (Compound 33, yield; 21.6%).

$^1$H-NMR (270 MHz, DMSO-d$_6$) δ ppm: 1.25–1.55 (m, 4H, —(CH$_2$)$_2$—), 1.68–1.80 (m, 1H, 3'-Ha), 1.95–2.18 (m, 3H, 3'-Hb and =CHCH$_2$), 3.05–3.25(m, 2H, CH$_2$N), 3.50–3.60 (m, 1H, 5'-Ha), 3.70–3.85 (m, 1H, 5'-Hb), 4.15–4.36 (m, 2H, 2'-H and 4'-H), 5.22 (t, 1H, J=5.1 Hz, 5'-OH), 5.54 (d, 1H, J=4.3 Hz, 2'-OH), 5.66 (d, 1H, J=1.6

Hz, 1'-H), 6.03 (d, 1H, J=15.7 Hz, —C̲H̲=CHCH₂—), 6.38 (dt, 1H, J=7.0, 16.2 Hz, —CH=C̲H̲CH₂—), 8.18 (s, 1H, 6-H), 9.39 (brs, 1H, NHTfa), 11.32 (s, 1H, 3-NH)

Synthesis Example 59
Synthesis of 3'-deoxy-5-(6"-trifluoroacetamido-1"-hexenyl)uridine (Compound 33)

To a solution of 3'-deoxy-5-iodouridine (Compound 2, 300 mg, 0.85 mmol) in DMF (4.25 ml), the 6-trifluoroacetamido-1-hexene obtained in Synthesis Example 57 (496 mg, 2.54 mmol), cuprous (I) iodide (32.3 mg, 0.17 mmol), tetrakis(triphenylphosphine) palladium (0) (97.9 mg, 0.085 mmol), and triethylamine (0.24 ml, 1.69 mmol) were added, and allowed to react at 60° C. for 18 hours under nitrogen gas flow. The reaction mixture was diluted with a methylene chloride-methanol mixture (9.3 ml), added with ion exchange resin AG1X8 (BIO-RAD, HCO₃⁻ type, 0.68 g), and stirred for 30 minutes. After filtration of the reaction mixture, the filtrate was concentrated, and the resulting residue was purified by silica gel column chromatography (eluent; methylene chloride-methanol mixed solution), and HPLC (column; Wakosil II 5C18 RS Prep, 20.0×250 mm, eluent; acetonitrile-water mixed solution) to afford 127 mg of a novel substance, 3'-deoxy-5-(6"-trifluoroacetamido-1"-hexenyl)uridine (Compound 33, yield; 35.5%).

¹H-NMR (270 MHz, DMSO-d₆) δ ppm: 1.25–1.55 (m, 4H, —(CH₂)₂—), 1.68–1.80 (m, 1H, 3'-Ha), 1.95–2.18 (m, 3H, 3'-Hb and =CHCH₂), 3.05–3.25 (m, 2H, CH₂N), 3.50–3.60 (m, 1H, 5'-Ha), 3.70–3.85 (m, 1H, 5'-Hb), 4.15–4.36 (m, 2H, 2'-H and 4'-H), 5.22 (t, 1H, J=5.1 Hz, 5'-OH), 5.54 (d, 1H, J=4.3 Hz, 2'-OH), 5.66 (d, 1H, J=1.6 Hz, 1'-H), 6.03 (d, 1H, J=15.7 Hz, —C̲H̲=CHCH₂—), 6.38 (dt, 1H, J=7.0, 16.2 Hz, —CH=C̲H̲CH₂—), 8.18 (s, 1H, 6-H), 9.39 (brs, 1H, NHTfa), 11.32 (s, 1H, 3-NH)

Synthesis Example 60
Synthesis of 5-(6"-amino-1"-hexenyl)-3'-deoxyuridine-5'-triphosphate (Compound 34)

3'-Deoxy-5-(6"-trifluoroacetamido-1"-hexenyl)uridine (Compound 33, 126.4 mg, 0.3 mmol) was dissolved in triethyl phosphate (1.26 ml), cooled to –20° C., added with phosphorus oxychloride (41.9 μl), and stirred at –20° C. After 30 minutes, the reaction mixture was added with further phosphorus oxychloride (55.9 μl), and further stirred for 23 hours. This reaction mixture was added to 0.5 M solution of tris(tri-n-butylammonium) pyrophosphate in DMF (3.6 ml) cooled to –20° C., and stirred at room temperature for three hours. After the reaction was completed, the reaction mixture was added with a triethylamine-water mixture (15 ml), and left stand overnight. The reaction mixture was washed with ether, and purified by DEAE-Toyopearl ion exchange column chromatography (1.7×40 cm, eluent; triethylammonium hydrogencarbonate buffer (pH 7.5), 0 M→0.3 M linear gradient (total volume; 1 L)). The purified product was added with 17% aqueous ammonia (60 ml), and left stand at 5° C. for 17 hours, and then concentrated under reduced pressure, and the obtained residue was purified again by DEAE-Toyopearl ion exchange column chromatography (1.7×40 cm, eluent; triethylammonium hydrogencarbonate buffer (pH 7.5), 0 M→0.3 M linear gradient (total volume; 1 L)) to afford 65.3 mg of a novel substance, 5-(6"-amino-1"-hexenyl)-3'-deoxyuridine-5'-triphosphate (Compound 34, yield; 22.4%).

Synthesis Example 61
Synthesis of TMR-labeled 3'-deoxyuridine-5'-triphosphate (A Compound of the General Formula [I] Where V is —CH=CH— and n=4)

To 5-(6"-amino-1"-hexenyl)-3'-deoxyuridine-5'-triphosphate (Compound 34, 14.8 μmol) dissolved in a mixture of DMF (300 μl) and water (300 μl), triethylamine (10 μl) and 6-carboxytetramethylrhodamine succinimide ester (Molecular Probe, 15.9 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.05 M→0.65 M linear gradient (total volume; 1L)) to afford 7.62 μmol (yield; 51.4%) of TMR-labeled 3'-deoxyuridine-5'-triphosphate represented by the following formula where the linker portion has a double bond and the number of n in the methylene chain is 4 [a compound of the general formula [I] where V is —CH=CH— and n=4, abbreviated as TMR-Allyl-3'dUTP(n4) hereinafter].

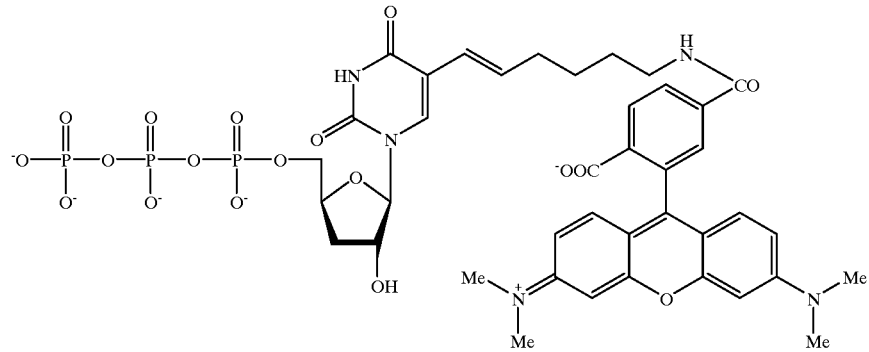

In the formula, Me represents a methyl group.

Figure 25:
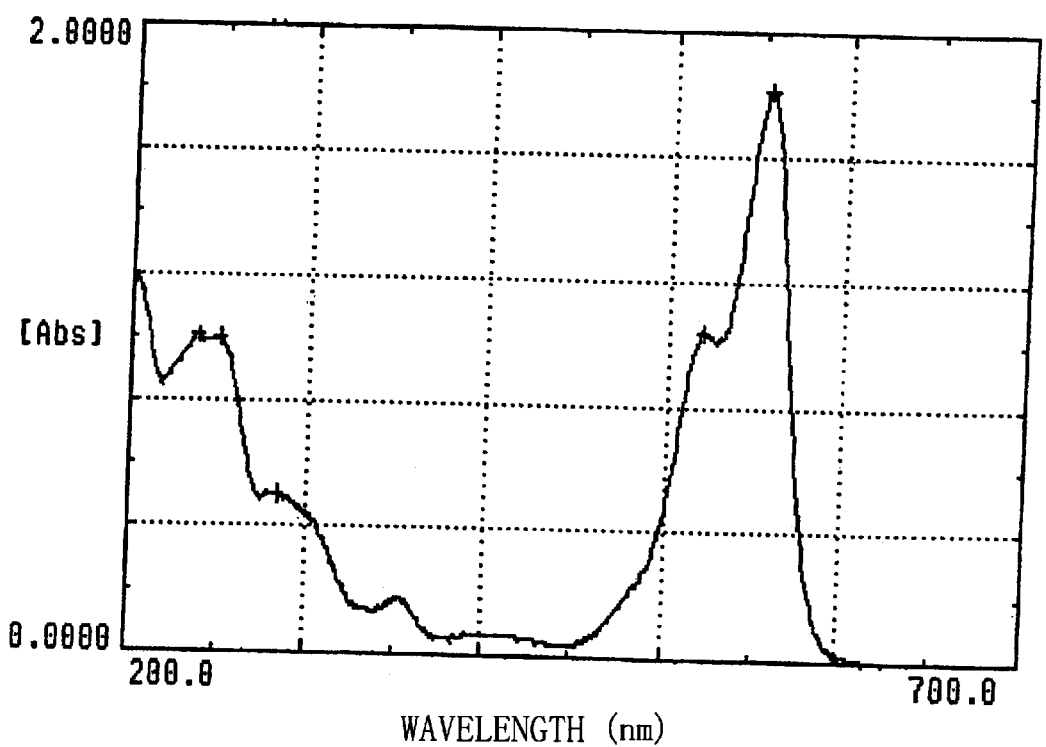
FIG. 25 shows the result of UV-visible region spectrophotometry of the carboxytetramethylrhodamine-labeled 3'-deoxyuridine-5'-triphosphate (a compound of the general formula [I] where V is —CH═CH— and n=4) obtained in Synthesis Example 61.

The absorption spectrum for UV-visible region resulting from spectrophotometry of the obtained TMR-Allyl-3'dUTP (n4) (measurement wavelength; 700 nm to 200 nm, reference; distilled water) performed by using DU640 UV-visible region spectrophotometer [Beckman] is shown in FIG. 25.

Synthesis Example 62
Synthesis of 3'-deoxy-5-(6"-trifluoroacetamido-1"-hexenyl) cytidine (Compound 35)

To a solution of 3'-deoxy-5-iodocytidine (Compound 6, 600 mg, 1.70 mmol) in DMF (8.5 ml), the 6-trifluoroacetamido-1-hexene obtained in Synthesis Example 57 (995 mg, 5.1 mmol), cuprous (I) iodide (64.7 mg, 0.34 mmol), tetrakis(triphenylphosphine) palladium (0)

(196mg, 0.17 mmol), and triethylamine (0.47 ml, 3.4 mmol) were added, and allowed to react at 60° C. for 18 hours under nitrogen gas flow. The reaction mixture was diluted with a methylene chloride-methanol mixture (20 ml), added with ion exchange resin AG1X8 (BIO-RAD, $HCO_3^-$ type, 1.36 g), and stirred for 30 minutes. After filtration of the reaction mixture, the filtrate was concentrated, and the resulting residue was purified by silica gel column chromatography (eluent; methylene chloride-methanol mixed solution), and HPLC (column; Wakosil II 5C18 RS Prep, 20.0×250 mm, eluent; acetonitrile-water mixed solution) to afford 187 mg of a novel substance, 3'-deoxy-5-(6"-trifluoroacetamido-1"-hexenyl)cytidine (Compound 35, yield; 26.2%).

$^1$H-NMR (400 MHz, DMSO-$d_6$) δ ppm: 1.37–1.52 (m, 4H, —($CH_2$)$_2$—), 1.64–1.68 (m, 1H, 3'-Ha), 1.90–1.97 (m, 1H, 3'-Hb), 2.07–2.12 (m, 2H, =CHCH$_2$), 3.18 (dd, 2H, J=6.8, 12.8 Hz, CH$_2$N), 3.53–3.56 (m, 1H, 5'-Ha), 3.80–3.82 (m, 1H, 5'-Hb), 4.10–4.30 (m, 2H, 2'-H and 4'-H), 5.15 (t, 1H, J=5.0 Hz, 5'-OH), 5.48 (d, 1H, J=4.0 Hz, 2'-OH), 5.65 (s, 1H, 1'-H), 5.87 (dt, 1H, J=6.8, 15.6 Hz, —CH=CHCH$_2$—), 6.18 (d, 1H, J=15.6 Hz, —CH=CHCH$_2$—), 6.91, 7.10 (2 br s, 2H, 4-NH$_2$), 8.26 (s, 1H, 6-H), 9.38 (brs, 1H, NHTfa)

Synthesis Example 63
Synthesis of 5-(6"-amino-1"-hexenyl)-3'-deoxycytidine-5'-triphosphate (Compound 36)

3'-Deoxy-5-(6"-trifluoroacetamido-1"-hexenyl)cytidine (Compound 35, 126.1 mg, 0.3 mmol) was dissolved in triethyl phosphate (1.26 ml), cooled to −20° C., added with phosphorus oxychloride (25.1 μl), and stirred at −20° C. After 30 minutes, the reaction mixture was added with further phosphorus oxychloride (22.3 μl), and further stirred for four hours. This reaction mixture was added to 0.5 M solution of tris (tri-n-butylammonium) pyrophosphate in DMF (3.6 ml) cooled to −20° C., and stirred at room temperature for three hours. After the reaction was completed, the reaction mixture was added with a triethylamine-water mixture (5 ml), and left stand overnight. The reaction mixture was washed with ether, and purified by DEAE-Toyopearl ion exchange column chromatography (1.7×40 cm, eluent; triethylammonium hydrogencarbonate buffer (pH 7.5), 0 M→0.3 M linear gradient (total volume; 1 L)). The purified product was added with 17% aqueous ammonia (60 ml), and left stand at 5° C. for 15 hours, and then concentrated under reduced pressure, and the obtained residue was purified again by DEAE-Toyopearl ion exchange column chromatography (1.7×40 cm, eluent; triethylammonium hydrogencarbonate buffer (pH 7.5), 0 M→0.3 M linear gradient (total volume; 1 L)) to afford 175 mg of a novel substance, 5-(6"-amino-1"-hexenyl)-3'-deoxycytidine-5'-triphosphate (Compound 36, yield; 60.2%).

Synthesis Example 64

Synthesis of XR-labeled 3'-deoxycytidine-5'-triphosphate (A Compound of the General Formula [I] Where V is —CH=CH— and n=4)

To 5-(6"-amino-1"-hexenyl)-3'-deoxycytidine-5'-triphosphate (Compound 36, 10 μmol) dissolved in a mixture of DMF (300 μl) and water (300 μl), triethylamine (10 μl) and 6-carboxy-X-rhodamine succinimide ester (Molecular Probe, 25 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH$_{7.5}$), 0.05 M→0.65 M linear gradient (total volume; 1 L)) to afford 6.55 μmol (yield; 65.5%) of XR-labeled 3'-deoxycytidine-5'-triphosphate represented by the following formula where the linker portion has a double bond and the number of n in the methylene chain is 4 [a compound of the general formula [I] where V is —CH=CH— and n=4, abbreviated as XR-Allyl-3'dCTP(n4) hereinafter].

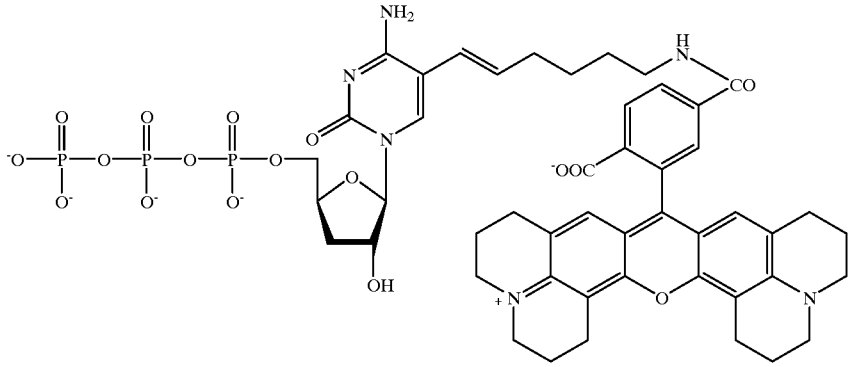

Figure 26:
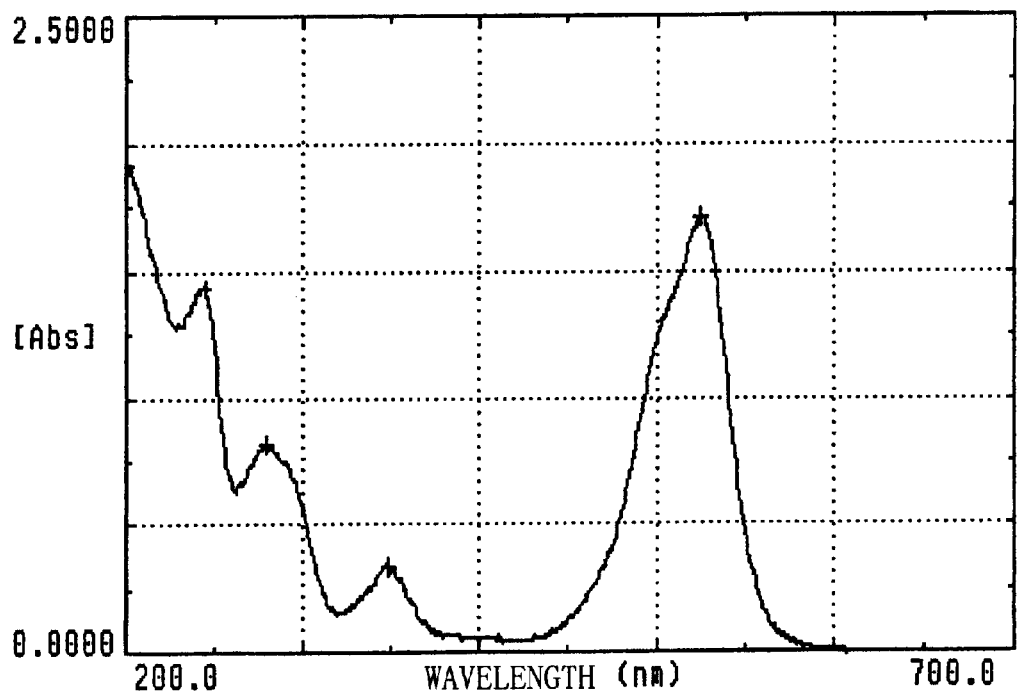
FIG. 26 shows the result of UV-visible region spectrophotometry of the carboxyrhodamine-X-labeled 3'-deoxycytidine-5'-triphosphate (a compound of the general formula [I] where V is —CH═CH— and n=4) obtained in Synthesis Example 64.

The absorption spectrum for UV-visible region resulting from spectrophotometry of the obtained XR-Allyl-3'dCTP (n4) (measurement wavelength; 700 nm to 200 nm, reference; distilled water) performed by using DU640 UV-visible region spectrophotometer [Beckman] is shown in FIG. 26.

Synthesis Example 65
Synthesis of 7-(6"-trifluoroacetamido-1"-hexenyl)-3'-deoxy-7-deazaadenosine (Compound 37)

To a solution of 7-iodo-3'-deoxy-7-deazaadenosine (Compound 18, 600 mg, 1.60 mmol) in DMF (8.0 ml), the 6-trifluoroacetamido-1-hexene obtained in Synthesis Example 57 (912 mg, 4.80 mmol), cuprous (I) iodide (62 mg, 0.32 mmol), tetrakis(triphenylphosphine) palladium (0) (184 mg, 0.16 mmol), and triethylamine (0.44 ml, 3.2 mmol) were added, and allowed to react at 60° C. for 18 hours under nitrogen gas flow. The reaction mixture was diluted with a methylene chloride-methanol mixture (16 ml), added with ion exchange resin AG1X8 (BIO-RAD, $HCO_3^-$ type, 1.50 g), and stirred for 30 minutes. After filtration of the reaction mixture, the filtrate was concentrated, and the resulting residue was purified by silica gel column chromatography (eluent; methylene chloride-methanol mixed solution), and HPLC (column; Wakosil II 5C18 RS Prep, 20.0×250 mm, eluent; acetonitrile-water mixed solution) to afford 175 mg of a novel substance, 7-(6"-trifluoroacetamido-1"-hexenyl)-3'-deoxy-7-deazaadenosine (Compound 37, yield; 24.8%).

$^1$H-NMR (400 MHz, DMSO-d$_6$) δ ppm: 1.23–1.54 (m, 4H, —(CH$_2$)$_2$—), 1.87–1.90 (m, 1H, 3'-Ha), 2.19–2.20 (m, 3H, 3'-Hb and =CHCH$_2$), 3.20 (dd, 2H, J=6.6, 13.0 Hz, CH$_2$N), 3.46–3.62 (m, 2H, 5'-Ha and 5'-Hb), 4.25–4.38 (m, 2H, 2'-H and 4'-H), 5.01 (t, 1H, J=5.6 Hz, 5'-OH), 5.50 (d, 1H, J=4.8 Hz, 2'-OH), 5.95 (dt, 1H, J=7.2, 15.2 Hz, —CH=CHCH$_2$—), 6.01 (d, 1H, J=2.4 Hz, 1'-H), 6.62 (br s, 2H, 6-NH2), 6.74 (d, 1H, J=15.2 Hz, —CH=CHCH$_2$—), 7.48 (s, 1H, 8-H), 8.03 (s, 1H, 2-H), 9.40 (brs, 1H, NHTfa)

Synthesis Example 66
Synthesis of 7-(6"-amino-1"-hexenyl)-3'-deoxy-7-deazaadenosine-5'-triphosphate (Compound 38)

7-(6"-trifluoroacetamido-1"-hexenyl)-3'-deoxy-7-deazaadenosine (Compound 37, 133 mg, 0.3 mmol) was dissolved in triethyl phosphate (1.26 ml), cooled to −20° C., added with phosphorus oxychloride (25.1 μl), and stirred at −20° C. After 30 minutes, the reaction mixture was added with further phosphorus oxychloride (22.3 μl), and further stirred for six hours. This reaction mixture was added to 0.5 M solution of tris (tri-n-butylammonium) pyrophosphate in DMF (3.6 ml) cooled to −20° C., and stirred at room temperature for three hours. After the reaction was completed, the reaction mixture was added with a triethylamine-water mixture (5 ml), and left stand overnight. The reaction mixture was washed with ether, and purified by DEAE-Toyopearl ion exchange column chromatography (1.7×40 cm, eluent; triethylammonium hydrogencarbonate buffer (pH 7.5), 0 M→0.3 M linear gradient (total volume; 1 L)). The purified product was added with 17% aqueous ammonia (60 ml), and left stand at 5° C. for 15 hours, and then concentrated under reduced pressure, and the obtained residue was purified again by DEAE-Toyopearl ion exchange column chromatography (1.7×40 cm, eluent; triethylammonium hydrogencarbonate buffer (pH 7.5), 0 M→0.3 M linear gradient (total volume; 1 L)) to afford 126 mg of a novel substance, 7-(6"-amino-1"-hexenyl)-3'-deoxy-7-deazaadenosine-5'-triphosphate (Compound 38, yield; 42.2%).

Synthesis Example 67
Synthesis of R6G-labeled 3'-deoxy-7-deazaadenosine-5'-triphosphate (A Compound of the General Formula [I] Where V is —CH=CH— and n=4)

To 7-(6"-amino-1"-hexenyl)-3'-deoxy-7-deazaadenosine-5'-triphosphate (Compound 38, 8 μmol) dissolved in a mixture of DMF (2 ml) and water (1 ml), triethylamine (10 μl) and 5-carboxyrhodamine 6G succinimide ester (Molecular Probe, 16 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.05 M→0.65 M linear gradient (total volume; 1 L)) to afford 3.90 μmol (yield; 48.7%) of R6G-labeled 3'-deoxy-7-deazaadenosine-5'-triphosphate represented by the following formula where the linker portion has a double bond and the number of n in the methylene chain is 4 [a compound of the general formula [I] where V is —CH=CH— and n=4, abbreviated as R6G-Allyl-3'dATP(n4) hereinafter].

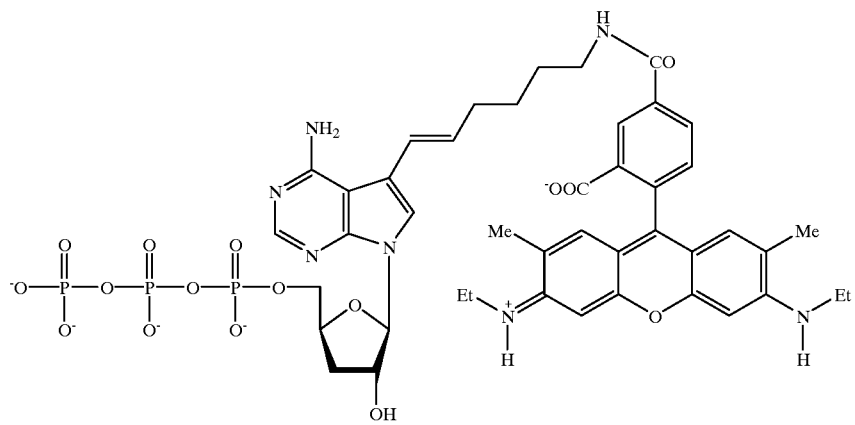

60

In the formula, Et represents an ethyl group, and Me represents a methyl group.

Figure 27:
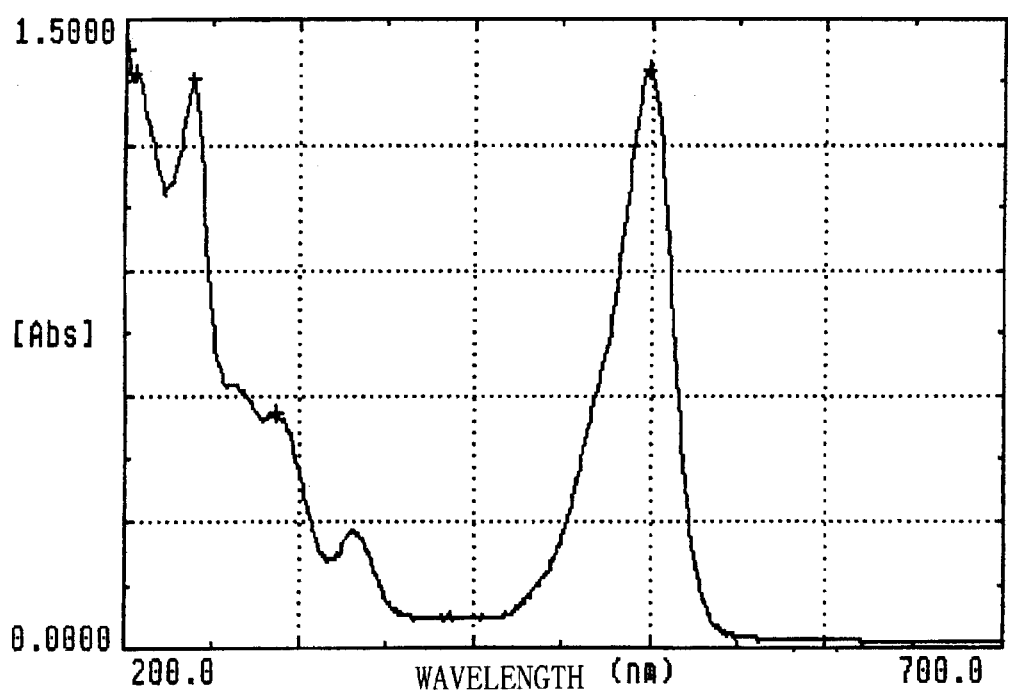
FIG. 27 shows the result of UV-visible region spectrophotometry of the carboxyrhodamine-6G-labeled 3'-deoxy-7-deazaadenosine-5'-triphosphate (a compound of the general formula [I] where V is —CH=CH— and n=4) obtained in Synthesis Example 67.

The absorption spectrum for UV-visible region resulting from spectrophotometry of the obtained R6G-Allyl-3'dATP- (n4) (measurement wavelength; 700 nm to 200 nm, reference; distilled water) performed by using DU640 UV-visible region spectrophotometer [Beckman] is shown in FIG. 27.

Synthesis Example 68

Synthesis of 7-(6"-trifluoroacetamido-1"-hexenyl)-3'-deoxy-7-deazaguanosine (Compound 39)

To a solution of 7-iodo-3'-deoxy-7-deazaguanosine (Compound 30, 1.31 g, 3.33 mmol) in DMF (16.67 ml), the 6-trifluoroacetamido-1-hexene obtained in Synthesis Example 57 (1.90 g, 9.99 mmol), cuprous (I) iodide (130 mg, 0.66 mmol), tetrakis(triphenylphosphine) palladium (0) (385mg, 0. 33 mmol), and triethylamine (0.93 ml, 6.66 mmol) were added, and allowed to react at 60° C. for 18 hours under nitrogen gas flow. The reaction mixture was diluted with a methylene chloride-methanol mixture (40 ml), added with ion exchange resin AG1X8 (BIO-RAD, $HCO_3^-$ type, 2.96 g), and stirred for 30 minutes. After filtration of the reaction mixture, the filtrate was concentrated, and the resulting residue was purified by silica gel column chromatography (eluent; methylene chloride-methanol mixed solution), and HPLC (column; Wakosil II 5C18 RS Prep, 20.0×250 mm, eluent; acetonitrile-water mixed solution) to afford 439 mg of a novel substance, 3'-deoxy-7-(6"-trifluoroacetamido-1"-hexenyl)-7-deazaguanosine (Compound 39, yield; 28.7%).

$^1$H-NMR (400 MHz, DMSO-$d_6$) δ ppm: 1.35–1.53 (m, 4H, —(CH$_2$)$_2$—), 1.85–1.89 (m, 1H, 3'-Ha), 2.09–2.15 (m, 3H, 3'-Hb and =CHCH$_2$), 3.19 (dd, 2H, J=6.8, 12.8 Hz, CH$_2$N), 3.43–3.56 (m, 2H, 5'-Ha and 5'-Hb), 4.10–4.30 (m, 2H, 2'-H and 4'-H), 4.84 (t, 1H, J=5.6 Hz, 5'-OH), 5.42 (d, 1H, J=4.4 Hz, 2'-OH), 5.81 (d, 1H, J=2.8 Hz, 1'-H), 6.21 (br s, 2H, 2-NH$_2$), 6.37 (d, 1H, J=15.6 Hz, —CH=CHCH$_2$—), 6.57 (dt, 1H, J=7.1, 15.6 Hz, —CH=CHCH$_2$—), 6.93 (s, 1H, 8-H), 9.39 (brs, 1H, NHTfa), 10.29 (s, 1H, 1-H)

Synthesis Example 69

Synthesis of 7-(6"-amino-1"-hexenyl)-3'-deoxy-7-deazaguanosine-5'-triphosphate (Compound 40)

7-(6"-Trifluoroacetamido-1"-hexenyl)-3'-deoxy-7-deazaguanosine (Compound 39, 138 mg, 0.3 mmol) was dissolved in triethyl phosphate (1.26 ml), cooled to −20° C., added with phosphorus oxychloride (25.1 μl), and stirred at −20° C. After 30 minutes, the reaction mixture was added with further phosphorus oxychloride (22.3 μl), and further stirred for 8 hours. This reaction mixture was added to 0.5 M solution of tris (tri-n-butylammonium) pyrophosphate in DMF (3.6 ml) cooled to −20° C., and stirred at room temperature for three hours. After the reaction was completed, the reaction mixture was added with a triethylamine-water mixture (5 ml), and left stand overnight. The reaction mixture was washed with ether, and purified by DEAE-Toyopearl ion exchange column chromatography (1.7×40 cm, eluent; triethylammonium hydrogencarbonate buffer (pH 7.5), 0 M→0.3 M linear gradient (total volume; 1 L)). The purified product was added with 17% aqueous ammonia (60 ml), left stand at 5° C. for 16 hours, and then concentrated under reduced pressure, and the obtained residue was purified again by DEAE-Toyopearl ion exchange column chromatography (1.7×40 cm, eluent; triethylammonium hydrogencarbonate buffer (pH 7.5), 0 M→0.3 M linear gradient (total volume; 1 L)) to afford 122 mg of a novel substance, 7-(6"-amino-1"-hexenyl)-3'-deoxy-7-deazaguanosine-5'-triphosphate (Compound 40, yield; 40.4%).

Synthesis Example 70

Synthesis of R110-labeled 3'-deoxy-7-deazaguanosine-5'-triphosphate (A Compound of the General Formula [I] Where V is —CH=CH— and n=4)

To 7-(6"-amino-1"-hexenyl)-3'-deoxy-7-deazaguanosine-5'-triphosphate (Compound 40, 10 μmol) dissolved in a mixture of DMF (500 μl) and water (375 μl), triethylamine (25 μl) and 5-carboxyrhodamine-110-bis(trifluoroacetate) succinimide ester (Molecular Probe, 25 μmol) were added, and stirred at room temperature overnight. The reaction mixture was diluted with water (30 ml), and purified by DEAE-Toyopearl ion exchange column chromatography (1.7×15 cm, eluent; triethylammonium hydrogencarbonate buffer (pH 7.5), 0.05 M→0.65 M linear gradient (total volume; 1 L)) to afford 5.1 μmol (yield; 51.0%) of R110-labeled 3'-deoxy-7-deazaguanosine-5'-triphosphate represented by the following formula where the linker portion has a double bond and the number of n in the methylene chain is 4 [a compound of the general formula [I] where V is —CH=CH— and n=4, abbreviated as R110-Allyl-3'dGTP (n4) hereinafter].

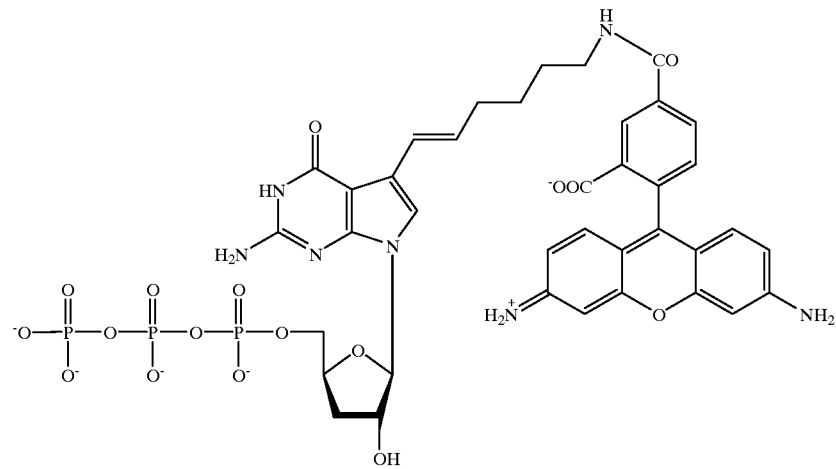

Figure 28:
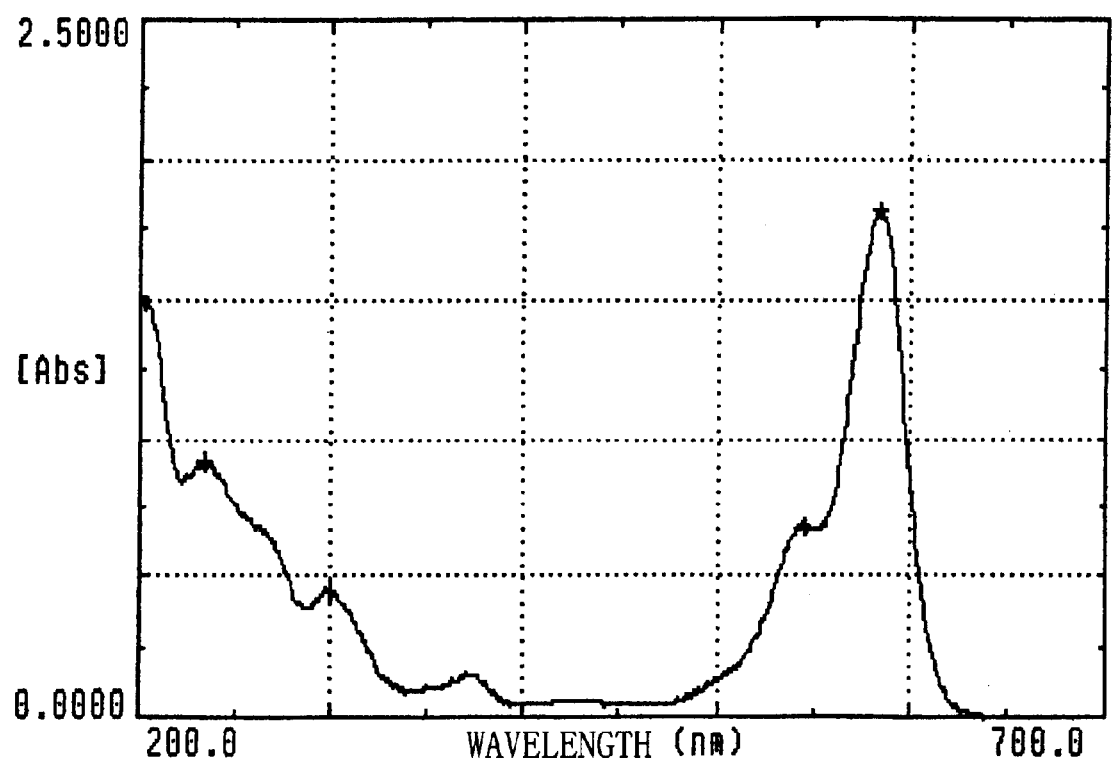
FIG. 28 shows the result of UV-visible region spectrophotometry of the carboxyrhodamine-110-labeled 3'-deoxy-7-deazaadenosine-5'-triphosphate (a compound of the general formula [I] where V is —CH=CH—and n=4) obtained in Synthesis Example 70.

The absorption spectrum for UV-visible region resulting from spectrophotometry of the obtained R110-Allyl-3'dGTP (n4) (measurement wavelength; 700 nm to 200 nm, reference; distilled water) performed by using DU640 UV-visible region spectrophotometer [Beckman] is shown in FIG. 28.

EXAMPLE 1

3'-dNTP incorporation efficiency of the purified mutant T7 RNA polymerases F644Y and L665P/F667Y was compared with that of wild type T7 RNA polymerase as follows. In vitro transcription reaction was performed by, for example, a partially modified version of the method of Melton, D. A., [Nucleic Acids Res., 12:7035–7056 (1984)]. More specifically, the reaction was performed in a total volume of 10 µl containing a plasmid vector pBluescriptKS (+) having T7 promoter (Stratagene) linearized by the reaction with a restriction endonuclease PvuII or ScaI as a template, 150 µM of the dye terminator XR-3'dCTP(n=1) synthesized in Synthesis Example 46 as a derivative of 3'-dNTP, 500 µM of GTP and UTP, 250 µM of ATP and CTP, 8 mM of $MgCl_2$, 2 mM of spermidine-$(HCl)_3$, 5 mM of DTT, 40 mM of Tris/HCl pH 8.0 (BRL, Gibco) and 25 units of wild type T7 RNA polymerase (BRL, Gibco or Nippon Gene) or the mutant T7 RNA polymerase F644Y or L665P/F667Y at 37° C. for 1 hour. Then, to remove the unreacted dye terminator remained in the reaction product, the transcription product was purified by gel filtration using a Sephadex G-50 column (Pharmacia Biotech), and the purification product was evaporated to dryness using a centrifugal evaporator.

Figure 29:
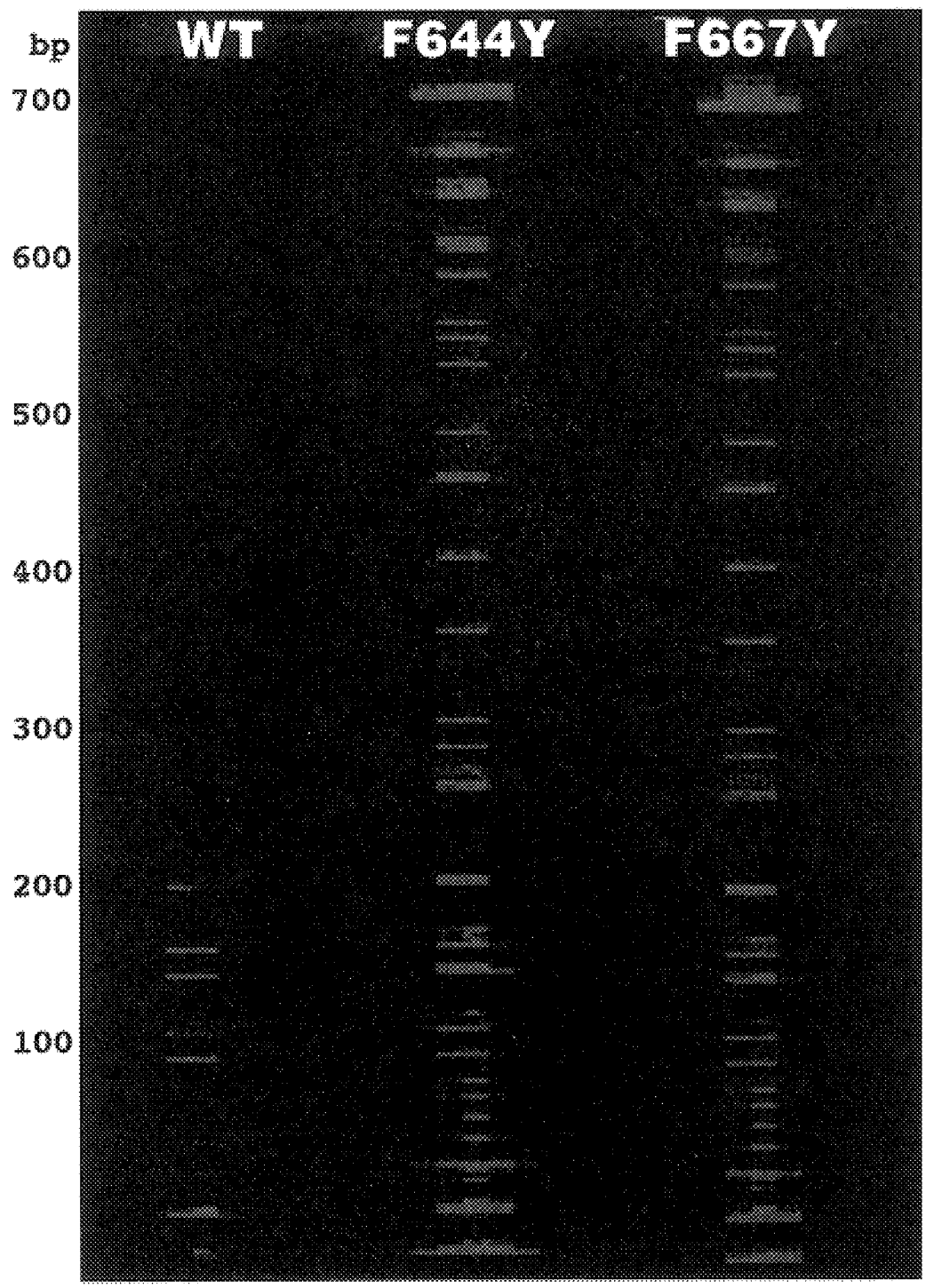
FIG. 29 represents improvement of incorporation rate of dye terminator by mutant T7 RNA polymerases. As the dye terminator, Rox-3'-dCTP was used. WT: wild type T7 RNA polymerase, F644Y: mutant T7 RNA polymerase F644Y, and F667Y: mutant T7 RNA polymerase L665P/F667Y.

The dried reaction product was dissolved in 6 µl of formamide/EDTA/Blue dextran loading buffer according to the instruction manual Ver.1.0 of ABI PRISM 377 DNA Sequencing System available from Perkin-Elmer Japan, and 2 µl of the solution was analyzed by ABI 377 DNA Sequencer and an analysis program using denatured gel for sequencing analysis which contained 6M urea/4% Long Ranger™ acrylamide solution (FMC). The results are shown in FIG. 29 as a gel image. It was found that the mutant T7 RNA polymerase F644Y could afford a sequence ladder 3 times longer than that afforded by the wild type T7 RNA polymerase, and a transcription product of about 700 bases was also confirmed.

Figure 30:
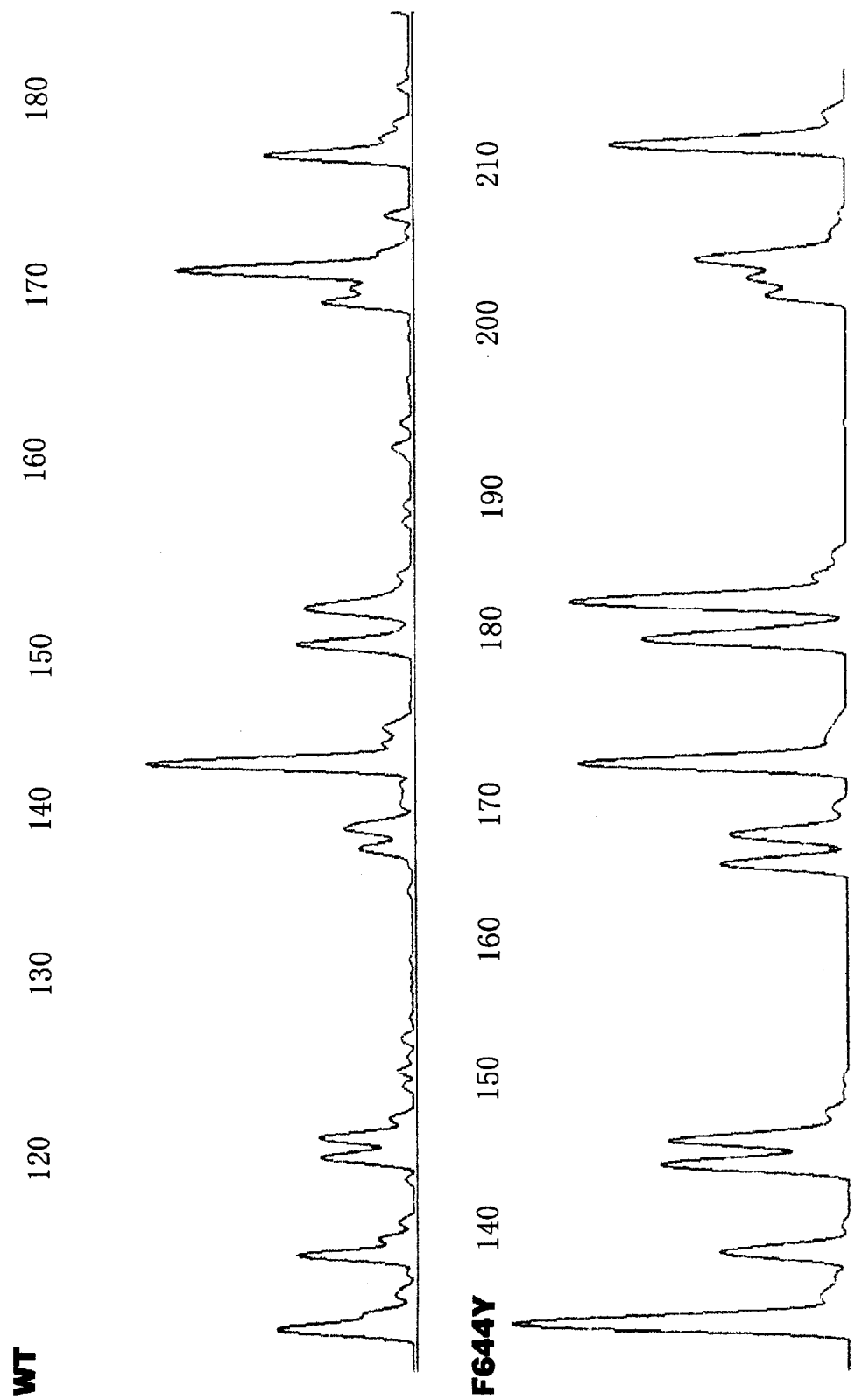
FIG. 30 represents improvement of incorporation rate of dye terminator by the mutant T7 RNA polymerase F644Y, which is shown as electrogram. As the dye terminator, Rox-3'-dCTP was used. WT: wild type T7 RNA polymerase, and F644Y: mutant T7 RNA polymerase F644Y.
Figure 31:
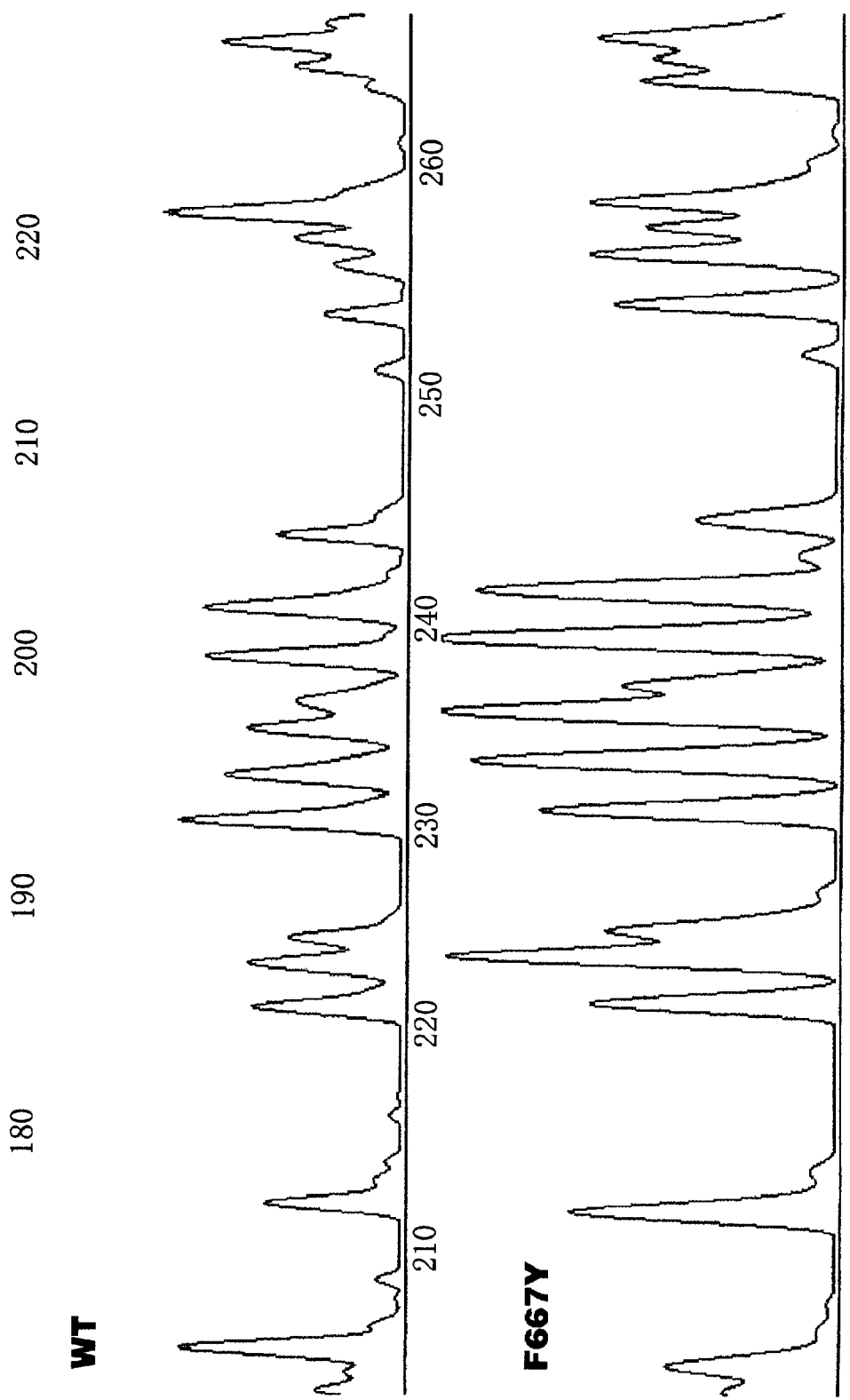
FIG. 31 represents improvement of incorporation rate of dye terminator by the mutant T7 RNA polymerase L665P/F667Y, which is shown as electrogram. As the dye terminator Rox-3'-dCTP was used. WT: wild type T7 RNA polymerase, F667Y: mutant T7 RNA polymerase L665P/F667Y.
Figure 32:
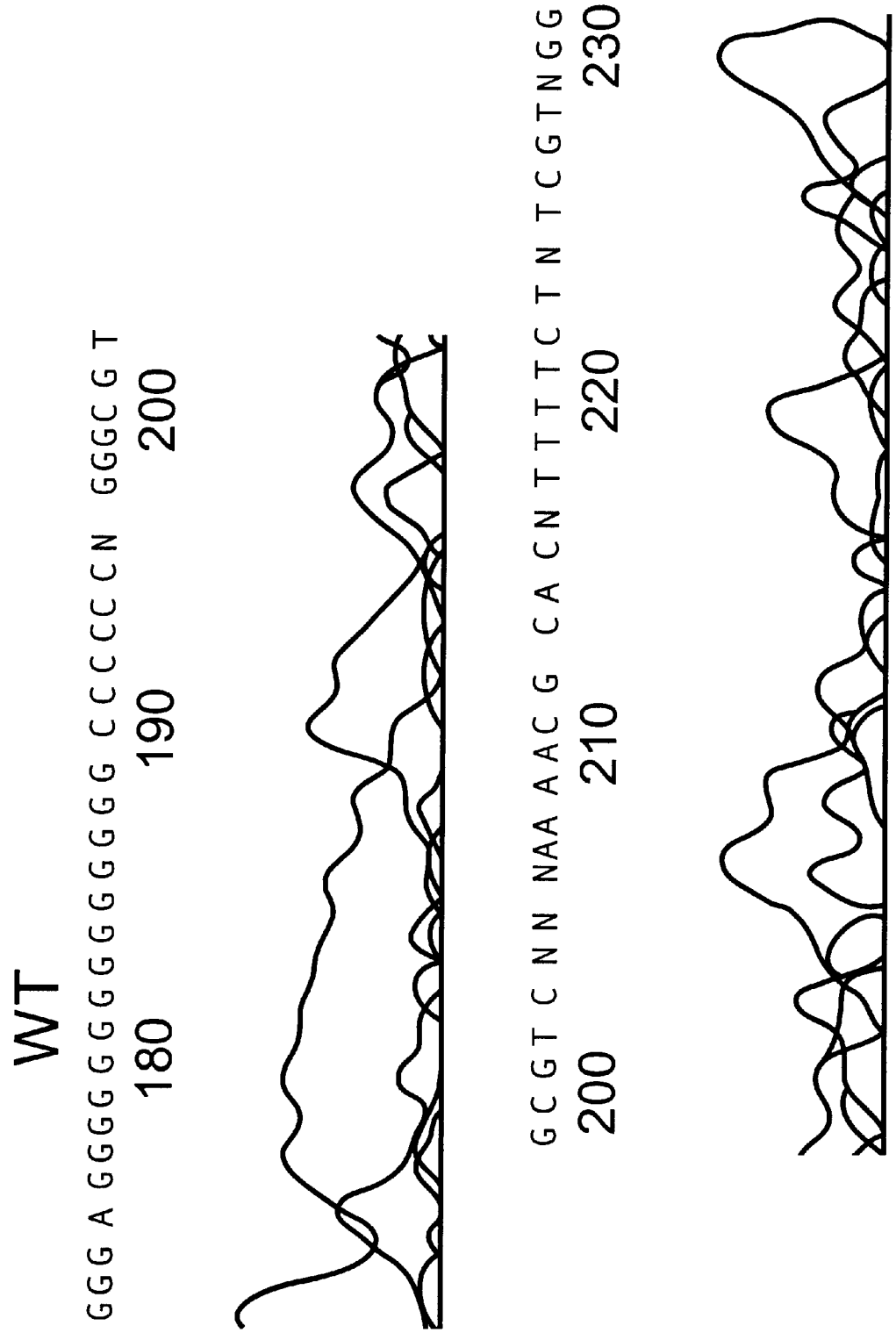
FIG. 32 represents the results of examples of sequence reaction utilizing wild type T7 RNA polymerase (WT) [SEQ ID NO.: 31], mutant T7 RNA polymerase F644Y [SEQ ID NO.: 33] (F644Y), or mutant T7 RNA polymerase L665P/F667Y (F667Y) [SEQ ID NO.: 35]. All of them were sequence patterns of the same area. It can be seen that, in the case of the wild type T7 RNA polymerase (WT, top section), the base call did not correctly function, intervals of bases were narrowed (representations of bases overlap) [SEQ ID NOS.: 32, 34 & 36], and thus sequencing was not performed correctly.
Figure 32:
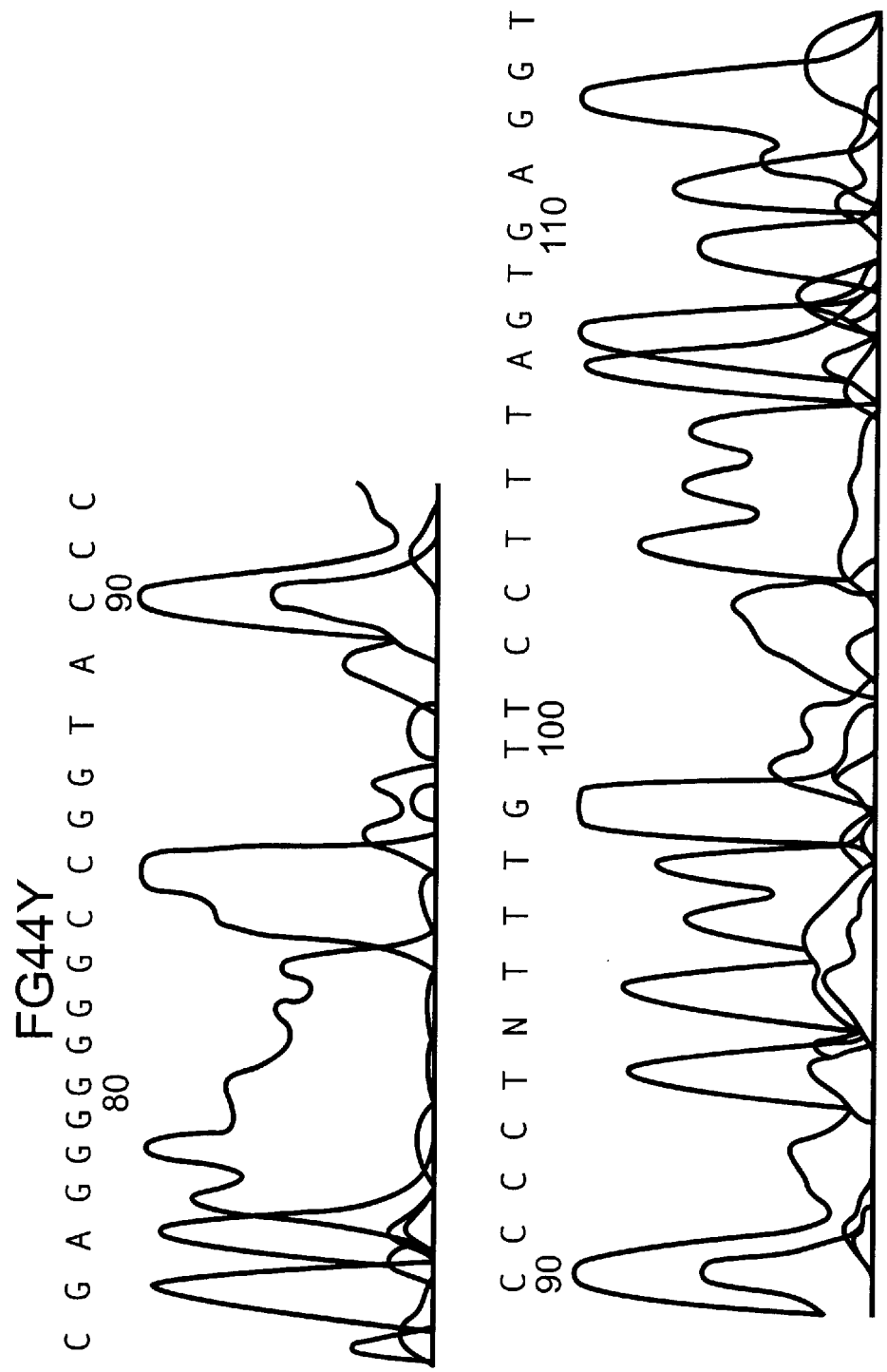
Figure 32:
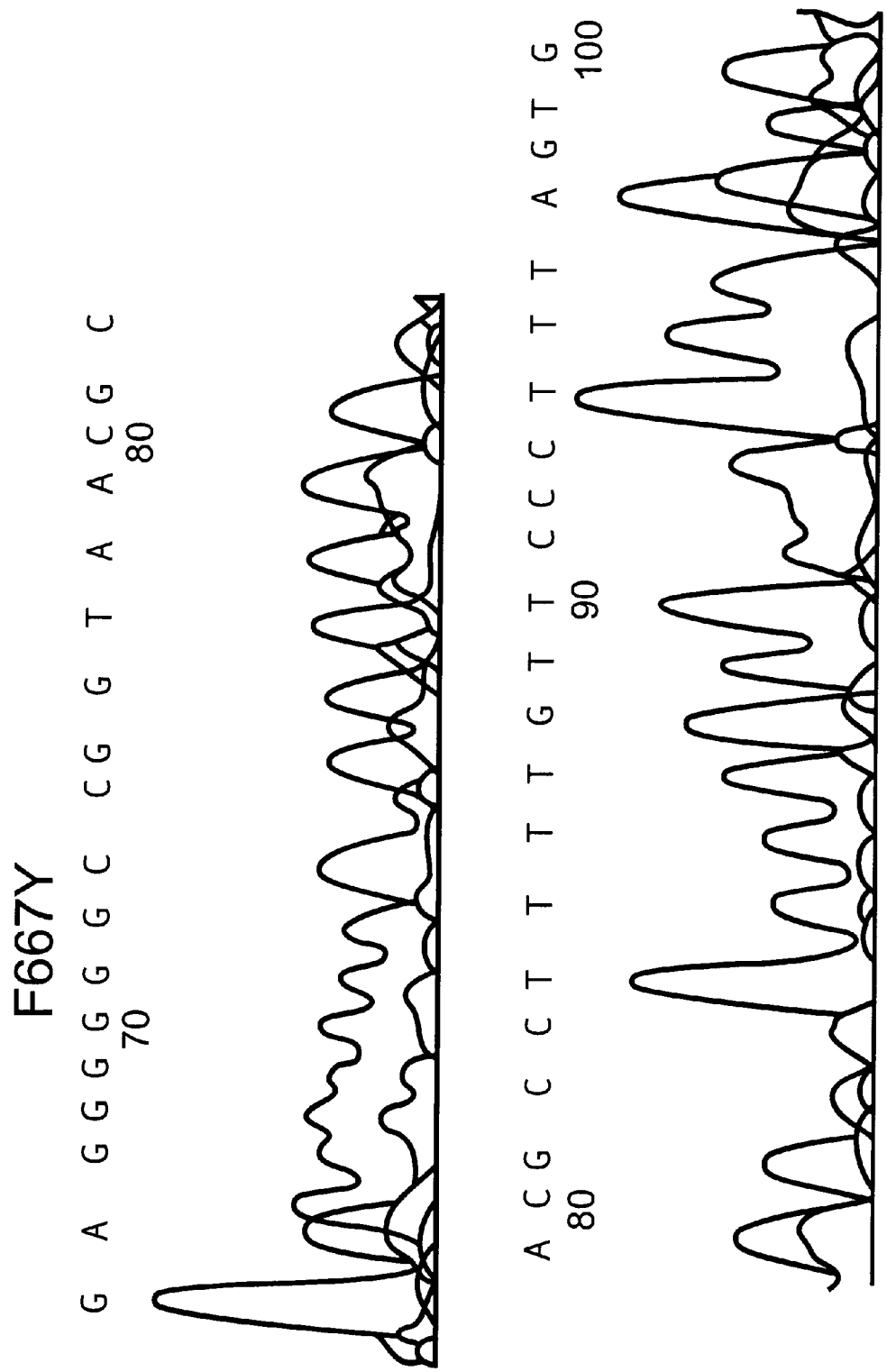

The peak intensities of the sequence ladder obtained by using the mutant T7 RNA polymerase F644Y are shown in FIG. 30 with the peak intensities obtained by using wild type T7 RNA polymerase for comparison. The peak intensities of the sequence ladder obtained by using the mutant T7 RNA polymerase L665P/F667Y are shown in FIG. 31 with the peak intensities obtained by using wild type T7 RNA polymerase for comparison. From these comparisons, it was confirmed that altitude of the peaks for the mutant enzymes showed less fluctuation in comparison with the wild type, and the peak showed stronger signals. This indicates that the mutation of F644Y or L665P/F667Y improved the incorporation efficiency for 3'-dCTP derivatives for this case, and that transcription reaction by these mutant T7 RNA polymerases exhibits ladder extension characteristic comparable to the data productivity of the conventional methods for determining nucleotide sequence using a DNA polymerase.

EXAMPLE 2

Example of Sequencing Reaction by the Dye Terminator Method Utilizing Mutant T7 RNA Polymerase Sequencing reaction by the dye terminator method was performed utilizing the purified mutant T7 RNA polymerases F644Y and L665P/F667Y, and the wild type T7 RNA polymerase as follows for comparison.

For the in vitro transcription reaction, the method of Melton, D. A. (1984, Nucleic Acids Res., 12:7035–7056) exemplified in Example 1 was used. More specifically, the reaction was performed in a total reaction volume of 10 µl containing a plasmid vector pBluescriptKS(+) having T7 promoter linealized by the reaction with a restriction endonuclease PvuII or ScaI as a template, 250 µM of R6G-3'-dATP(n=1), 25 µM of R110-3'-dGTP(n=1), 150 µM of XR-3'-dCTP(n=1), 50 µM of TMR-3'-dUTP(n=1), which were the dye terminators synthesized in the above Synthesis Examples 49, 52, 46 and 43 respectively, as derivatives of 3'-dNTP, 500 µM of GTP and UTP, 250 µM of ATP and CTP, 8 mM of $MgCl_2$, 2 mM of spermidine-$(HCl)_3$, 5 mM of DTT, 40 mM of Tris/HCl pH 8.0 (BRL, Gibco) and 25 units of wild type T7 RNA polymerase (BRL, Gibco or Nippon Gene) or the mutant T7 RNA polymerase F644Y at 37° C. for 1 hour. Then, to remove the unreacted dye terminators remained in the reaction product, the transcription product was purified by gel filtration using a Sephadex G-50 column (Pharmacia Biotech), and the purification product was evaporated to dryness using a centrifugal evaporator.

The dried reaction product was dissolved in 6 µl of formamide/EDTA/Blue dextran loading buffer according to the instruction manual Ver.1.0 of ABI PRISM 377 DNA Sequencing System available from Perkin-Elmer Japan, and 2 µl of the solution was analyzed by ABI 377 DNA Sequencer and an analysis program using denatured gel for sequencing analysis which contained 6 M urea/4% Long Ranger™ acrylamide solution (FMC). As a result, it was found that the mutant T7 RNA polymerases F644Y and L665P/F667Y could afford higher peak intensity with less fluctuation in comparison with the wild type T7 RNA polymerase, and their sequence reading was possible. When the wild type T7 RNA polymerase was used, its sequence reading was almost impossible.

EXAMPLE 3

For the in vitro transcription reaction, the method of Melton, D. A. (1984, Nucleic Acids Res., 12:7035–7056) was used as in Examples 1 and 2.

Specifically, 0.25 µg per reaction of a plasmid vector pBluescriptKS(+) having T7promoter (Stratagene) linearized by the reaction with a restriction endonuclease PvuII was used as a template.

The reaction was performed in a total reaction volume of 10 µl containing 4 µM R6G-3'dATP(n=4), 4 µM R110-3'dGTP(n=4), 80 µM XR-3'dCTP(n=4), and 20 µM TMR-3'dUTP(n=4) as the dye terminators (4×linker dye terminators), 500 µM of GTP and UTP, 250 µM of ATP and CTP, 8 mM of $MgCl_2$, 2 mM of spermidine-$(HCl)_3$, 5 mM of DTT, 40 mM of Tris/HCl pH 8.0 (BRL, Gibco) and 25 units of the mutant T7 RNA polymerase F644Y similarly at 37° C. for 1 hour. Then, to remove the unreacted dye terminators remained in the reaction product, the transcription product was purified by gel filtration using a Sephadex G-50 column (Pharmacia Biotech), and the purification product was evaporated to dryness using a centrifugal evaporator. The dried reaction product was dissolved in 6 µl of formamide/EDTA/Blue dextran loading buffer according to the instruction manual Ver.1.0 of ABI PRISM 377 DNA Sequencing System available from Perkin-Elmer Japan, and 2 µl of the solution was analyzed by ABI 377 DNA Sequencer and an analysis program using denatured gel for sequencing analysis which contained 6 M urea/4% Long Ranger™ acrylamide solution (FMC).

Figure 33:
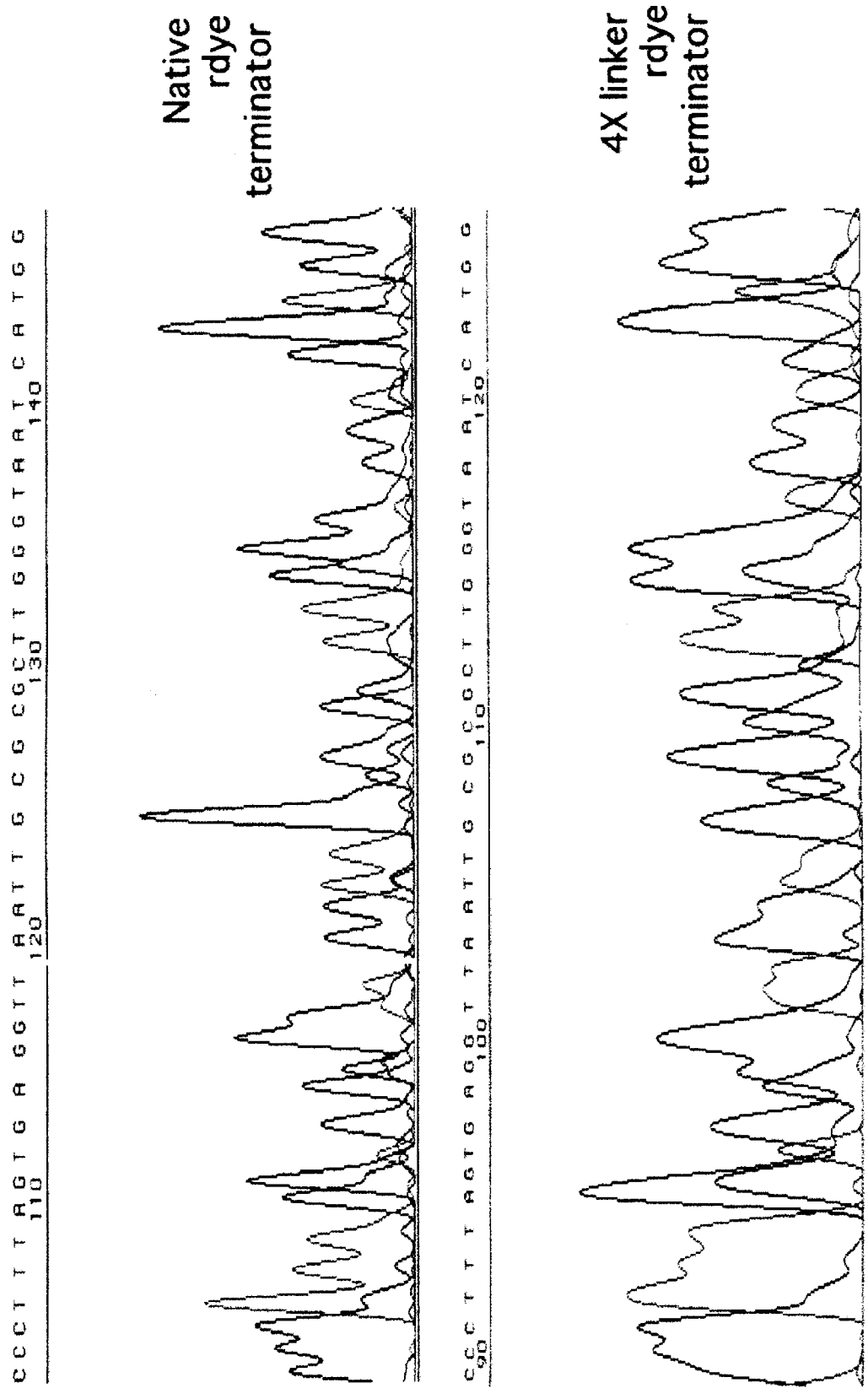
FIG. 33 [SEQ ID NOS.: 37–38] shows comparison of the results of the sequencing using T7 RNA polymerase, when the mutant T7 RNA polymerase L665P/F667Y, and dye terminators different in the linker length were used.

The results were shown in FIG. 33. In FIG. 33, the upper section shows the result obtained by using the dye terminator used in Example 2, and the lower section shows the result obtained by using the dye terminator having a longer linker length. It can be seen that the combination of the dye terminator having a longer linker length and the mutant T7

RNA polymerase exhibited more uniform incorporation efficiency compared with that of the conditions of Example 2 where a dye terminator having a shorter linker length was used. These results indicate that the nucleotide sequence analysis utilizing in vitro transcription reaction can be performed at a practical level.

EXAMPLE 4
Example of Sequencing Reaction Using Vector Having T7 Promoter as Template For the in vitro transcription reaction, the method of Melton, D. A. (1984, Nucleic Acids Res., 12:7035–7056) was used as in Examples 1–3.

Specifically, a plasmid vector pBluescriptKS(+) having T7 promoter (Stratagene) linearized by the reaction with a restriction endonuclease PvuII was used as a template. The reaction was performed in a total reaction volume of 10 μl containing 4 μM R6G-3'dATP(n=4), 4 μM R110-3'dGTP(n=4), 80 μM XR-3'dCTP(n=4), and 20 μM TMR-3'dUTP(n=4), 500 μM of GTP and UTP, 250 μM of ATP and CTP, 8 mM of $MgCl_2$, 2 mM of spermidine-$(HCl)_3$, 5 mM of DTT, 40 mM of Tris/HCl, pH 8.0 (BRL, Gibco) and 25 units of the mutant T7 RNA polymerase F644Y (or L665P/F667Y) similarly at 37° C. for 1 hour. Then, to remove the unreacted dye terminators remained in the reaction product, the transcription product was purified by gel filtration using a Sephadex G-50 column (Pharmacia Biotech), and the purification product was evaporated to dryness using a centrifugal evaporator.

The dried reaction product was dissolved in 6 μl of formamide/EDTA/Blue dextran loading buffer according to the instruction manual Ver.1.0 of ABI PRISM 377 DNA Sequencing System available from Perkin-Elmer Japan, and 2 μl of the solution was analyzed by ABI 377 DNA Sequencer and an analysis program (Sequencing Analysis Ver. 3.0) using denatured gel for sequencing analysis which contained 6 M urea/4% Long Ranger™ acrylamide solution (FMC). The results were shown in FIG. 34. As a result, a sequence electrogram which can be sufficiently used at a practical level was obtained, though a few sections difficult to be determined were still remained.

EXAMPLE 5
Example of Sequencing Reaction Using PCR Product as Template

In this example, a human thyroid-stimulating hormone (hTSH-β) cDNA subcloned into the EcoRI site of pBluescript KS(+) (Stratagene) was used as a template of PCR reaction, but the template is not limited to the hTSH-β cDNA, and any genes may be used. An important point in the explanation of this example is that, if a T7 promoter which is recognized by T7 RNA polymerase can be provided in the PCR product, a subject of nucleotide sequencing, sequencing becomes possible as in this example. One means for providing the T7 promoter in the PCR product that allows the sequencing is an addition of a T7 promoter sequence and transcription origin required for the transcription to a 5' end of either one of the primers when PCR is performed, and it can be achieved in any DNA. Another means, which will be explained in this example, is use of a plasmid already having the T7 promoter and primers that should at least be present on the both sides of the T7 promoter, and this makes it possible to obtain a PCR product having the T7 promoter. Vectors useful for performing PCR of the latter method are commercially available, which include pBluescript series vectors, pBC Phagemid vector (those are from Stratagene) and PGEM series vectors (Promega). The PCR reaction was performed by using 100 fg of a plasmid having the hTSH-β cDNA, and primers present on the both sides of the cloning site, L220 primer [SEQ ID NO.:13] (5'-TAA CAA TTT CAC ACA GGA AAC A-3') and 1211 primer [SEQ ID NO.:14] (5'-ACG TTG TAA AAC GAC GGC CAG T-3') in a reaction volume of 20 μl with the following profile; 94° C. for 2 minutes for one cycle, 94° C. for 1 minute, 55° C. for 1 minute, and 72° C. for 1.5 minute for 30 cycles, and 72° C. for 5 minutes. In the PCR product obtained in the above PCR reaction, the T7 promoter was present in the downstream of the 1211 primer. 1 μl (about 10 ng) of the above PCR product was used for the sequencing reaction. The reaction was performed in a total reaction volume of 10 μl containing 4 μM R6G-3'dATP(n=4), 4 μM R110-3'dGTP(n=4), 80 μM XR-3'dCTP(n=4), 20 μM TMR-3'dUTP(n=4), 500 μM of GTP and UTP, 250 μM of ATP and CTP, 8 mM of $MgCl_2$, 2 mM of spermidine-$(HCl)_3$, 5 mM of DTT, 40 mM of Tris/HCl, pH 8.0 (BRL, Gibco) and 25 units of the mutant T7 RNA polymerase F644Y similarly at 37° C. for 1 hour. Then, to remove the unreacted dye terminators remained in the reaction product, the transcription product was purified by gel filtration using a Sephadex G-50 column (Pharmacia Biotech), and the purification product was evaporated to dryness using a centrifugal evaporator.

The dried reaction product was dissolved in 6 μl of formamide/EDTA/Blue dextran loading buffer according to the instruction manual Ver.1.0 of ABI PRISM 377 DNA Sequencing System available from Perkin-Elmer Japan, and 2 μl of the solution was analyzed by ABI 377 DNA Sequencer and an analysis program (Sequencing Analysis Ver. 3.0) using denatured gel for sequencing analysis which contained 6 M urea/4% Long Ranger™ acrylamide solution (FMC). The results are shown in FIG. 35. From these results, a sequence electrogram sufficiently used at a practical level could be obtained, though a few sections difficult to be determined were still remained.

Reference Example 6
Purification of Inorganic Pyrophosphatase Free From RNase Activity Inorganic pyrophosphatase (PPase) free from RNase was produced as follows, but its production method is not limited to the method described below.

As a starting material of the purification of inorganic pyrophosphatase, a roughly purified product derived from yeast, which was available from Sigma (Sigma I-1643, EC.3.6.1.1), was used, and 4 mg (680 units) of the product was suspended in a buffer (20 mM Tris-HCl, 1 mM EDTA, pH 7.9, 1 ml), and dialyzed against the same buffer for two hours for desalting, and the dialyzed product was subjected to column chromatography in an SP Sepharose column having a column volume of 1 ml (Pharmacia Biotech). More specifically, the column was sufficiently washed with the same buffer until any material absorbing ultraviolet ray at 280 nm disappeared, and eluted with a linear gradient of 0 to 0.1 M NaCl in the same buffer of about 20 times volume of the column volume. The eluent was collected in test tubes as fractions of a suitable volume, and immediately subjected to SDS-12.5% polyacrylamide gel electrophoresis for protein analysis to identify fractions containing a protein of about 32 kDa. In typical examples, the PPase fractions should be found in the unabsorbed portion. The fractions containing the protein were collected, absorbed by Q-Sepharose column (Pharmacia Biotech) having a column volume of 1 ml, and eluted with a linear gradient of 0 to 0.1 M NaCl in the same buffer of about 20 times volume of the column volume. The eluent was collected in test tubes as fractions of a suitable volume, and immediately subjected to SDS-12.5% polyacrylamide gel electrophoresis to identify fractions containing a protein of about 32 kDa. In typical examples, it should be found around 0.35 M NaCl. The fractions containing the protein of 32 kDa were collected, dialyzed against 500 ml of storage buffer (20 mM Tris-HCl, 1 mM EDTA, 50% glycerol, pH 7.9) for 16 hours, and stored at −20° C. until use. In typical examples, a specimen containing 425 units of the PPase protein, i.e., 0.425 units/μl, could be obtained with a collection yield of 62.5%.

RNase contamination degree of the above specimen was examined by using 8 μg of E. coli rRNA (16S and 23S) as substrates. More specifically, the PPase in an amount corresponding to 0.17 units was added to the E. coli rRNA in a buffer containing 8 mM $MgCl_2$, 2 mM spermidine-$(HCl)_3$, 5 mM DTT, 40 mM Tris/HCl, pH 8.0, and allowed to react at 37° C. for four hours. The RNA was subjected to 1.0% agarose gel electrophoresis under a denaturation condition where formamide was present, and electrophoresis was finished when simultaneously added xylenecyanol dye reached the height of about ⅓ of the agarose gel. The gel was irradiated with ultraviolet light (wavelength: 254 nm), and photographed to examine degree of the RNA degradation. The PPase in the roughly purified product and the PPase after purification were compared, and degradation of RNA was observed in the roughly purified product, whereas significant RNA degradation activity was not observed in the purified product.

EXAMPLE 6
Effect of Adding Dye Terminator Having Linker and Inorganic Pyrophosphatase on Sequencing Reaction Utilizing Mutant T7 RNA Polymerase Effect of the PPase purified in Reference Example 6 on in vitro sequencing transcription reaction was examined. First, to examine the effect of added amount, the reaction was performed with various addition amounts of PPase. For the sequencing reaction, the method of Melton, D. A. (1984, Nucleic Acids Res., 12:7035–7056) was used. More specifically, a plasmid vector pBluescriptKS(+) having T7promoter (Stratagene) linearized by the reaction with a restriction endonuclease PvuII was used as a template. The reaction was performed in a total reaction volume of 10 μl containing 4 μM R6G-3'dATP(n=4), 4 μM R110-3'dGTP(n=4), 80 μM XR-3'dCTP(n=4), and 20 μM TMR-3'dUTP(n=4), 500 μM of GTP and UTP, 250 μM of ATP and CTP, 8 mM of $MgCl_2$, 2 mM of spermidine-$(HCl)_3$, 5 mM of DTT, 40 mM of Tris/HCl, pH 8.0 (BRL, Gibco) and 25 units of the mutant T7 RNA polymerase F644Y similarly at 37° C. for 1 hour. To examine the effect of PPase, the above reaction was performed with no addition of the enzyme, or addition of the enzyme in an amount corresponding to 0.425 units, 0.0425 units, or 0.00425 units. Then, to remove the unreacted dye terminators remained in the reaction product, the transcription product was purified by gel filtration using a Sephadex G-50 column (Pharmacia Biotech), and the purification product was evaporated to dryness using a centrifugal evaporator.

The dried reaction product was dissolved in 6 μl of formamide/EDTA/Blue dextran loading buffer according to the instruction manual Ver.1.0 of ABI PRISM 377 DNA Sequencing System available from Perkin-Elmer Japan, and 2 μl of the solution was analyzed by ABI 377 DNA Sequencer and an analysis program (Sequencing Analysis Ver. 3.0) using denatured gel for sequencing analysis which contained 6 M urea/4% Long Ranger™ acrylamide solution (FMC). The results were shown in FIGS. 36 and 37. As seen from these results, the separation of the peaks was improved, and uniformity of the peak altitudes was also increased in all of the cases where the PPase was added. Since the same effect was obtained even with the addition of 0.00425 units of the PPase, the addition amount of the PPase was fixed to 0.00425 units hereafter.

Then, effect on the sequencing reaction utilizing the PCR product as a template was examined. The sequencing reaction was performed as follows. In this example, a human thyroid-stimulating hormone (hTSH-β) CDNA subcloned into the EcoRI site of pBluescript KS(+) (Stratagene) was used as a template of PCR reaction, but the template is not limited to the hTSH-β cDNA, and any genes may be used. The PCR reaction was performed by using 100 fg of a plasmid having the hTSH-β cDNA, and primers present on the both sides of the cloning site, L220 primer [SEQ ID NO.:13] (5'-TAA CAA TTT CAC ACA GGA AAC A-3') and 1211 primer [SEQ ID NO.:14] (5'-ACG TTG TAA AAC GAC GGC CAG T-3') in a reaction volume of 20 μl with the following profile; 94° C. for 2 minutes for one cycle, 94° C. for 1 minute, 55° C. for 1 minute, and 72° C. for 1.5 minute for 30 cycles, and 72° C. for 5 minutes. 1 μl (about 10 ng) of the above PCR product was used for the sequencing reaction. The reaction was performed in a total reaction volume of 10 μl containing 4 μM R6G-3'dATP(n=4), 4 μM R110-3'dGTP(n=4), 80 μM XR-3'-dCTP(n=4), 20 μM TMR-3'dUTP(n=4), 500 μM of GTP and UTP, 250 μM of ATP and CTP, 8 μM of $MgCl_2$, 2 mM of spermidine-$(HCl)_3$, 5 mM of DTT, 40 mM of Tris/HCl, pH 8.0 (BRL, Gibco) and 25 units of the mutant T7 RNA polymerase F644Y similarly at 37° C. for 1 hour. When the PPase was added, it was added in an amount corresponding to 0.00425 units. Then, to remove the unreacted dye terminators remained in the reaction product, the transcription product was purified by gel filtration using a Sephadex G-50 column (Pharmacia Biotech), and the purification product was evaporated to dryness using a centrifugal evaporator.

The dried reaction product was dissolved in 6 μl of formamide/EDTA/Blue dextran loading buffer according to the instruction manual Ver.1.0 of ABI PRISM 377 DNA Sequencing System available from Perkin-Elmer Japan, and 2 μl of the solution was analyzed by ABI 377 DNA Sequencer and an analysis program (Sequencing Analysis Ver. 3.0) using denatured gel for sequencing analysis which contained 6 M urea/4% Long Ranger™ acrylamide solution (FMC). A part of the results are shown in FIG. 38. As seen from these results, when the PPase was added, the separation of the peaks was improved, and uniformity of the peak altitudes was also increased. Thus, the same results were obtained as the case where the above plasmid was used as a template for sequencing. This suggests that the use of PPase increases the sequence reading precision.

EXAMPLE 7
Specific Example of Sequencing Reaction Utilizing Addition of Inorganic Pyrophosphatase The sequencing reaction was performed with the same conditions as the case of Example 6 where the PCR product was used as a template with addition of inorganic pyrophosphatase, and the obtained sequencing precision was used for comparison.

Figures 39G, 39H:
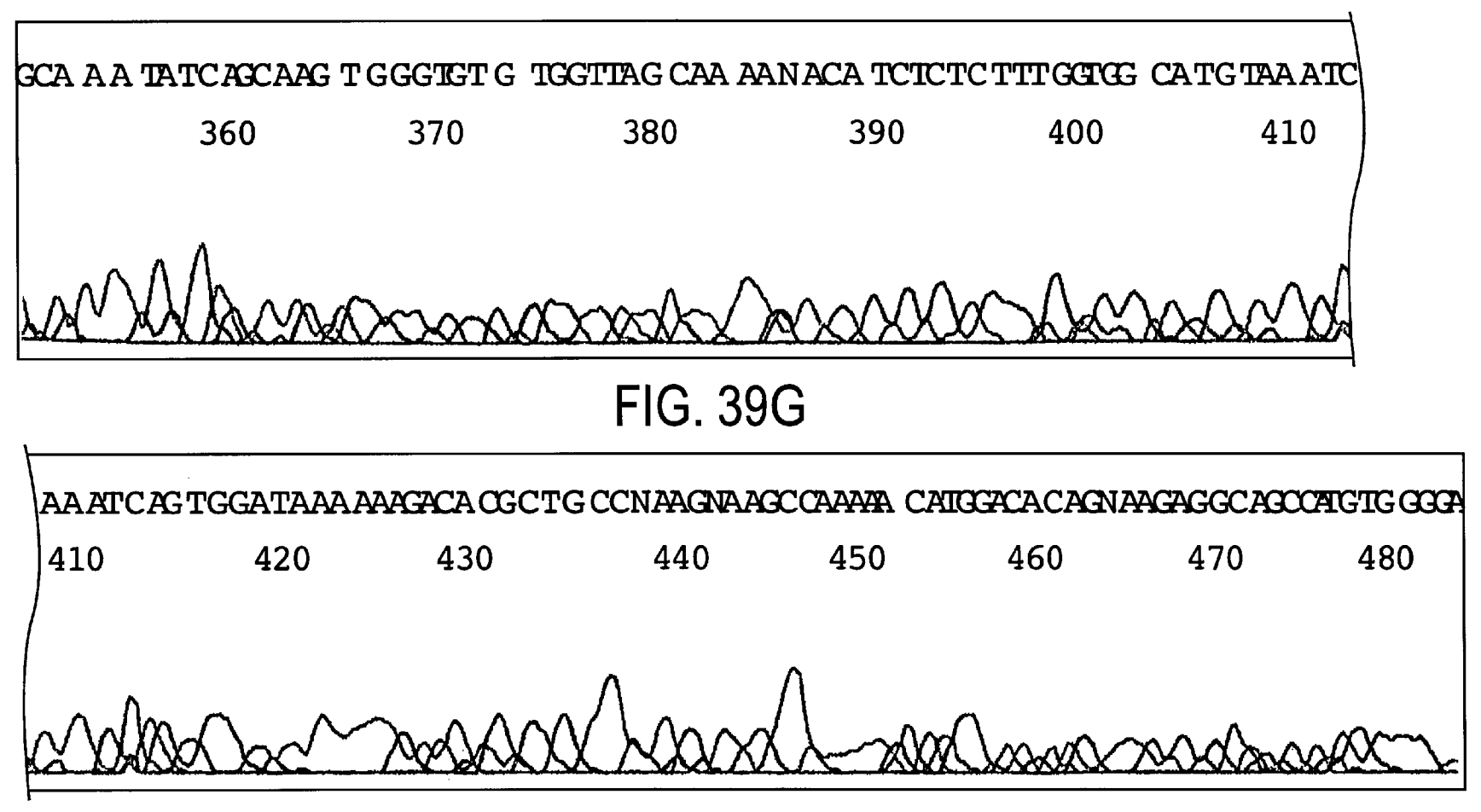

FIG. 39 shows the results obtained with no addition of inorganic pyrophosphatase, and FIG. 40 shows the results obtained from the reaction with addition of inorganic pyrophosphatase. As a result of comparison with the hTSH-β cDNA which nucleotide sequence determined is already reported, it was found that, as for the 510 base pairs determined, 90% of precision was obtained for the case with no addition of the inorganic pyrophosphatase, whereas 98% of precision was obtained for the case with addition of inorganic pyrophosphatase. FIG. 38 referred to in Example 6 was obtained by processing a part of the results of this experiment for comparison of the effect of the addition of inorganic pyrophosphatase.

From the above, it is demonstrated that, by using a mutant T7 RNA polymerase, dye terminator and inorganic pyrophosphatase, nucleotide sequences can be determined with a precision equivalent to, or higher than that obtainable by the methods for determining nucleotide sequences of current mainstream, i.e., the methods utilizing DNA polymerases.

Reference Example 7
Improvement of Incorporation Rate of 3'-dNTP Derivatives

Ribonucleotide (NTP) and 3'-deoxynucleotide (3'-dNTP) incorporation rates of the mutant T7 RNA polymerase purified in Reference Example 5 were measured as follows. pBluescript(KS+) plasmid (Stratagene) linearized by reaction with a restriction endonuclease, PvuII, was used as a template for the transcription reaction, and 250 μM each of ATP, CTP, GTP, and UTP, 2 mM of spermidine-(HCl)$_3$, 5 mM of DTT, 40 mM Tris/HCl pH 8.0, 0.1 μl of [α-$^{32}$P]UTP (3000 Ci/mmole), and 25 units of the mutant T7 RNA polymerase F644Y/L665P/F667Y were also used for the reaction. For two kinds of reaction mixture (with or without 3'-DATP, final concentration was 100 μM), the reaction was performed at 37° C. for 60 minutes. The whole reaction mixture was spotted on DE81 paper (Whatman), washed three times with phosphate buffer, and dried. The DE81 paper was placed into a scintillation vial, and radioactivity was measured using a scintillation counter (Beckman) for each reaction. Degree of inhibition of the [α-$^{32}$P]UTP incorporation was calculated by comparing the values obtained with and without 3'-dATP based on the measured radioactivity. The relative activity obtained from calculated inhibition degree and defined as a relative value to the inhibition degree of the wild type T7 RNA polymerase normalized to 1.000 was shown in Table 1.

The inhibition degree was calculated by using the wild type T7 RNA polymerase, T7 RNA polymerase F644Y, L665P/F667Y obtained in Reference Example 3, mutant T7 RNA polymerase F644Y/L665P, F782Y, F733Y, F646Y or Y639F constructed and purified in the same manner as in Examples 2 and 3 for the reaction instead of the above F644Y/L665P/F667Y mutant, and results concerning inhibition were obtained. The relative activities are shown in Table 1.

In the results of Table 1, a larger value indicates that the corresponding mutant enzyme has a mutation making 3'-dATP incorporation easier in a higher degree. For example, it is meant that the mutant T7 RNA polymerase F644Y/L665P/F667Y is 5.58 times more likely to incorporate 3'-dATP in comparison with the wild type enzyme. It has been demonstrate that the F644Y/L665P/F667Y mutant was the mutant enzyme exhibiting the least bias for the 3'-dATP incorporation among the mutant enzymes prepared.

TABLE 1

| Mutation site | Relative activity of RNA polymerase for 3'-dATP |
|---|---|
| F644Y | 5.130 |
| F644Y/L665P | 5.130 |
| L665P/F667Y | 4.711 |
| F644Y/L665P/F667Y | 5.580 |
| F782Y | 1.173 |
| F733Y | 1.075 |

TABLE 1-continued

| Mutation site | Relative activity of RNA polymerase for 3'-dATP |
|---|---|
| F646Y | 0.459 |
| Y639F | 0.930 |
| Wild type | 1.000 |

EXAMPLE 8
Example of Sequencing Reaction Utilizing Mutant T7 RNA Polymerase F644Y/L665P/F667Y A template used as a template for sequencing reaction was prepared by PCR as follows.

As the template for PCR, human thyroid-stimulating hormone (hTSH-β) cDNA subcloned into a plasmid derived from BS750 having T7 promoter was used. By using this plasmid 100 fg having hTSH-β with L220 primer [SEQ ID NO: 13] (5'-TAA CAA TTT CAC ACA GGA AAC A-3') and 1211 primer [SEQ ID NO: 14] (5'-ACG TTG TAA AAC GAC GGC CAG T-3') existing at both sides of the cloning site, PCR reaction was performed in a reaction volume of 20 μl (1 cycle of 94° C. for 2 minutes, 30 cycles of 94° C. for 1 minute, 55° C. for 1 minute, and 72° C. for 1.5 minutes, followed by 72° C. for 5 minutes). The T7 promoter existed in the downstream of 1211 primer of the PCR product obtained from the above PCR reaction.

The transcriptional sequencing reaction was performed by the method of Melton, D. A, [Nucleic Acids Res., 12: 7035–7056 (1984)].

1 μl (about 10 ng) of the above PCR product was used for the sequencing reaction. The reaction was performed in a total reaction volume of 10 μl containing the same dye terminators as used in Example 2, 4 μM R6G-3'dATP [5-carboxyrhodamine 6G-labeled 3'-deoxyadenosine-5-triphosphate (n=4)], 4 μM R110-3'dGTP [5-carboxyrhodamine 110-labeled 3'-deoxyguanosine-5-triphosphate (n=4)], 80 μM XR-3'dCTP [5-carboxy-X-rhodamine-labeled 3'-deoxycytidine-5-triphosphate (n=4)], 20 μM TMR-3'dUTP [5-carboxytetramethylrhodamine-labeled 3'-deoxyuridine-5-triphosphate (n=4)], 500 μM UTP, 250 μM ATP, 200 μM CTP, 500 μM GTP, 2 mM spermidine-(HCl)$_3$, 5 mM DTT, 40mM Tris/HCl pH 8.0 (BRL, Gibco) and 25 units of the mutant T7 RNA polymerase F644Y/L665P/F667Y at 37° C. for 1 hour.

Then, to remove the unreacted dye terminator remained in the reaction product, the transcription product was purified by gel filtration using a Sephadex G-50 column (Pharmacia Biotech), and the purification product was evaporated to dryness using a centrifugal evaporator.

The dried reaction product was dissolved in 6 μl of formamide/EDTA/Blue dextran loading buffer according to the instruction manual Ver.1.0 of ABI PRISM 377 DNA Sequencing System available from Perkin-Elmer Japan, and 2 μl of the solution was analyzed by ABI 377 DNA Sequencer and an analysis program (Sequencing Analysis Ver. 3.0) using denatured gel for sequencing analysis which contained 6M urea/4% Long Ranger™ acrylamide solution (FMC) to afford an electropherogram. The results are shown in FIG. 41. Excellent sequencing analysis was possible as demonstrated.

Reference Example 8
Examination of 3'-deoxyterminators With Different Methylene Chains as Linker Portion
[Template DNA]

PCR was performed by using the following materials (96° C. for one minute, 55° C. for 30 seconds, and 72° C. for one minute for one cycle, and 96° C. for 30 seconds, 55° C. for 30 seconds, 72° C. for one minute for 24 cycles), and the resulting PCR product (amplified DNA fragment of human thyroid stimulating hormone (TSH) β-subunit) was used as a template DNA.

Each material in a predetermined amount was added to a sample tube, filled up to a total volume of 10 μl with EXTaq buffer (Takara Shuzo), and used as a PCR mixture.

[Materials]

| | |
|---|---|
| Bluescript II (Stratagene) introduced with human TSHβ subunit DNA (accession No.S70586) | 1 pg |
| Forward primer [SEQ ID NO.:14] (5'-ACGTTGTAAAACGACGGCCAGT-3') | 0.1 M |
| Reverse primer [SEQ ID NO:13] (5'-TAACAATTTCACAGGAAACA-3') | 0.1 M |
| 2'-dGTP | 200 μM |
| 2'-dTTP | 200 μM |
| 2'-dATP | 200 μM |
| 2'-dCTP | 200 μM |
| EXTaq polymerase (Takara Shuzo) | 0.5 units |

[Terminator]

TMR-3'dUTP(n4) (the compound of Synthesis Example 30)

TMR-Allyl-3'dUTP(n4) (the compound of Synthesis Example 61)

[Experimental Procedure]

The template DNA (10 ng) was added to a sample tube containing each of the terminators, guanosine-5'-triphosphate (rGTP), uridine-5'-triphosphate (rUTP), adenosine-5'-triphosphate (rATP), and cytidine-5'-triphosphate (rCTP), MgCl$_2$, spermidine-(HCl)$_3$, dithiothreitol (DTT), Tris/HCl (pH 7.5), yeast inorganic pyrophosphatase (PPase) and T7 RNA polymerase in such amounts as their final concentrations should be as follows, filled up to a total amount of 10 μl with distilled water, and used as a sample.

| | |
|---|---|
| • Terminater | 10 μM |
| • rGTP | 500 μM |
| • rUTP | 500 μM |
| • rATP | 250 μM |
| • rCTP | 250 μM |
| • MgCl$_2$ | 8 mM |
| • Spermidine-(HCl)$_3$ | 2 mM |
| • DTT | 5 mM |
| • Tris/HCl (pH 7.5) | 40 mM |
| • Yeast PPase | 10 units |
| • T7 RNA polymerase (Gibco BRL) | 25 units |

After 30 minutes incubation of the sample at 37° C., the terminators not incorporated were removed by gel filtration using a Sephadex G25 column (Pharmacia), and the precipitates were collected by centrifugal separation. Subsequently, the precipitates were dissolved in 4 μl of formamide dye (10 mM EDTA containing 95% formamide), and heated to 90° C. for two minutes. After cooling, 2 μl of the solution was applied to 4% sequencing gel, and electrophoresed on ABI377 fluorescence automatic sequencer (ABI). The matrix-converted gel image (termination pattern) obtained in the sequencer with TMR-3'dUTP(n4) is shown in FIG. 42A, and the similarly matrix-converted gel image (termination pattern) obtained in the sequencer with TMR-Allyl-3'dUTP(n4) is shown in FIG. 42B.

[Results]

As clearly seen from FIGS. 42A and 42B, difference is not recognized between the termination patterns obtained with TMR-3'dUTP(n4) and TMR-Allyl-3'dUTP(n4), and therefore it was demonstrated that TMR-Allyl-3'dUTP(n4) is incorporated as efficiently as TMR-3'dUTP(n4).

Similar results were obtained when the experiment was repeated with the same conditions except that the amount of the terminator used was changed from 10 μM to 0.5μM.

What is claimed is:

1. A method for determining DNA nucleotide sequences comprising
providing ribonucleoside 5'-triphosphates, wherein said ribonucleoside triphosphates are selected from the group consisting of ATP, GTP, CTP, UTP, and derivatives thereof,
reacting said ribonucleoside 5' triphosphates with one or more kinds of 3'-dNTP derivatives in the presence of an RNA polymerase and a DNA fragment containing a promoter sequence for the RNA polymerase to obtain a nucleic acid transcription product, wherein said 3'-dNTP derivatives are 3'-deoxyribonucleoside 5'-triphosphates selected from the group consisting of 3'-dATP, 3'-dGTP, 3'-dCTP, 3'-dUTP, and derivatives thereof,
separating the resulting nucleic acid transcription product, and
determining a nucleic acid sequence from the resulting separated fraction,
wherein the RNA polymerase is a mutant promoter-specific RNA polymerase selected from the group consisting of F644Y, L665P, F667Y, F644Y/L665P, F644Y/F667Y, L665P/F667Y and F644Y/L665P/F667Y mutants of an RNA polymerase derived from T7 phage,
said mutant RNA polymerase having an enhanced ability for incorporating the 3'-dNTP derivatives in comparison with the corresponding wild type RNA polymerase.

2. The method of claim 1, wherein the mutant RNA polymerase is an RNA polymerase derived from T7 phage, and has tyrosine at amino acid residue 644 or 667.

3. The method of claim 1, wherein the mutant RNA polymerase is an RNA polymerase consisting of a wild type T7 RNA polymerase provided that 644th amino acid residue of the wild type T7 RNA polymerase, phenylalanine, has been replaced with tyrosine.

4. The method of claim 1, wherein the mutant RNA polymerase is an RNA polymerase consisting of a wild type T7 RNA polymerase provided that 667th amino acid residue, phenylalanine, of the wild type T7 RNA polymerase has been replaced with tyrosine.

5. The method of claim 1, wherein the mutant RNA polymerase is an RNA polymerase consisting of a wild type T7 RNA polymerase provided that 644th amino acid residue, phenylalanine, of the wild type T7 RNA polymerase has been replaced with tyrosine, and 667th amino acid residue, phenylalanine, of the wild type T7 RNA polymerase has been replaced with tyrosine.

6. The method of claim 1, wherein the 3'-dNTP derivatives are 3'-deoxynucleotide derivatives represented by the following general formula [I]:

$$Q\text{—}V\text{—}(CH_2)_n\text{—}NH\text{—}R \qquad [I]$$

wherein Q represents a 3'-deoxyribonucleotide residue, n represents an integer not less than 1, V represents —C≡C— or —CH=CH—, and R represents a fluorescent group.

7. The method of claim 1, wherein the DNA fragment containing a promoter sequence is a DNA product amplified by polymerase chain reaction.

8. The method of claim 1, wherein the nucleic acid transcription reaction is performed in the presence of an inorganic pyrophosphatase.

9. The method of claim 3, wherein the mutant RNA polymerase is an RNA polymerase consisting of a wild type T7 RNA polymerase provided that 665th amino acid residue, leucine, of the wild type T7 RNA polymerase has been replaced with proline.

10. The method of claim 5, wherein the mutant RNA polymerase is an RNA polymerase consisting of a wild type T7 RNA polymerase provided that 665th amino acid residue, leucine, of the wild type T7 RNA polymerase has further been replaced with proline.

11. The method of claim 6, wherein n in the general formula [I] represents an integer of 4–10.

12. The method of claim 6, wherein R in the general formula [I] is represented by the following general formula [VII]:

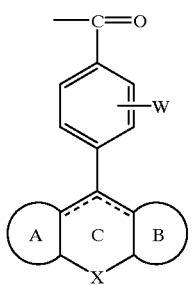

[VII]

wherein W represents a carboxyl group,
X represents —O—, —S—, —NR'— where R' represents hydrogen atom, a lower alkyl group, an aralkyl group or an aryl group, or —CH$_2$—, one of the ring A and the ring B represents

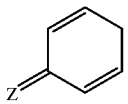

and the other one represents

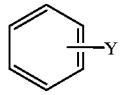

where Z represents O or =N$^+$R$_1$R$_2$, and Y represents OH or —NR$_1$R$_2$ where R$_1$ and R$_2$ each independently represent hydrogen atom or a lower alkyl group, or both of R$_1$ and R$_2$ represent a trimethylene group (provided that R$_1$ and R$_2$ represent two trimethylene groups, of which other end is bonded to either one of the carbon atoms next to the nitrogen atom to which the trimethylene group is bonded),
the broken line ------ in the ring C:

represents a bond present at a position decided by the structures of the ring A and the ring B, and the rings A, B and C and the benzene ring having W may optionally have one or more additional substituents.

13. The method of claim 2, wherein the nucleic acid transcription reaction is performed with the amplified product without removing primers and/or 2'-deoxyribonucleoside 5'-triphosphates and/or derivatives thereof used for the polymerase chain reaction.

14. A method for determining DNA nucleotide sequences comprising providing ribonucleoside 5'-triphosphates wherein said ribonucleoside triphosphates are selected from the group consisting of ATP, GTP, CTP, UTP, and derivatives thereof, reacting said ribonucleoside 5' triphosphates with one or more kinds of 3'-dNTP derivatives in the presence of an RNA polymerase and a DNA fragment containing a promoter sequence for the RNA polymerase to obtain a nucleic acid transcription product, wherein said 3'-dNTP derivatives are 3'-deoxyribonucleoside 5'-triphosphates selected from the group consisting of 3'-dATP, 3'-dGTP, 3'-dCTP, 3'-dUTP, and derivatives thereof separating the resulting nucleic acid transcription product, and determining a nucleic acid sequence from the resulting separated fraction, wherein the RNA polymerase is a mutant promoter-specific RNA polymerase selected from the group consisting of F645Y, L666P, F668Y, F645Y/L666P, F645Y/F668Y, L666/F668Y and F645Y/L666P/F668Y mutants of an RNA polymerase derived from T3 phage, said mutant RNA polymerase having an enhanced ability for incorporating the 3'-dNTP derivatives in comparison with the corresponding wild type RNA polymerase.

15. The method of claim 14, wherein the mutant RNA polymerase is an RNA polymerase derived from T3 phage, and has tyrosine at amino acid residue 645 or 668.

16. A method for determining DNA nucleotide sequences comprising providing ribonucleoside 5'-triphosphates wherein said ribonucleoside triphosphates are selected from the group consisting of ATP, GTP, CTP, UTP, and derivatives thereof, reacting said ribonucleoside 5' triphosphates with one or more kinds of 3'-dNTP derivatives in the presence of an RNA polymerase and a DNA fragment containing a promoter sequence for the RNA polymerase to obtain a nucleic acid transcription product, wherein said 3'-dNTP derivatives are 3'-deoxyribonucleoside 5'-triphosphates selected from the group consisting of 3'-dATP, 3'-dGTP, 3'-dCTP, 3'-dUTP, and derivatives thereof separating the resulting nucleic acid transcription product, and determining a nucleic acid sequence from the resulting separated fraction, wherein the RNA polymerase is a mutant promoter-specific RNA polymerase selected from the group consisting of L668P, F690Y, L688P/F690Y of K11 RNA polymerase and F670Y of SP6 RNA polymerase, said mutant RNA polymerase having an enhanced ability for incorporating the 3'-dNTP derivatives in comparison with the corresponding wild type RNA polymerase.

17. The method of claim 16, wherein the mutant RNA polymerase is an RNA polymerase derived from K11 phage, and has tyrosine at one or more amino acid residues 663–668 and 690.

18. The method of claim 16, wherein the mutant RNA polymerase is an RNA polymerase derived from SP6 phage, and has tyrosine at one or more amino acid residues 633–638 and 670.

* * * * *